United States Patent
Bartels et al.

(10) Patent No.: US 10,562,903 B2
(45) Date of Patent: Feb. 18, 2020

(54) BRIDGED PIPERIDINE DERIVATIVES

(71) Applicant: Hoffmann-La Roche Inc., Little Falls, NJ (US)

(72) Inventors: Bjoern Bartels, Basel (CH); Hasane Ratni, Basel (CH); Karlheinz Baumann, Basel (CH); Guido Galley, Basel (CH); Georg Jaeschke, Basel (CH); Roland Jakob-Roetne, Basel (CH); Anja Limberg, Basel (CH); Werner Neidhart, Basel (CH); Rosa Maria Rodriguez-Sarmiento, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/004,145

(22) Filed: Jun. 8, 2018

(65) Prior Publication Data

US 2019/0010156 A1    Jan. 10, 2019

Related U.S. Application Data

(63) Continuation of application No. PCT/EP2016/079816, filed on Dec. 6, 2016.

(30) Foreign Application Priority Data

Dec. 10, 2015  (EP) .................................... 15199260

(51) Int. Cl.
  *C07D 487/04* (2006.01)
  *C07D 471/04* (2006.01)
  *A61P 25/28* (2006.01)

(52) U.S. Cl.
  CPC ............ *C07D 487/04* (2013.01); *A61P 25/28* (2018.01); *C07D 471/04* (2013.01)

(58) Field of Classification Search
  CPC .............. A61K 31/4985; A61K 31/437; C07D 451/04; C07D 487/04; C07D 471/04
  See application file for complete search history.

(56) References Cited

U.S. PATENT DOCUMENTS

| 8,703,763 | B2 * | 4/2014 | Baumann | ............ | C07D 451/04 514/217.04 |
| 2002/0099208 | A1 | 7/2002 | Yu et al. | | |
| 2012/0225884 | A1 * | 9/2012 | Baumann | ............ | C07D 451/04 514/249 |

FOREIGN PATENT DOCUMENTS

| DE | 23 45 064 A1 | 4/1974 |
| FR | 2 914 188 A1 | 10/2008 |
| WO | 02/062290 A2 | 8/2002 |
| WO | 2005/061513 A1 | 7/2005 |
| WO | 2009/151546 A2 | 12/2009 |
| WO | 2010/019326 A1 | 2/2010 |
| WO | 2012/116965 | * 9/2012 |
| WO | 2012/116965 A1 | 9/2012 |
| WO | 2013/020993 A1 | 2/2013 |
| WO | 2013/068769 A1 | 5/2013 |
| WO | 2013/101974 A1 | 7/2013 |
| WO | 2013/112788 A1 | 8/2013 |

(Continued)

OTHER PUBLICATIONS

Brunhilde Wirth et al., "Moving towards treatments for spinal muscular atrophy: hopes and limits" Expert Opinion on Emerging Drugs 20(3):353-356 (Apr. 28, 2015).

(Continued)

*Primary Examiner* — D Margaret M Seaman
(74) *Attorney, Agent, or Firm* — Genentech, Inc.; Richard G. A. Bone

(57) ABSTRACT

The present invention relates to a compound of formula

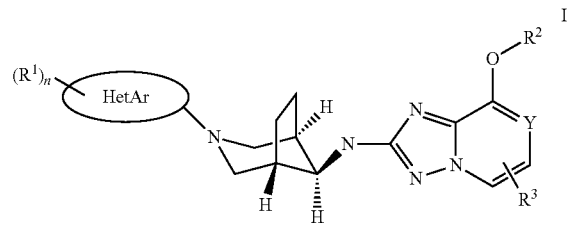

wherein
HetAr is a five or six membered hetaryl group, containing one, two or three heteroatoms, selected from N, O or S;
$R^1$ is hydrogen, lower alkyl, lower alkyl substituted by halogen, halogen, or lower alkoxy;
$R^2$ is lower alkyl substituted by halogen, $-CH_2-C_{3-6}$-cycloalkyl, substituted by one or two substituents, selected from lower alkyl substituted by halogen or halogen, or is lower alkenyl substituted by halogen;
$R^3$ is hydrogen, lower alkyl substituted by halogen, lower alkyl, halogen, $C_{3-6}$-cycloalkyl or lower alkyl substituted by hydroxy;
n is 1 or 2; for n=2, $R^1$ can be independent to each other;
Y is CH or N;
or to a pharmaceutically active acid addition salt thereof, to a racemic mixture or its corresponding enantiomer and/or optical isomer and/or stereoisomer thereof.

The compounds may be used for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome.

24 Claims, No Drawings

(56) References Cited

FOREIGN PATENT DOCUMENTS

| WO | 2013/119916 A2 | 8/2013 |
| WO | 2014/012050 A2 | 1/2014 |
| WO | 2014/184163 A1 | 11/2014 |
| WO | 2014/209841 A2 | 12/2014 |
| WO | 2015/173181 A1 | 11/2015 |
| WO | 2015/110446 A1 | 7/2016 |
| WO | 2017/080967 A1 | 5/2017 |

OTHER PUBLICATIONS

Chiara Zanetta et al., "Molecula Therapeutic Strategies for Spinal Muscular Atrophies: Current and Future Clinical Trials" Clinical Therapeutics 36(1):128-140 (Dec. 17, 2013).

Combrink et al., "Respiratory syncytial virus fusion inhibitors. Part 6: An examination of the effect of structural variation of the benzimidazol-2-one heterocycle moiety" Bioorganic & Medicinal Chemistry Letters 17(17):4784-4790 (Aug. 4, 2007)

IPRP for PCT/EP2015/060343.

ISR and Written Opinion of PCT/EP2016/076905 (dated Feb. 9, 2017).

ISR and Written Opinion of PCT/EP2016/077190 (dated Mar. 1, 2017).

ISR for PCT/EP2015/063894.

ISR of PCT/EP2012/065499 (dated Sep. 20, 2012) WO2013/020993.

ISR of PCT/EP2014/059699 (dated Jul. 10, 2014) WO2014/184163.

ISR of PCT/EP2015/051066 (dated Feb. 6, 2015) WO2015/110446A1.

ISR of PCT/EP2015/060343 (dated Jul. 6, 2015) WO2015/173181.

ISR of PCT/EP2016/060952 (dated Jun. 16, 2016).

ISR of PCT/EP2016/079816 (dated Jan. 19, 2017).

Markus Riessland et al., "The benzamide M344, a novel histone deacetylase inhibitior, significantly increases SMN2 RNA/protein levels in spinal muscular atrophy cells" Hum Genet 120:101-110 (May 25, 2006).

N.A. Naryshkin et al., "SMN2 splicing modifiers improve motor function and lngevity in mice with spinal muscular atrophy" Science 345(6197):688-693 (Aug. 8, 2014).

Seisuke Mimori et al., "Protective Effects of 4-Phenylbutyrate Derivatives on the Neuronal Cell Death and Endoplasmic Reticulum Stress" Biological & Pharmaceutical Bulletin of Japan 35(1):84-90 (Jan. 1, 2012).

Sin et al., "Respiratory syncytial virus fusion inhibitors. Part 7: Structure-activity relationships associated with a series of isatin oximes that demonstrate antiviral activity in vivo" Bioorganic & Medicinal Chemistry Letters 19(16):4857-4862 (Aug. 15, 2009).

* cited by examiner

BRIDGED PIPERIDINE DERIVATIVES

CROSS-REFERENCE TO RELATED APPLICATIONS

This application is a continuation of, and claims priority to, International Patent Application No. PCT/EP2016/079816, filed on Dec. 6, 2016. This application also claims priority to European Patent Application No. 15199260.9, filed on Dec. 10, 2015. The entire contents of each of the above patent applications are hereby incorporated by reference.

The present invention relates to a compound of formula

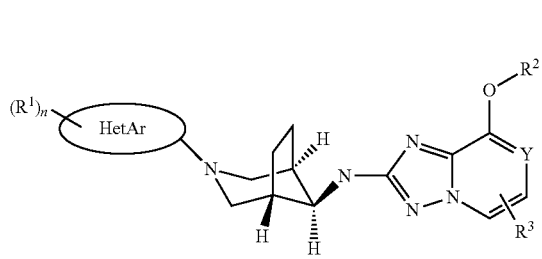

I wherein
HetAr is a five or six membered hetaryl group, containing one, two or three heteroatoms, selected from N, O or S;
$R^1$ is hydrogen, lower alkyl, lower alkyl substituted by halogen, halogen, or lower alkoxy;
$R^2$ is lower alkyl substituted by halogen, —$CH_2$—$C_{3-6}$-cycloalkyl substituted by one or two substituents selected from lower alkyl substituted by halogen or halogen, or is lower alkenyl substituted by halogen;
$R^3$ is hydrogen, lower alkyl substituted by halogen, lower alkyl, halogen, $C_{3-6}$-cycloalkyl or lower alkyl substituted by hydroxy;
n is 1 or 2; for n=2, $R^1$ can be independent to each other;
Y is CH or N;
or to a pharmaceutically active acid addition salt thereof, to a racemic mixture or to its corresponding enantiomer and/or optical isomer and/or stereoisomer thereof.

Now it has been found that the present compounds of formula I are modulators of γ-secretase, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, doi: 10.1038/nature14892). The presenilins are bearing the catalytic site and represent a group of atypical aspartyl proteases which cleave their substrates within the TM of and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease. Therefore, it was believed that selective and potent inhibition of γ-secretase might be useful for the prevention and treatment of AD.

An alternative mode of treatment is the modulation of the γ-secretase activity which results in a selective reduction of the Aβ42 production. This will lead in an increase of shorter Aβ isoforms, such as Aβ38, Aβ37 or others, which have no or reduced capability for aggregation and plaque formation, and are not or less neurotoxic. Compounds which show this effect on modulating γ-secretase activity include certain non-steroidal anti-inflammatory drugs (NSAIDs) and related analogues (Weggen et al. Nature, 414 (2001) 212-16).

Thus, the compounds of this invention will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Numerous documents describe the current knowledge on γ-secretase modulation, for example the following publications:
Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91

Ebke et al, J. Biol. Chem., 286 (2011) 37181-86
Hall et al, Progress in Med. Chem., 53 (2014) 101-145
The following definitions for compounds of formula I are used:

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by halogen" denotes an alkyl group as defined above, wherein at least one hydrogen atom is replaced by halogen, for example $CF_3$, $CHF_2$, $CH_2F$, $CHFCF_3$, $CH_2CHF_2$, $CH_2CH_2F$, $CH_2C(CH_3)_2CF_3$, $CH_2CF_2CF_3$, $CH(CF_3)_2$, $CH_2CF_3$, $(CH_2)_2CF_3$, $(CH_2)_3CF_3$, $CH(CH_3)CF_3$, $CF_2CF_3$, and the like.

As used herein, "lower alkenyl substituted by halogen" denotes an alkenyl group, wherein at least one hydrogen atom is replaced by halogen, for example $CH=CFCF_3$.

As used herein, the term "lower alkyl substituted by hydroxy" denotes an alkyl group as defined above, wherein at least one hydrogen atom is replaced by hydroxy, for example $C(CH_3)_2OH$.

The term "halogen" denotes chlorine, iodine, fluorine and bromine.

The term "five or six membered hetaryl group, containing one, two or three heteroatoms, selected from N, O or S" is selected from the group consisting of

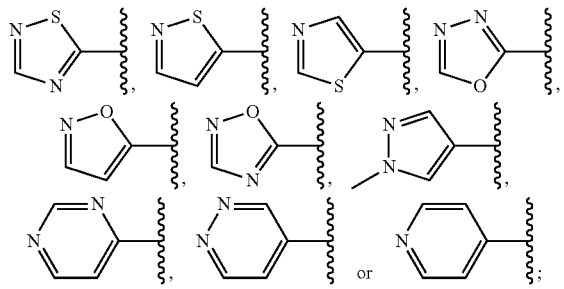

The term "—$CH_2$—$C_{3-6}$-cycloalkyl, substituted by one or two substituents, selected from lower alkyl substituted by halogen or halogen, is selected from the group consisting of

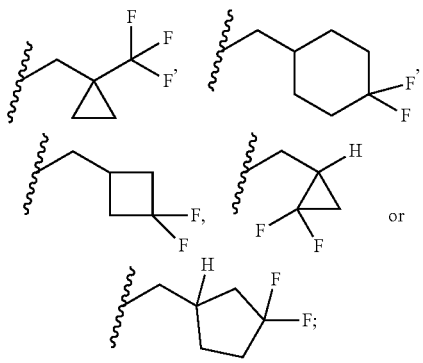

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Objects of the present invention are compounds of formula I, the use of such compounds for the preparation of medicaments for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, their manufacture and medicaments based on a compound of formula I in accordance with the invention.

Further objects of the invention are all forms of optically pure enantiomers, racemates or diastereomeric mixtures for compounds of formula I.

One object of the invention is a compound of formula I-1

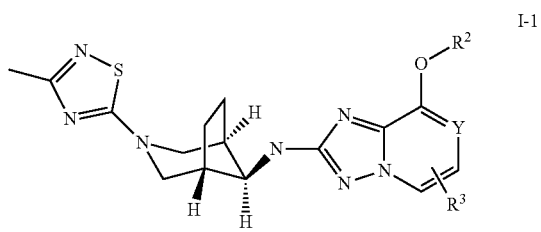

wherein
$R^2$ is lower alkyl substituted by halogen,

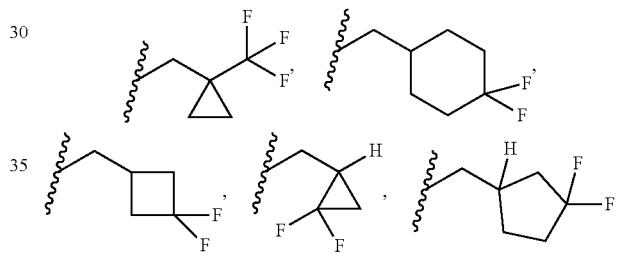

or is lower alkenyl substituted by halogen;
$R^3$ is hydrogen, lower alkyl substituted by halogen, lower alkyl, halogen, $C_{3-6}$-cycloalkyl or lower alkyl substituted by hydroxy;
Y is CH or N;
or a pharmaceutically active acid addition salt thereof, a racemic mixture or its corresponding enantiomer and/or optical isomer and/or stereoisomer thereof, for example the following compounds
N-[(8 endo)-3-(3-methyl-1,2,4-thiadiazol-5-yl)-3-azabicyclo[3.2.1]octan-8-yl]-8-(4,4,4-trifluorobutoxy)-[1,2,4]triazolo[1,5-a]pyridin-2-amine
N-[(8-endo)-3-(3-methyl-1,2,4-thiadiazol-5-yl)-3-azabicyclo[3.2.1]octan-8-yl]-8-(3,3,3-trifluoropropoxy)-[1,2,4]triazolo[1,5-a]pyridin-2-amine
N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine
N-[(8-endo) 3-(3-methyl-1,2,4-thiadiazol-5-yl)-3-azabicyclo[3.2.1]octan-8-yl]-8-[(2R/S)-1,1,1-trifluoropropan-2-yl]oxy-[1,2,4]triazolo[1,5-a]pyridin-2-amine
N-[(8-endo)-3-(3-methyl-1,2,4-thiadiazol-5-yl)-3-azabicyclo[3.2.1]octan-8-yl]-8-[(2R or 2S)-1,1,1-trifluoropropan-2-yl]oxy-[1,2,4]triazolo[1,5-a]pyridin-2-amine
N-[(8 endo)-3-(3-methyl-1,2,4-thiadiazol-5-yl)-3-azabicyclo[3.2.1]octan-8-yl]-8-[(2S or 2R)-1,1,1-trifluoropropan-2-yl]oxy-[1,2,4]triazolo[1,5-a]pyridin-2-amine N-[(8 endo)-3-(3-methyl-1,2,4-thiadiazol-5-yl)-3-azabicyclo[3.2.1]octan-8-yl]-8-[[1-(trifluoromethyl)cyclopropyl]methoxy]-[1,2,4]triazolo[1,5-a]pyridin-2-amine 8-[(4,4-difluorocyclohexyl)methoxy]-N [(8-endo)-3-(3-methyl-1,2,4-thiadiazol-5-yl)-3-azabicyclo[3.2.1]octan-8-yl]-[1,2,4]triazolo[1,5-a]pyridin-2-amine 8-[(3,3-difluorocyclobutyl)methoxy]-N-[(8 endo)-3-(3-methyl-1,2,4-thiadiazol-5-yl)-3-azabicyclo[3.2.1]octan-8-yl]-[1,2,4]triazolo[1,5-a]pyridin-2-amine N-[(8 endo)-3-(3-methyl-1,2,4-thiadiazol-5-yl)-3-azabicyclo[3.2.1]octan-8-yl]-8-(1,2,2,2-tetrafluoroethoxy)-[1,2,4]triazolo[1,5-a]pyridin-2-amine 8-[2,2-difluorocyclopropyl] methoxy]-N-[(8endo)-3-(3-methyl-1,2,4-thiadiazol-5-yl)-3-azabicyclo[3.2.1]octan-8-yl]-[1,2,4]triazolo[1,5-a]pyridin-2-amine 8-((3,3-difluorocyclopentyl)methoxy)-N-[(8 endo) 3-(3-methyl-1,2,4-thiadiazol-5-yl)-3-azabicyclo[3.2.1]octan-8-yl]-[1,2,4]triazolo[1,5-a]pyridin-2-amine N-[(8-endo)-3-(3-methyl-1,2,4-thiadiazol-5-yl)-3-azabicyclo[3.2.1]octan-8-yl]-8-(3,3,3-trifluoro-2,2-dimethylpropoxy)-[1,2,4]triazolo[1,5-a]pyridin-2-amine 5-methyl-N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine 6-Methyl-N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine or 6-chloro-N-[8-endo-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine.

One object of the invention is a compound of formula I-2

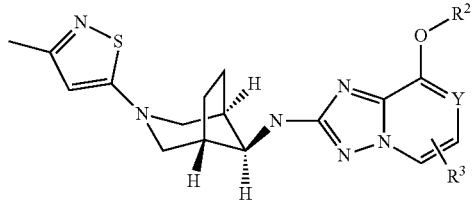

I-2 wherein
R² is lower alkyl substituted by halogen,

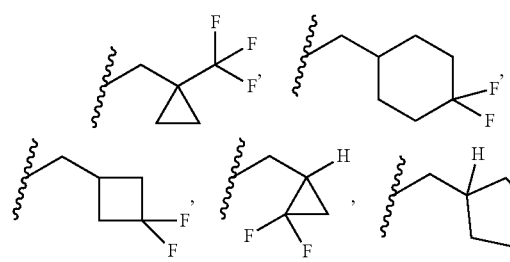

or is lower alkenyl substituted by halogen;
R³ is hydrogen, lower alkyl substituted by halogen, lower alkyl, halogen, $C_{3-6}$-cycloalkyl or lower alkyl substituted by hydroxy;
Y is CH or N;
or a pharmaceutically active acid addition salt thereof, a racemic mixture or its corresponding enantiomer and/or optical isomer and/or stereoisomer thereof, for example the following compounds N-[(8-endo)-3-(3-methyl-1,2-thiazol-5-yl)-3-azabicyclo[3.2.1]octan-8-yl]-8-(3,3,3-trifluoropropoxy)-[1,2,4]triazolo[1,5-a]pyridin-2-amine N-[(8 endo)-3-(3-methylisothiazol-5-yl)-3-azabicyclo[3.2.1]octan-8-yl]-8-(2,2,3,3,3-pentafluoropropoxy)-[1,2,4]triazolo[1,5-a]pyridin-2-amine N-[(8 endo) 3-(3-methylisothiazol-5-yl)-3-azabicyclo[3.2.1]octan-8-yl)]-8-(2,2,2-trifluoroethoxy)-[1,2,4]triazolo[1,5-a]pyridin-2-amine N-[(8 endo)-3-(3-methylisothiazol-5-yl)-3-azabicyclo[3.2.1]octan-8-yl]-8-((1,1,1,1-trifluoropropan-2-yl)oxy)-[1,2,4]triazolo[1,5-a]pyridin-2-amine N-((8 endo)-3-(3-methylisothiazol-5-yl)-3-azabicyclo[3.2.1]octan-8-yl)-8-((2R or 2S)-1,1,1-trifluoropropan-2-yl)oxy)-[1,2,4]triazolo[1,5-a]pyridin-2-amine N-[(8-endo)-3-(3-methylisothiazol-5-yl)-3-azabicyclo[3.2.1]octan-8-yl)]-8-((2S or 2R)-1,1,1-trifluoropropan-2-yl)oxy)-[1,2,4]triazolo[1,5-a]pyridin-2-amine N-[(8 endo)-3-(3-methylisothiazol-5-yl)-3-azabicyclo[3.2.1]octan-8-yl]-8-(trifluoromethoxy)-[1,2,4]triazolo[1,5-a]pyridin-2-amine N [(8 endo)-3-(3-methyl-1,2-thiazol-5-yl)-3-azabicyclo[3.2.1]octan-8-yl]-8-[[1-(trifluoromethyl) cyclopropyl]methoxy]-[1,2,4]triazolo[1,5-a]pyridin-2-amine 8-[(4,4-difluorocyclohexyl)methoxy]-N-[(8 endo)-3-(3-methyl-1,2-thiazol-5-yl)-3-azabicyclo[3.2.1]octan-8-yl]-[1,2,4]triazolo[1,5-a]pyridin-2-amine 8-[(3,3-difluorocyclobutyl)methoxy]-N-[(8 endo)-3-(3-methyl-1,2-thiazol-5-yl)-3-azabicyclo[3.2.1]octan-8-yl]-[1,2,4]triazolo[1,5-a]pyridin-2-amine N-[(8 endo)-3-(3-methyl-1,2-thiazol-5-yl)-3-azabicyclo[3.2.1]octan-8-yl]-8-[1,2,2,2-tetrafluoroethoxy]-[1,2,4]triazolo[1,5-a]pyridin-2-amine 8-[2,2-difluorocyclopropyl]methoxy]-N-[(8-endo)-3-(3-methylisothiazol-5-yl)-3-azabicyclo[3.2.1]octan-8-yl)]-[1,2,4]triazolo[1,5-a]pyridin-2-amine 8-[3,3-difluorocyclopentyl] methoxy]-N-[(8 endo)-3-(3-methyl-1,2-thiazol-5-yl)-3-azabicyclo[3.2.1]octan-8-yl]-[1,2,4]triazolo[1,5-a]pyridin-2-amine N-[(8 endo)-3-(3-methyl-1,2-thiazol-5-yl)-3-azabicyclo[3.2.1]octan-8-yl]-8-(3,3,3-trifluoro-2,2-dimethylpropoxy)-[1,2,4]triazolo[1,5-a]pyridin-2-amine N-[(8 endo) (3-(3-methylisothiazol-5-yl))-3-azabicyclo[3.2.1]octan-8-yl)]-8-(2,2,2-trifluoroethoxy)-[1,2,4]triazolo[1,5-a]pyridin-2-amine N-[(8 endo)-3-(3-methylisothiazol-5-yl)-3-azabicyclo[3.2.1]octan-8-yl)]-8-(3,3,3-trifluoropropoxy)-[1,2,4]triazolo[1,5-a]pyrazin-2-amine 8-(2,2-difluoroethoxy)-N-[(8-endo)-3-(3-methylisothiazol-5-yl)-3-azabicyclo[3.2.1]octan-8-yl]-[1,2,4]triazolo[1,5-a]pyrazin-2-amine N-[(8-endo)-3-(3-methylisothiazol-5-yl)-3-azabicyclo[3.2.1]octan-8-yl]-8-(2,2,3,3,3-pentafluoropropoxy)-[1,2,4]triazolo[1,5-a]pyrazin-2-amine 8-((1,1,1,3,3,3-hexafluoropropan-2-yl)oxy)-N-[(8 endo)-3-(3-methylisothiazol-5-yl)-3-azabicyclo[3.2.1]octan-8-yl)-[1,2,4]triazolo[1,5-a]pyrazin-2-amine N-[(8 endo)-3-(3-methylisothiazol-5-yl)-3-azabicyclo[3.2.1]octan-8-yl]-8-((1-(trifluoromethyl)cyclopropyl)methoxy)-[1,2,4]triazolo[1,5-a]pyrazin-2-amine N-[(8 endo)-3-(3-methylisothiazol-5-yl)-3-azabicyclo[3.2.1]octan-8-yl]-8-((1,1,1,1-trifluoropropan-2-yl)oxy)-[1,2,4]triazolo[1,5-a]pyrazin-2-amine N-[(8 endo)-3-(3-methylisothiazol-5-yl)-3-azabicyclo[3.2.1]octan-8-yl]-8-((2R or 2S)-1,1,1-trifluoropropan-2-yl)oxy)-[1,2,4]triazolo[1,5-a]pyrazin-2-amine N-[(8 endo)-3-(3-methylisothiazol-5-yl)-3-azabicyclo[3.2.1]octan-8-yl]-8-((2S or 2R)-1,1,1-trifluoropropan-2-yl)oxy)-[1,2,4]triazolo[1,5-a]pyrazin-2-amine N-[8-endo-3-(3-methylisothiazol-5-yl)-3-azabicyclo[3.2.1]octan-8-yl]-8-(2,2,2-trifluoroethoxy)-5-(trifluoromethyl)-[1,2,4]triazolo[1,5-a]pyridin-2-amine N-[(8-endo-3-(3-methylisothiazol-5-yl)-3-azabicyclo[3.2.1]octan-8-yl]-5-(trifluoromethyl)-8-[[1-(trifluoromethyl)cyclopropyl]methoxy]-[1,2,4]triazolo[1,5-a]pyridin-2-amine or 6-Fluoro-N-[(8-endo)-3-(3-methylisothiazol-5-yl)-3-azabicyclo[3.2.1]octan-8-yl]-8-(2,2,2-trifluoroethoxy)-[1,2,4]triazolo[1,5-a]pyridin-2-amine.

One object of the invention is a compound of formula I-3

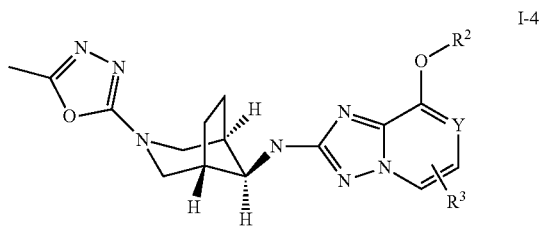

wherein
R² is lower alkenyl substituted by halogen;

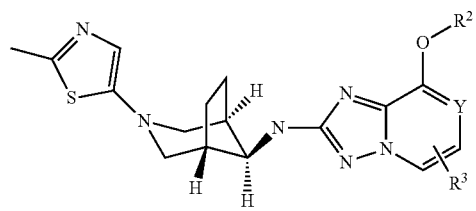

R³ is hydrogen, lower alkyl substituted by halogen, lower alkyl, halogen, C₃₋₆-cycloalkyl or lower alkyl substituted by hydroxy;
Y is CH or N;
or a pharmaceutically active acid addition salt thereof, a racemic mixtures or its corresponding enantiomer and/or optical isomer and/or stereoisomer thereof, for example the following compounds N-[(8 endo)-3-(2-methyl-1,3-thiazol-5-yl)-3-azabicyclo[3.2.1]octan-8-yl]-8-(4,4,4-trifluorobutoxy)-[1,2,4]triazolo[1,5-a]pyridin-2-amine N-[(8 endo)-3-(2-methyl-1,3-thiazol-5-yl)-3-azabicyclo[3.2.1]octan-8-yl]-8-(3,3,3-trifluoropropoxy)-[1,2,4]triazolo[1,5-a]pyridin-2-amine N-[8 endo-3-(2-methyl-1,3-thiazol-5-yl)-3-azabicyclo[3.2.1]octan-8-yl]-8-(2,2,2-trifluoroethoxy)-[1,2,4]triazolo[1,5-a]pyridin-2-amine or N-[(8 endo-3-(2-methyl-1,3-thiazol-5-yl)-3-azabicyclo[3.2.1]octan-8-yl]-8-[1,1,1-trifluoropropan-2-yl]oxy-[1,2,4]triazolo[1,5-a]pyridin-2-amine.

One object of the invention is a compound of formula I-4

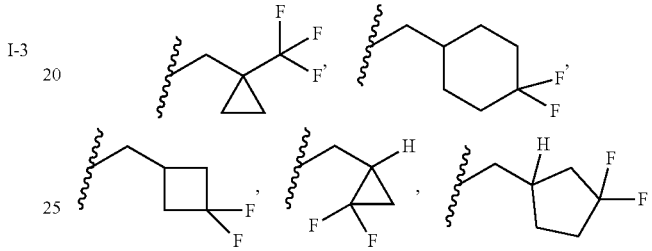

wherein
R² is lower alkyl substituted by halogen,

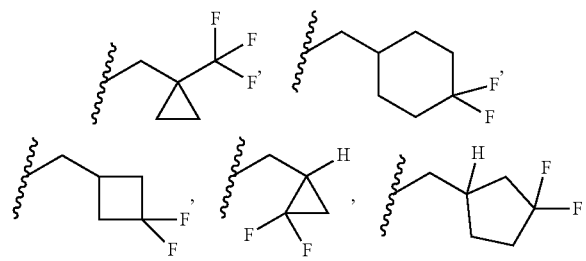

or is lower alkenyl substituted by halogen;
R³ is hydrogen, lower alkyl substituted by halogen, lower alkyl, halogen, C₃₋₆-cycloalkyl or lower alkyl substituted by hydroxy;
Y is CH or N;
or a pharmaceutically active acid addition salt thereof, a racemic mixtures or its corresponding enantiomer and/or optical isomer and/or stereoisomer thereof, for example the following compounds N-[(8 endo)-3-(5-methyl-1,3,4-oxadiazol-2-yl)-3-azabicyclo[3.2.1]octan-8-yl]-8-(4,4,4-trifluorobutoxy)-[1,2,4]triazolo[1,5-a]pyridin-2-amine N-[8-endo-3-(5-methyl-1,3,4-oxadiazol-2-yl)-3-azabicyclo[3.2.1]octan-8-yl]-8-(2,2,2-trifluoroethoxy)-5-(trifluoromethyl)-[1,2,4]triazolo[1,5-a]pyridin-2-amine N-[(8-endo)-3-(5-methyl-1,3,4-oxadiazol-2-yl)-3-azabicyclo[3.2.1]octan-8-yl]-5-(trifluoromethyl)-8-(2,2,2-trifluoro-1-methyl-ethoxy)-[1,2,4]triazolo[1,5-a]pyridin-2-amine N-[(8-endo)-3-(5-methyl-1,3,4-oxadiazol-2-yl)-3-azabicyclo[3.2.1]octan-8-yl]-5-(trifluoromethyl)-8-[(1R or 1S)-2,2,2-trifluoro-1-methyl-ethoxy]-[1,2,4]triazolo[1,5-a]pyridin-2-amine or N-[(8-endo)-3-(5-methyl-1,3,4-oxadiazol-2-yl)-3-azabicyclo[3.2.1]octan-8-yl]-5-(trifluoromethyl)-8-[(1S or 1R)-2,2,2-trifluoro-1-methyl-ethoxy]-[1,2,4]triazolo[1,5-a]pyridin-2-amine.

One object of the invention is a compound of formula I-5

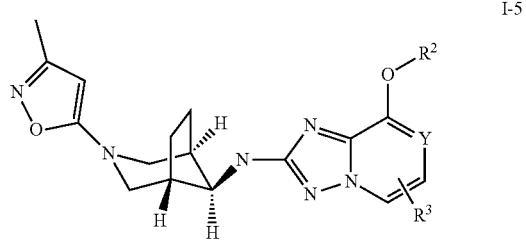

wherein
R² is lower alkyl substituted by halogen,

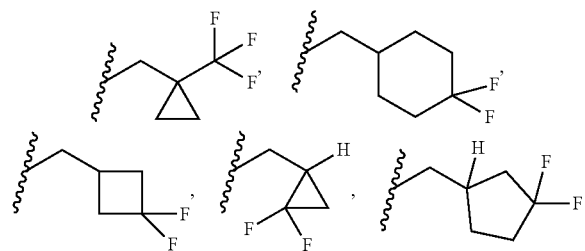
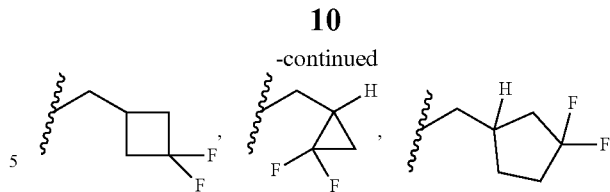

or is lower alkenyl substituted by halogen;
R³ is hydrogen, lower alkyl substituted by halogen, lower alkyl, halogen, C₃₋₆-cycloalkyl or lower alkyl substituted by hydroxy;
Y is CH or N;
or a pharmaceutically active acid addition salt thereof, a racemic mixtures or its corresponding enantiomer and/or optical isomer and/or stereoisomer thereof, for example the following compounds N-[(8 endo)-3-(3-methyl-1,2-oxazol-5-yl)-3-azabicyclo[3.2.1]octan-8-yl]-8-[1,1,1-trifluoropropan-2-yl]oxy-[1,2,4]triazolo[1,5-a]pyridin-2-amine N-[(8 endo)-3-(3-methyl-1,2-oxazol-5-yl)-3-azabicyclo[3.2.1]octan-8-yl]-8-[(2R or 2S)-1,1,1-trifluoropropan-2-yl]oxy-[1,2,4]triazolo[1,5-a]pyridin-2-amine N-[(8 endo)-3-(3-methyl-1,2-oxazol-5-yl)-3-azabicyclo[3.2.1]octan-8-yl]-8-[[1 (trifluoromethyl)cyclopropyl]methoxy]-[1,2,4]triazolo[1,5-a]pyridin-2-amine N-[(8 endo)-3-(3-methyl-1,2-oxazol-5-yl)-3-azabicyclo[3.2.1]octan-8-yl]-8-(2,2,3,3,3-pentafluoropropoxy)-[1,2,4]triazolo[1,5-a]pyridin-2-amine N-[(8-endo)-3-(3-methylisoxazol-5-yl)-3-azabicyclo[3.2.1]octan-8-yl]-8-(2,2,2-trifluoroethoxy)-5-(trifluoromethyl)-[1,2,4]triazolo[1,5-a]pyridin-2-amine or N-[(8-endo)-3-(3-methylisoxazol-5-yl)-3-azabicyclo[3.2.1]octan-8-yl]-5-(trifluoromethyl)-8-[2,2,2-trifluoro-1-methyl-ethoxy]-[1,2,4]triazolo[1,5-a]pyridin-2-amine.

One object of the invention is a compound of formula I-6

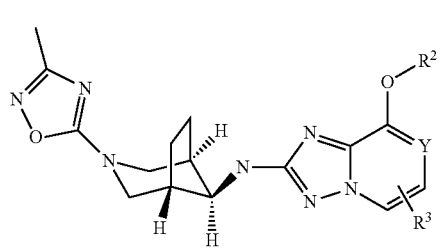

wherein
R² is lower alkyl substituted by halogen,

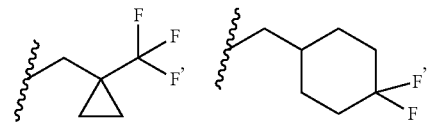

or is lower alkenyl substituted by halogen;
R³ is hydrogen, lower alkyl substituted by halogen, lower alkyl, halogen, C₃₋₆-cycloalkyl or lower alkyl substituted by hydroxy;
Y is CH or N;
or a pharmaceutically active acid addition salt thereof, a racemic mixture or its corresponding enantiomer and/or optical isomer and/or stereoisomer thereof, for example the following compounds N-[(8 endo)-3-(3-methyl-1,2,4-oxadiazol-5-yl)-3-azabicyclo[3.2.1]octan-8-yl]-8-(1,1,1-trifluoropropan-2-yloxy)-[1,2,4]triazolo[1,5-a]pyridin-2-amine N-[(8 endo)-3-(3-methyl-1,2,4-oxadiazol-5-yl)-3-azabicyclo[3.2.1]octan-8-yl]-8-(2,2,3,3,3-pentafluoropropoxy)-[1,2,4]triazolo[1,5-a]pyridin-2-amine N-[(8 endo)-3-(3-methyl-1,2,4-oxadiazol-5-yl)-3-azabicyclo[3.2.1]octan-8-yl]-8-[(Z)-2,3,3,3-tetrafluoroprop-1-enoxy]-[1,2,4]triazolo[1,5-a]pyridin-2-amine N-[(8 endo)-3-(3-methyl-1,2,4-oxadiazol-5-yl)-3-azabicyclo[3.2.1]octan-8-yl]-8-(2,2,3,3,3-pentafluoropropoxy)-[1,2,4]triazolo[1,5-a]pyrazin-2-amine N-[(8-endo)-3-(3-methyl-1,2,4-oxadiazol-5-yl)-3-azabicyclo[3.2.1]octan-8-yl]-8-(2,2,2-trifluoroethoxy)-5-(trifluoromethyl)-[1,2,4]triazolo[1,5-a]pyridin-2-amine N-[(8-endo)-3-(3-methyl-1,2,4-oxadiazol-5-yl)-3-azabicyclo[3.2.1]octan-8-yl]-5-(trifluoromethyl)-8-(2,2,2-trifluoro-1-methyl-ethoxy)-[1,2,4]triazolo[1,5-a]pyridin-2-amine N-[(8-endo)-3-(3-methyl-1,2,4-oxadiazol-5-yl)-3-azabicyclo[3.2.1]octan-8-yl]-5-(trifluoromethyl)-8-[(1R or 1S)-2,2,2-trifluoro-1-methyl-ethoxy]-[1,2,4]triazolo[1,5-a]pyridin-2-amine or 5-Methyl-N-[8-endo-3-(3-methyl-1,2,4-oxadiazol-5-yl)-3-azabicyclo[3.2.1]octan-8-yl]-8-(2,2,3,3,3-pentafluoropropoxy)-[1,2,4]triazolo[1,5-a]pyridin-2-amine.

One object of the invention is a compound of formula I-7

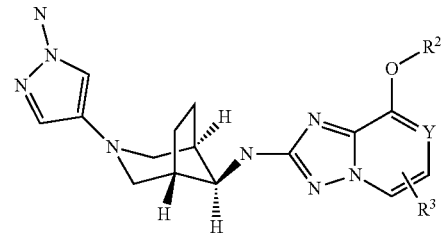

wherein
R² is lower alkyl substituted by halogen,

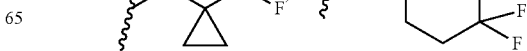

-continued

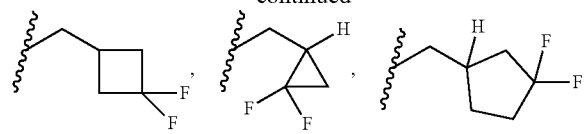

or is lower alkenyl substituted by halogen;
R³ is hydrogen, lower alkyl substituted by halogen, lower alkyl, halogen, C₃₋₆-cycloalkyl or lower alkyl substituted by hydroxy;
Y is CH or N;
or a pharmaceutically active acid addition salt thereof, a racemic mixture or its corresponding enantiomer and/or optical isomer and/or stereoisomer thereof, for example the following compound
N-[(8 endo)-3-(1-methylpyrazol-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine.

One object of the invention is a compound of formula I-8

I-8

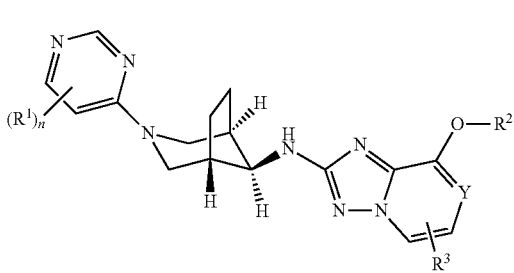

wherein
R¹ is hydrogen, lower alkyl, lower alkyl substituted by halogen, halogen, or lower alkoxy;
R² is lower alkyl substituted by halogen,

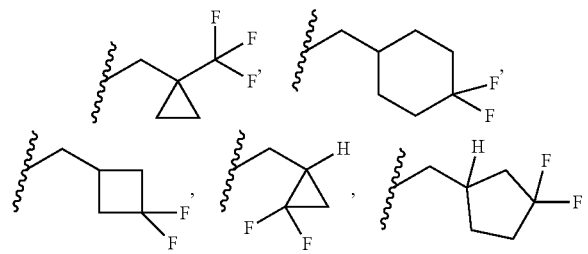

or is lower alkenyl substituted by halogen;
R³ is hydrogen, lower alkyl substituted by halogen, lower alkyl, halogen, C₃₋₆-cycloalkyl or lower alkyl substituted by hydroxy;
Y is CH or N;
n is 1 or 2; for n=2, R¹ can be independent to each other;
or a pharmaceutically active acid addition salt thereof, a racemic mixture or its corresponding enantiomer and/or optical isomer and/or stereoisomer thereof, for example the following compounds
N-[(8 endo)-3-(6-methylpyrimidin-4-yl)-3-azabicyclo[3.2.1]octan-8-yl]-8-(3,3,3-trifluoropropoxy)-[1,2,4]triazolo[1,5-a]pyridin-2-amine
N-[(8 endo)-3-(6-methylpyrimidin-4-yl)-3-azabicyclo[3.2.1]octan-8-yl]-8-(2,2,2-trifluoroethoxy)-[1,2,4]triazolo[1,5-a]pyridin-2-amine
N-[(8 endo)-3-(6-methylpyrimidin-4-yl)-3-azabicyclo[3.2.1]octan-8-yl]-8-1,1,1-trifluoropropan-2-yloxy)-[1,2,4]triazolo[1,5-a]pyridin-2-amine
N-[(8 endo)-3-(6-methylpyrimidin-4-yl)-3-azabicyclo[3.2.1]octan-8-yl]-8-(2,2,3,3,3-pentafluoropropoxy)-[1,2,4]triazolo[1,5-a]pyridin-2-amine
N-[(8 endo)-3-(2-methylpyrimidin-4-yl)-3-azabicyclo[3.2.1]octan-8-yl]-44,44-trifluorobutoxy)-[1,2,4]triazolo[1,5-a]pyridin-2-amine
N-[(8 endo)-3-(2-methylpyrimidin-4-yl)-3-azabicyclo[3.2.1]octan-8-yl]-8-1,1,1-trifluoropropan-2-yloxy)-[1,2,4]triazolo[1,5-a]pyridin-2-amine
8-(2,2,3,3,3-pentafluoropropoxy)-N-[(8 endo)-3-[6-(trifluoromethyl)pyrimidin-4-yl]-3-azabicyclo[3.2.1]octan-8-yl]-[1,2,4]triazolo[1,5-a]pyridin-2-amine
N-[(8 endo)-3-(5-fluoropyrimidin-4-yl)-3-azabicyclo[3.2.1]octan-8-yl]-8-(2,2,3,3,3-pentafluoropropoxy)-[1,2,4]triazolo[1,5-a]pyridin-2-amine
N-[(8 endo)-3-(5-fluoro-6-methylpyrimidin-4-yl)-3-azabicyclo[3.2.1]octan-8-yl]-8-(2,2,3,3,3-pentafluoropropoxy)-[1,2,4]triazolo[1,5-a]pyridin-2-amine
N-[(8 endo)-3-(5-fluoro-2-methylpyrimidin-4-yl)-3-azabicyclo[3.2.1]octan-8-yl]-8-(2,2,2-trifluoroethoxy)-[1,2,4]triazolo[1,5-a]pyridin-2-amine
N-[(8 endo)-3-(6-chloropyrimidin-4-yl)-3-azabicyclo[3.2.1]octan-8-yl]-8-(2,2,2-trifluoroethoxy)-[1,2,4]triazolo[1,5-a]pyridin-2-amine
N-[(8-endo)-3-(6-methylpyrimidin-4-yl)-3-azabicyclo[3.2.1]octan-8-yl]-8-(2,2,2 trifluoroethoxy)-5-(trifluoromethyl)-[1,2,4]triazolo[1,5-a]pyridin-2-amine
N-[(8-endo)-3-(5-fluoropyrimidin-4-yl)-3-azabicyclo[3.2.1]octan-8-yl]-8-(2,2,2-trifluoroethoxy) 5-(trifluoromethyl)-[1,2,4]triazolo[1,5-a]pyridin-2-amine
N-[(8-endo)-3-(5-fluoro-6-methyl-pyrimidin-4-yl)-3-azabicyclo[3.2.1]octan-8-yl]-8-(2,2,2 trifluoroethoxy)-5-(trifluoromethyl)-[1,2,4]triazolo[1,5-a]pyridin-2-amine amine
N-[(8-endo)-3-(6-chloropyrimidin-4-yl)-3-azabicyclo[3.2.1]octan-8-yl]-8-(2,2,2 trifluoroethoxy)-5-(trifluoromethyl)-[1,2,4]triazolo[1,5-a]pyridin-2-amine
N-[(8-endo)-3-pyrimidin-4-yl-3-azabicyclo[3.2.1]octan-8-yl]-8-(2,2,2-trifluoroethoxy)-5-(trifluoromethyl)-[1,2,4]triazolo[1,5-a]pyridin-2-amine
N-[(8-endo)-3-(5-fluoro-2-methyl-pyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine
N-[(8-endo-3-(6-methoxypyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine
N-[(8-endo)-3-(6-fluoropyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine
2-[2-[[(8 endo)-3-(6-methylpyrimidin-4-yl)-3-azabicyclo[3.2.1]octan-8-yl]amino]-8-(2,2,2-trifluoroethoxy)-[1,2,4]triazolo[1,5-a]pyridin-5-yl]propan-2-ol
2-[2-[[(8 endo)-3-(5-fluoropyrimidin-4-yl)-3-azabicyclo[3.2.1]octan-8-yl]amino]-8-(2,2,2 trifluoroethoxy)-[1,2,4 triazolo[1,5-a]pyridin-5-yl]propan-2-ol
2-[2-[[(8 endo)-3-(5-fluoro-6-methylpyrimidin-4-yl)-3-azabicyclo[3.2.1]octan-8-yl]amino]-8 (2,2,2-trifluoroethoxy)-[1,2,4]triazolo[1,5-a]pyridin-5-yl]propan-2-ol
2-[2-[[(8endo)-3-(5-fluoro-2-methylpyrimidin-4-yl)-3-azabicyclo[3.2.1]octan-8-yl]amino]-8 (2,2,2-trifluoroethoxy)-[1,2,4]triazolo [1,5-a]pyridin-5-yl]propan-2-ol
8-(2,2-difluoroethoxy)-N-[(8 endo)-3-(6-methylpyrimidin-4-yl)-3-azabicyclo[3.2.1]octan-8-yl]-5-(trifluoromethyl)-[1,2,4]triazolo[1,5-a]pyridin-2-amine 8-(2-fluoroethoxy)-N-[(8 endo)-3-(6-methylpyrimidin-4-yl)-3-azabicyclo[3.2.1]octan-8-yl]-5-(trifluoromethyl)-[1,2,4]triazolo[1,5-a]pyridin-2-amine 5-cyclopropyl-N-[(1R,5S,8s)-3-(6-methylpyrimidin-4-yl)-3-azabicyclo[3.2.1]octan-8-yl]-8-(2,2,2-trifluoroethoxy)-[1,2,4]triazolo[1,5-a]pyridin-2-amine or N-[(1R,5S,8s)-3-(6-chloropyrimidin-4-yl)-3-azabicyclo[3.2.1]octan-8-yl]-5-cyclopropyl-8-(2,2,2-trifluoroethoxy)-[1,2,4]triazolo[1,5-a]pyridin-2-amine.

One object of the invention is a compound of formula I-9

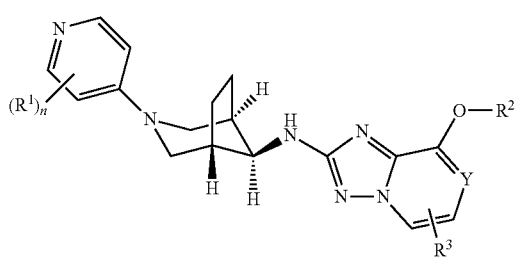

I-9 wherein $R^1$ is hydrogen, lower alkyl, lower alkyl substituted by halogen, halogen, or lower alkoxy;

$R^2$ is lower alkyl substituted by halogen,

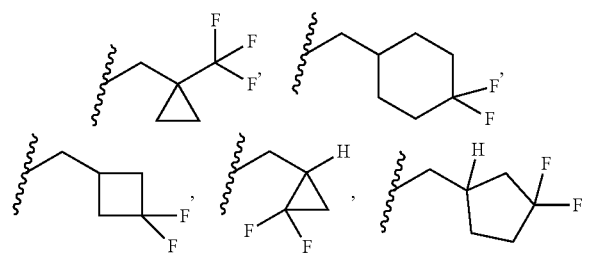

or is lower alkenyl substituted by halogen;

$R^3$ is hydrogen, lower alkyl substituted by halogen, lower alkyl, halogen, $C_{3-6}$-cycloalkyl or lower alkyl substituted by hydroxy;

Y is CH or N;

n is 1 or 2; for n=2, $R^1$ can be independent to each other;

or a pharmaceutically active acid addition salt thereof, a racemic mixture or its corresponding enantiomer and/or optical isomer and/or stereoisomer thereof, for example the following compounds 8-(2,2,2-trifluoroethoxy)-N-[(8 endo)-3-(2-(trifluoromethyl)pyridin-4-yl)-3-azabicyclo[3.2.1]octan-8-yl)-[1,2,4]triazolo[1,5-a]pyridin-2-amine 8-[1,2,2,2-tetrafluoroethoxy]-N-[(8 endo)-3-[2-(trifluoromethyl)pyridin-4-yl]-3-azabicyclo[3.2.1]octan-8-yl]-[1,2,4]triazolo[1,5-a]pyridin-2-amine 8-((1-(trifluoromethyl) cyclopropyl)methoxy)-N-[(8 endo)-3-(2-(trifluoromethyl)pyridin-4-yl)-3 azabicyclo[3.2.1]octan-8-yl]-[1,2,4]triazolo[1,5-a]pyridin-2-amine 8-(2,2,3,3-pentafluoropropoxy)-N-[(8 endo)-3-(2-(trifluoromethyl)pyridin-4-yl)-3 azabicyclo[3.2.]octan-8-yl]-[1,2,4]triazolo[1,5-a]pyridin-2-amine N-((8 endo)-3-(2-(2-(trifluoromethyl)pyridin-4-yl)-3-azabicyclo[3.2.1]octan-8-yl)-8-((1,1,1-trifluoropropan-2-yl)oxy)-[1,2,4]triazolo[1,5-a]pyrazin-2-amine 8-(2,2,3,3,3-pentafluoropropoxy)-N-((8 endo)-3-(2-(trifluoromethyl)pyridin-4-yl)-3-azabicyclo[3.2.1]octan-8-yl)-[1,2,4]triazolo[1,5-a]pyrazin-2-amine N-[(8 endo)-3-(3-fluoropyridin-4-yl)-3-azabicyclo[3.2.1]octan-8-yl]-8-(2,2,2-trifluoroethoxy)-[1,2,4]triazolo[1,5-a]pyridin-2-amine N-[(8 endo)-3-(2-chloropyridin-4-yl)-3-azabicyclo[3.2.1]octan-8-yl]-8-(2,2,2-trifluoroethoxy)-[1,2,4]triazolo[1,5-a]pyridin-2-amine N-[(8 endo)-3-(5-fluoro-2-methylpyridin-4-yl)-3-azabicyclo[3.2.1]octan-8-yl]-8-(2,2,3,3,3-pentafluoropropoxy)-[1,2,4]triazolo[1,5-a]pyridin-2-amine 8-(2,2,2-trifluoroethoxy)-5-(trifluoromethyl)-N-[(8-endo)-3-[2-(trifluoromethyl)-4-pyridyl]-3-azabicyclo[3.2.1]octan-8-yl]-[1,2,4]triazolo[1,5-a]pyridin-2-amine 5-(trifluoromethyl)-8-(2,2,2-trifluoro-1-methyl-ethoxy)-N-[8-endo-3-[2-(trifluoromethyl)-4-pyridyl]-3-azabicyclo[3.2.1]octan-8-yl]-[1,2,4]triazolo[1,5-a]pyridin-2-amine N-[(8-endo)-3-(5-fluoro-2-methyl-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine N-[(8-endo)-3-(2-chloro-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine N-[(8 endo)-3-(3-fluoro-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine N-[(8 endo)-3-(2-chloro-6-methyl-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine N-[(8-endo)-3-(2-chloro-5-fluoro-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine 5-Methyl-8-(2,2,2-trifluoroethoxy)-N-[(8-endo)-3-[2-(trifluoromethyl)-4-pyridyl]-3-azabicyclo[3.2.1]octan-8-yl]-[1,2,4]triazolo[1,5-a]pyridin-2-amine 2-[8-(2,2,2-trifluoroethoxy)-2-[[(8-endo)-3-[2-(trifluoromethyl)pyridin-4-yl]-3-azabicyclo[3.2.1]octan-8-yl]amino]-[1,2,4]triazolo [1,5-a]pyridin-5-yl]propan-2-ol 2-[2-[[(8endo)-3-(2-chloropyridin-4-yl)-3-azabicyclo[3.2.1]octan-8-yl]amino]-8-(2,2,2 trifluoroethoxy)-[1,2,4]triazolo [1,5-a]pyridin-5-yl]propan-2-ol 2-[2-[[(8 endo)-3-(2-chloro-5-fluoropyridin-4-yl)-3-azabicyclo[3.2.1]octan-8-yl]amino]-8-(2,2,2-trifluoroethoxy)-[1,2,4]triazolo[1,5-a]pyridin-5-yl]propan-2-ol N-[(8 endo)-3-(2-chloropyridin-4-yl)-3-azabicyclo[3.2.1]octan-8-yl]-8-(2,2-difluoroethoxy)-5-(trifluoromethyl)-[1,2,4]triazolo[1,5-a]pyridin-2-amine N-[(8 endo)-3-(2-chloropyridin-4-yl)-3-azabicyclo[3.2.1]octan-8-yl]-8-(2-fluoroethoxy)-5-(trifluoromethyl)-[1,2,4]triazolo[1,5-a]pyridin-2-amine 2-[2-[[(1R,5S,8s)-3-(5-fluoro-2-methyl-4-pyridyl)-3-azabicyclo[3.2.1]octan-8-yl]amino]-8-(2,2,2-trifluoroethoxy)-[1,2,4]triazolo[1,5-a]pyridin-5-yl]propan-2-ol 2-[2-[[(1R,5S,8s)-3-(3-fluoro-4-pyridyl)-3-azabicyclo[3.2.1]octan-8-yl]amino]-8-(2,2,2-trifluoroethoxy)-[1,2,4]triazolo[1,5-a]pyridin-5-yl]propan-2-ol or N-[(1R,5S,8s)-3-(2-chloro-4-pyridyl)-3-azabicyclo[3.2.1]octan-8-yl]-5-cyclopropyl-8-(2,2,2-trifluoroethoxy)-[1,2,4]triazolo[1,5-a]pyridin-2-amine.

One object of the invention is a compound of formula I-10

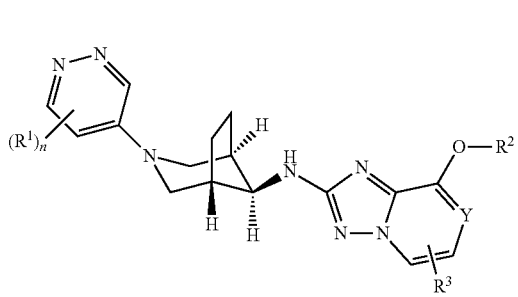

wherein
R¹ is hydrogen, lower alkyl, lower alkyl substituted by halogen, halogen, or lower alkoxy;
R² is lower alkyl substituted by halogen,

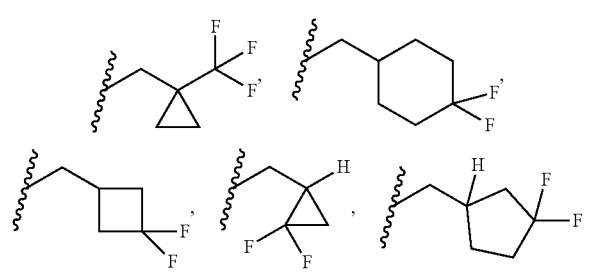

or is lower alkenyl substituted by halogen;
R³ is hydrogen, lower alkyl substituted by halogen, lower alkyl, halogen, $C_{3-6}$-cycloalkyl or lower alkyl substituted by hydroxy;
Y is CH or N;
n is 1 or 2; for n=2, R¹ can be independent to each other;
or a pharmaceutically active acid addition salt thereof, a racemic mixture or its corresponding enantiomer and/or optical isomer and/or stereoisomer thereof, for example the following compounds N-[(1R,5S,8s)-3-(6-chloropyridazin-4-yl)-3-azabicyclo [3.2.1]octan-8-yl]-5-cyclopropyl-8-(2,2,2-trifluoroethoxy)-[1,2,4]triazolo[1,5-a]pyridin-2-amine 5-cyclopropyl-N-[(1R,5S,8s)-3-(6-methoxypyridazin-4-yl)-3-azabicyclo[3.2.1]octan-8-yl]-8-(2,2,2-trifluoroethoxy)-[1,2,4]triazolo[1,5-a]pyridin-2-amine N-[(1R,5S,8s)-3-(6-chloropyridazin-4-yl)-3-azabicyclo [3.2.1]octan-8-yl]-8-(2,2,2-trifluoroethoxy)-5-(trifluoromethyl)-[1,2,4]triazolo[1,5-a]pyridin-2-amine or N-[(1R,5S,8s)-3-(6-methoxypyridazin-4-yl)-3-azabicyclo [3.2.1]octan-8-yl]-8-(2,2,2-trifluoroethoxy)-5-(trifluoromethyl)-[1,2,4]triazolo[1,5-a]pyridin-2-amine.

The present compounds of formula I and their pharmaceutically acceptable salts can be prepared by methods known in the art, for example, by processes described below, which processes comprise a) reacting a compound of formula

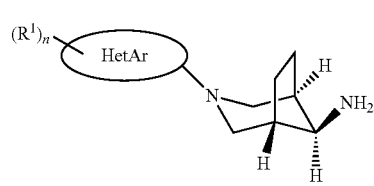

with a compound of formula 3

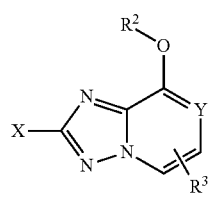

to a compound of formula

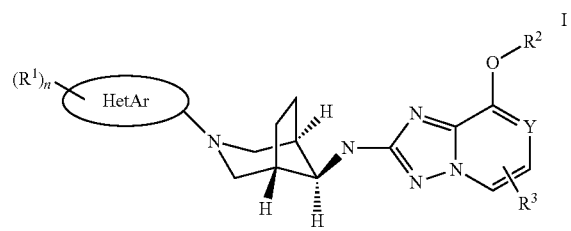

wherein the substituents have the meaning as described above and X is halogen, and,
if desired, converting the compounds obtained into pharmaceutically acceptable acid addition salts;
or b) reacting a compound of formula

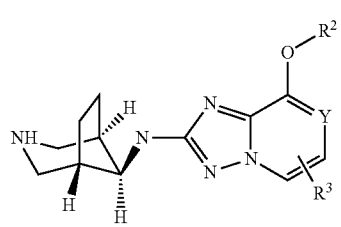

with a compound of formula

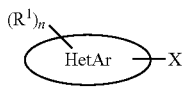

to a compound of formula

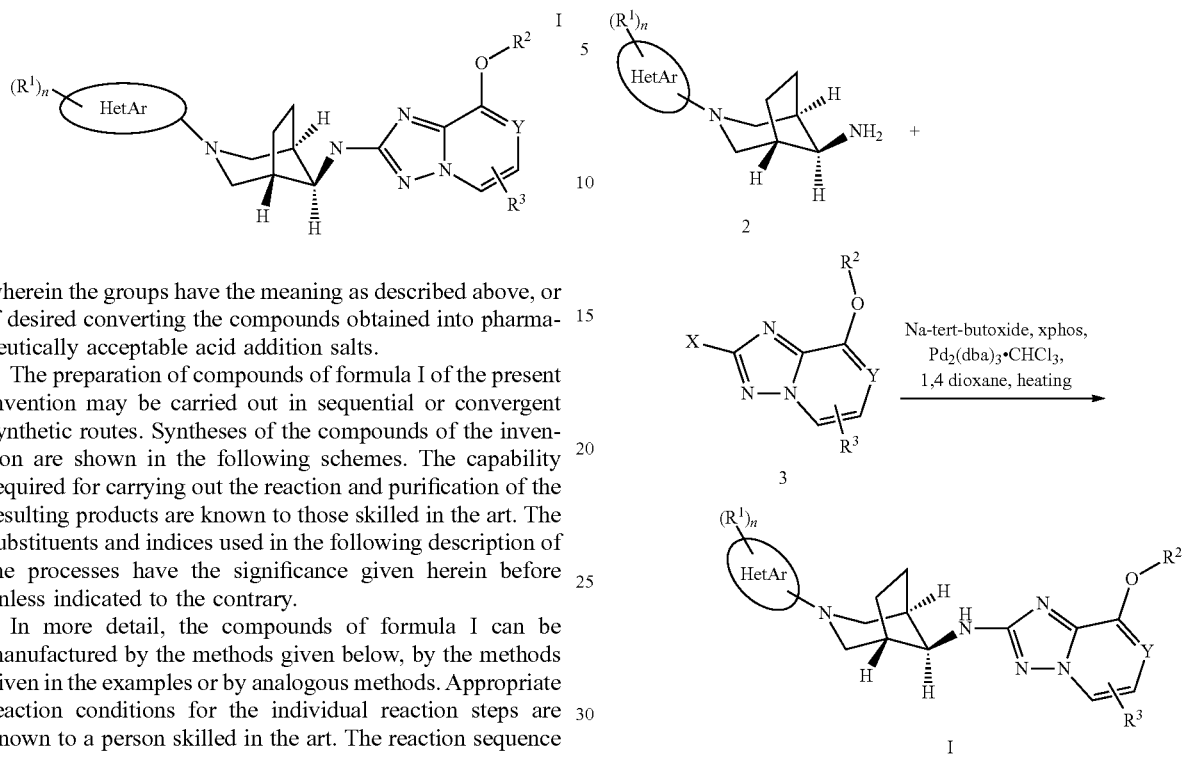

wherein the groups have the meaning as described above, or if desired converting the compounds obtained into pharmaceutically acceptable acid addition salts.

The preparation of compounds of formula I of the present invention may be carried out in sequential or convergent synthetic routes. Syntheses of the compounds of the invention are shown in the following schemes. The capability required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Particularly, compounds of formula I can be prepared following standard methods in accordance with any of the Schemes 1 to 8.

According to Scheme 1 the present compounds of formula I and their pharmaceutically acceptable salts can be prepared by coupling of amines of general formula 2 and halides of general formula 3. This reaction can be accomplished using generally known procedures, e.g. displacement reactions under thermal conditions or under catalytic conditions (like e.g. palladium(0) catalysis) such as the Buchwald coupling (X=halogen).

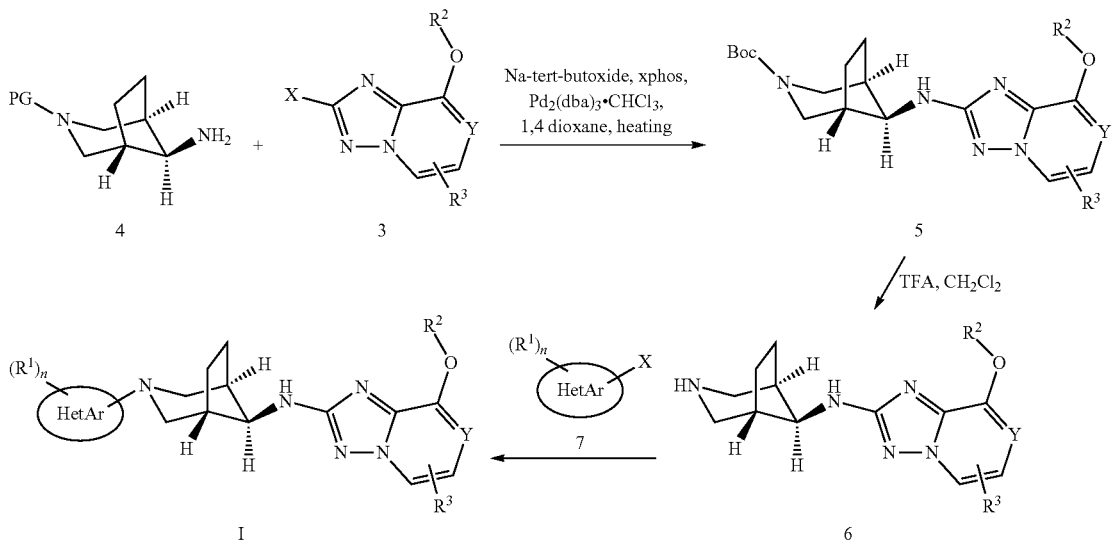

Alternatively halo-triazolopyridines 3 can react under conditions as described above with amines of general formula 4 which bear a protective group PG, e.g. Boc, on the piperidine nitrogen (see Scheme 2). After deprotection with e.g. trifluoro acetic acid, the piperidines 6 can be coupled with a hetaryl halides of formula 7 to provide compounds of formula I.

Halo-triazolopyridines intermediates of general formula 3, which can be used as starting materials for the preparation of compounds of formula I can be prepared as described below.

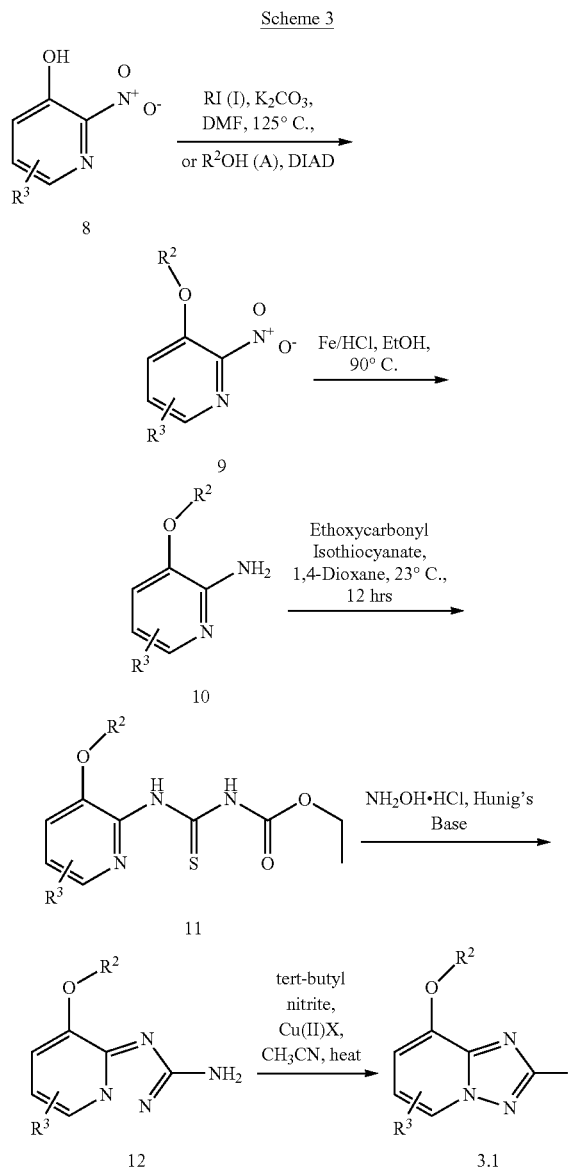

Compounds of formula 3.1 can be prepared as described in Scheme 3. An appropriately substituted 2-nitropyridin-3-ol is reacted with an alkyl halide in a SN2 type reaction in an aprotic solvent such as DMF. Alternatively the 2-nitro-pyridin-3-ol can be reacted with an alcohol A ($R^2OH$) under "Mitsunobu" conditions employing a trialkylphosphine such as tributylphosphine ($(n-Bu)_3P$) or a triarylphosphine such as triphenylphosphine ($Ph_3P$) and the like and a diazo-compound like diethyl-azodicarboxylate (DEAD), diisopropyl-azodicarboxylate (DIAD) (optionally polymer bound), tetramethyl azodicarboxamide and the like in a solvent commonly used in such transformations like tetrahydrofurane (THF), toluene, dichloromethane and the like. Bechamp reduction of nitro compound 9 using e.g. Fe and HCl yields amine 10. It is also possible to reduce the nitro group through a hydrogenation reaction with Pd/C catalyst and $H_2$. Formation of triazole 12 was accomplished by a two steps procedure reported by M. Nettkoven et al. (Synthesis, 2003, 11, 1649-1652). Reaction of the amine with ethoxy carbonyl isothiocyanate provides carbamate 11 which undergoes cyclization under elimination of $CO_2$ upon treatment with aqueous hydroxylamine, in the presence of a base such as diisopropylethylamine in a solvent such as methanol to obtain the amino-triazolo pyridine of formula 12. The amino triazole 12 can be converted into halo triazole 3.1 by a Sandmeyer reaction. i.e. formation of the corresponding diazonium salt and subsequent decomposition in the presence of a halide source like copper (II) bromide.

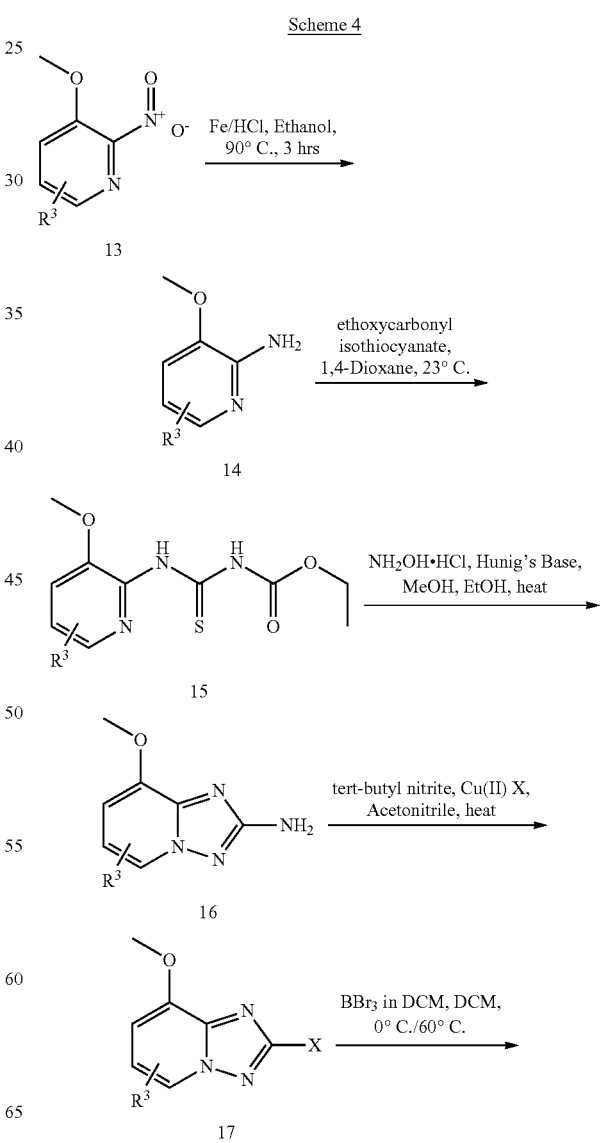

-continued

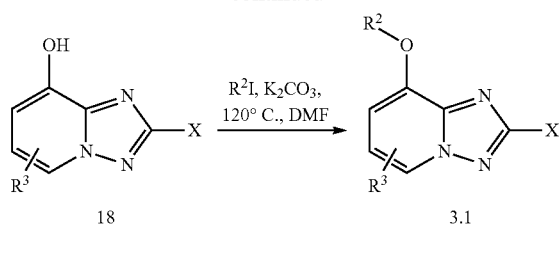

18 → 3.1

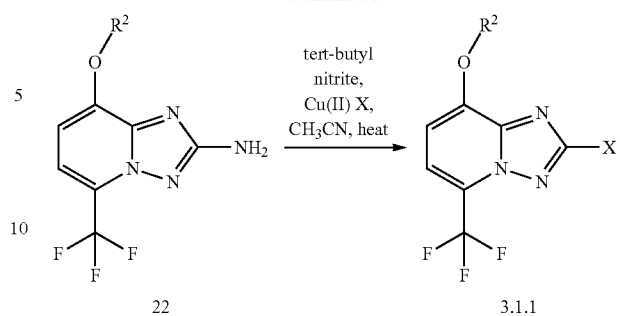

22 → 3.1.1

The sequence of reaction steps can be freely altered (scheme 4) starting with a protected 2-nitro pyridine alcohol analog (e.g. protected as methyl ether) followed by similar transformations as described in scheme 3 to produce the halo analog 17. Removal of the methyl protecting group with an acid as for example $BBr_3$, in an appropriate solvent such as dichloromethane gives access to alcohol 18 which can be converted into alkoxy derivatives of formula 3 by "alkylation" or "mitsunobu" reactions as already described for the first step of scheme 3.

Substituted halo alkoxy triazolo-pyridines of general formula 3.1.1 can be prepared as described in scheme 5 starting from substituted bromo amino-pyridine 19 bearing an electron withdrawing group on para position such as $CF_3$ by following similar synthetic steps as described in scheme 3. Key intermediate 8-bromo-5-(trifluoromethyl)-[1,2,4]triazolo[1,5-a]pyridin-2-amine of formula 21 undergoes Ullmann coupling with a range of alcohols $R^2OH$ to produce alkoxy derivatives of formula 22. Sandmeyer reaction provides the substituted halo triazole 3.1.1.

The synthesis of isoproanolyl intermediates of general formula 3.1.2 is outlined in scheme 6.

Scheme 5

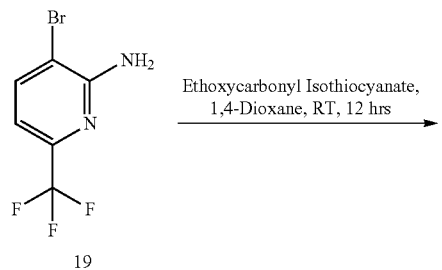

19

Scheme 6

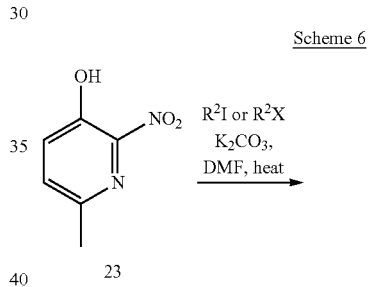

23

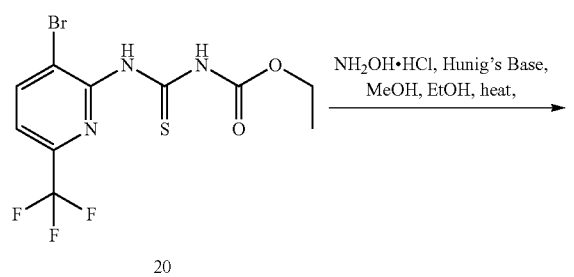

20

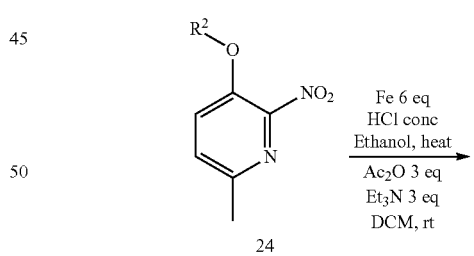

24

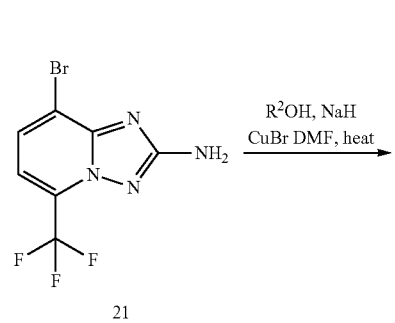

21

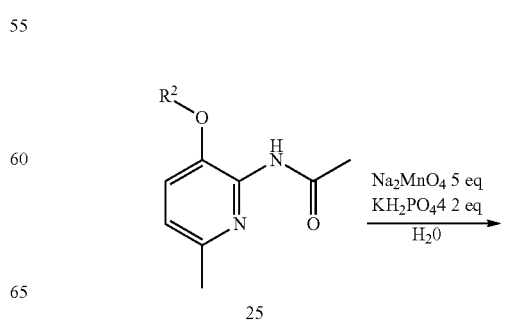

25 already described in scheme 3, the methoxcarbonyl substituted triazolo-pyridine of formula 29 is obtained. Sandmeyer reaction leads to the substituted halo triazole 30 which is then converted into the desired intermediate 3.1.2 via Grignard addition.

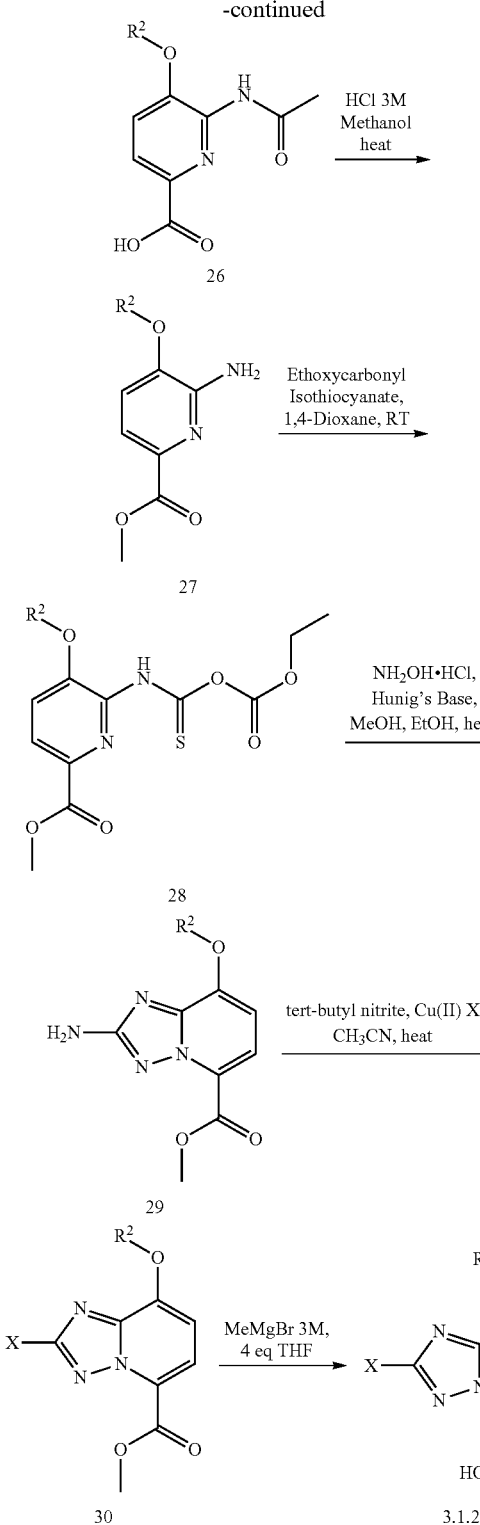

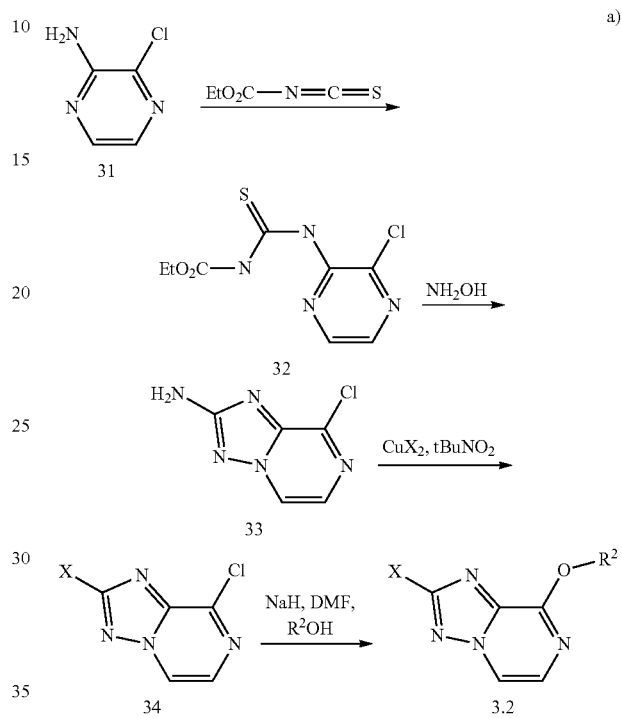

The compound 3.1.2 is obtained via alkylation of 6-methyl-2-nitro-3-(2,2,2-trifluoroethoxy)pyridine to provide analog 24. Bechamp reduction of the nitro group of 24 followed by acetylation gives intermediate 25. Oxidation of the methyl group with $Na_2MnO_4$ followed by esterification with methanol produces the methyl ester 27 in a one pot reaction without isolation of the carboxylic acid intermediate 26. Following similar synthetic steps for the cyclization as

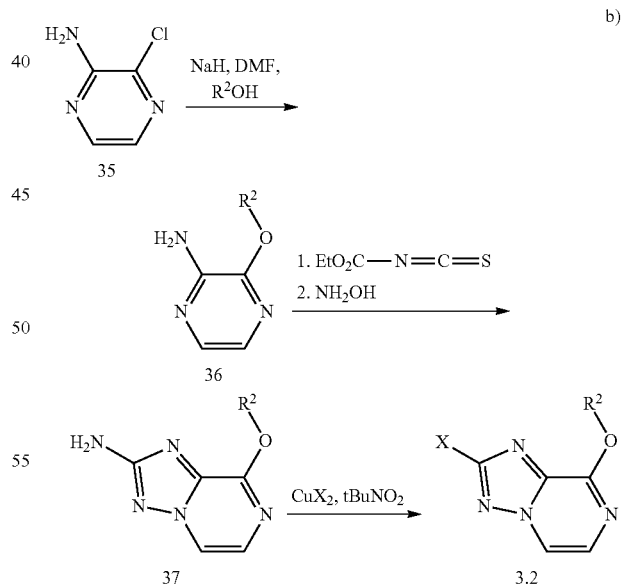

Halo-pyrazolopyrazines of general formula 3.2 can be prepared from 3-chloropyrazin-2-amine 31 (Scheme 7a). Reaction with ethoxycarbonyl isothiocyanate yield thiourea derivatives 32 which undergo a cyclization reaction upon treatment with hydroxylamine in the presence of a base under liberation of carbon dioxide to annelated triazoles 33

(as e.g. described by M. Nettekoven et al., Synthesis 2003, 11, 1649-1652). Conversion of the amine under Sandmeyer conditions gives halogen 34 which then undergoes substitution of the chloride with deprotonated alcohols to yield intermediate 3.2.

Alternatively the sequence of reaction steps can be freely altered as outlined in scheme 7b to produce the same intermediate compound of formula 3.2. For example introducing first the alkoxy group to produce 36 and then performing the cyclization to produce compound 37 as precursor of 3.2.

The different types of intermediates 3 undergo Pd catalysed coupling reactions (e.g. Buchwald coupling reactions) with amines of formula 2 or 4 as described in schemes 1 and 2. Different synthetic access to intermediates 2 are described in scheme 8.

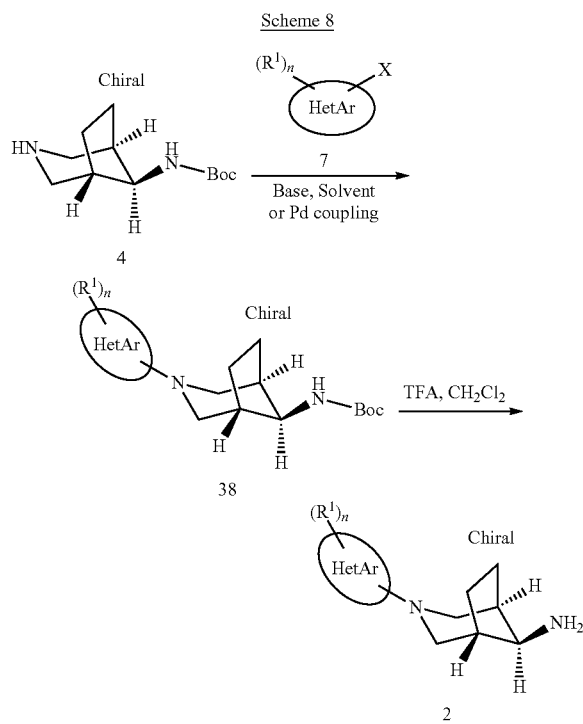

Scheme 8

Compounds of formula 2 in scheme 8, can be synthesized starting from meso [(8-endo)-3-azabicyclo[3,2,1] oct-8-yl]-carbamic acid tert-butyl ester 4 (CAS 847862-26-4). Compound 4 can be obtained from (meso)-8-endo-3-benzyl-3-azabicyclo[3,2,1] octan-8-amine (WO2012116965, page 33) by protective group modifications such as the one described in WO2012116965, page 37-38. The coupling of 4 with heterocyclic halides of general formula 7 can be accomplished under thermal conditions in a solvent such as ethanol or NMP in the presence of a base such as $Et_3N$ or by using displacement reactions under catalytic conditions (like e.g. palladium(0) or copper(II) catalysis) to provide compounds of formula 38. After deprotection with acid e.g. trifluoro acetic acid compounds of formula 2 can be submitted to coupling reactions as described in scheme 1 to provide compounds of formula I.

The heterocycles halides are either commercial available, known in the literature so they can be prepared by methods known in the art or alternatively could be prepared as described in the specification.

The compounds were investigated in accordance with the test given hereinafter.

Description of γ-Secretase Assay

Cellular γ-Secretase Assay

Human neuroglioma H4 cells overexpressing human APP695 with the Swedish double mutation (K595N/M596L) were plated at 30,000 cells/well/100 µl in 96-well plates in IMDM media containing 10% FCS, 0.2 mg/l Hygromycin B and incubated at 37° C., 5% $CO_2$.

3-4 hr post plating, compounds are a diluted in media and 50 µl is added as 1.5-fold concentrate to achieve the final concentration. Compound incubation is performed for 24 hr. Final doses typically range from 4 µM down to 0.0013 µM in half-log steps resulting in a eight point dose response curve.

Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa assay kit (Human Amyloid beta 1-42 Kit: Cat # AL203C, Perkin Elmer). 20 µl of the cell culture supernatant was transferred to an assay plate. Then 10 µl of a mixture of the AlphaLisa coupled capture antibody and the biotinylated detection antibody was added and incubated for 3 hours at room temperature while softly shaking the assay plate. After a further addition of 20 µl of the Donor beads the assay plate was incubated for 30 min at room temperature and constant shaking without exposure to direct light. The assay plate was then read on a Paradigm AlphaLisa Reader using the build-in program with excitation at 680 nm and emission at 570 nm.

The measured signals were then used to calculate $IC_{50}$ values for inhibition of Aβ42 secretion by nonlinear regression fit analysis using XLfit 5.3 software (IDBS).

In the list below are described the data for all compounds to the inhibition of Aβ42 secretion (nM):

| Example No. | $EC_{50}$ Aβ42 (nM) |
| --- | --- |
| 1 | 14 |
| 2 | 16 |
| 3 | 23 |
| 4 | 27 |
| 5 | 27 |
| 6 | 16 |
| 7 | 24 |
| 8 | 13 |
| 9 | 26 |
| 10 | 18 |
| 11 | 37 |
| 12 | 28 |
| 13 | 21 |
| 14 | 13 |
| 15 | 9 |
| 16 | 4 |
| 17 | 7 |
| 18 | 7 |
| 19 | 5 |
| 20 | 20 |
| 21 | 2 |
| 22 | 8 |
| 23 | 11 |
| 24 | 7 |
| 25 | 22 |
| 26 | 11 |
| 27 | 9 |
| 28 | 34 |

| Example No. | EC$_{50}$ Aβ42 (nM) |
|---|---|
| 29 | 16 |
| 30 | 34 |
| 31 | 5 |
| 32 | 39 |
| 33 | 8 |
| 34 | 15 |
| 35 | 6 |
| 36 | 6 |
| 37 | 23 |
| 38 | 21 |
| 39 | 32 |
| 40 | 21 |
| 41 | 45 |
| 42 | 28 |
| 43 | 27 |
| 44 | 37 |
| 45 | 4 |
| 46 | 36 |
| 47 | 30 |
| 48 | 40 |
| 49 | 28 |
| 50 | 21 |
| 51 | 59 |
| 52 | 30 |
| 53 | 40 |
| 54 | 14 |
| 55 | 37 |
| 56 | 45 |
| 57 | 47 |
| 58 | 24 |
| 59 | 8.9 |
| 60 | 38 |
| 61 | 15.8 |
| 62 | 25 |
| 63 | 37 |
| 64 | 21 |
| 65 | 16 |
| 66 | 49 |
| 67 | 21 |
| 68 | 43 |
| 69 | 14 |
| 70 | 12 |
| 71 | 1 |
| 72 | 2 |
| 73 | 46 |
| 74 | 25 |
| 75 | 26 |
| 76 | 16 |
| 77 | 20 |
| 78 | 21 |
| 79 | 19 |
| 80 | 36 |
| 81 | 43 |
| 82 | 36 |
| 83 | 20 |
| 84 | 39 |
| 85 | 19 |
| 86 | 28 |
| 87 | 17 |
| 88 | 17 |
| 89 | 5 |
| 90 | 9 |
| 91 | 22.5 |
| 92 | 24 |
| 93 | 13 |
| 94 | 34 |
| 95 | 33.6 |
| 96 | 10.5 |
| 97 | 19.7 |
| 98 | 24 |
| 99 | 44 |
| 100 | 22 |
| 101 | 49 |
| 102 | 5 |
| 103 | 41 |
| 104 | 28 |
| 105 | 47 |
| 106 | 16.9 |
| 107 | 31 |
| 108 | 15.6 |
| 109 | 5 |
| 110 | 27 |
| 111 | 24 |
| 112 | |
| 113 | 26 |
| 114 | 8 |
| 115 | 16 |
| 116 | 12 |
| 117 | 12 |
| 118 | 15 |
| 119 | 14 |
| 120 | 16 |
| 121 | 16 |
| 122 | 19 |
| 123 | |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions. The administration can also be effected topically, e.g. transdermal administration, or in form of eye drops or ear drops.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

N-(8 endo)-3-(3-methyl-1,2,4-thiadiazol-5-yl)-3-azabicyclo[3.2.1]octan-8-yl)-8-(4,4,4-trifluorobutoxy)-[1,2,4]triazolo[1,5-a]pyridin-2-amine

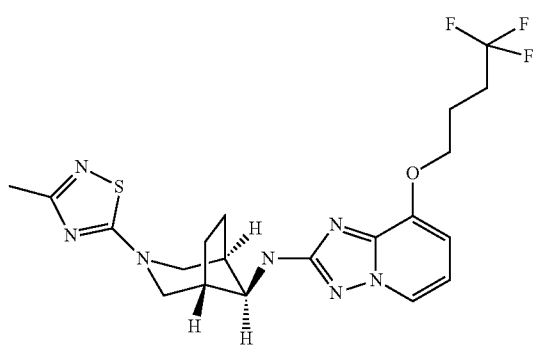 [SMILES: Cc1nsc(N2C[C@H]3CC[C@@H](C2)[C@@H]3Nc2nc3c(OCCCC(F)(F)F)cccn3n2)n1]

Intermediate 3

2-Bromo-8-(4,4,4-trifluorobutoxy)-[1,2,4]triazolo[1,5-a]pyridine

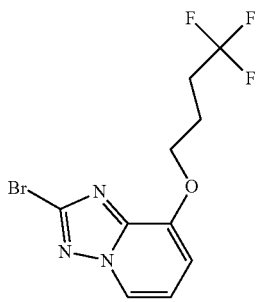 [SMILES: FC(F)(F)CCCOc1cccn2nc(Br)nc12]

Step 1

2-Nitro-3-(4,4,4-trifluorobutoxy)pyridine

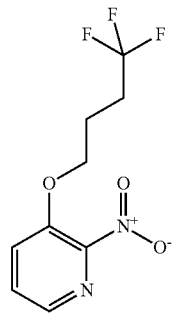 [SMILES: O=[N+]([O-])c1ncccc1OCCCC(F)(F)F]

To a solution of triphenylphosphine (8.42 g, 32.1 mmol) in THF (100 ml) at 0° C. was added dropwise diisopropyl azodicarboxylate (6.5 g, 6.25 ml, 32.1 mmol). After 30 minutes a solution of 2-nitropyridin-3-ol (3 g, 21.4 mmol) and 4,4,4-trifluorobutan-1-ol (4.11 g, 32.1 mmol) in THF (15 ml) was added dropwise. The resulting mixture was stirred at room temperature for 2 hours. The solvent was evaporated. The residue was dissolved in a small amount of AcOEt and heptane was added until beginning of precipitation. After 12 hours the precipitate was filtered off and the solvent was evaporated. The residue was purified by flash chromatography on silica gel using a gradient 0% to 100% EtOAc in hexanes.

The title compound was obtained as light yellow liquid (5.29 g, 99%).

MS ES+ (m/z): 251.1 (100%) [(M+H)$^+$]

Step 2

3-(4,4,4-Trifluorobutoxy)pyridin-2-amine

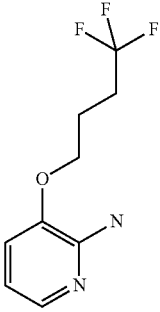 [SMILES: Nc1ncccc1OCCCC(F)(F)F]

To a solution of 2-nitro-3-(4,4,4-trifluorobutoxy)pyridine (example A-1a, 2.5 g, 9.99 mmol) in ethanol (150 ml) and hydrochloric acid (55.4 g, 46.2 ml, 380 mmol) iron (3.35 g, 60.0 mmol) was added. The reaction mixture was heated to 90° C. for 2 h. The crude reaction mixture was filtered and the solvent was removed in vacuo. Saturated NaHCO₃ solution was added. The aqueous phase was separated and extracted four times with AcOEt (100 ml). The combined organic layers were dried over Na₂SO₄ and the solvent was removed in vacuo. The crude material was purified by flash chromatography on silica gel using a gradient from 0% to 70% EtOAc in heptane. The title compound was obtained as light yellow solid (2.05 g, 93%). MS ES+ (m/z): 221.1 [(M+H)⁺]

Step 3

Ethyl N-[[3-(4,4,4-trifluorobutoxy)pyridin-2-yl]carbamothioyl]carbamate

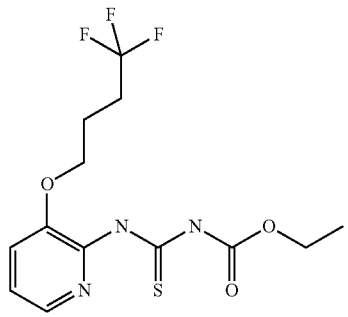 [SMILES: CCOC(=O)NC(=S)Nc1ncccc1OCCCC(F)(F)F]

To a solution of 3-(4,4,4-trifluorobutoxy)pyridin-2-amine (example A-1b, 3.7 g, 16.8 mmol) in dioxane (90 ml) was added ethoxycarbonyl isothiocyanate (2.2 g, 1.98 ml, 16.8 mmol). The reaction mixture was stirred for 6 h at room temperature. The solvent was removed in vacuo and the crude material was used in the next step without purification.

The title compound was obtained as yellow solid (5.7 g, 97%). MS ES+ (m/z): 352.1 [(M+H)⁺]

Step 4

8-(4,4,4-Trifluorobutoxy)-[1,2,4]triazolo[1,5-a]pyridin-2-amine

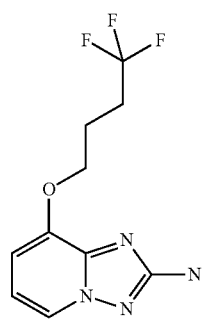 [SMILES: Nc1nc2c(OCCCC(F)(F)F)cccn2n1]

To suspension of hydroxylamine hydrochloride (5.69 g, 81.8 mmol) and Hunig's base (6.35 g, 8.57 ml, 49.1 mmol) in MeOH (20 ml) and Ethanol (20.0 ml) was added Ethyl N-[[3-(4,4,4-trifluorobutoxy)pyridin-2-yl]carbamothioyl]carbamate (5.75 g, 16.4 mmol). The reaction mixture was heated to 60° C. for 3 h. A saturated aqueous solution of NaHCO₃ was added, the aqueous phase was separated and extracted with CH₂Cl₂. The combined organic layers were dried over Na₂SO₄ and the solvent was removed in vacuo. The title compound was obtained as white solid (4.23 g, 99%). MS ES+ (m/z): 261.1 [(M+H)⁺]

Step 5

2-Bromo-8-(4,4,4-trifluorobutoxy)-[1,2,4]triazolo[1,5-a]pyridine

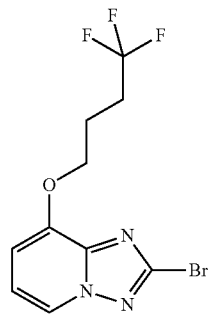 [SMILES: FC(F)(F)CCCOc1cccn2nc(Br)nc12]

To a solution of tert-butyl nitrite (1.78 g, 2.06 ml, 17.3 mmol) and copper (II) bromide (3.86 g, 17.3 mmol) in acetonitrile (110 ml) was heated to 60° C. and 8-(4,4,4-trifluorobutoxy)-[1,2,4]triazolo[1,5-a]pyridin-2-amine (3 g, 11.5 mmol) was added in portions over 15 minutes. The reaction mixture was stirred at 60° C. for 30 minutes. An aqueous HCl solution (1M, 40 ml) was added, the aqueous phase was separated and extracted with AcOEt. The combined organic layers were washed with brine, dried over Na₂SO₄ and the solvent was removed in vacuo. The crude material was purified by flash chromatography on silica gel using CH₂Cl₂ as eluent.

The title compound was obtained as white solid (3.0 g, 80%).

MS ES+ (m/z): 324.0/326.0 [(M+H)⁺]

Intermediate 2

(8-endo)-3-(3-methyl-1,2,4-thiadiazol-5-yl)-3-azabicyclo[3.2.1]octan-8-amine

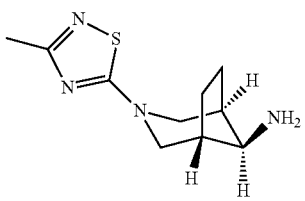

Step 1

Tert-butyl N-[(8 endo)-3-(3-methyl-1,2,4-thiadiazol-5-yl)-3-azabicyclo[3.2.1]octan-8-yl]carbamate

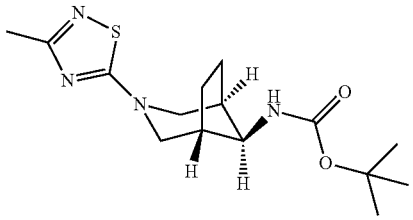 [SMILES: Cc1nsc(N2C[C@H]3CC[C@@H](C2)[C@@H]3NC(=O)OC(C)(C)C)n1]

To solution of tert-butyl N-[(8 endo)-3-azabicyclo[3.2.1]octan-8-yl]carbamate (750 mg, 3.31 mmol) (as described in WO2012116965) in ethanol (10 ml) was added triethylamine (503 mg, 693 μl, 4.97 mmol) followed by 5-chloro-3-methyl-1,2,4-thiadiazole (535 mg, 395 μl, 3.98 mmol). The reaction mixture was stirred over night at 80° C. The crude reaction mixture was concentrated under reduced pressure. The residue was purified by column chromatography on silica gel using a gradient from 0% to 100% EtOAc in as eluent.

The title compound was obtained as a solid (991 mg, 92.2% yield)

MS ES+ (m/z): 325.2 (100%) [(M+H)$^+$]

Step 2

(8-endo)-3-(3-methyl-1,2,4-thiadiazol-5-yl)-3-azabicyclo[3.2.1]octan-8-amine

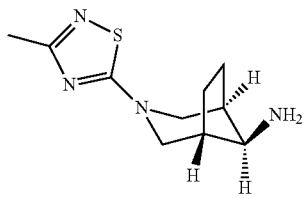

To a light yellow solution of tert-butyl (8 endo)-3-(3-methyl-1,2,4-thiadiazol-5-yl)-3-azabicyclo[3.2.1]octan-8-ylcarbamate (990 mg, 3.05 mmol) in dichloromethane (30 ml) was added TFA (3.48 g, 2.35 ml, 30.5 mmol). The reaction mixture was stirred at room temperature over night. Saturated aqueous NaHCO$_3$ was added and the aqueous phase extracted with DCM. The organic layers were dried over MgSO$_4$ and concentrated to obtain the title compound as a white solid (644 mg, 2.87 mmol, 94.1% yield). MS ES+ (m/z): 325.1 [(M+H)$^+$]

Final Coupling Step 3

N-[(8 endo)-3-(3-methyl-1,2,4-thiadiazol-5-yl)-3-azabicyclo[3.2.1]octan-8-yl]-8-(4,4,4-trifluorobutoxy)-[1,2,4]triazolo[1,5-a]pyridin-2-amine

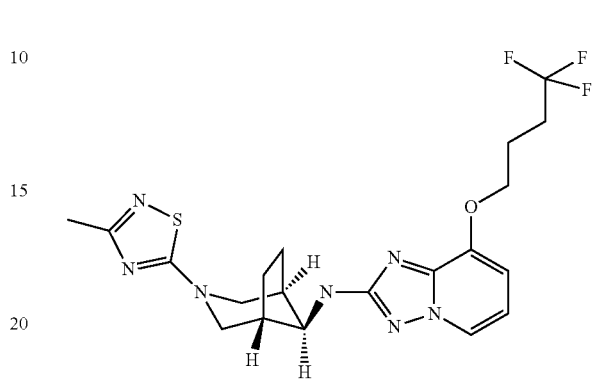

To a solution of 2-bromo-8-(4,4,4-trifluorobutoxy)-[1,2,4]triazolo[1,5-a]pyridine (43.3 mg, 134 μmol) in dry 1,4-dioxane (2 mL) were added (8 endo)-3-(3-methyl-1,2,4-thiadiazol-5-yl)-3-azabicyclo[3.2.1]octan-8-amine (30 mg, 134 μmol), sodium phenoxide (24.8 mg, 214 μmol) and xantphos (12.4 mg, 21.4 μmol). The mixture was purged with argon for 5 minutes and tris(dibenzylideneacetone)dipalladium (0) chloroform adduct (Pd$_2$(dba)$_3$.CHCl$_3$, 11.1 mg, 10.7 mol) was added. The reaction mixture was purged again with argon for 5 minutes, sealed and heated to 130° C. for 0.5 hours in the microwave. The mixture was diluted with EtOAc (10 mL), and washed with water (5 mL). The organic layer was dried over anhydrous sodium sulfate, filtered, and the solvent was evaporated in vacuo. The resulting crude material was purified by flash chromatography (silica gel, 20 g, 0% to 100% EtOAc in heptane) to yield the title compound as a white solid (39 mg, 62%). MS ES+ (m/z): 468.2 [(M+H)$^+$]

EXAMPLE 2

N-[(8-endo)-3-(3-methyl-1,2,4-thiadiazol-5-yl)-3-azabicyclo[3.2.1]octan-8-yl]-8-(3,3,3-trifluoropropoxy)-[1,2,4]triazolo[1,5-a]pyridin-2-amine

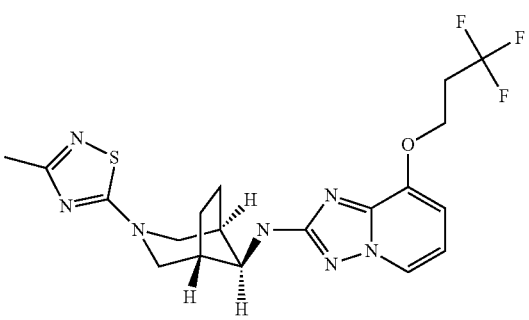 [SMILES: Cc1nsc(N2C[C@H]3CC[C@@H](C2)[C@@H]3Nc2nc3c(OCCC(F)(F)F)cccn3n2)n1]

Intermediate 3

2-bromo-8-(3,3,3-trifluoropropoxy)-[1,2,4]triazolo[1,5-a]pyridine

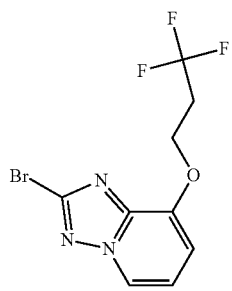

Step 1

2-nitro-3-(3,3,3-trifluoropropoxy)pyridine

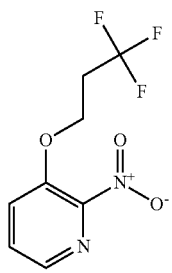 [SMILES: O=[N+]([O-])c1ncccc1OCCC(F)(F)F]

Prepared in analogy to example 1, intermediate 3, step 1 from 2-nitropyridin-3-ol (3 g, 21.4 mmol) and 3,3,3-trifluoropropan-1-ol (3.66 g, 32.1 mmol) with triphenyl phosphine and diisopropyl azodicarboxilate. The title compound was obtained as a colorless liquid (3.57 g, 71%). MS ES+ (m/z): 237.1 [(M+H)⁺]

Step 2

3-(4,4,4-Trifluorobutoxy)pyridin-2-amine

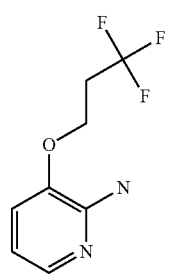 [SMILES: Nc1ncccc1OCCC(F)(F)F]

Prepared in analogy to example 1, intermediate 3, step 2 from 2-nitro-3-(3,3,3-trifluoropropoxy) pyridine (3.57 g, 15.05 mmol). The title compound was obtained as a white solid (2.73 g, 88%). MS ES+ (m/z): 207.1 [(M+H)⁺]

Step 3

Ethyl N-[[3-(3,3,3-trifluoropropoxy)pyridin-2-yl]carbamothioyl]carbamate

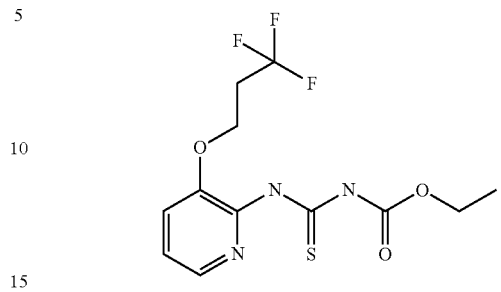

The title compound was prepared in analogy to example 1, intermediate 3, step 3 from 3-(3,3,3-trifluoropropoxy)pyridin-2-amine (2.6 g, 12.6 mmol) and Ethoxycarbonyl isothiocyanate (1.65 g, 1.49 ml, 12.6 mmol). The title compound was obtained as a light yellow solid (4.25 g, 100%).
MS ES+ (m/z): 338.1 [(M+H)⁺]

Step 4

8-(3,3,3-trifluoropropoxy)-[1,2,4]triazolo[1,5-a]pyridin-2-amine

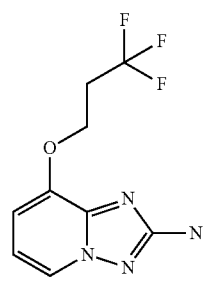 [SMILES: Nc1nc2c(OCCC(F)(F)F)cccn2n1]

Prepared in analogy to example 1, intermediate 3, step 4 from Ethyl N-[[3-(3,3,3-trifluoropropoxy)pyridin-2-yl]carbamothioyl]carbamate (4.25 g, 12.6 mmol) with hydroxylamine hydrochloride and Hunig's base. The title compound, was obtained as a light yellow solid (2.83 g, 93%).
MS ES+ (m/z): 247.1 [(M+H)⁺]

Step 5

2-Bromo-8-(4,4,4-trifluorobutoxy)-[1,2,4]triazolo[1,5-a]pyridine

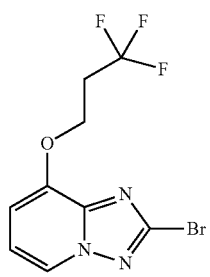 [SMILES: FC(F)(F)CCOc1cccn2nc(Br)nc12]

The title compound, was prepared in analogy to example 1, intermediate 3, step 5 from 8-(3,3,3-trifluoropropoxy)-[1,2,4]triazolo[1,5-a]pyridin-2-amine (1.8 g, 7.31 mmol), tert-butyl nitrite and copper (II) bromide as a white solid (2.03 g, 89.5%).

MS ES+ (m/z): 310.0/313.0 [(M+H)⁺]

Final Coupling Step 6

N-[(8 endo)-3-(3-methyl-1,2,4-thiadiazol-5-yl)-3-azabicyclo[3.2.1]octan-8-yl)-8-(3,3,3-trifluoro-propoxy]-[1,2,4]triazolo[1,5-a]pyridin-2-amine

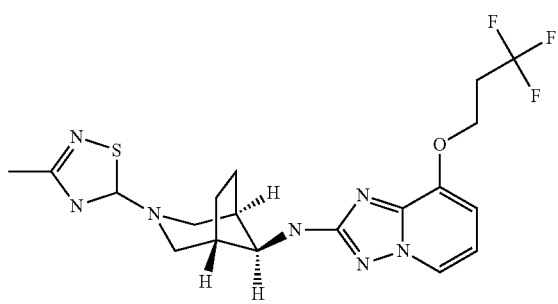 [SMILES: CC1=NSC(N2C[C@H]3CC[C@@H](C2)[C@@H]3Nc2nc3c(OCCC(F)(F)F)cccn3n2)N1]

The title compound, was prepared by Buchwald coupling in analogy to example 1, from 2-Bromo-8-(4,4,4-trifluoro-propoxy)-[1,2,4]triazolo[1,5-a]pyridine (41.5 mg, 134 µmol) and (8-endo)-3-(3-methyl-1,2,4-thiadiazol-5-yl)-3-azabicyclo[3.2.1]octan-8-amine (intermediate 2, example 1), (30 mg, 134 µmol) with Pd₂(dba)₃.CHCl₃ in the presence of Sodium phenoxide and xantphos as a white solid (26 mg, 43%) MS ES+ (m/z): 454.2 [(M+H)⁺]

EXAMPLE 3

N-[(8-endo)-3-(3-methyl-1,2,4-thiadiazol-5-yl)-3-azabicyclo[3.2.1]octan-8-yl]-8-(2,2,2-trifluoroeth-oxy)-[1,2,4]triazolo[1,5-a]pyridin-2-amine

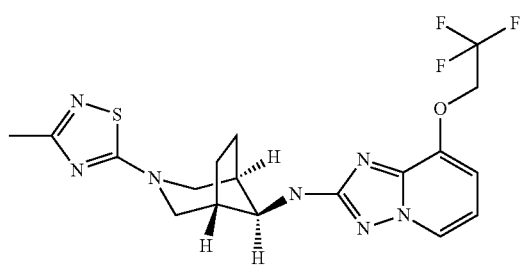 [SMILES: Cc1nsc(N2C[C@H]3CC[C@@H](C2)[C@@H]3Nc2nc3c(OCC(F)(F)F)cccn3n2)n1]

Intermediate 3

2-Nitro-3-(2,2,2-trifluoroethoxy)-[1,2,4]triazolo[1,5-a]pyridine

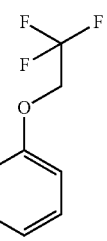

Step 1

2-Nitro-3-(2,2,2-trifluoroethoxy)pyridine

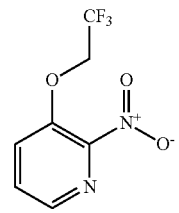 [SMILES: O=[N+]([O-])c1ncccc1OCC(F)(F)F]

2-Nitropyridin-3-ol (3 g, 21.4 mmol) and K₂CO₃ (5.92 g, 42.8 mmol) were combined in DMF (50 ml) and the orange suspension was heated to 90° C. for 1 h. 1,1,1-Trifluoro-2-iodoethane (13.48 g, 6.32 ml, 64.2 mmol) was added at room temperature and the reaction mixture was heated to 125° C. and stirred for 2 days. The solvent was removed under reduced pressure, and the residue was diluted with water and extracted with dichloromethane. The combined organic layers were washed with concentrated aqueous sodium chloride solution, dried over sodium sulfate, filtered and concentrated under reduced pressure. The residue was purified by column chromatography on silica gel using a gradient (0% to 100% EtOAc in heptane) to yield 2-nitro-3-(2,2,2-trifluoroethoxy) pyridine (3.32 g, 70%) as a light yellow liquid. MS ES+ (m/z): 223.1 [(M+H)⁺]

Step 2

3-(2,2,2-trifluoroethoxy)pyridin-2-amine

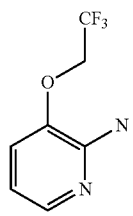

The title compound was prepared in analogy to example 1, intermediate 3, step 2 from 2-nitro-3-(2,2,2-trifluoroethoxy)pyridine (2.66 g, 12 mmol) as an off white solid (1.68 g, 73%). MS ES+ (m/z): 193.1 [(M+H)⁺]

Step 3

Ethyl N-[[3-(2,2,2-trifluoroethoxy)pyridin-2-yl]car-bamothioyl]carbamate

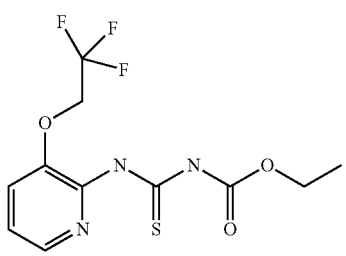 [SMILES: CCOC(=O)NC(=S)Nc1ncccc1OCC(F)(F)F]

The title compound as a solid, was prepared in analogy to example 1, intermediate 3, step 3 from (3-(2,2,2-trifluoroethoxy)pyridin-2-amine (1.61 g, 8.4 mmol) and Ethoxycarbonyl isothiocyanate (1.1 g, 0.940 ml, 8.4 mmol) as a light yellow solid (2.7 g, 100%) that was used as crude on the next step without purification.

MS ES+ (m/z): 324.1 [(M+H)⁺]

Step 4

8-(2,2,2-trifluoroethoxy)-[1,2,4]triazolo[1,5-a]pyridin-2-amine

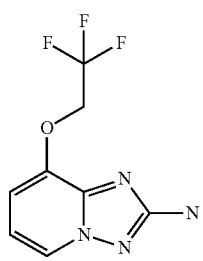 [SMILES: Nc1nc2c(OCC(F)(F)F)cccn2n1]

The title compound, was prepared in analogy to example 1, intermediate 3, step 4 from ethyl N-[[3-(2,2,2-trifluoroethoxy)pyridin-2-yl]carbamothioyl]carbamate (2.7 g, 8.35 mmol) with hydroxylamine hydrochloride and Hunig's base as a light yellow solid (1.69 g, 87.5%).

MS ES+ (m/z): 233.1 [(M+H)⁺]

Step 5

Bromo-8-(2,2,2-trifluoroethoxy)-[1,2,4]triazolo[1,5-a]pyridine

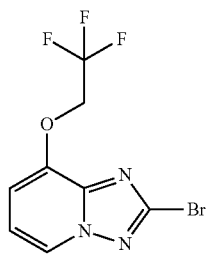 [SMILES: FC(F)(F)COc1cccn2nc(Br)nc12]

The title compound, was prepared in analogy to example 1, intermediate 3 (step 5) from 8-(2,2,2-trifluoroethoxy)-[1,2,4]triazolo[1,5-a]pyridin-2-amine (1.25 g, 5.2 mmol), tert-butyl nitrite and copper (II) bromide as a white solid (1.46 g, 93%). MS ES+ (m/z): 298 [(M+H)⁺]

Coupling Step 6

N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine

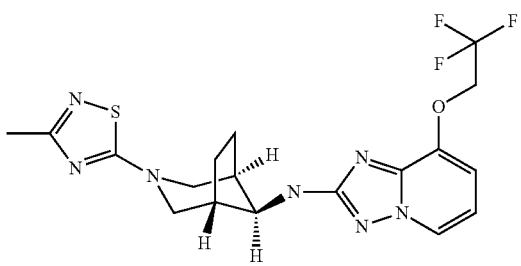 [SMILES: Cc1nsc(N2C[C@H]3CC[C@@H](C2)[C@@H]3Nc2nc3c(OCC(F)(F)F)cccn3n2)n1]

The title compound was prepared by Buchwald coupling in analogy to example 1, from Bromo-8-(2,2,2-trifluoroethoxy)-[1,2,4]triazolo[1,5-a]pyridine (39.6 mg, 134 μmol) and intermediate 2 (example 1), (8-endo)-3-(3-methyl-1,2,4-thiadiazol-5-yl)-3-azabicyclo[3.2.1]octan-8-amine (30 mg, 134 μmol) with Pd₂(dba)₃.CHCl₃ in the presence of sodium phenoxide and xantphos as a white solid (39.3 mg, 67%) MS ES+ (m/z): 440.2 [(M+H)⁺]

EXAMPLE 4

N-[(8-endo) 3-(3-methyl-1,2,4-thiadiazol-5-yl)-3-azabicyclo[3.2.1]octan-8-yl]-8-[(2R/S)-1,1,1-trifluoropropan-2-yl]oxy-[1,2,4]triazolo[1,5-a]pyridin-2-amine

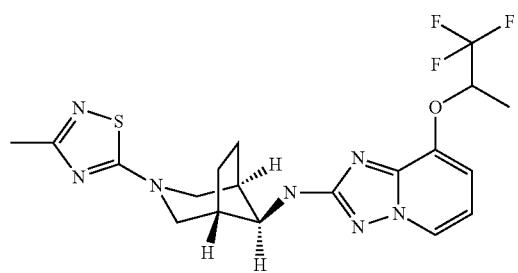 [SMILES: Cc1nsc(N2C[C@H]3CC[C@@H](C2)[C@@H]3Nc2nc3c(OC(C)C(F)(F)F)cccn3n2)n1]

Intermediate 3

2-bromo-8-(1,1,1-trifluoropropan-2-yloxy)-[1,2,4]triazolo[1,5-a]pyridine

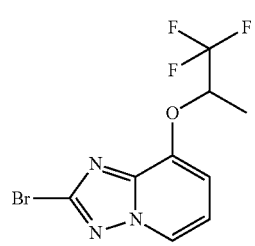 [SMILES: CC(Oc1cccn2nc(Br)nc12)C(F)(F)F]

Step 1

Ethyl N-[(3-methoxypyridin-2-yl)carbamothioyl]carbamate

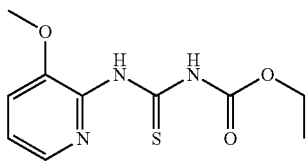 [SMILES: CCOC(=O)NC(=S)Nc1ncccc1OC]

To a stirred solution of 3-methoxypyridin-2-amine (8 g, 64.4 mmol) in 1,4-dioxane (120 mL) was added Ethoxycarbonyl Isothiocyanate (8.45 g, 7.29 ml, 64.4 mmol) and the reaction was stirred over night. The solvent was evaporated in vacuo to yield the title compound (15.82 g, 96%) as a light yellow solid. MS ES+ (m/z): 256.2 (100%) [(M+H)+]

Step 2

8-Methoxy-[1,2,4]triazolo[1,5-a]pyridin-2-ylamine

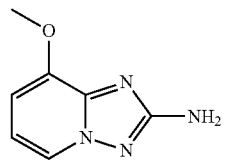

Hydroxylamine hydrochloride (21.5 g, 310 mmol) and Hunig's base (24 g, 32.4 ml, 186 mmol) were dissolved in a mixture of MeOH (105 ml) and EtOH (105 ml). Ethyl N-[(3-methoxypyridin-2-yl)carbamothioyl]carbamate (15.81 g, 61.9 mmol) was added and the mixture was allowed to stir for 3 h at 60° C. The reaction mixture was poured into 600 mL of sat NaHCO$_3$ and extracted with dichloromethane (5×650 mL). The combined organic layers were dried over MgSO$_4$ and concentrated in vacuo. The crude material was purified by flash chromatography on silica gel (0% to 100% EtOAc in heptane) to yield 9.99 g (98.2%) of the title compound as a white solid. MS ES+ (m/z): 165.1 (100%) [(M+H)+]

Step 3

Bromo-8-methoxy-[1,2,4]triazolo[1,5-a]pyridine

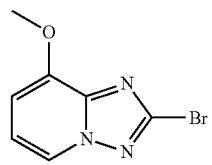

Copper (II) bromide (14.3 g, 64 mmol) and tert-Butyl nitrite (6.6 g, 7.63 ml, 64 mmol) were dissolved in acetonitrile (280 ml) and the reaction mixture was heated to 60° C. 8-methoxy-[1,2,4]triazolo[1,5-a]pyridin-2-amine (7 g, 42.6 mmol) was added portion wise during 30 minutes and the reaction mixture was stirred for 2 hrs at 60° C. The reaction was poured into 350 mL 1 M HCl and extracted with dichloromethane (3×400 mL). The organic layers were dried over MgSO$_4$ and concentrated in vacuo. The crude material was purified by flash chromatography on silica gel (solid application) (0% to 100% EtOAc in heptane) to yield 6.06 g (62%) of the title compound as a white solid. MS ES+ (m/z): 228.1-230.1 (100%) [(M+H)+]

Step 4

2-bromo-[1.2.4]triazolo[1,5-a]pyridin-8-ol

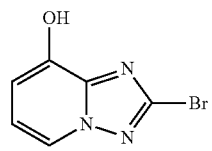 [SMILES: Oc1cccn2nc(Br)nc12]

To a light yellow solution of 2-bromo-8-methoxy-[1,2,4]triazolo[1,5-a]pyridine (5.0 g, 21.9 mmol) in dichloromethane (100 ml) at 0° C. was added drop wise a solution of BBr$_3$ 1M in dichloromethane (110 ml, 110 mmol). After the addition the reaction mixture was stirred at 0° C. for 2 hours and at room temperature for 3 days. The excess of BBr$_3$ was quenched by adding methanol (around 20 ml) with a dropping funnel. The reaction mixture was poured into a solution of ammonium chloride (60 ml) and extracted with dichloromethane (5×200 ml). The organic layers were dried over MgSO$_4$ and concentrated in vacuo to obtain the title compound (3.85 g, 81% yield) as an off-white solid. MS ES+ (m/z): 214.0-216.0 (100%) [(M+H)$^+$]

Step 5

2-Bromo-8-(1,1,1-trifluoropropan-2-yloxy)-[1,2,4]triazolo[1,5-a]pyridine

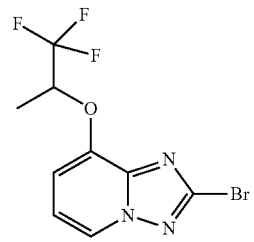

To a colorless solution of 2-bromo-[1,2,4]triazolo[1,5-a]pyridin-8-ol (50 mg, 234 μmol) in DMF (1 ml), freshly prepared 1,1,1-trifluoropropan-2-yl 1,1,2,2,3,3,4,4,4-nonafluorobutane-1-sulfonate (CAS number 118334-94-4) (139 mg, 350 μmol) and K$_2$CO$_3$ (64.6 mg, 467 μmol) were added. The reaction mixture was stirred over night at 120° C. in a closed vial. The reaction mixture was poured into 20 mL H$_2$O and extracted with DCM (3×20 mL). The organic layers were dried over MgSO$_4$ and concentrated in vacuo. The crude material was purified by flash chromatography (silica gel, 0% to 80% EtOAc in heptane) to afford the title compound (38.7 mg, 125 μmol, 53.4% yield) as a white solid. MS ES+ (m/z): 310.0 [(M+H)$^+$]

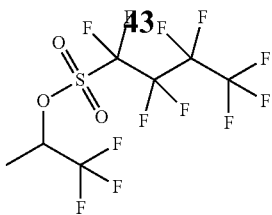

The reagent for the alkylation step 1,1,1-trifluoropropan-2-yl 1,1,2,2,3,3,4,4,4-nonafluorobutane-1-sulfonate (or 1,1,1-Trifluoroisopropyl Nonaflate with CAS number 118334-94-4), was prepared from 1,1,1-trifluoropropan-2-ol with 1,1,2,2,3,3,4,4,4-nonafluorobutane-1-sulfonyl fluoride and triethylamine in dichloromethane as described in J. Org. Chem 1989, 54, 1432-1435.

Final Coupling Step 6

N-[(8-endo)-3-(3-methyl-1,2,4-thiadiazol-5-yl)-3-azabicyclo[3.2.1]octan-8-yl]-8-[rac-1,1,1-trifluoro-propan-2-yl]oxy-[1,2,4]triazolo[1,5-a]pyridin-2-amine

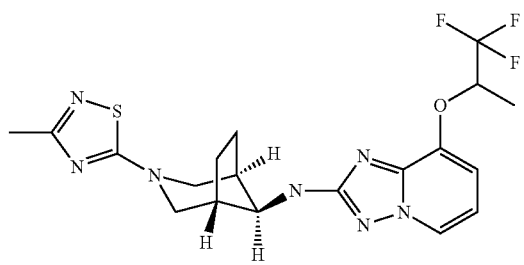 [SMILES: Cc1nsc(N2C[C@H]3CC[C@@H](C2)[C@@H]3Nc2nc3c(OC(C)C(F)(F)F)cccn3n2)n1]

The title compound was prepared by Buchwald coupling in analogy to example 1, from 2-bromo-8-(1,1,1-trifluoropropan-2-yloxy)-[1,2,4]triazolo[1,5-a]pyridine (76.0 mg, 245 µmol) (intermediate 3) and (8 endo)-3-(3-methyl-1,2,4-thiadiazol-5-yl)-3-azabicyclo[3.2.1]octan-8-amine (intermediate 2, example 1), (50 mg, 223 µmol) with Pd$_2$(dba)$_3$·CHCl$_3$ in the presence of sodium tert-butoxide (64.3 mg, 669 µmol) as base instead of sodium phenoxide, and xantphos (20.6 mg, 35.7 µmol). The title compound was obtained as a white solid (81 mg, 80.1% yield).

MS ES+ (m/z): 454.2 [(M+H)$^+$]

EXAMPLE 5

N-[(8-endo)-3-(3-methyl-1,2,4-thiadiazol-5-yl)-3-azabicyclo[3.2.1]octan-8-yl]-8-[(2R or 2S)-1,1,1-trifluoropropan-2-yl]oxy-[1,2,4]triazolo[1,5-a]pyridin-2-amine

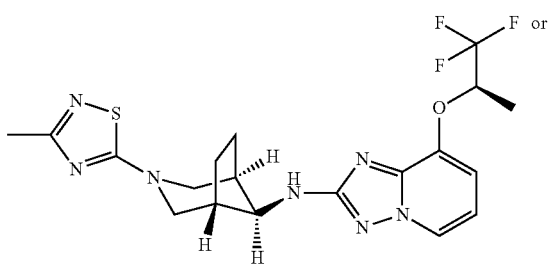

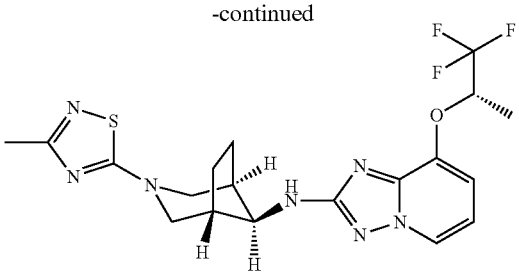

The title compound was obtained from separation using a chiral column (chiralpak AD) of N-[(8-endo)-3-(3-methyl-1,2,4-thiadiazol-5-yl)-3-azabicyclo[3.2.1]octan-8-yl]-8-[rac-1,1,1-trifluoropropan-2-yl]oxy-[1,2,4]triazolo[1,5-a]pyridin-2-amine (Example 4).

MS ES+ (m/z): 454.3 (100%) [(M+H)$^+$]

EXAMPLE 6

N-[(8 endo)-3-(3-methyl-1,2,4-thiadiazol-5-yl)-3-azabicyclo[3.2.1]octan-8-yl]-8-[(2S or 2R)-1,1,1-trifluoropropan-2-yl]oxy-[1,2,4]triazolo[1,5-a]pyridin-2-amine

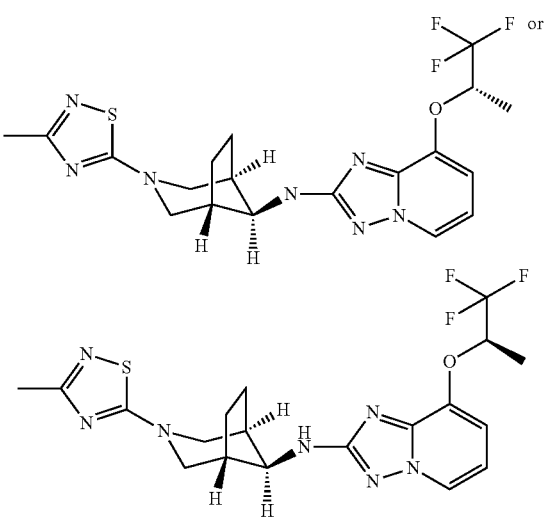

The title compound was obtained from separation using a chiral column (chiralpak AD) of N-[(8-endo)-3-(3-methyl-1,2,4-thiadiazol-5-yl)-3-azabicyclo[3.2.1]octan-8-yl]-8-[rac-1,1,1-trifluoropropan-2-yl]oxy-[1,2,4]triazolo[1,5-a] pyridin-2-amine (Example 4).

MS ES+ (m/z): 454.2 [(M+H)$^+$]

Preparation of Intermediates 3

According to the procedure described for the synthesis of intermediate 3 (example 4) further derivatives have been synthesized from the respective 2-bromo-[1,2,4]triazolo[1,5-a]pyridin-8-ol (example 4, step 5) and the corresponding alkylating agent. They comprise intermediates 3-14 on table I.

TABLE I

| Intermediate 3 | Systematic name Yield of reaction | Starting materials | MW found (M + H)+ |
|---|---|---|---|
| 7 | 2-bromo-8-[[1-(trifluoromethyl)cyclopropyl]methoxy]-[1,2,4]triazolo[1,5-a]pyridine (65.4 mg, 83.3% yield). | 2-Bromo-[1,2,4]triazolo[1,5-a]pyridin-8-ol (50 mg, 234 µmol) and (1-(trifluoromethyl)cyclopropyl)methyl 4-methylbenzenesulfonate (CAS number 865833-72-3) (82.5 mg, 280 µmol) | 336.1 |
| 8 | 2-bromo-8-((4,4-difluorocyclohexyl)methoxy)-[1,2,4]triazolo[1,5-a]pyridine (99.2 mg, 61.3% yield). | 2-Bromo-[1,2,4]triazolo[1,5-a]pyridin-8-ol (100 mg, 467 µmol) and 4-(bromomethyl)-1,1-difluorocyclohexane (CAS number 858121-94-5 (119 mg, 84.7 µl, 561 µmol) | 346.1 |
| 9 | 2-bromo-8-[(3,3-difluorocyclobutyl)methoxy]-[1,2,4]triazolo[1,5-a]pyridine (120 mg, 80.7% yield) | 2-Bromo-[1,2,4]triazolo[1,5-a]pyridin-8-ol (100 mg, 467 µmol) and 3 (Bromomethyl)-1,1-Difluorocyclobutane (104 mg, 561 µmol) | 318.1 |
| 10 | 2-bromo-8-(1,2,2,2-tetrafluoroethoxy)-[1,2,4]triazolo[1,5-a]pyridine (51 mg, 23.2% yield) | 2-Bromo-[1,2,4]triazolo[1,5-a]pyridin-8-ol (150 mg, 701 µmol) and 1,2,2,2-Tetrafluoroethyl-iodide (319 mg, 152 µl, 1.4 mmol) | 314.0 |

TABLE I-continued

| Intermediate 3 | Systematic name Yield of reaction | Starting materials | MW found (M + H)+ |
|---|---|---|---|
| 11 | 2-bromo-8-[(2,2-difluorocyclopropyl)methoxy]-[1,2,4]triazolo[1,5-a]pyridine (134.3 mg, 94.5% yield) | 2-Bromo-[1,2,4]triazolo[1,5-a]pyridin-8-ol (100 mg, 467 μmol) and 1-Bromomethyl-2,2-Diflurocyclopropane (120 mg, 701 μmol) | 304.0-306.0 |
| 12 | 2-bromo-8-((3,3-difluorocyclopentyl)methoxy)-[1,2,4]triazolo[1,5-a]pyridine (145 mg, 93.4% yield). | 2-Bromo-[1,2,4]triazolo[1,5-a]pyridin-8-ol (100 mg, 467 μmol) and (3,3-difluorocyclopentyl)methyl 4-methyl-benzenesulfonate (prepared from alcohol as described on US2009/325942, WO2008/89892, page 55) (163 mg, 561 μmol) | 332.1 |
| 13 | 2-bromo-8-(3,3,3-trifluoro-2,2-dimethylpropoxy)-[1,2,4]triazolo[1,5-a]pyridine (52.3 mg, 66.2% yield). | 2-Bromo-[1,2,4]triazolo[1,5-a]pyridin-8-ol (50 mg, 234 μmol) and 3-bromo-1,1,1-trifluoro-2,2-dimethylpropane (71.8 mg, 350 μmol) | 338.1 |
| 14 | 2-bromo-8-(2,2,3,3,3-pentafluoropropoxy)-[1,2,4]triazolo[1,5-a]pyridine (399.5 mg, 49.4% yield). | 2-Bromo-[1,2,4]triazolo[1,5-a]pyridin-8-ol (500 mg, 2.34 mmol) and 1,1,1,2,2-pentafluoro-3-iodopropane (1.21 g, 581 μl, 4.67 mmol) | 346.0 |

Preparation of Final Examples with Selected Intermediates 3

According to the procedure described for the synthesis of example 1 (final coupling step) further derivatives have been synthesized from the respective intermediates 3 and intermediate 2 from example, (8-endo)-3-(3-methyl-1,2,4-thiadiazol-5-yl)-3-azabicyclo[3.2.1]octan-8-amine, with Pd2(dba)3.CHCl$_3$ in the presence of a base such as sodium phenoxide or sodium tert-butoxide and xantphos, They comprise example 7 to example 13 described on the table below.

TABLE 2

| Examples number | Systematic name | Starting materials | MW found (M + H)$^+$ |
|---|---|---|---|
| 7<br />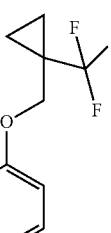 | N-[(8 endo)-3-(3-methyl-1,2,4-thiadiazol-5-yl)-3-azabicyclo[3.2.1]octan-8-yl]-8-[[1-(trifluoromethyl)cyclopropyl]methoxy]-[1,2,4]triazolo[1,5-a]pyridin-2-amine (23.6 mg, 73.6% yield). | 2-bromo-8-((1-(trifluoromethyl)cyclopropyl)methoxy)-[1,2,4]triazolo[1,5-a]pyridine (23.6 mg, 70.2 μmol) and (8 endo)-3-(3-methyl-1,2,4-thiadiazol-5-yl)-3-azabicyclo[3.2.1]octan-8-amine (15 mg, 66.9 μmol) | 480.4 |
| 8<br /> | 8-[(4,4-difluorocyclohexyl)methoxy]-N [(8-endo)-3-(3-methyl-1,2,4-thiadiazol-5-yl)-3-azabicyclo[3.2.1]octan-8-yl]-8-[(4,4-difluorocyclohexyl)methoxy]-[1,2,4]triazolo[1,5-a]pyridin-2-amine | 2-bromo-8-((4,4-difluorocyclohexyl)methoxy)-[1,2,4]triazolo[1,5-a]pyridine (24.3 mg, 70.2 μmol) and (8-endo)-3-(3-methyl-1,2,4-thiadiazol-5-yl)-3-azabicyclo[3.2.1]octan-8-amine (15 mg, 66.9 μmol) | 490.4 |
| 9<br /> | 8-[(3,3-difluorocyclobutyl)methoxy]-N-[(8 endo)-3-(3-methyl-1,2,4-thiadiazol-5-yl)-3-azabicyclo[3.2.1]octan-8-yl]-[1,2,4]triazolo[1,5-a]pyridin-2-amine (22 mg, 71.3% yield). | 2-bromo-8-((3,3-difluorocyclobutyl)methoxy)-[1,2,4]triazolo[1,5-a]pyridine (22.3 mg, 70.2 μmol) and (8-endo)-3-(3-methyl-1,2,4-thiadiazol-5-yl)-3-azabicyclo[3.2.1]octan-8-amine (15 mg, 66.9 μmol) | 462.4 |

TABLE 2-continued

| Examples number | Systematic name | Starting materials | MW found (M + H)+ |
|---|---|---|---|
| 10 | N-[(8 endo)-3-(3-methyl-1,2,4-thiadiazol-5-yl)-3-azabicyclo[3.2.1]octan-8-yl]-8-(1,2,2,2-tetrafluoroethoxy)-[1,2,4]triazolo[1,5-a]pyridin-2-amine (15.1 mg, 49.4% yield). | 2-bromo-8-(1,2,2,2-tetrafluoroethoxy)-[1,2,4]triazolo[1,5-a]pyridine (31.5 mg, 100 μmol) and (8 endo)-3-(3-methyl-1,2,4-thiadiazol-5-yl)-3-azabicyclo[3.2.1]octan-8-amine (15 mg, 66.9 μmol) | 458.3 |
| 11 | 8-[2,2-difluorocyclopropyl]methoxy]-N-[(8endo)-3-(3-methyl-1,2,4-thiadiazol-5-yl)-3-azabicyclo[3.2.1]octan-8-yl]-[1,2,4]triazolo[1,5-a]pyridin-2-amine (22.6 mg, 75.5% yield) | 2-bromo-8-((2,2-difluorocyclopropyl)methoxy)-[1,2,4]triazolo[1,5-a]pyridine (24.4 mg, 80.2 μmol) and 8-endo)-3-(3-methyl-1,2,4-thiadiazol-5-yl)-3-azabicyclo[3.2.1]octan-8-amine (15 mg, 66.9 μmol) | 448.3 |
| 12 | 8-((3,3-difluorocyclopentyl)methoxy)-N-[(8 endo) 3-(3-methyl-1,2,4-thiadiazol-5-yl)-3-azabicyclo[3.2.1]octan-8-yl]-[1,2,4]triazolo[1,5-a]pyridin-2-amine (19.5 mg, 61.3% yield). | 2-bromo-8-((3,3-difluorocyclopentyl)methoxy)-[1,2,4]triazolo[1,5-a]pyridine (23.3 mg, 70.2 μmol) and (8-endo)-3-(3-methyl-1,2,4-thiadiazol-5-yl)-3-azabicyclo[3.2.1]octan-8-amine (15 mg, 66.9 μmol) | 476.4 |
| 13 | N-[(8-endo)-3-(3-methyl-1,2,4-thiadiazol-5-yl)-3-azabicyclo[3.2.1]octan-8-yl]-8-(3,3,3-trifluoro-2,2-dimethylpropoxy)-[1,2,4]triazolo[1,5-a]pyridin-2-amine (7 mg, 21% yield). | 2-bromo-8-(3,3,3-trifluoro-2,2-dimethylpropoxy)-[1,2,4]triazolo[1,5-a]pyridine (22.6 mg, 66.9 μmol) and (8-endo)-3-(3-methyl-1,2,4-thiadiazol-5-yl)-3-azabicyclo[3.2.1]octan-8-amine (15 mg, 66.9 μmol) | 482.2 |

EXAMPLE 14

N-[(8-endo)-3-(3-methyl-1,2-thiazol-5-yl)-3-azabicyclo[3.2.1]octan-8-yl]-8-(3,3,3-trifluoropropoxy)-[1,2,4]triazolo[1,5-a]pyridin-2-amine

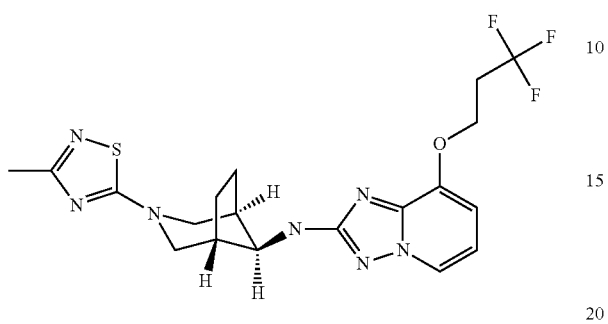

Intermediate 2

(8-endo)-3-(3-Methylisothiazol-5-yl)-3-azabicyclo[3.2.1]octan-8-amine

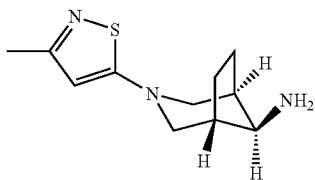

Step 1

Tert-Butyl ((8-meso)-3-(3-Methylisothiazol-5-yl)-3-azabicyclo[3.2.1]octan-8-yl)carbamate

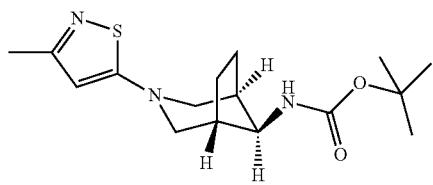 [SMILES: Cc1cc(N2C[C@H]3CC[C@@H](C2)[C@@H]3NC(=O)OC(C)(C)C)sn1]

In a 250 mL round-bottomed flask, 4-methyl-6-thioxo-3,6-dihydro-2H-1,3-thiazin-2-one (CAS 97309-82-5, 1.50 g, 9.42 mmol), tert-butyl (8-anti)-3-azabicyclo[3.2.1]octan-8-ylcarbamate (CAS 847862-26-4, 2.13 g, 9.42 mmol), 4-methylmorpholine (2.86 g, 3.11 ml, 28.3 mmol) and 4-dimethylaminopyridine (11.5 mg, 94.2 µmol) were combined with dioxane (150 ml) to give a light brown solution. The reaction mixture was heated to 80° C. and stirred overnight. Diisopropylethyl amine (4.87 g, 6.58 ml, 37.7 mmol) was added and the mixture was cooled in an icebath. Iodine (4.78 g, 18.8 mmol) in dioxane (10 ml) was added and the reaction mixture was stirred overnight while warming to room temperature. The crude reaction mixture was concentrated in vacuo and purified by chromatography (silica gel-NH$_2$, 40 g, ethylacetate/heptane=50:50 to 100:0) to yield the title compound as light brown solid (1.09 g, 36%). MS: m/z=324.2 [M+H]$^+$.

Step 2

(8 endo)-3-(3-Methylisothiazol-5-yl)-3-azabicyclo[3.2.1]octan-8-amine

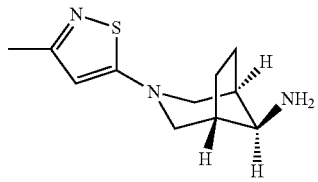

In a 250 mL round-bottomed flask, tert-butyl ((8-anti)-3-(3-methylisothiazol-5-yl)-3-azabicyclo[3.2.1]octan-8-yl)carbamate (2.99 g, 9.24 mmol) was combined with dichloromethane (180 ml) to give a brown solution. Hydrochloric acid (25%, 10 ml) was added and the reaction mixture was stirred at room temperature for 2 hours. The reaction mixture was cooled in an icebath, water (50 ml) was added and the mixture was basified with aqueous sodium hydroxide (4N). Extraction with dichloromethane and chromatography (silica gel-NH2, 40 g, ethylacetate/heptane=50:50 to 100:0) yielded the title compound as light brown solid (1.64 g, 80%). MS: m/z=224.2 [M+H]$^+$.

Final Coupling Step 3

N-[(8 endo)-3-(3-methyl-1,2-thiazol-5-yl)-3-azabicyclo[3.2.1]octan-8-yl]-8-(3,3,3-trifluoropropoxy)-[1,2,4]triazolo[1,5-a]pyridin-2-amine

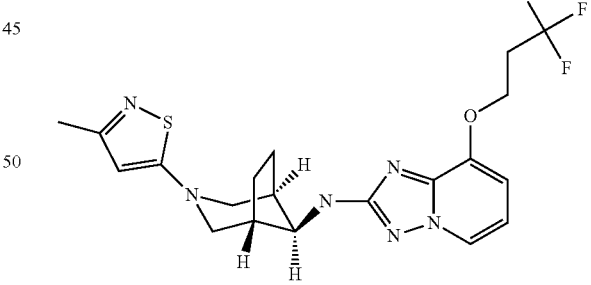

The title compound, was prepared by Buchwald coupling in analogy to example 1, from 2-bromo-8-(3,3,3-trifluoropropoxy)-[1,2,4]triazolo[1,5-a]pyridine (21.9 mg, 70.5 µmol), or intermediate 3 from example 2 (prepared on steps 1-5), and intermediate 2 described (8-endo)-3-(3-Methylisothiazol-5-yl)-3-azabicyclo[3.2.1]octan-8-amine (15 mg, 67.2 µmol) with Tris(dibenzylideneacetone)dipalladium (0) chloroform adduct or Pd$_2$(dba)$_3$.CHCl$_3$ in the presence of Sodium phenoxide and xantphos. The compound was obtained as a white solid (6 mg, 30%), MS ES+ (m/z): 453.3 [(M+H)$^+$]

EXAMPLE 15

N-[(8 endo)-3-(3-methylisothiazol-5-yl)-3-azabicyclo[3.2.1]octan-8-yl]-8-(2,2,3,3,3-pentafluoropropoxy)-[1,2,4]triazolo[1,5-a]pyridin-2-amine

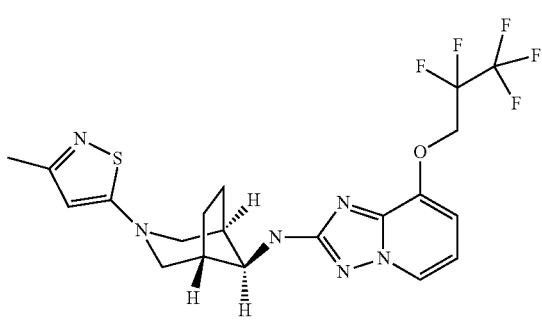 [SMILES: Cc1cc(N2C[C@H]3CC[C@@H](C2)[C@@H]3Nc2nc3c(OCC(F)(F)C(F)(F)F)cccn3n2)sn1]

The title compound, was prepared by Buchwald coupling in analogy to example 1, from 2-bromo-8-(2,2,3,3,3-pentafluoropropoxy)-[1,2,4]triazolo[1,5-a]pyridine (65.1 mg, 188 µmol), described as intermediate 3-14 on table I, and (8-endo))-3-(3-Methylisothiazol-5-yl)-3-azabicyclo[3.2.1] octan-8-amine (42 mg, 188 µmol) with Tris(dibenzylideneacetone) dipalladium (0) chloroform adduct or Pd$_2$(dba)$_3$·CHCl$_3$ in the presence of Sodium phenoxide and Xantphos. The compound was obtained as an off-white solid (50 mg, 54.4%)

MS ES+ (m/z): 489.9 [(M+H)$^+$]

EXAMPLE 16

N-[(8 endo) 3-(3-methylisothiazol-5-yl)-3-azabicyclo[3.2.1]octan-8-yl)]-8-(2,2,2-trifluoroethoxy)-[1,2,4]triazolo[1,5-a]pyridin-2-amine

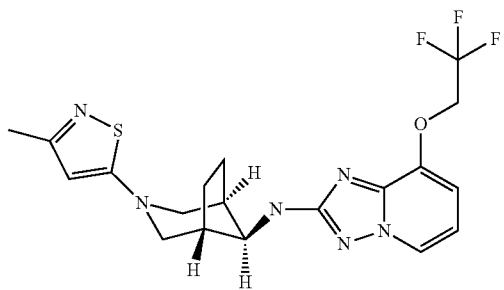 [SMILES: Cc1cc(N2C[C@H]3CC[C@@H](C2)[C@@H]3Nc2nc3c(OCC(F)(F)F)cccn3n2)sn1]

The title compound, was prepared by Buchwald coupling in analogy to example 1, from 2-bromo-8-(2,2,2-trifluoroethoxy)-[1,2,4]triazolo[1,5-a]pyridine (39.8 mg, 134 mol), intermediate 3 from example 3 (steps 1-5) and intermediate 2 (from example 14) (8-endo)-3-(3-Methylisothiazol-5-yl)-3-azabicyclo[3.2.1]octan-8-amine (30 mg, 134 µmol) with Tris(dibenzylideneacetone) dipalladium (0) chloroform adduct or Pd$_2$(dba)$_3$·CHCl$_3$ in the presence of Sodium phenoxide and xantphos. The compound was obtained as an off-white solid (15 mg, 25.5%) MS ES+ (m/z): 439.2 [(M+H)$^+$]

EXAMPLE 17

N-[(8 endo)-3-(3-methylisothiazol-5-yl)-3-azabicyclo[3.2.1]octan-8-yl]-8-((1,1,1-trifluoropropan-2-yl)oxy)-[1,2,4]triazolo[1,5-a]pyridin-2-amine

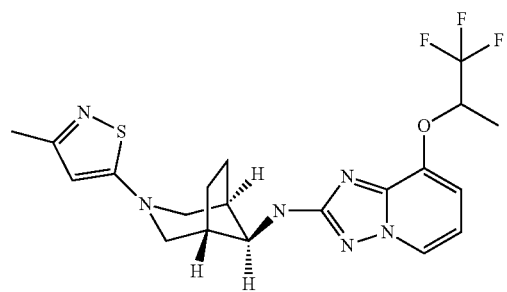 [SMILES: Cc1cc(N2C[C@H]3CC[C@@H](C2)[C@@H]3Nc2nc3c(OC(C)C(F)(F)F)cccn3n2)sn1]

The title compound, was prepared by Buchwald coupling in analogy to example 1, from 2-bromo-8-((1,1,1-trifluoropropan-2-yl)oxy)-[1,2,4]triazolo[1,5-a]pyridine (27.8 mg, 89.6 µmol), intermediate 3 from example 4 and (8-endo)-3-(3-Methylisothiazol-5-yl)-3-azabicyclo[3.2.1]octan-8-amine or intermediate 2 from example 14 (20 mg, 89.6 µmol) with Tris(dibenzylideneacetone) dipalladium (0) chloroform adduct (7.42 mg, 7.16 µmol) in the presence of sodium tert-butoxide (25.8 mg, 269 µmol) and xantphos (8.29 mg, 14.3 µmol) in Dioxane in a microwave at 145° C. during 30 min. The compound was obtained as an off-white solid (29.2 mg, 72.1% yield) MS ES+ (m/z): 453.3 [(M+H)$^+$]

EXAMPLE 18

N-((8 endo)-3-(3-methylisothiazol-5-yl)-3-azabicyclo[3.2.1]octan-8-yl)-8-((2R or 2S)-1,1,1-trifluoropropan-2-yl)oxy)-[1,2,4]triazolo[1,5-a]pyridin-2-amine

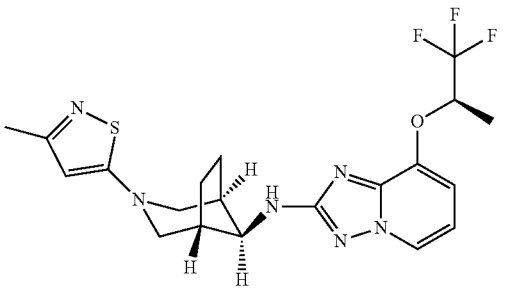

or

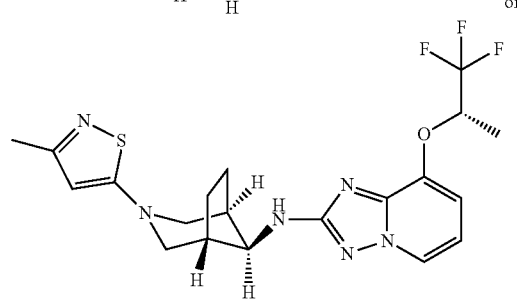

57

Intermediate 3

2-bromo-8-[(2R or 2S)-1,1,1-trifluoropropan-2-yl]oxy-[1,2,4]triazolo[1,5-a]pyridine

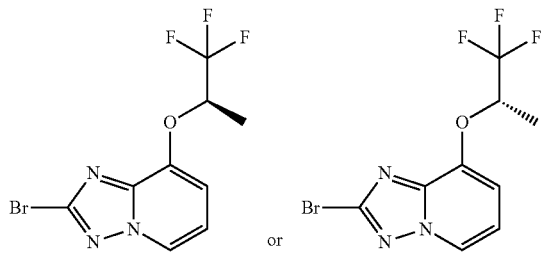 [SMILES: C[C@@H](Oc1cccn2nc(Br)nc12)C(F)(F)F ; C[C@H](Oc1cccn2nc(Br)nc12)C(F)(F)F]

The title compound was obtained from separation of racemic 2-bromo-8-(1,1,1-trifluoropropan-2-yloxy)-[1,2,4]triazolo[1,5-a]pyridine (intermediate 3 from example 4) using a chiral column (Chiralcel OD, 90% Heptane/10% Isopropanol, K-2979).

Coupling Step

N-((8 endo)-3-(3-methylisothiazol-5-yl)-3-azabicyclo[3.2.1]octan-8-yl)-8-((2R or 2S)-1,1,1-trifluoropropan-2-yl)oxy)-[1.2.4]triazolo[1,5-a]pyridin-2-amine

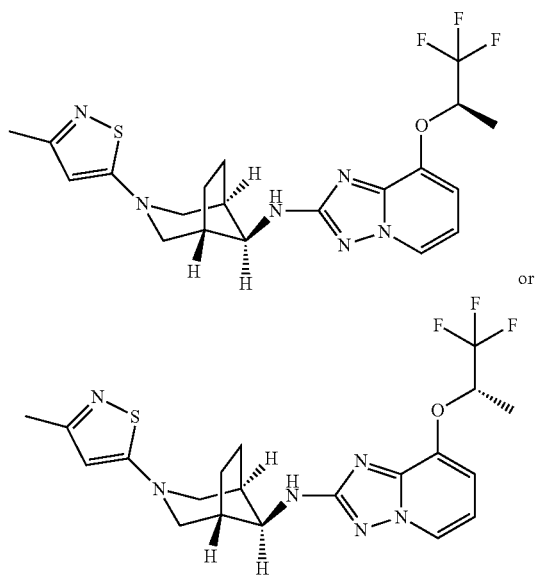

The title compound, was prepared by Buchwald coupling from the corresponding chiral 2-bromo-8-[(2R)-1,1,1-trifluoropropan-2-yl]oxy-[1,2,4]triazolo[1,5-a]pyridine or 2-bromo-8-[(2S)-1,1,1-trifluoropropan-2-yl]oxy-[1,2,4]triazolo[1,5-a]pyridine (intermediate 3-18) and (8 endo))-3-(3-Methylisothiazol-5-yl)-3-azabicyclo[3.2.1]octan-8-amine as described in example 1. The compound was obtained as light yellow solid (33.1 mg, 65.3% yield) MS ES+ (m/z): 453.4 (100%) [(M+H)+]

58

EXAMPLE 19

N-[(8-endo)-3-(3-methylisothiazol-5-yl)-3-azabicyclo[3.2.1]octan-8-yl)]-8-((2S or 2R)-1,1,1-trifluoropropan-2-yl)oxy)-[1,2,4]triazolo[1,5-a]pyridin-2-amine Intermediate 3

2-bromo-8-[(2S or 2R)-1,1,1-trifluoropropan-2-yl]oxy-[1,2,4]triazolo[1,5-a]pyridine

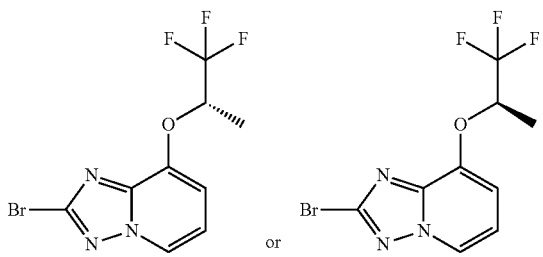 [SMILES: C[C@H](Oc1cccn2nc(Br)nc12)C(F)(F)F ; C[C@@H](Oc1cccn2nc(Br)nc12)C(F)(F)F]

The title compound was obtained from separation of racemic 2-bromo-8-(1,1,1-trifluoropropan-2-yloxy)-[1,2,4]triazolo[1,5-a]pyridine (intermediate 3 from example 4) using a chiral column (Chiralcel OD, 90% Heptan/10% Isopropanol, K-2979).

Coupling Step

N-[(8 endo)-3-(3-methylisothiazol-5-yl)-3-azabicyclo[3.2.1]octan-8-yl]-8-((2S or 2R)-1,1,1-trifluoropropan-2-yl)oxy)-[1,2,4]triazolo[1,5-a]pyridin-2-amine

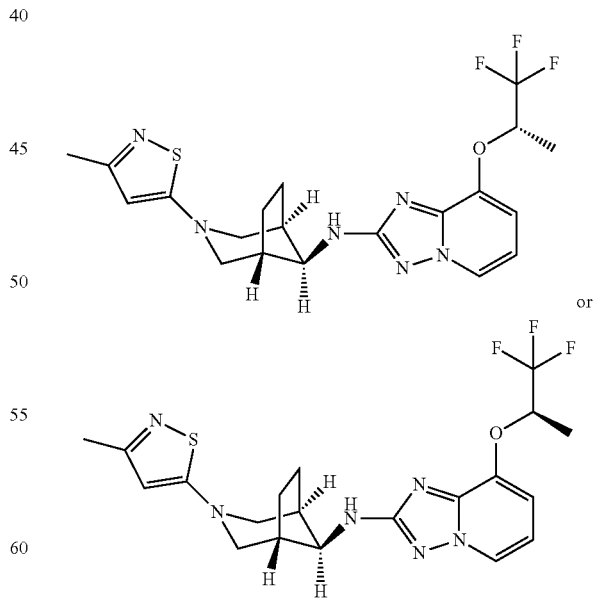

The title compound, was prepared by Buchwald coupling from the corresponding chiral 2-bromo-8-[(2S)-1,1,1-trifluoropropan-2-yl]oxy-[1,2,4]triazolo[1,5-a]pyridine or 2-bromo-8-[(2R)-1,1,1-trifluoropropan-2-yl]oxy-[1,2,4]triazolo[1,5-a]pyridine (intermediate 3-19) and (8 endo)-3-(3-Methylisothiazol-5-yl)-3-azabicyclo[3.2.1]octan-8-amine similarly as described in example 1. The compound was obtained as a light yellow solid (41.9 mg, 66.2% yield).

MS ES+ (m/z): 453.4 [(M+H)+]

EXAMPLE 20

N-[(8 endo)-3-(3-methylisothiazol-5-yl)-3-azabicyclo[3.2.1]octan-8-yl]-8-(trifluoromethoxy)-[1,2,4]triazolo[1,5-a]pyridin-2-amine Intermediate 3

Step 1

Ethyl N-[[3-(trifluoromethoxy)pyridin-2-yl]carbamothioyl]carbamate

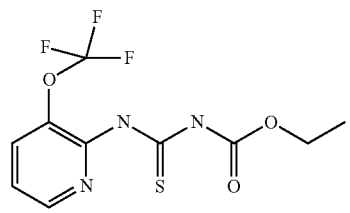 [SMILES: CCOC(=O)NC(=S)Nc1ncccc1OC(F)(F)F]

The title compound was prepared by reaction of 3-(trifluoromethoxy)pyridin-2-amine (CAS 1206981-49-83, 500 mg, 2.81 mmol) with Ethoxycarbonyl isothiocyanate in Dioxane at room temp over night as described in example 1 (step 3). The title compound was used as a crude on the next step (909 mg, 105% yield). MS ES+ (m/z): 310.1 [(M+H)+]

Step 2

8-(trifluoromethoxy)-[1,2,4]triazolo[1,5-a]pyridin-2-amine

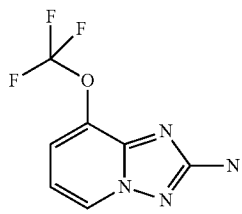 [SMILES: Nc1nc2c(OC(F)(F)F)cccn2n1]

The title compound was prepared by cyclization of Ethyl N-[[3-(trifluoromethoxy)pyridin-2-yl]carbamothioyl]carbamate (900 mg, 2.62 mmol) in a mixture of EtOH/MeOH with Hunig's base as described in example 1 (step 4). The title compound (442 mg, 77.4% yield) was obtained as a white solid, MS ES+ (m/z): 219.1 [(M+H)+]

Step 3

2-bromo-8-(trifluoromethoxy)-[1,2,4]triazolo[1,5-a]pyridine

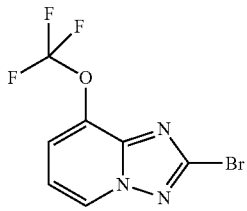 [SMILES: FC(F)(F)Oc1cccn2nc(Br)nc12]

The title compound was prepared from 8-(trifluoromethoxy)-[1,2,4]triazolo[1,5-a]pyridin-2-amine with tert-butyl nitrite and copper (II) bromide in acetonitrile at 60-75° C. during 2 hours similarly as described in example 1 (step 5). The title compound (395 mg, 77.3% yield) was obtained as a white solid. MS ES+ (m/z): 282.0 [(M+H)+]

Final Coupling

N-[(8 endo)-3-(3-methylisothiazol-5-yl)-3-azabicyclo[3.2.1]octan-8-yl]-8-(trifluoromethoxy)-[1,2,4]triazolo[1,5-a]pyridin-2-amine

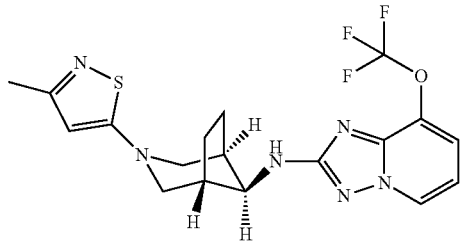 [SMILES: Cc1cc(N2C[C@H]3CC[C@@H](C2)[C@@H]3Nc2nc3c(OC(F)(F)F)cccn3n2)sn1]

The title compound, was prepared by Buchwald coupling from the corresponding Intermediate 3 (2-bromo-8-(trifluoromethoxy)-[1,2,4]triazolo[1,5-a]pyridine (33.1 mg, 118 μmol)) and (8-endo)-3-(3-Methylisothiazol-5-yl)-3-azabicyclo[3.2.1]octan-8-amine (25 mg, 112 μmol) as described in example 1 with sodium tert-butoxide, tris(dibenzylideneacetone)dipalladium (0) chloroform adduct and xantphos in 1,4-Dioxane. The compound was obtained as a light yellow solid (20.2 mg, 42.5% yield). MS ES+ (m/z): 425.3 [(M+H)+]

Preparation of Final Examples with Selected Intermediates 3

According to the procedure described for the synthesis of example 1 (final coupling step) further derivatives have been synthesized by Buchwald coupling from the respective intermediates 3 (described on table 1) and 8-endo (1R,5S))-3-(3-Methylisothiazol-5-yl)-3-azabicyclo[3.2.1]octan-8-amine with Pd2(dba)3.CHCl₃ in the presence of a base such as sodium phenoxide or sodium tert-butoxide and xantphos in dioxane at 145° C. during 30 min in a microwave. They comprise examples 21 to example 27 described on the table below.

TABLE 3

| Examples number | Systematic name | Starting materials | MW found (M + H)+ |
| --- | --- | --- | --- |
| 21 | N [(8 endo)-3-(3-methyl-1,2-thiazol-5-yl)-3-azabicyclo[3.2.1]octan-8-yl]-8-[[1-(trifluoromethyl)cyclopropyl]methoxy]-[1,2,4]triazolo[1,5-a]pyridin-2-amine (27.1 mg, 42% yield) | 2-bromo-8-((1-(trifluoromethyl)cyclopropyl)methoxy)-[1,2,4]triazolo[1,5-a]pyridine (56.8 mg, 161 μmol) and (8 endo)-3-(3-Methylisothiazol-5-yl)-3-azabicyclo[3.2.1]octan-8-amine (30 mg, 134 μmol) | 479.3 |
| 22 | 8-[(4,4-difluorocyclohexyl)methoxy]-N-[(8 endo)-3-(3-methyl-1,2-thiazol-5-yl)-3-azabicyclo[3.2.1]octan-8-yl]-[1,2,4]triazolo[1,5-a]pyridin-2-amine (9.1 mg, 27.7% yield) | 2-bromo-8-((4,4-difluorocyclohexyl)methoxy)-[1,2,4]triazolo[1,5-a]pyridine (24.4 mg, 70.5 μmol) and (8 endo))-3-(3-Methylisothiazol-5-yl)-3-azabicyclo[3.2.1]octan-8-amine (15 mg, 67.2 μmol) | 489.4 |
| 23 | 8-[(3,3-difluorocyclobutyl)methoxy]-N-[(8 endo)-3-(3-methyl-1,2-thiazol-5-yl)-3-azabicyclo[3.2.1]octan-8-yl]-[1,2,4]triazolo[1,5-a]pyridin-2-amine (31 mg, 46% yield) | 2-bromo-8-((3,3-difluorocyclobutyl)methoxy)-[1,2,4]triazolo[1,5-a]pyridine (22.4 mg, 70.5 μmol) and (8 endo))-3-(3-Methylisothiazol-5-yl)-3-azabicyclo[3.2.1]octan-8-amine (15 mg, 67.2 μmol) | 461.4 |
| 24 | N-[(8 endo)-3-(3-methyl-1,2-thiazol-5-yl)-3-azabicyclo[3.2.1]octan-8-yl]-8-[1,2,2,2-tetrafluoroethoxy]-[1,2,4]triazolo[1,5-a]pyridin-2-amine (21.9 mg, 71.4% yield) | 2-bromo-8-(1,2,2,2-tetrafluoroethoxy)-[1,2,4]triazolo[1,5-a]pyridine (22.1 mg, 70.5 μmol) and (8 endo))-3-(3-Methylisothiazol-5-yl)-3-azabicyclo[3.2.1]octan-8-amine (15 mg, 67.2 μmol) | 457.3 |

TABLE 3-continued

| Examples number | Systematic name | Starting materials | MW found (M + H)+ |
|---|---|---|---|
| 25 | 8-[2,2-difluorocyclopropyl]methoxy]-N-[(8-endo)-3-(3-methylisothiazol-5-yl)-3-azabicyclo[3.2.1]octan-8-yl)]-[1,2,4]triazolo[1,5-a]pyridin-2-amine (17.7 mg, 59% yield) | 2-bromo-8-((2,2-difluorocyclopropyl)methoxy)-[1,2,4]triazolo[1,5-a]pyridine (22.5 mg, 73.9 μmol) and (8 endo))-3-(3-Methylisothiazol-5-yl)-3-azabicyclo[3.2.1]octan-8-amine (15 mg, 67.2 μmol) | 447.3 |
| 26 | 8-[3,3-difluorocyclopentyl]methoxy]-N-[(8 endo)-3-(3-methyl-1,2-thiazol-5-yl)-3-azabicyclo[3.2.1]octan-8-yl]-[1,2,4]triazolo[1,5-a]pyridin-2-amine (20.3 mg, 63.7% yield) | 2-bromo-8-((3,3-difluorocyclopentyl)methoxy)-[1,2,4]triazolo[1,5-a]pyridine (23.4 mg, 70.5 μmol) and (8 endo))-3-(3-Methylisothiazol-5-yl)-3-azabicyclo[3.2.1]octan-8-amine (15 mg, 67.2 μmol) | 475.4 |
| 27 | N-[(8 endo)-3-(3-methyl-1,2-thiazol-5-yl)-3-azabicyclo[3.2.1]octan-8-yl]-8-(3,3,3-trifluoro-2,2-dimethylpropoxy)-[1,2,4]triazolo[1,5-a]pyridin-2-amine (21.3 mg, 66% yield) | 2-bromo-8-(3,3,3-trifluoro-2,2-dimethylpropoxy)-[1,2,4]triazolo[1,5-a]pyridine (23.8 mg, 70.5 μmol) and (8 endo))-3-(3-Methylisothiazol-5-yl)-3-azabicyclo[3.2.1]octan-8-amine (15 mg, 67.2 μmol) | 481.3 |

EXAMPLE 28

N-[(8 endo) (3-(3-methylisothiazol-5-yl)-3-azabicyclo[3.2.1]octan-8-yl)]-8-(2,2,2-trifluoroethoxy)-[1,2,4]triazolo[1,5-a]pyridin-2-amine

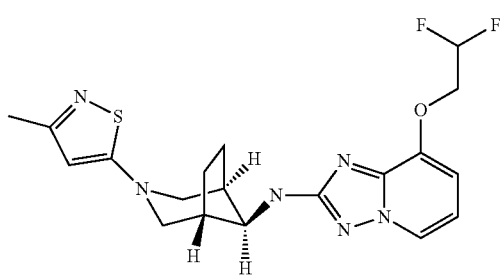 [SMILES: Cc1cc(N2C[C@H]3CC[C@@H](C2)[C@@H]3Nc2nc3c(OCC(F)F)cccn3n2)sn1]

Intermediate 3

2-bromo-8-(2,2-difluoroethoxy)-[1,2,4]triazolo[1,5-a]pyridine

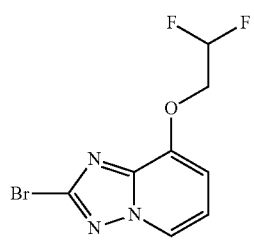 [SMILES: FC(F)COc1cccn2nc(Br)nc12]

The title compound (116.2 mg, 89.4% yield) was prepared in analogy to the procedure described for the synthesis of intermediate 3 (example 4) from the respective 2-bromo-[1,2,4]triazolo[1,5-a]pyridin-8-ol (example 4, step 5) and 2-Iodo-1,1-Difluoroethane (135 mg, 61.7 µl, 701 µmol) in DMF (2 mL) with K$_2$CO$_3$ (129 mg, 934 µmol) as base. MS ES+ (m/z): 425.3 [(M+H)$^+$]

Final Coupling 8-(2,2-difluoroethoxy)-N-[(8 endo)-3-(3-methyl-1,2-thiazol-5-yl)-3-azabicyclo[3.2.1]octan-8-yl]-[1,2,4]triazolo[1,5-a]pyridin-2-amine

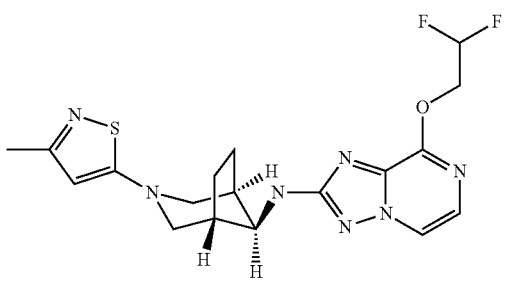 [SMILES: Cc1cc(N2C[C@H]3CC[C@@H](C2)[C@@H]3Nc2nc3c(OCC(F)F)nccn3n2)sn1]

The title compound, was prepared by Buchwald coupling from the corresponding Intermediate 3 2-bromo-8-(2,2-difluoroethoxy)-[1,2,4]triazolo[1,5-a]pyridine (22.4 mg, 80.6 µmol) and (8-endo)-3-(3-Methylisothiazol-5-yl)-3-azabicyclo[3.2.1]octan-8-amine (15 mg, 67.2 µmol) as described in example 1 with sodium tert-butoxide, tris(dibenzylideneacetone) dipalladium (0) chloroform adduct and xantphos in 1,4-Dioxane. The compound was obtained as an off-white solid (12.6 mg; 44.6% yield) MS ES+ (m/z): 421.2 [(M+H)$^+$]

EXAMPLE 29

N-[(8 endo)-3-(3-methylisothiazol-5-yl)-3-azabicyclo[3.2.1]octan-8-yl)]-8-(3,3,3-trifluoropropoxy)-[1,2,4]triazolo[1,5-a]pyrazin-2-amine

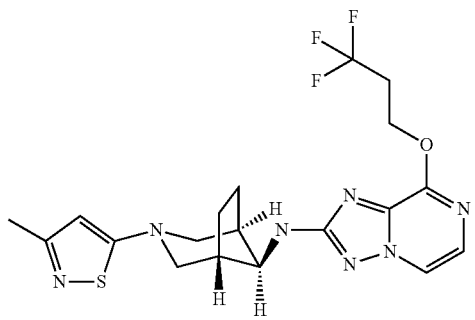 [SMILES: Cc1cc(N2C[C@H]3CC[C@@H](C2)[C@@H]3Nc2nc3c(OCCC(F)(F)F)nccn3n2)sn1]

Intermediate 3

2-Bromo-8-(3,3,3-trifluoropropoxy)-[1,2,4]triazolo[1,5-a]pyrazine

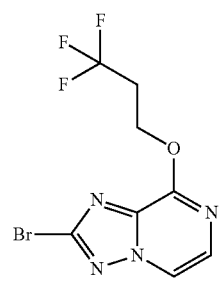 [SMILES: FC(F)(F)CCOc1nccn2nc(Br)nc12]

Step 1

Ethyl N-[(3-chloroprazin-2-yl)carbamothioyl]carbamate

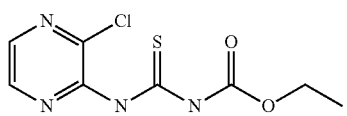 [SMILES: CCOC(=O)NC(=S)Nc1nccnc1Cl]

To a solution of 3-chloropyrazin-2-amine (7 g, 54 mmol) in dioxane (600 ml) was added dropwise O-ethyl carbonisothiocyanatidate (8.15 g, 7.33 ml, 62.1 mmol). After 48 h at room temperature the solvent was evaporated and the residue was purified by flash chromatography on silica gel using a gradient 0% to 5% MeOH in CH$_2$Cl$_2$.

The title compound was obtained as yellow solid (7.89 g, 56%). MS ES+ (m/z): 261.1 [(M+H)$^+$]

Step 2

8-Chloro-[1,2,4]triazolo[1,5-a]pyrazin-2-ylamine

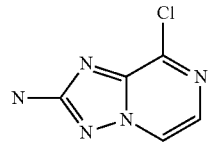 [SMILES: Nc1nc2c(Cl)nccn2n1]

To a mixture of hydroxylamine hydrochloride (5.16 g, 74.2 mmol), diisopropylethylamine (5.75 g, 7.78 ml, 44.5 mmol), MeOH (20 ml) and EtOH (20 ml) Ethyl N-[(3-chloropyrazin-2-yl)carbamothioyl]carbamate (3.869 g, 14.8 mmol) was added.

The reaction mixture was heated to 60° C. for 3 hours. The solvent was evaporated and the residue was suspended in CH$_2$Cl$_2$ (100 ml) and water (20 ml). The suspension was stirred for 10 minutes and the solid was filtered off. The aqueous phase was extracted four times with CH$_2$Cl$_2$, the combined organic layers were dried over Na$_2$SO$_4$ and the solvent was removed in vacuo. The residue was combined with the filtered solid (4.4 g) and used in the next step without purification. MS ES+ (m/z): 170.0/172.1 [(M+H)$^+$]

Step 3

2-Bromo-8-chloro-[1,2,4]triazolo[1,5-a]pyrazine

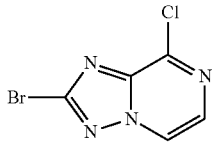 [SMILES: Clc1nccn2nc(Br)nc12]

A solution of copper(II) bromide (5.33 g, 23.9 mmol) and tert-butyl nitrite (2.74 g, 3.17 ml, 23.9 mmol) in acetonitril (270 ml) was heated to 60° C. and 8-chloro-[1,2,4]triazolo[1,5-a]pyrazin-2-amine (2.7 g, 15.9 mmol) was added. The reaction mixture was heated to 75° C. for 35 minutes and then cooled to room temperature. Saturated NaHCO$_3$ solution was added. The aqueous phase was separated and extracted with EtOAc (100 ml). The combined organic layers were dried over Na$_2$SO$_4$ and the solvent was removed in vacuo. The crude material was purified by flash chromatography on silica gel using a gradient from 0% to 50% EtOAc in heptane.

The title compound was obtained as off-white solid (1.08 g, 29%).
MS ES+ (m/z): 232.9/234.9/236.9 [(M+H)$^+$]

Step 4

2-Bromo-8-(3,3,3-trifluoropropoxy)-[1,2,4]triazolo[1,5-a]pyrazine

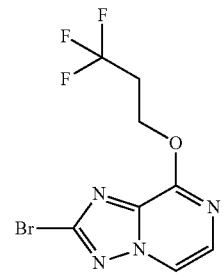 [SMILES: FC(F)(F)CCOc1nccn2nc(Br)nc12]

To a solution of 3,3,3-trifluoropropan-1-ol (36.3 mg, 28 µl, 308 µmol) in DMF (200 µl) at room temperature was added NaH 55% (16.8 mg, 386 µmol). After 10 minutes a solution of 2-bromo-8-chloro-[1,2,4]triazolo[1,5-a]pyrazine (60 mg, 257 µmol) in DMF (500 µl) was added at 10° C. After warming to room temperature the reaction mixture was stirred for 2 hours. Water (200 ul) was added dropwise at 10° C. and the solvent was evaporated. The residue was purified by flash chromatography on amine silica gel using a gradient from 0% to 16% EtOAc in heptane.

The title compound was obtained as light yellow solid (33 mg, 42%).
MS ES+ (m/z): 311.0/313.0 [(M+H)$^+$]

Final Coupling

N-((8 endo)-3-(3-methylisothiazol-5-yl)-3-azabicyclo[3.2.1]octan-8-yl)-8-(3,3,3-trifluoropropoxy)-[1,2,4]triazolo[1,5-a]pyrazin-2-amine

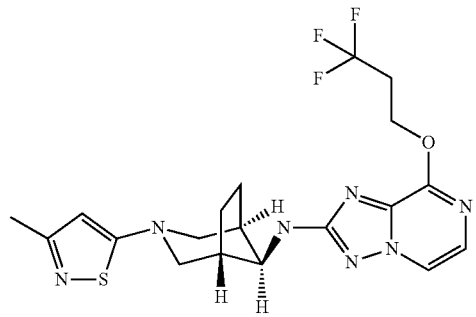 [SMILES: Cc1cc(N2C[C@H]3CC[C@@H](C2)[C@@H]3Nc2nc3c(OCCC(F)(F)F)nccn3n2)sn1]

The title compound, was prepared by Buchwald coupling in analogy to example 1, from (8-endo)-3-(3-methylisothiazol-5-yl)-3-azabicyclo[3.2.1]octan-8-amine (23 mg, 103 µmol) and 2-bromo-8-(3,3,3-trifluoropropoxy)-[1,2,4]triazolo[1,5-a]pyrazine (32 mg, 103 µmol) in Dioxane (1.5 ml) in the presence of sodium tert-butoxide (20.3 mg, 211 µmol), xantphos (9.53 mg, 16.5 µmol) and tris(dibenzylideneacetone) dipalladium (0) chloroform adduct (8.53 mg, 8.24 µmol) by heating at 145° C. in a microwave, during 20 min. The compound was obtained as a light yellow solid (11 mg, 23% yield). MS ES+ (m/z): 454.2 [(M+H)$^+$].

EXAMPLE 30

8-(2,2-difluoroethoxy)-N-[(8-endo)-3-(3-methylisothiazol-5-yl)-3-azabicyclo[3.2.1]octan-8-yl]-[1,2,4]triazolo[1,5-a]pyrazin-2-amine

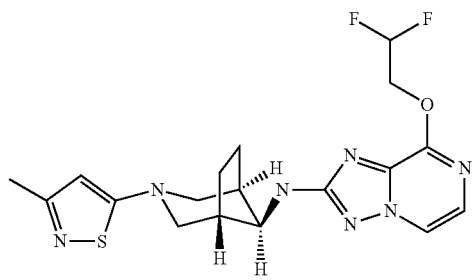 [SMILES: Cc1cc(N2C[C@H]3CC[C@@H](C2)[C@@H]3Nc2nc3c(OCC(F)F)nccn3n2)sn1]

Intermediate 3

2-Bromo-8-(2,2-difluoroethoxy)-[1,2,4]triazolo[1,5-a]pyrazine

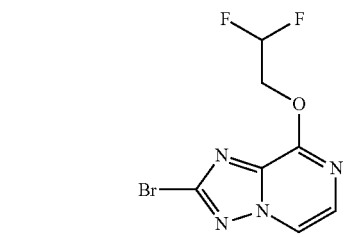 [SMILES: FC(F)COc1nccn2nc(Br)nc12]

Step 1

3-(2,2-Difluoroethoxy)pyrazin-2-amine

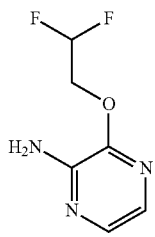

NaH 55% (774 mg, 18.5 mmol) was added to 2,2-difluoroethanol (1.52 g, 1.17 ml, 18.5 mmol) in DMF (5 ml). After stirring for 10 minutes, a solution of 3-chloropyrazin-2-amine (800 mg, 6.18 mmol) in DMF (5 ml) was added dropwise and the reaction mixture was heated at 75° C. for 4 hours. The reaction mixture was partitioned between water and EtOAc, the organic layer was separated, the aqueous layer was extracted once with EtOAc, the combined organic layers was dried over magnesium sulfate, filtered and evaporated over SiO$_2$. The crude material was purified by flash chromatography (silica gel, 50 g, 10% to 4 0% EtOAc in heptane) to give the desired product as a light yellow solid (0.672 g, 62% yield). MS ES+ (m/z): 391.4 [(M+H)$^+$].

Step 2

Ethyl N-[[3-(2,2-difluoroethoxy)pyrazin-2-yl]carbamothioyl]carbamate

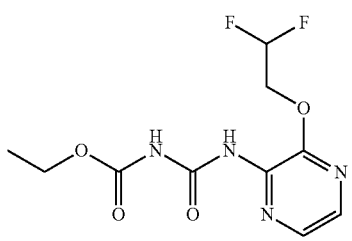 [SMILES: CCOC(=O)NC(=O)Nc1nccnc1OCC(F)F]

The title compound was prepared in analogy to example 1, intermediate 3, step 3, from 3-(2,2-difluoroethoxy)pyrazin-2-amine (0.67 g, 3.83 mmol) and ethoxycarbonyl isithiocyanate (577 mg, 519 µl, 4.4 mmol) as light yellow solid (0.99 g, 84.5% yield). MS ES+ (m/z): 325.2 [(M+H)$^+$].

Step 3

8-(2,2-Difluoroethoxy)-[1,2,4]triazolo[1,5-a]pyrazin-2-amine

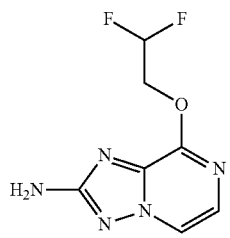 [SMILES: Nc1nc2c(OCC(F)F)nccn2n1]

The title compound was prepared in analogy to example 1, intermediate 3, step 4, from ethyl N-[[3-(2,2-difluoroethoxy)pyrazin-2-yl]carbamothioyl]carbamate (0.99 g, 3.23 mmol) and hydroxylamine hydrochloride (1.12 g, 16.2 mmol as light yellow solid (0.61 g, 87% yield).
MS ES+ (m/z): 217.1 [(M+H)$^+$].

Step 4

2-Bromo-8-(2,2-difluoroethoxy)-[1,2,4]triazolo[1,5-a]pyrazine

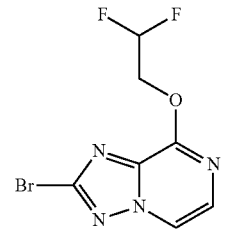 [SMILES: FC(F)COc1nccn2nc(Br)nc12]

The title compound was prepared in analogy to example 1, intermediate 3, step 5, from 8-(2,2-difluoroethoxy)-[1,2,4]triazolo[1,5-a]pyrazin-2-amine (0.61 g, 2.84 mmol), tert-butyl nitrite and copper (II) bromide as light yellow solid (0.757 g, 95.7% yield). MS ES+ (m/z): 279 [(M+H)$^+$]

Final Coupling Step 8-(2,2-difluoroethoxy)-N-[(8-endo)-3-(3-methyliso-thiazol-5-yl)-3-azabicyclo[3.2.1]octan-8-yl]-[1,2,4]triazolo[1,5-a]pyrazin-2-amine

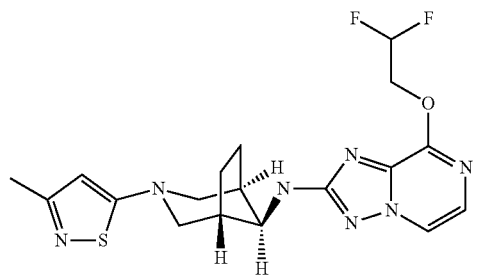 [SMILES: Cc1cc(N2C[C@H]3CC[C@@H](C2)[C@@H]3Nc2nc3c(OCC(F)F)nccn3n2)sn1]

The title compound, was prepared by Buchwald coupling in analogy to example 1, from (8-endo)-3-(3-methylisothiazol-5-yl)-3-azabicyclo[3.2.1]octan-8-amine (30 mg, 134 µmol) and 2-bromo-8-(2,2-difluoroethoxy)-[1,2,4]triazolo[1,5-a]pyrazine (45 mg, 161 umol) in the presence of sodium tert-butoxide, xantphos and tris(dibenzylideneacetone)dipalladium (0) chloroform adduct. The compound was obtained as a light yellow solid (24.4 mg, 43% yield). MS ES+(m/z): 422.2 [(M+H)$^+$]

According to the procedure described for the synthesis of intermediate 3 further derivatives have been synthesized from the respective 2-Bromo-8-chloro-[1,2,4]triazolo[1,5-a]pyrazine and the corresponding alcohol. They comprise intermediates on table 4.

TABLE 4

| Intermediate N-IIII number | | Systematic name Yield | Starting materials | MW found (M + H)$^+$ |
|---|---|---|---|---|
| 31 | ![structure] | 2-Bromo-8-(2,2,3,3,3-pentafluoropropoxy)-[1,2,4]triazolo[1,5-a]pyrazine (76 mg, 63.9 mg) | 2-bromo-8-chloro-[1,2,4]triazolo[1,5-a]pyrazine (80 mg, 343 µmol) and 2,2,3,3,3-pentafluoropropan-1-ol (63 mg, 41.8 µl, 411 µmol) | 279.0/ 281.0 |
| 32 | ![structure] | 2-Bromo-8-((1,1,1,3,3,3-hexafluoropropan-2-yl)oxy)-[1,2,4]triazolo[1,5-a]pyrazine (73.2 mg, 78% yield) | 2-bromo-8-chloro-[1,2,4]triazolo[1,5-a]pyrazine (60 mg, 257 µmol) and and 1,1,1,3,3,3-hexafluoropropan-2-ol (51.8 mg, 32.5 µl, 308 µmol) | 347.0/ 349.0 |
| 33 | ![structure] | 2-Bromo-8-((1-(trifluoromethyl)cyclopropyl)methoxy)-[1,2,4]triazolo[1,5-a]pyrazine (54 mg, 48.6% yield) | 2-bromo-8-chloro-[1,2,4]triazolo[1,5-a]pyrazine (77 mg, 330 µmol) and (1-(trifluoromethyl)cyclopropyl)methanol (55.5 mg, 396 µmol) | 365.0/ 367.0 |

TABLE 4-continued

| Intermediate N-IIII number | Systematic name | Yield | Starting materials | MW found (M + H)+ |
|---|---|---|---|---|
| 34 | 2-bromo-8-((1,1,1-trifluoropropan-2-yl)oxy)-[1,2,4]triazolo[1,5-a]pyrazine | (55.2 mg, 52% yield) | 2-bromo-8-chloro-[1,2,4]triazolo[1,5-a]pyrazine (80 mg, 343 µmol) and 1,1,1-trifluoropropan-2-ol (47.9 mg, 38 µl, 411 µmol) | 337.0/ 339.0 |

EXAMPLE 31

N-[(8-endo)-3-(3-methylisothiazol-5-yl)-3-azabicyclo[3.2.1]octan-8-yl]-8-(2,2,3,3,3-pentafluoropropoxy)-[1,2,4]triazolo[1,5-a]pyrazin-2-amine

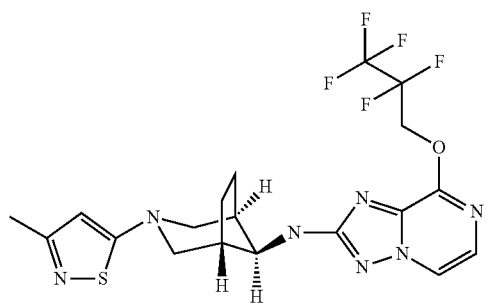 [SMILES: Cc1cc(N2C[C@H]3CC[C@@H](C2)[C@@H]3Nc2nc3c(OCC(F)(F)C(F)(F)F)nccn3n2)sn1]

The title compound, was prepared by Buchwald coupling in analogy to example 1, from (8-endo)-3-(3-methylisothiazol-5-yl)-3-azabicyclo[3.2.1]octan-8-amine (30 mg, 134 µmol) and 2-bromo-8-(2,2,3,3,3-pentafluoropropoxy)-[1,2,4]triazolo[1,5-a]pyrazine (55.9 mg, 161 µmol) (intermediate on table 4) in the presence of sodium tert-butoxide, xantphos and tris(dibenzylideneacetone) dipalladium (0) chloroform adduct. The compound was obtained as a light yellow solid (38 mg, 57.8% yield). MS ES+ (m/z): 490.2 [(M+H)+]

EXAMPLE 32

8-((1,1,1,3,3,3-hexafluoropropan-2-yl)oxy)-N-[(8 endo)-3-(3-methylisothiazol-5-yl)-3-azabicyclo[3.2.1]octan-8-yl)-[1,2,4]triazolo[1,5-a]pyrazin-2-amine

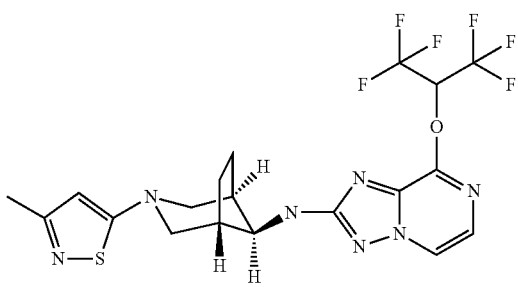 [SMILES: Cc1cc(N2C[C@H]3CC[C@@H](C2)[C@@H]3Nc2nc3c(OC(C(F)(F)F)C(F)(F)F)nccn3n2)sn1]

The title compound, was prepared by Buchwald coupling in analogy to example 1, from (8-endo)-3-(3-methylisothiazol-5-yl)-3-azabicyclo[3.2.1]octan-8-amine (27 mg, 121 µmol) and 2-bromo-8-((1,1,1,3,3,3-hexafluoropropan-2-yl)oxy)-[1,2,4]triazolo[1,5-a]pyrazine (44.1 mg, 121 mol) (intermediate on table 4) in the presence of sodium tert-butoxide, xantphos and tris(dibenzylideneacetone) dipalladium (0) chloroform adduct. The compound was obtained as a light yellow solid (10 mg, 16.3% yield). MS ES+ (m/z): 508.2 [(M+H)+]

EXAMPLE 33

N-[(8 endo)-3-(3-methylisothiazol-5-yl)-3-azabicyclo[3.2.1]octan-8-yl]-8-((1-(trifluoromethyl)cyclopropyl)methoxy)-[1,2,4]triazolo[1,5-a]pyrazin-2-amine

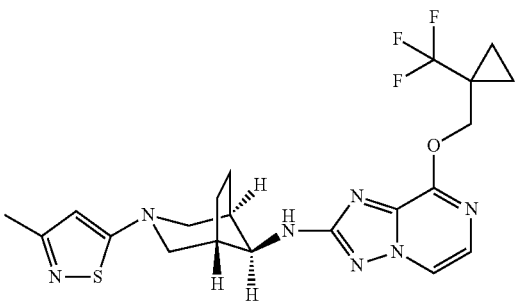 [SMILES: Cc1cc(N2C[C@H]3CC[C@@H](C2)[C@@H]3Nc2nc3c(OCC4(C(F)(F)F)CC4)nccn3n2)sn1]

The title compound, was prepared by Buchwald coupling in analogy to example 1, from (8-endo)-3-(3-methylisothiazol-5-yl)-3-azabicyclo[3.2.1]octan-8-amine (30 mg, 134 µmol) and 2-bromo-8-((1-(trifluoromethyl)cyclopropyl)methoxy)-[1,2,4]triazolo[1,5-a]pyrazine (45.3 mg, 134 µmol), (table 4) in the presence of sodium tert-butoxide, xantphos and tris(dibenzylideneacetone) dipalladium (0) chloroform adduct. The compound was obtained as a white foam (31 mg, 48.3% yield). MS ES+ (m/z): 480.3 (100%) [(M+H)+]

EXAMPLE 34

N-[(8 endo)-3-(3-methylisothiazol-5-yl)-3-azabicyclo[3.2.1]octan-8-yl]-8-((1,1,1-trifluoropropan-2-yl)oxy)-[1,2,4]triazolo[1,5-a]pyrazin-2-amine

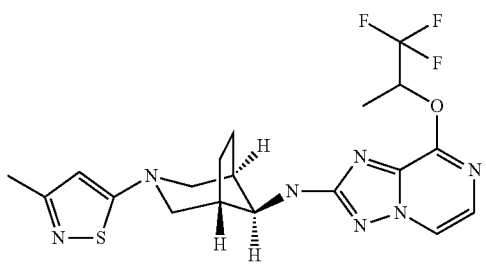 [SMILES: Cc1cc(N2C[C@H]3CC[C@@H](C2)[C@@H]3Nc2nc3c(OC(C)C(F)(F)F)nccn3n2)sn1]

The title compound, was prepared by Buchwald coupling in analogy to example 1, from (8-endo)-3-(3-methylisothiazol-5-yl)-3-azabicyclo[3.2.1]octan-8-amine (30 mg, 134 μmol) and 2-bromo-8-((1,1,1-trifluoropropan-2-yl)oxy)-[1,2,4]triazolo[1,5-a]pyrazine (50.1 mg, 161 μmol) in the presence of sodium tert-butoxide, xantphos and tris(dibenzylideneacetone) dipalladium (0) chloroform adduct. The compound was obtained as a white foam (34 mg, 55.8% yield).

MS ES+ (m/z): 454.2 [(M+H)$^+$]

EXAMPLE 35

N-[(8 endo)-3-(3-methylisothiazol-5-yl)-3-azabicyclo[3.2.1]octan-8-yl]-8-((2R or 2S)-1,1,1-trifluoropropan-2-yl)oxy)-[1,2,4]triazolo[1,5-a]pyrazin-2-amine

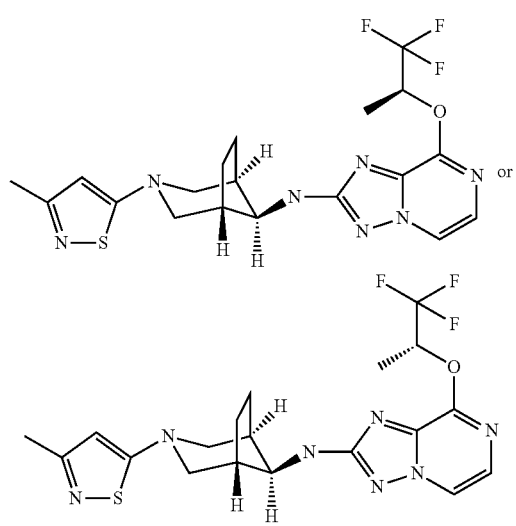

The title compound was obtained from separation using a chiral column (chiralpak AD) of N-[(8 endo)-3-(3-methylisothiazol-5-yl)-3-azabicyclo[3.2.1]octan-8-yl]-8-((1,1,1-trifluoropropan-2-yl)oxy)-[1,2,4]triazolo[1,5-a]pyrazin-2-amine (Example 34).

MS ES+ (m/z): 454.2 [(M+H)$^+$]

EXAMPLE 36

N-[(8 endo)-3-(3-methylisothiazol-5-yl)-3-azabicyclo[3.2.1]octan-8-yl]-8-((2S or 2R)-1,1,1-trifluoropropan-2-yl)oxy)-[1,2,4]triazolo[1,5-a]pyrazin-2-amine

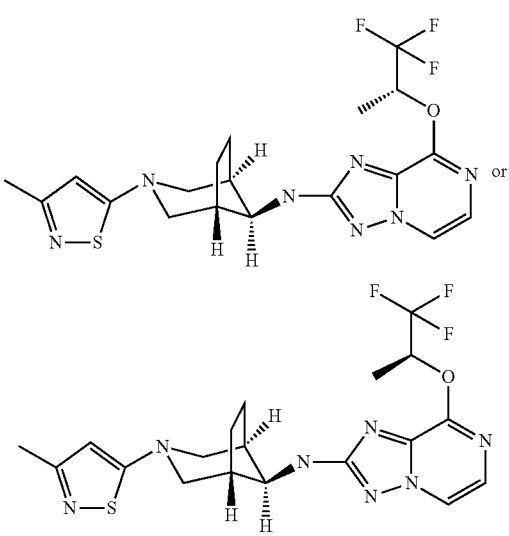

The title compound was obtained from separation using a chiral column (chiralpak AD) of N-[(8 endo)-3-(3-methylisothiazol-5-yl)-3-azabicyclo[3.2.1]octan-8-yl]-8-((1,1,1-trifluoropropan-2-yl)oxy)-[1,2,4]triazolo[1,5-a]pyrazin-2-amine (Example 39).

MS ES+ (m/z): 454.2 (100%) [(M+H)$^+$]

EXAMPLE 37

N-[(8 endo)-3-(2-methyl-1,3-thiazol-5-yl)-3-azabicyclo[3.2.1]octan-8-yl]-8-(4,4,4-trifluorobutoxy)-[1,2,4]triazolo[1,5-a]pyridin-2-amine

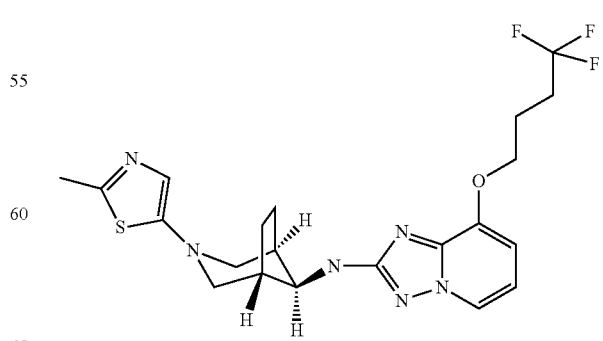

Intermediate II 8 endo-3-(2-methyl-1,3-thiazol-5-yl)-3-azabicyclo[3.2.1]octan-8-amine

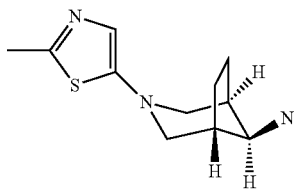

Step 1

Tert-butyl N-[8-endo-3-(2-acetamidoacetyl)-3-azabicyclo[3.2.1]octan-8-yl]carbamate

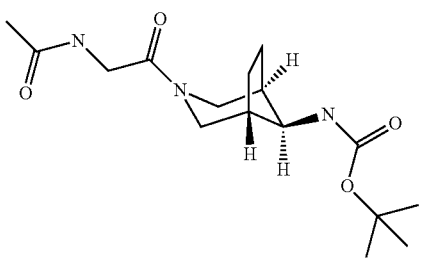 [SMILES: CC(=O)NCC(=O)N1C[C@H]2CC[C@@H](C1)[C@@H]2NC(=O)OC(C)(C)C]

The title compound was prepared by adding to a solution Tert-butyl N [(8 endo)-3-azabicyclo[3.2.1]octan-8-yl]carbamate (600 mg, 2.65 mmol in dichloromethane (15 ml), 2-acetamidoacetic acid (326 mg, 2.78 mmol) followed by dichloromethane (574 mg, 2.78 mmol) and stirring the reaction mixture at room temp overnight. The reaction mixture was poured into a saturated solution of NaHCO$_3$ and the aqueous phase was extracted with dichloromethane. The organic layers were dried over MgSO$_4$ and concentrated in vacuum. The crude material was purified by flash chromatography to afford the title compound (861 mg, 99.8% yield) MS ES+ (m/z): 326.2 [(M+H)$^+$]

Step 2

Tert-butyl N-[(8 endo)-3-(2-methyl-1,3-thiazol-5-yl)-3-azabicyclo[3.2.1]octan-8-yl]carbamate

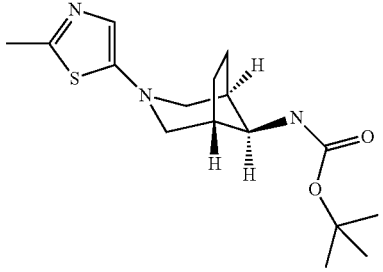 [SMILES: Cc1ncc(N2C[C@H]3CC[C@@H](C2)[C@@H]3NC(=O)OC(C)(C)C)s1]

The reaction was performed similarly as published in Bioorganic and Medicinal Chemistry, 2008, vol. 16, #4 p. 1613-1631 with Lawesson's reagent in Pyridine at 100° C. over night: To a light yellow solution of Tert-butyl N-[(8 endo)-3-(2-methyl-1,3-thiazol-5-yl)-3-azabicyclo[3.2.1]octan-8-yl]carbamate (840 mg, 2.58 mmol) in Pyridine (15 ml) was added Lawesson's reagent (1.04 g, 2.58 mmol). The reaction mixture was heated to 100° C. and stirred overnight. The crude reaction mixture was concentrated in vacuum. The crude material was purified by flash chromatography (0% to 100% EtOAc in heptane) to afford the title compound (459 mg, 55.1% yield) as a light yellow solid. MS ES+ (m/z): 324.1 [(M+H)$^+$]

Step 3

8 endo-3-(2-methyl-1,3-thiazol-5-yl)-3-azabicyclo[3.2.1]octan-8-amine

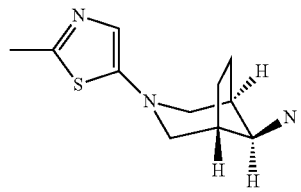

To a light yellow solution of Tert-butyl N-[(8 endo)-3-(2-methyl-1,3-thiazol-5-yl)-3-azabicyclo[3.2.1]octan-8-yl]carbamate (285 mg, 881 µmol in Dichloromethane (6 ml) was added Trifluoroacetic acid (1.00 g, 679 µl, 8.81 mmol) The reaction mixture at room temperature over night. Saturated aqueous NaHCO$_3$ was added and the aqueous phase was extracted with Dichloromethane. The organic layers were dried over MgSO$_4$ and concentrated in vacuo to obtain the title compound as a white solid (194 mg, 98.6% yield) MS ES+ (m/z): 224.1 [(M+H)$^+$]

Final Coupling

N-[(8 endo)-3-(2-methyl-1,3-thiazol-5-yl)-3-azabicyclo[3.2.1]octan-8-yl]-8-(4,4,4-trifluorobutoxy)-[1,2,4]triazolo[1,5-a]pyridin-2-amine

The title compound, was prepared by Buchwald coupling in analogy to example 1, from 2-bromo-8-(4,4,4-trifluorobutoxy)-[1,2,4]triazolo[1,5-a]pyridine (intermediate 3, example 1) (23.9 mg, 73.9 µmol) and (8 endo)-3-(2-methyl-1,3-thiazol-5-yl)-3-azabicyclo[3.2.1]octan-8-amine (15 mg, 67.2 µmol) with Pd₂(dba)₃.CHCl₃ in the presence of sodium phenoxide and xantphos as a light yellow solid (15.4 mg, 33.0 µmol, 49.1% yield).

MS ES+ (m/z): 467.3 [(M+H)⁺]

EXAMPLE 38

N-[(8 endo)-3-(2-methyl-1,3-thiazol-5-yl)-3-azabicyclo[3.2.1]octan-8-yl]-8-(3,3,3-trifluoropropoxy)-[1,2,4]triazolo[1,5-a]pyridin-2-amine

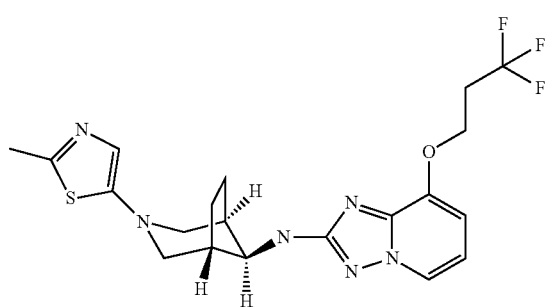 [SMILES: Cc1ncc(N2C[C@H]3CC[C@@H](C2)[C@@H]3Nc2nc3c(OCCC(F)(F)F)cccn3n2)s1]

The title compound, was prepared by Buchwald coupling in analogy to example 1, from 2-bromo-8-(4,4,4-trifluoropropoxy)-[1,2,4]triazolo[1,5-a]pyridine (intermediate 3, example 2) (22.9 mg, 73.9 µmol), and (8 endo)-3-(2-methyl-1,3-thiazol-5-yl)-3-azabicyclo[3.2.1]octan-8-amine (15 mg, 67.2 µmol) with Pd₂(dba)₃.CHCl₃ (5.56 mg, 5.37 µmol) in the presence of sodium phenoxide (12.5 mg, 107 µmol) and xantphos (6.22 mg, 10.7 µmol) as a light yellow solid (9.9 mg, 32.6% yield). MS ES+ (m/z): 453.2 [(M+H)⁺]

EXAMPLE 39

N-[8 endo-3-(2-methyl-1,3-thiazol-5-yl)-3-azabicyclo[3.2.1]octan-8-yl]-8-(2,2,2-trifluoroethoxy)-[1,2,4]triazolo[1,5-a]pyridin-2-amine

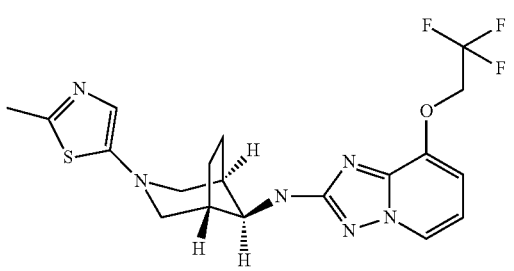 [SMILES: Cc1ncc(N2C[C@H]3CC[C@@H](C2)[C@@H]3Nc2nc3c(OCC(F)(F)F)cccn3n2)s1]

The title compound, was prepared by Buchwald coupling in analogy to example 1, from 2-Bromo-8-(2,2,2-trifluoroethoxy)-[1,2,4]triazolo[1,5-a]pyridine (intermediate III, example 4) (25.5 mg, 86.2 µmol), and 8 endo-3-(2-methyl-1,3-thiazol-5-yl)-3-azabicyclo[3.2.1]octan-8-amine (17.5 mg, 78.4 µmol) with Pd₂(dba)₃. CHCl₃ in the presence of sodium phenoxide and xantphos as a light yellow solid (24.2 mg, 70.4% yield). MS ES+ (m/z): 439.2 [(M+H)⁺]

EXAMPLE 40

N-[(8 endo-3-(2-methyl-1,3-thiazol-5-yl)-3-azabicyclo[3.2.1]octan-8-yl]-8-[1,1,1-trifluoropropan-2-yl]oxy-[1,2,4]triazolo[1,5-a]pyridin-2-amine

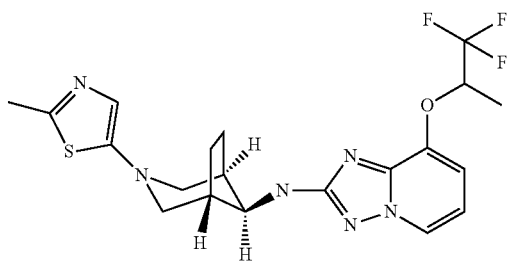 [SMILES: Cc1ncc(N2C[C@H]3CC[C@@H](C2)[C@@H]3Nc2nc3c(OC(C)C(F)(F)F)cccn3n2)s1]

The title compound, was prepared by Buchwald coupling in analogy to example 1, from 2-bromo-8-(1,1,1-trifluoropropan-2-yloxy)-[1,2,4]triazolo[1,5-a]pyridine (22.9 mg, 73.9 µmol) (intermediate 3, example 4) and 8 endo-3-(2-methyl-1,3-thiazol-5-yl)-3-azabicyclo[3.2.1]octan-8-amine (15 mg, 67.2 µmol) with Pd₂(dba)₃.CHCl₃ in the presence of sodium phenoxide and xantphos as a light yellow solid (19.6 mg, 64.5% yield). MS ES+ (m/z): 453.2 [(M+H)⁺]

EXAMPLE 41

N-[(8 endo)-3-(5-methyl-1,3,4-oxadiazol-2-yl)-3-azabicyclo[3.2.1]octan-8-yl]-8-(4,4,4-trifluorobutoxy)-[1,2,4]triazolo[1,5-a]pyridin-2-amine

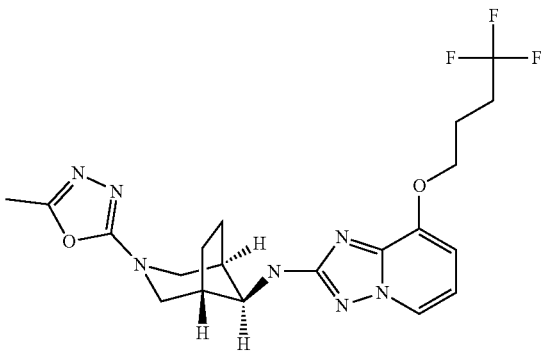 [SMILES: Cc1nnc(N2C[C@H]3CC[C@@H](C2)[C@@H]3Nc2nc3c(OCCCC(F)(F)F)cccn3n2)o1]

Intermediate II (8 endo)-3-(5-methyl-1,3,4-oxadiazol-2-yl)-3-azabicyclo[3.2.1]octan-8-amine

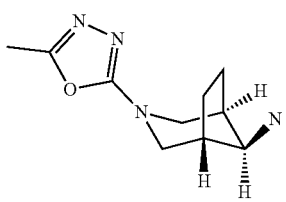

Step 1

Tert-butyl N-[(8 endo)-3-(5-methyl-1,3,4-oxadiazol-2-yl)-3-azabicyclo[3.2.1]octan-8-yl]carbamate

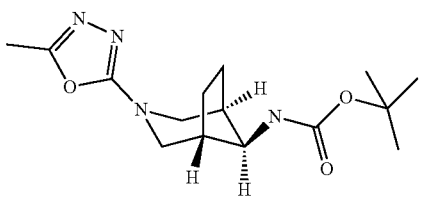 [SMILES: Cc1nnc(N2C[C@H]3CC[C@@H](C2)[C@@H]3NC(=O)OC(C)(C)C)o1]

To a solution of tert-butyl (8 endo)-3-azabicyclo[3.2.1]octan-8-ylcarbamate (200 mg, 884 μmol) in ethanol (10 ml), was added triethylamine (358 mg, 493 μl, 3.53 mmol) followed by 2-bromo-5-methyl-1,3,4-oxadiazole (288 mg, 1.77 mmol). The reaction mixture was stirred at 130° C. over night. The crude reaction mixture was concentrated in vacuum. Water was added and the aqueous phase was extracted with dichloromethane. The organic layers were dried over MgSO$_4$ and concentrated in vacuum. The crude material was purified by flash chromatography (0% to 5% MeOH in DCM) to afford the title compound as a white solid (230 mg, 84.4% yield).

MS ES+ (m/z): 309.2 [(M+H)$^+$]

Step 2

(8 endo)-3-(5-methyl-1,3,4-oxadiazol-2-yl)-3-azabicyclo[3.2.1]octan-8-amine

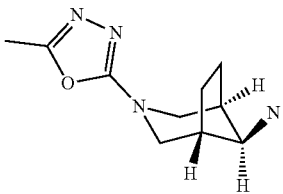

To a light yellow solution of Tert-butyl (8 endo)-3-(5-methyl-1,3,4-oxadiazol-2-yl)-3-azabicyclo[3.2.1]octan-8-ylcarbamate (230 mg, 746 μmol) in dichloromethane (6 ml) was added trifluoroacetic acid (850 mg, 575 μl, 7.46 mmol). The reaction mixture was stirred at room temp over night. Next morning TFA (85.0 mg, 57.5 μl, 746 μmol) was added and after 3 hrs the reaction was finished by MS/TLC. The reaction mixture was concentrated in vacuo. The crude material was purified by Ion-exchange column (Si-SCX-2, 10 g, washed with MeOH and liberated with MeOH (NH$_3$ 7M)) to afford the title compound as a light yellow solid (124.5 mg, 80.2% yield). MS ES+ (m/z): 209.1 [(M+H)$^+$]

Final Coupling

N-[(8 endo)-3-(5-methyl-1,3,4-oxadiazol-2-yl)-3-azabicyclo[3.2.1]octan-8-yl]-8-(4,4,4-trifluorobutoxy)-[1,2,4]triazolo[1,5-a]pyridin-2-amine

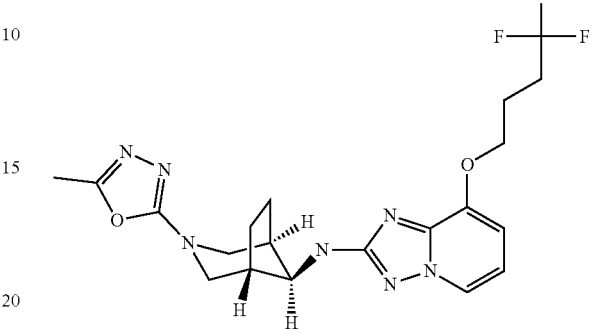

The title compound, was prepared by Buchwald coupling in analogy to example 1, from 2-bromo-8-(4,4,4-trifluorobutoxy)-[1,2,4]triazolo[1,5-a]pyridine (20 mg, 61.7 μmol) (intermediate 3, example 1) and intermediate 2 (8 endo)-3-(5-methyl-1,3,4-oxadiazol-2-yl)-3-azabicyclo[3.2.1]octan-8-amine (12.9 mg, 61.7 μmol) with Pd$_2$(dba)$_3$.CHCl$_3$ (5.11 mg, 4.94 mol) in the presence of sodium phenoxide and xantphos (5.71 mg, 9.87 μmol) as an off-white solid (8.5 mg, 30.5% yield) MS ES+ (m/z): 452.2 (100%) [(M+H)$^+$]

EXAMPLE 42

N-[(8 endo)-3-(3-methyl-1,2-oxazol-5-yl)-3-azabicyclo[3.2.1]octan-8-yl]-8-[1,1,1-trifluoropropan-2-yl]oxy-[1,2,4]triazolo[1,5-a]pyridin-2-amine

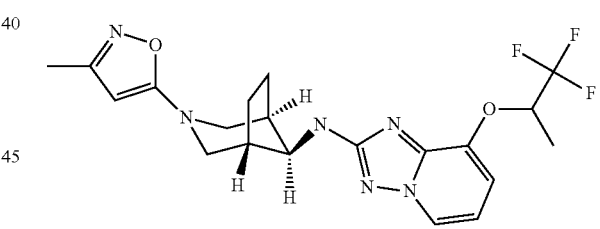

Step 1

Tert-butyl-(8 endo)-[8-[1,1,1-trifluoropropan-2-yl]oxy-[1,2,4]triazolo[1,5-a]pyridin-2-yl]amino]-3-azabicyclo[3.2.1]octane-3-carboxylate

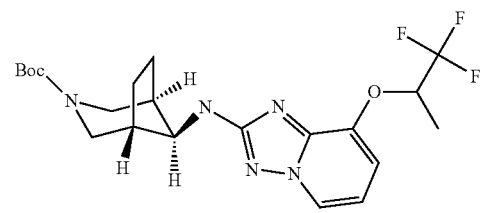 [SMILES: CC(Oc1cccn2nc(N[C@@H]3[C@@H]4CC[C@H]3CN(C(=O)OC(C)(C)C)C4)nc12)C(F)(F)F]

The title compound was prepared by Buchwald coupling in analogy to example 1, from 2-bromo-8-((1,1,1-trifluoropropan-2-yl)oxy)-[1,2,4]triazolo[1,5-a]pyridine (575 mg, 1.86 mmol) (intermediate 3 from example 4), tert-butyl (8 endo)-amino-3-azabicyclo[3.2.1]octane-3-carboxylate (CAS Registry Number: 1330763-51-3) (400 mg, 1.77 mmol) and sodium tert-butoxide (510 mg, 5.3 mmol) with Pd$_2$(dba)$_3$.CHCl$_3$ (146 mg, 141 μmol) in the presence of xantphos (164 mg, 283 μmol) in 1,4-Dioxane (12 ml) at 145° C. during 30 min in a microwave. The compound was obtained as a light brown solid (541 mg, 67.2% yield).)

MS ES+ (m/z): 456.4 [(M+H)$^+$]

Step 2

N-[(8 endo)-3-azabicyclo[3.2.1]octan-8-yl]-8-((1,1,1-trifluoropropan-2-yl)oxy]-[1,2,4]triazolo[1,5-a]pyridin-2-amine

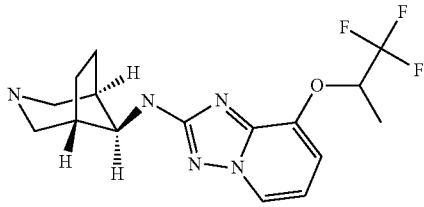 [SMILES: CC(Oc1cccn2nc(N[C@@H]3[C@@H]4CC[C@H]3CNC4)nc12)C(F)(F)F]

To a light yellow solution of Tert-butyl-(8 endo)-((8-((1,1,1-trifluoropropan-2-yl)oxy)-[1,2,4]triazolo[1,5-a]pyridin-2-yl)amino)-3-azabicyclo[3.2.1]octane-3-carboxylate (520 mg, 1.14 mmol) in dichloromethane (6 ml) was added TFA (1.3 g, 880 μl, 11.4 mmol). The reaction mixture was stirred over night at room temp and the reaction was quenched by adding sat. Na$_2$CO$_3$. The aqueous layer was extracted with dichloromethane. The organic layers were dried over MgSO$_4$ and concentrated in vacuum to obtain the title compound (390 mg, 96.1% yield) as crude. MS ES+ (m/z): 356.3 [(M+H)$^+$]

Final Step 3

N-[(8 endo)-3-(3-methyl-1,2-oxazol-5-yl)-3-azabicyclo[3.2.1]octan-8-yl]-8-[(1,1,1-trifluoropropan-2-yl)oxy-[1,2,4]triazolo[1,5-a]pyridin-2-amine

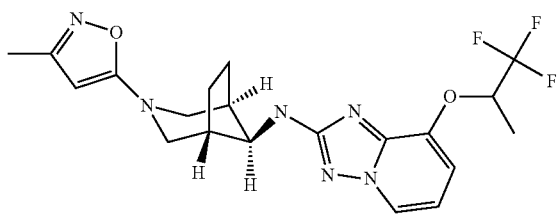 [SMILES: Cc1cc(N2C[C@H]3CC[C@@H](C2)[C@@H]3Nc2nc3c(OC(C)C(F)(F)F)cccn3n2)on1]

To a light yellow solution of N-((8 endo)-3-azabicyclo[3.2.1]octan-8-yl)-8-((1,1,1,1-trifluoropropan-2-yl)oxy)-[1,2,4]triazolo[1,5-a]pyridin-2-amine (250 mg, 704 μmol) in DMF (8 ml) were added copper (I) iodide (13.4 mg, 70.4 μmol), tripotassium phosphate (299 mg, 1.41 mmol) and N,N-diethylsalicylamide (40.8 mg, 211 μmol). The reaction mixture was cooled down to −5° C. before 5-iodo-3-methylisoxazole (CAS Number 126085-92-5) (147 mg, 704 μmol) was added. After the addition, the reaction mixture was stirred for 6 hours at −5° C. and it was poured into 50 mL of saturated NaHCO$_3$. The aqueous phase was extracted with dichloromethane. The organic layers were dried over MgSO$_4$ and concentrated in vacuum. The crude material was purified by flash chromatography (0% to 80% EtOAc in heptane) to afford the title compound (20 mg, 6.5% yield). MS ES+ (m/z): 437.2 [(M+H)$^+$]

EXAMPLE 43

N-[(8 endo)-3-(3-methyl-1,2-oxazol-5-yl)-3-azabicyclo[3.2.1]octan-8-yl]-8-[(2R or 2S)-1,1,1-trifluoropropan-2-yl]oxy-[1,2,4]triazolo[1,5-a]pyridin-2-amine

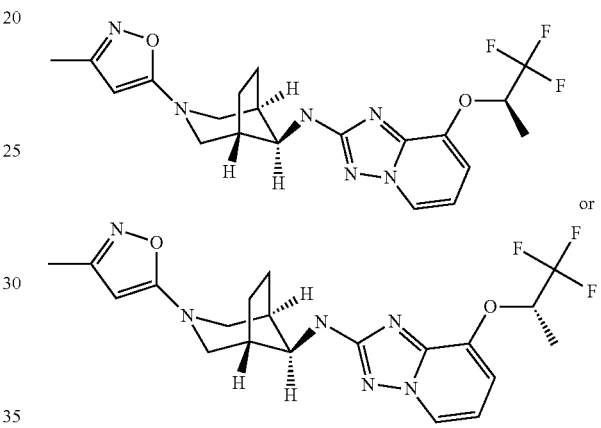

Step 1

Tert-butyl-(8-endo)-[[8-[(2R or 2S)-1,1,1-trifluoropropan-2-yl]oxy-[1.2.4]triazolo[1,5-a]pyridin-2-yl]amino]-3-azabicyclo[3.2.1]octane-3-carboxylate

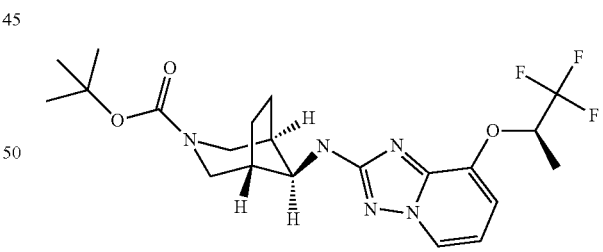

The title compound was prepared by Buchwald coupling in analogy to example 42, from 2-bromo-8-[(2R)-1,1,1-trifluoropropan-2-yl]oxy-[1,2,4]triazolo[1,5-a]pyridine or 2-bromo-8-[(2S)-1,1,1-trifluoropropan-2-yl]oxy-[1,2,4]triazolo[1,5-a]pyridine ((320 mg, 1.03 mmol) (Intermediate 3-18 from example 18), Tert-butyl (8 endo)-amino-3-azabicyclo[3.2.1]octane-3-carboxylate (CAS Registry Number: 1330763-51-3) ((280 mg, 1.24 mmol) and sodium tert-butoxide with Pd$_2$(dba)$_3$. CHCl$_3$ in the presence of xantphos in 1,4-Dioxane. The compound was obtained as a light yellow solid (303 mg, 64.5% yield).) MS ES+ (m/z): 456.3 [(M+H)$^+$]

Step 2

N-[(8 endo)-3-azabicyclo[3.2.1]octan-8-yl]-8-[(2R or 2S)-1,1,1-trifluoropropan-2-yl]oxy-[1,2,4]triazolo[1,5-a]pyridin-2-amine

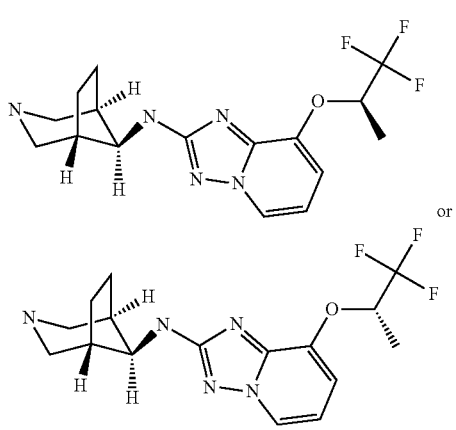

or

The title compound was prepared in analogy to example 42 (step 2) from tert-butyl-(8-endo)-[[8-[(2R or 2S)-1,1,1-trifluoropropan-2-yl]oxy-[1,2,4]triazolo[1,5-a]pyridin-2-yl]amino]-3-azabicyclo[3.2.1]octane-3-carboxylate (300 mg, 659 µmol) in dichloromethane (6 ml) with TFA (751 mg, 507 µl, 6.59 mmol). The compound was obtained as an off-white solid (227 mg, 97% yield) as crude. MS ES+ (m/z): 356.2 [(M+H)+]

Final Step 3

N-[(8 endo)-3-(3-methyl-1,2-oxazol-5-yl)-3-azabicyclo[3.2.1]octan-8-yl]-8-[(2R or 2S)-1,1,1-trifluoropropan-2-yl]oxy-[124]triazolo[1,5-a]pyridin-2-amine

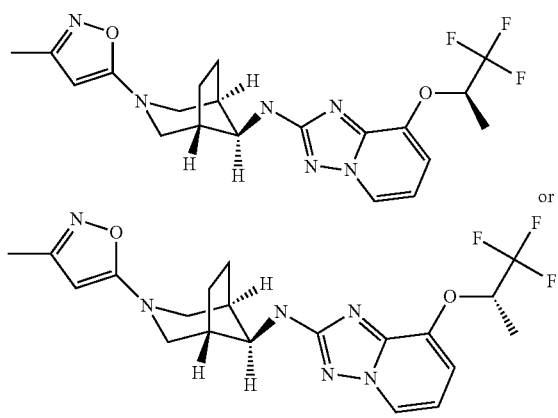

or

The compound was prepared in analogy to example 42 (step 3) from N-[(8 endo)-3-azabicyclo[3.2.1]octan-8-yl]-8-[(2R or 2S)-1,1,1-trifluoropropan-2-yl]oxy-[1,2,4]triazolo[1,5-a]pyridin-2-amine (225 mg, 633 µmol) and 5-iodo-3-methylisoxazole (159 mg, 760 µmol) in the presence of copper (I) iodide (12.1 mg, 63.3 µmol), tripotassium phosphate (269 mg, 1.27 mmol, Eq: 2) and N,N-diethyl salicylamide (36.7 mg, 190 µmol) at −5° C. in DMF. The title compound was obtained as a light yellow solid (26.1 mg, 9.45% yield).

MS ES+ (m/z): 437.3 [(M+H)+]

EXAMPLE 44

N-[(8 endo)-3-(3-methyl-1,2-oxazol-5-yl)-3-azabicyclo[3.2.1]octan-8-yl]-8-[[1 (trifluoromethyl)cyclopropyl]methoxy]-[1,2,4]triazolo[1,5-a]pyridin-2-amine

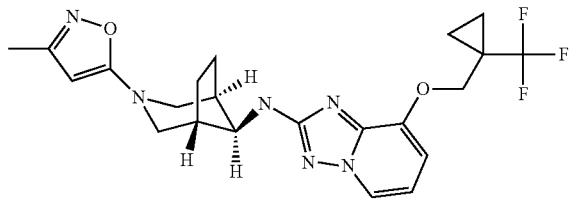 [SMILES: Cc1cc(N2C[C@H]3CC[C@@H](C2)[C@@H]3Nc2nc3c(OCC4(C(F)(F)F)CC4)cccn3n2)on1]

Step 1

Tert-butyl-(8 endo)-[8-[1,1,1-trifluoropropan-2-yl]oxy-[1,2,4]triazolo[1,5-a]pyridin-2-yl]amino]-3-azabicyclo[3.2.1]octane-3-carboxylate

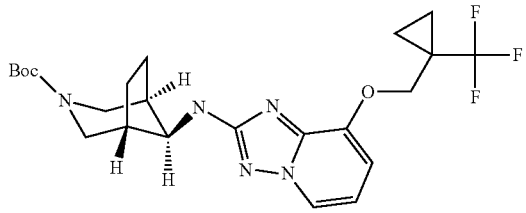 [SMILES: CC(C)(C)OC(=O)N1C[C@H]2CC[C@@H](C1)[C@@H]2Nc1nc2c(OCC3(C(F)(F)F)CC3)cccn2n1]

The title compound was prepared by Buchwald coupling in analogy to example 42, from 2-bromo-8-[[1-(trifluoromethyl) cyclopropyl] methoxy]-[1,2,4] triazolo [1,5-a] pyridine (intermediate 3-7 on table 1, 250 mg, 744 µmol), Tert-butyl-(8 endo)-amino-3-azabicyclo[3.2.1]octane-3-carboxylate (CAS Registry Number: 1330763-51-3) (168 mg, 744 µmol, mmol) and sodium tert-butoxide with Pd2(dba)3.CHCl3 (146 mg, 141 µmol) in the presence of xantphos in 1,4-Dioxane at 145° C. during 30 min in a microwave. The compound was obtained as a light yellow solid (198 mg, 411 µmol, 55.3% yield). MS ES+ (m/z): 482.4 [(M+H)+]

Step 2

N-[(8 endo)-3-azabicyclo[3.2.1]octan-8-yl]-8-((1-(trifluoromethyl)cyclopropyl)methoxy]-[1,2,4]triazolo[1,5-a]pyridin-2-amine

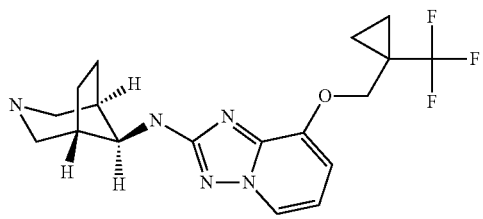 [SMILES: FC(F)(F)C1(COc2cccn3nc(N[C@@H]4[C@@H]5CC[C@H]4CNC5)nc23)CC1]

The title compound was prepared in analogy to example 42 (step 2) from Tert-butyl-(8 endo)-[8-[1,1,1-trifluoropropan-2-yl]oxy-[1,2,4]triazolo[1,5-a]pyridin-2-yl]amino]-3-azabicyclo[3.2.1]octane-3-carboxylate (190 mg, 395 μmol) in Dichloromethane with TFA (450 mg, 304 μl, 3.95 mmol). The compound was obtained as a light brown solid (147 mg, 98% yield) and used on the next step as crude. MS ES+ (m/z): 382.2 [(M+H)⁺]

Final Step 3

N-[(8 endo)-3-(3-methyl-1,2-oxazol-5-yl)-3-azabicyclo[3.2.1]octan-8-yl]-8-[[1 (trifluoromethyl)cyclopropyl]methoxy]-[1,2,4]triazolo[1,5-a]pyridin-2-amine

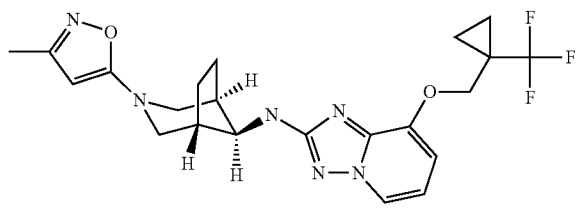 [SMILES: Cc1cc(N2C[C@H]3CC[C@@H](C2)[C@@H]3Nc2nc3c(OCC4(C(F)(F)F)CC4)cccn3n2)on1]

The compound was prepared in analogy to example 42 (step 3) from N-((8 endo)-3-azabicyclo[3.2.1]octan-8-yl)-8-((1-(trifluoromethyl)cyclopropyl)methoxy)-[1,2,4]triazolo[1,5-a]pyridin-2-amine (115 mg, 302 μmol) and 5-iodo-3-methylisoxazole (75.6 mg, 362 μmol) in the presence of copper (I) iodide, tripotassium phosphate and N,N-diethyl salicylamide at −5° C. in DMF. The title compound was obtained as a light yellow solid (9.1 mg, 19.7 μmol, 6.53% yield). MS ES+ (m/z): 463.3 [(M+H)⁺]

EXAMPLE 45

N-[(8 endo)-3-(3-methyl-1,2-oxazol-5-yl)-3-azabicyclo[3.2.1]octan-8-yl]-8-(2,2,3,3,3-pentafluoropropoxy)-[1,2,4]triazolo[1,5-a]pyridin-2-amine

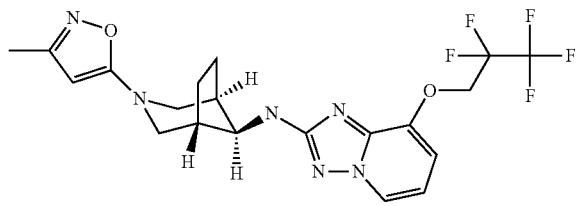 [SMILES: Cc1cc(N2C[C@H]3CC[C@@H](C2)[C@@H]3Nc2nc3c(OCC(F)(F)C(F)(F)F)cccn3n2)on1]

Step 1

Tert-butyl-(8 endo)-[8-(2,2,3,3,3-pentafluoropropoxy)-[1,2,4]triazolo[1,5-a]pyridin-2-yl]amino]-3-azabicyclo[3.2.1]octane-3-carboxylate

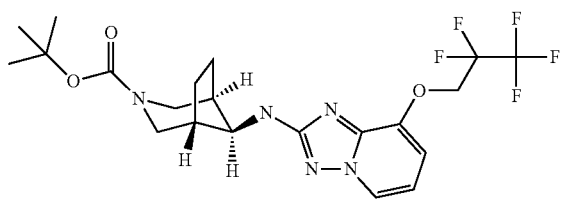 [SMILES: CC(C)(C)OC(=O)N1C[C@H]2CC[C@@H](C1)[C@@H]2Nc1nc2c(OCC(F)(F)C(F)(F)F)cccn2n1]

The title compound was prepared by Buchwald coupling in analogy to example 42, from 2-bromo-8-(2,2,3,3,3-pentafluoropropoxy)-[1,2,4] triazolo [1,5-a] pyridine (intermediate 3-14 on table 1, 317 mg, 916 μmol), Tert-butyl (8 endo)-amino-3-azabicyclo[3.2.1]octane-3-carboxylate (249 mg, 1.1 mmol) and sodium tert-butoxide with Pd₂(dba)₃.CHCl₃ (146 mg, 141 μmol) in the presence of xantphos in 1,4-Dioxane at 145° C. during 30 min in a microwave. The title compound was obtained as a light brown solid (146.2 mg, 33% yield).

MS ES+ (m/z): 492.2 [(M+H)⁺]

Step 2

N-[(8 endo)-3-azabicyclo[3.2.1]octan-8-yl]-8-(2,2,3,3,3-pentafluoropropoxy)-[1,2,4]triazolo[1,5-a]pyridin-2-amine

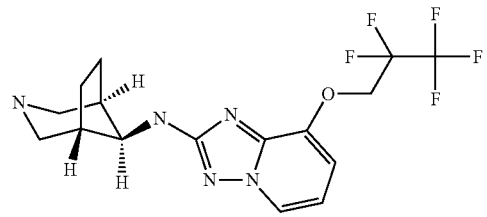 [SMILES: FC(F)(F)C(F)(F)COc1cccn2nc(N[C@@H]3[C@@H]4CC[C@H]3CNC4)nc12]

The title compound was prepared in analogy to example 42 (step 2) from Tert-butyl-8 (endo)-[[8-(2,2,3,3,3-pentafluoropropoxy)-[1,2,4]triazolo[1,5-a]pyridin-2-yl]amino]-3-azabicyclo[3.2.1]octane-3-carboxylate (140 mg, 285 μmol) in Dichloromethane with TFA (325 mg, 219 μl, 2.85 mmol). The compound was obtained as a white solid (104.1 mg, 93.4% yield) as crude. MS ES+ (m/z): 392.2 [(M+H)⁺]

Step 3

N-[(8 endo)-3-(3-methyl-1,2-oxazol-5-yl)-3-azabicyclo[3.2.1]octan-8-yl]-8-(2,2,3,3,3-pentafluoropropoxy)-[1,2,4]triazolo[1,5-a]pyridin-2-amine

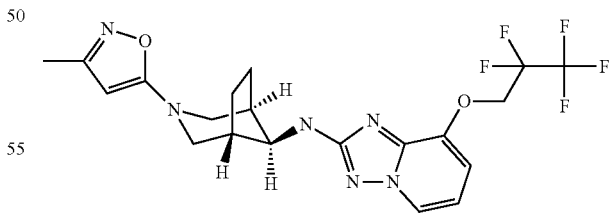

The compound was prepared in analogy to example 42 (step 3) from N-[(8 endo)-3-azabicyclo[3.2.1]octan-8-yl]-8-(2,2,3,3,3-pentafluoropropoxy)-[1,2,4]triazolo[1,5-a]pyridin-2-amine (100 mg, 256 μmol) and 5-iodo-3-methylisoxazole (64.1 mg, 307 μmol) in the presence of copper (I) iodide, tripotassium phosphate and N,N-diethyl salicylamide at −5° C. in DMF. The title compound was obtained as a white solid (12.1 mg, 10% yield).

MS ES+ (m/z): 473.2 [(M+H)+]

EXAMPLE 46

N-[(8 endo)-3-(3-methyl-1,2,4-oxadiazol-5-yl)-3-azabicyclo[3.2.1]octan-8-yl]-8-(1,1,1-trifluoropropan-2-yloxy)-[1,2,4]triazolo[1,5-a]pyridin-2-amine

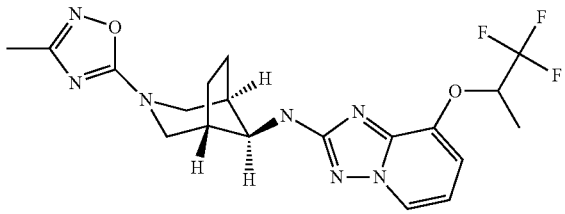 [SMILES: Cc1noc(N2C[C@H]3CC[C@@H](C2)[C@@H]3Nc2nc3c(OC(C)C(F)(F)F)cccn3n2)n1]

Step 1

8 (endo)-[[8-(1,1,1-trifluoropropan-2-yloxy)-[1,2,4]triazolo[1,5-a]pyridin-2-yl]amino]-3-azabicyclo[3.2.1]octane-3-carbonitrile

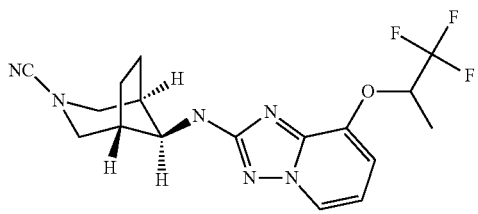 [SMILES: CC(Oc1cccn2nc(N[C@@H]3[C@@H]4CC[C@H]3CN(C#N)C4)nc12)C(F)(F)F]

To a light yellow solution of N-(8 endo)-[3-azabicyclo[3.2.1]octan-8-yl]-8-[-1,1,1-trifluoropropan-2-yl]oxy-[1,2,4]triazolo[1,5-a]pyridin-2-amine (prepared also for example 42, on steps 1 and 2) (100 mg, 281 µmol) in EtOH (1.5 ml) under argon, was added sodium bicarbonate (26 mg, 310 µmol, Eq: 1.1) followed by Cyanogen bromide (32.8 mg, 16.3 µl, 310 µmol), and the reaction mixture was stirred over night at room temp. The suspension was filtered and washed with some Ethanol and the organic solvents were concentrated in vacuum. The crude material was purified by flash chromatography (0% to 100% EtOAc in heptane) to afford the title compound (95 mg, 88.8% yield) as a white solid. MS ES+ (m/z): 381.2 [(M+H)+]

Step 2

N-[(8 endo)-3-(3-methyl-1,2,4-oxadiazol-5-yl)-3-azabicyclo[3.2.1]octan-8-yl]-8-(1,1,1-trifluoropropan-2-yloxy)-[1,2,4]triazolo[1,5-a]pyridin-2-amine

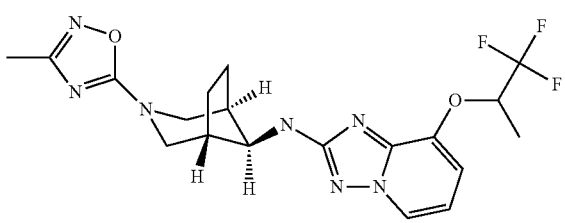 [SMILES: Cc1noc(N2C[C@H]3CC[C@@H](C2)[C@@H]3Nc2nc3c(OC(C)C(F)(F)F)cccn3n2)n1]

To a light yellow suspension of 8 (endo)-[[8-(1,1,1-trifluoropropan-2-yloxy)-[1,2,4]triazolo[1,5-a]pyridin-2-yl]amino]-3-azabicyclo[3.2.1]octane-3-carbonitrile (50 mg, 131 µmol) in Ethanol (600 µL) was added under argon, N-Hydroxyacetamidine (11.7 mg, 158 µmol) and zinc chloride (21.5 mg, 158 µmol) solved in Ethanol (250 µL). The reaction mixture was stirred at room temp for 2 hours, HCl 37% (32.9 µl, 394 µmol) was added and the reaction was warmed to 60° C. for 3 hrs and stirred to room temp over night. The crude reaction mixture was concentrated in vacuum, the residue solved in 25 mL sat NaHCO$_3$ and the aqueous phase extracted with DCM (3×25 mL). The organic layers were dried over Na$_2$SO$_4$ and concentrated in vacuum. The crude material was purified by flash chromatography (0% to 100% EtOAc in heptane) to afford the title compound (27.3 mg, 47.5% yield) as a white solid.

MS ES+ (m/z): 438.3 [(M+H)+]

EXAMPLE 47

N-[(8 endo)-3-(3-methyl-1,2,4-oxadiazol-5-yl)-3-azabicyclo[33.2.1]octan-8-yl]-8-(2,2,3,3,3-pentafluoropropoxy)-[1,2,4]triazolo[1,5-a]pyridin-2-amine

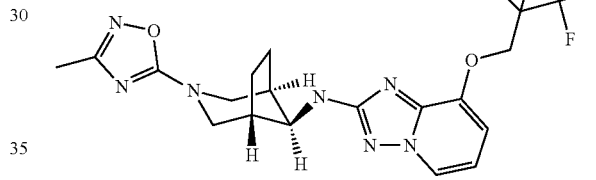

Step 3

8 (endo)-[[8-(2,2,3,3,3-pentafluoropropoxy)-[1,2,4]triazolo[1,5-a]pyridin-2-yl]amino]-3-azabicyclo[3.2.1]octane-3-carbonitrile

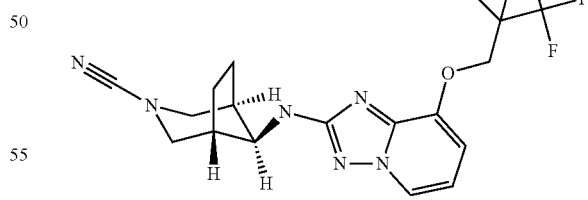

The compound was prepared in analogy to example 46 (step 3) from N-[(8 endo)-3-azabicyclo[3.2.1]octan-8-yl]-8-(2,2,3,3,3-pentafluoropropoxy)-[1,2,4]triazolo[1,5-a]pyridin-2-amine (35 mg, 89.4 µmol) described on example 45 (steps 1 and 2) in EtOH (1 ml), in the presence of sodium bicarbonate (8.26 mg, 98.4 µmol) and cyanogen bromide (10.4 mg, 5.17 µl, 98.4 µmol). The title compound was obtained as a light yellow solid (34.1 mg, 81.9 µmol, 91.6% yield). MS ES+ (m/z): 417.2 [(M+H)+]

Step 4

N-[(8 endo)-3-(3-methyl-1,2,4-oxadiazol-5-yl)-3-azabicyclo[3.2.1]octan-8-yl]-8-(2,2,3,3,3-pentafluoropropoxy)-[1,2,4]triazolo[1,5-a]pyridin-2-amine

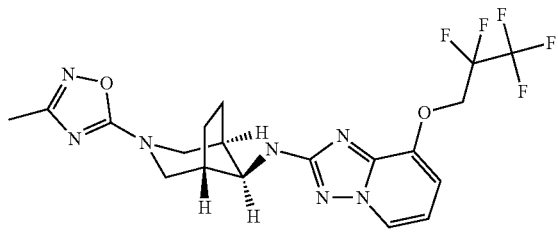 [SMILES: Cc1noc(N2C[C@H]3CC[C@@H](C2)[C@@H]3Nc2nc3c(OCC(F)(F)C(F)(F)F)cccn3n2)n1]

The compound was prepared in analogy to example 46 (step 4) from 8 (endo)-[[8-(2,2,3,3,3-pentafluoropropoxy)-[1,2,4]triazolo[1,5-a]pyridin-2-yl]amino]-3-azabicyclo[3.2.1]octane-3-carbonitrile (32 mg, 76.9 µmol, Eq: 1) in the presence of N-hydroxyacetamidine (6.83 mg, 92.2 mol), zinc chloride (12.6 mg, 92.2 µmol) in Ethanol (800 µl) as solvent and HCl 37% (19.2 µl, 231 µmol, Eq: 3) that was added 2 hrs later. The title compound was obtained after flash chromatoghraphy as a white solid (27.2 mg, 57.5 µmol, 74.8% yield).
MS ES+ (m/z): 474.2 [(M+H)+]

EXAMPLE 48

N-[(8 endo)-3-(3-methyl-1,2,4-oxadiazol-5-yl)-3-azabicyclo[3.2.1]octan-8-yl]-8-[(Z)-2,3,3,3-tetrafluoroprop-1-enoxy]-[1,2,4]triazolo[1,5-a]pyridin-2-amine

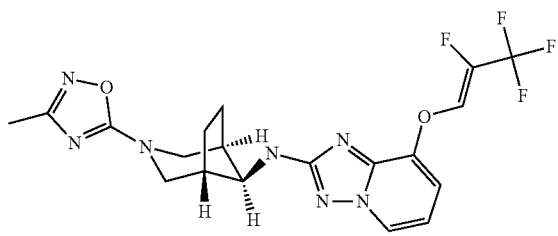 [SMILES: Cc1noc(N2C[C@H]3CC[C@@H](C2)[C@@H]3Nc2nc3c(O/C=C(\F)C(F)(F)F)cccn3n2)n1]

Step 1

Tert-butyl-(8 endo)-[[8-[(Z)-2,3,3,3-tetrafluoroprop-1-enoxy]-[1,2,4]triazolo[1,5-a]pyridin-2-yl]amino]-3-azabicyclo[3.2.1]octane-3-carboxylate

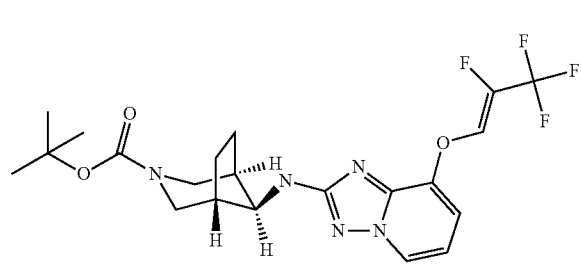 [SMILES: CC(C)(C)OC(=O)N1C[C@H]2CC[C@@H](C1)[C@@H]2Nc1nc2c(O/C=C(\F)C(F)(F)F)cccn2n1]

The title compound was obtained as secondary product on the Buchwald coupling directed to obtain Tert-butyl-(8 endo)-[[8-(2,2,3,3,3-pentafluoropropoxy)-[1,2,4]triazolo[1,5-a]pyridin-2-yl]amino]-3-azabicyclo[3.2.1]octane-3-carboxylate (described on example 45, step 1) from 2-bromo-8-(2,2,3,3,3-pentafluoropropoxy)-[1,2,4]triazolo[1,5-a]pyridine (330 mg, 954 µmol) and Tert-butyl (8 endo)-amino-3-azabicyclo[3.2.1]octane-3-carboxylate (259 mg, 1.14 mmol). Tert-butyl-(8 endo)-[[8-(2,2,3,3,3-pentafluoropropoxy)-[1,2,4]triazolo[1,5-a]pyridin-2-yl]amino]-3-azabicyclo[3.2.1]octane-3-carboxylate (example 45) was obtained as main product (142 mg, 31% yield) and the title compound was collected as yellow by-product by column chromatography (silica gel, 0% to 100% EtOAc in heptane) separately and repurified via HPLC (40.2 mg, 85.3 µmol, 8.94% yield). MS ES+ (m/z): 472.2 [(M+H)+]

Step 2

N-[(8 endo)-3-azabicyclo[3.2.1]octan-8-yl]-8-[(Z)-2,3,3,3-tetrafluoroprop-1-enoxy]-[1,2,4]triazolo[1,5-a]pyridin-2-amine

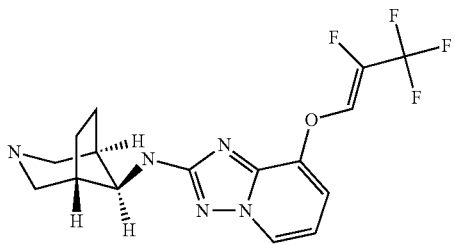 [SMILES: F/C(=C\Oc1cccn2nc(N[C@@H]3[C@@H]4CC[C@H]3CNC4)nc12)C(F)(F)F]

The title compound was prepared in analogy to example 45 (step 2) from Tert-butyl-8 (endo)-[[8-[(Z)-2,3,3,3-tetrafluoroprop-1-enoxy]-[1,2,4]triazolo[1,5-a]pyridin-2-yl]amino]-3-azabicyclo[3.2.1]octane-3-carboxylate in Dichloromethane with TFA. The compound was obtained as a white solid (32 mg, 85.9 µmol, 100%) as crude. MS ES+ (m/z): 372.1 [(M+H)+]

Step 3

8 (endo)-[[8-[(Z)-2,3,3,3-tetrafluoroprop-1-enoxy]-[1,2,4]triazolo[1,5-a]pyridin-2-yl]amino]-3-azabicyclo[3.2.1]octane-3-carbonitrile

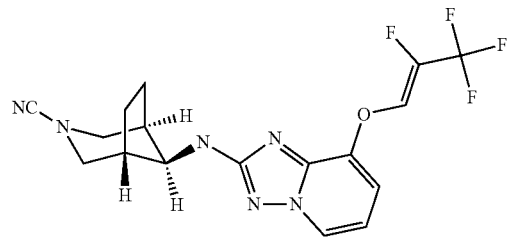 [SMILES: N#CN1C[C@H]2CC[C@@H](C1)[C@@H]2Nc1nc2c(O/C=C(\F)C(F)(F)F)cccn2n1]

The compound was prepared in analogy to example 46 (step 3) from N-[(8 endo)-3-azabicyclo[3.2.1]octan-8-yl]-8-[(Z)-2,3,3,3-tetrafluoroprop-1-enoxy]-[1,2,4]triazolo[1,5-a]pyridin-2-amine (32 mg, 86 µmol) in EtOH (500 µl), in the presence of sodium bicarbonate (7.8 mg, 92.8 µmol) and cyanogen bromide (11.5 mg, 5.71 µl, 109 µmol). The title compound was obtained as a white solid (22.8 mg, 57.5 µmol, 64.7% yield).

MS ES+ (m/z): 397.1 [(M+H)+]

Step 4

N-[(8 endo)-3-(3-methyl-1,2,4-oxadiazol-5-yl)-3-azabicyclo[3.2.1]octan-8-yl]-8-[(Z)-2,3,3,3-tetrafluoroprop-1-enoxy]-[124]triazolo[1,5-a]pyridin-2-amine

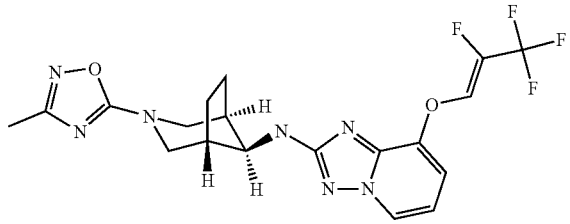 [SMILES: Cc1noc(N2C[C@H]3CC[C@@H](C2)[C@@H]3Nc2nc3c(O/C=C(\F)C(F)(F)F)cccn3n2)n1]

The compound was prepared in analogy to example 46 (step 4) from 8 (endo)-[[8-[(Z)-2,3,3,3-tetrafluoroprop-1-enoxy]-[1,2,4]triazolo[1,5-a]pyridin-2-yl]amino]-3-azabicyclo[3.2.1]octane-3-carbonitrile (21.6 mg, 54.5 µmol) in the presence of N-hydroxyacetamidine (4.84 mg, 65.4 µmol), zinc chloride (8.91 mg, 65.4 µmol) in Ethanol (600 µl) as solvent and HCl 37% (13.6 µl, 163 µmol) that was added 2 hrs later. The title compound was obtained after flash chromatoghraphy as a white solid (11 mg, 44.2 µmol, 74.8% yield). MS ES+ (m/z): 454.2 [(M+H)+]

EXAMPLE 49

N-[(8 endo)-3-(3-methyl-1,2,4-oxadiazol-5-yl)-3-azabicyclo[33.2.1]octan-8-yl]-8-(2,2,3,3,3-pentafluoropropoxy)-[1,2,4]triazolo[1,5-a]pyrazin-2-amine

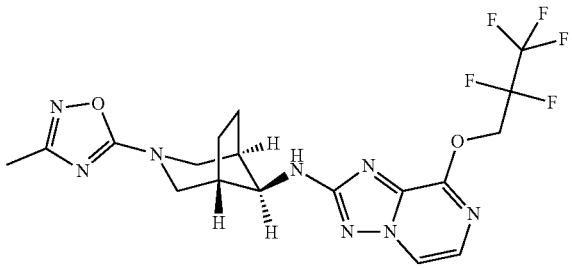 [SMILES: Cc1noc(N2C[C@H]3CC[C@@H](C2)[C@@H]3Nc2nc3c(OCC(F)(F)C(F)(F)F)nccn3n2)n1]

Intermediate 2

Step 1

Tert-butyl ((8 endo)-3-cyano-3-azabicyclo[3.2.1]octan-8-yl)carbamate

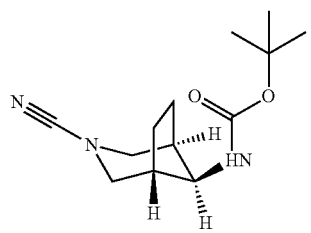 [SMILES: CC(C)(C)OC(=O)N[C@@H]1[C@@H]2CC[C@H]1CN(C#N)C2]

To a light yellow solution of tert-butyl ((8 endo)-3-azabicyclo[3.2.1]octan-8-yl) carbamate (250 mg, 1.1 mmol) described in WO 2012116965, in ethanol in EtOH (4 ml) was added sodium bicarbonate (102 mg, 1.22 mmol) followed by cyanogen bromide (129 mg, 1.22 mmol). The reaction was stirred over night at room temperature and the suspension was filtered off and washed with some Ethanol. The crude reaction mixture was concentrated in vacuum and the residue was purified by flash chromatography (silica gel, 12 g, 0% to 100% EtOAc in heptane) to afford the title compound as a light yellow solid (216 mg, 77.8% yield).

MS ES+ (m/z): 252.2 [(M+H)+]

Step 2

(8 endo)-3-(3-methyl-1,2,4-oxadiazol-5-yl)-3-azabicyclo[3.2.1]octan-8-amine

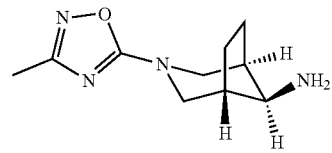

Tert-butyl (8 endo)-3-cyano-3-azabicyclo[3.2.1]octan-8-yl)carbamate (200 mg, 796 µmol) was dissolved in Ethanol (20 ml) and under Argon it was added N-hydroxyacetimidamide ((70.7 mg, 955 µmol) and zinc chloride ((130 mg, 955 µmol). The reaction mixture was stirred at room temperature for 2 hours. HCl 37% (199 µl, 2.39 mmol) was added and the reaction mixture was warmed and stirred at 60° for 3 hours. The solvent was removed in vacuum. LC-MS showed the removal of the BOC protecting group. The residue was taken up with 25 mL sat NaHCO3 and extracted with dichloromethane (3×25 mL). The organic layers were dried over Na2SO4 and concentrated in vacuum. The crude material was purified by flash chromatography (silica gel, 0% to 10% MeOH in DCM, at the end 7M NH3 in MeOH was used) to afford the debocylated title compound as an off-white powder (126 mg, 76% yield). MS ES+ (m/z): 209.1 [(M+H)+]

Step 4

N-((8 endo)-3-(3-methyl-1,2,4-oxadiazol-5-yl)-3-azabicyclo[3.2.1]octan-8-yl)-8-(2,2,3,3,3-pentafluoropropoxy)-[1,2,4]triazolo[1,5-a]pyrazin-2-amine

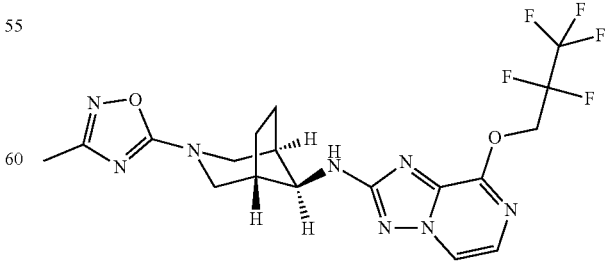

To a solution of (8 endo)-3-(3-methyl-1,2,4-oxadiazol-5-yl)-3-azabicyclo[3.2.1]octan-8-amine (20 mg, 96 µmol, Eq:

1) in 1,4-Dioxane (1.5 ml) in a microway vial, was added sodium tert-butoxide (18.9 mg, 197 μmol) and 2-bromo-8-(2,2,3,3,3-pentafluoropropoxy)-[1,2,4]triazolo[1,5-a]pyrazine (66.7 mg, 192 μmol). The mixture was purged with Argon for a 5 minutes and dibromo-bis-(tritert.-Butyl)-phosphine-palladium (7.46 mg, 9.6 μmol) was added. The reaction mixture was purged again with argon for 2 minutes, sealed and heated to 120° C. for 0.5 hours in the microwave. The mixture was concentrated in vacuum and the residue was diluted with dichloromethane, evaporated with silica gel to dryness and transferred to a column for purification (SILICYCLE Silia Sep™ Amine, eluent ethyl acetate 3:1 to 1:1). The title compound was obtained as a white powder (17 mg, 37.3% yield).

MS ES+ (m/z): 475.2 [(M+H)$^+$]

EXAMPLE 50

N-[(8 endo)-3-(6-methylpyrimidin-4-yl)-3-azabicyclo[3.2.1]octan-8-yl]-8-(4,4,4-trifluorobutoxy)-[1,2,4]triazolo[1,5-a]pyridin-2-amine

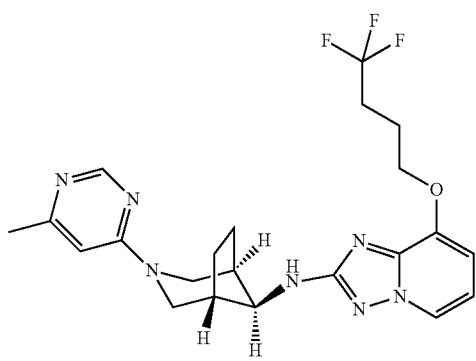 [SMILES: Cc1cc(N2C[C@H]3CC[C@@H](C2)[C@@H]3Nc2nc3c(OCCCC(F)(F)F)cccn3n2)ncn1]

Intermediate 2

Step 1

Tert-butyl N-[(8 endo)-3-(6-methylpyrimidin-4-yl)-3-azabicyclo[3.2.1]octan-8-yl]carbamate

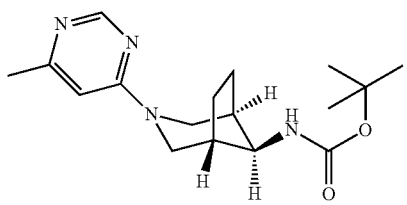 [SMILES: Cc1cc(N2C[C@H]3CC[C@@H](C2)[C@@H]3NC(=O)OC(C)(C)C)ncn1]

In a sealed tube Tert-butyl (8 endo)-3-azabicyclo[3.2.1]octan-8-ylcarbamate (500 mg, 2.21 mmol) was dissolved in EtOH (10 ml) and 4-chloro-6-methylpyrimidine (869 mg, 6.63 mmol) was added followed by triethylamine (894 mg, 1.23 ml, 8.84 mmol). The reaction mixture was stirred in the sealed tube at 130° C. overnight. The crude reaction mixture was concentrated in vacuum. The residue was diluted with 20 mL of dichloromethane and 20 mL of water. The organic phase were extracted with DCM (3×20 mL), dried over MgSO$_4$ and concentrated in vacuum. The crude material was purified by flash chromatography (0% to 100% EtOAc in heptane) to afford the title compound as a yellow solid (496 mg, 71% yield).

MS ES+ (m/z): 319.2 [(M+H)$^+$]

Step 2

(8 endo)-3-(6-methylpyrimidin-4-yl)-3-azabicyclo[3.2.1]octan-8-amine

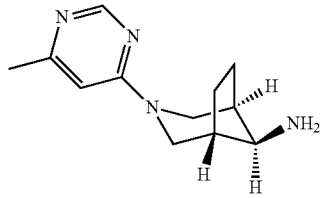 [SMILES: Cc1cc(N2C[C@H]3CC[C@@H](C2)[C@@H]3N)ncn1]

To a light yellow solution of Tert-butyl N-[(8 endo)-3-(6-methylpyrimidin-4-yl)-3-azabicyclo[3.2.1]octan-8-yl]carbamate (260 mg, 817 μmol) in dichloromethane (8 ml) was added TFA (931 mg, 629 μl, 8.17 mmol). The reaction mixture was stirred at room temperature over night and concentrated in vacuum. The crude material was purified by Ion-exchange column (Si-SCX-2, 10 g, washed with MeOH and liberated with MeOH(NH$_3$ 2M)) to afford the title compound (195 mg, 804 μmol, 98.5% yield) that was used in the next step without further purification. MS ES+ (m/z): 219.2 [(M+H)$^+$]

Final Coupling Step 3

N-[(8 endo)-3-(6-methylpyrimidin-4-yl)-3-azabicyclo[3.2.1]octan-8-yl]-8-(4,4,4-trifluorobutoxy)-[1,2,4]triazolo[1,5-a]pyridin-2-amine

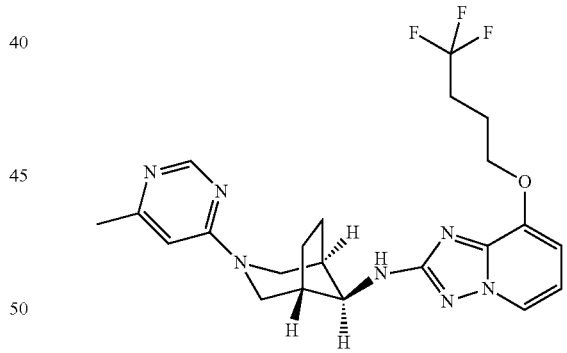

The title compound, was prepared by Buchwald coupling in analogy to example 1, from 2-bromo-8-(4,4,4-trifluorobutoxy)-[1,2,4]triazolo[1,5-a]pyridine (20 mg, 61.7 μmol) (intermediate 3, example 1) and intermediate 2 (8 endo)-3-(6-methylpyrimidin-4-yl)-3-azabicyclo[3.2.1]octan-8-amine (15.0 mg, 61.7 μmol) with Pd$_2$(dba)$_3$.CHCl$_3$ (5.11 mg, 4.94 μmol) in the presence of sodium phenoxide and xantphos (5.71 mg, 9.87 μmol) as a light yellow solid (7.5 mg, 26.3% yield). MS ES+ (m/z): 462.2 [(M+H)$^+$].

According to the procedure described for the synthesis of example 1, further derivatives have been synthesized by Buchwald coupling from the respective intermediate 2 (8 endo)-3-(6-methylpyrimidin-4-yl)-3-azabicyclo[3.2.1]octan-8-amine and the corresponding intermediate 3. They comprise examples 51-53 in table 5

TABLE 5

| Example | Systematic name / Yield of reaction | Starting materials | MW found (M + H)+ |
|---|---|---|---|
| 51 | N-[(8 endo)-3-(6-methylpyrimidin-4-yl)-3-azabicyclo[3.2.1]octan-8-yl]-8-(3,3,3-trifluoropropoxy)-[1,2,4]triazolo[1,5-a]pyridin-2-amine (10.1 mg, 21% yield) | 2-bromo-8-(3,3,3-trifluoropropoxy)-[1,2,4]triazolo[1,5-a]pyridine (31.6 mg, 91.6 µmol) (intermediate III, example 4) and (8 endo)-3-(6-methylpyrimidin-4-yl)-3-azabicyclo[3.2.1]octan-8-amine (20 mg, 91.6 µmol) | 448.2 |
| 52 | N-[(8 endo)-3-(6-methylpyrimidin-4-yl)-3-azabicyclo[3.2.1]octan-8-yl]-8-(2,2,2-trifluoroethoxy)-[1,2,4]triazolo[1,5-a]pyridin-2-amine (15.9 mg, 40% yield) | 2-bromo-8-(2,2,2-trifluoroethoxy)-[1,2,4]triazolo[1,5-a]pyridine (29.8, 101 µmol) (intermediate III, example 3) and (8 endo)-3-(6-methylpyrimidin-4-yl)-3-azabicyclo[3.2.1]octan-8-amine (20 mg, 91.6 µmol,) | 434.2 |
| 53 | N-[(8 endo)-3-(6-methylpyrimidin-4-yl)-3-azabicyclo[3.2.1]octan-8-yl]-8-1,1,1-trifluoropropan-2-yloxy)-[1,2,4]triazolo[1,5-a]pyridin-2-amine (16.3 mg, 45.4%) | 2-bromo-8-(1,1,1-trifluoropropan-2-yloxy)-[1,2,4]triazolo[1,5-a]pyridine (27.3 mg, 88.2 µmol) (intermediate III, example 4) and (8 endo)-3-(6-methylpyrimidin-4-yl)-3-azabicyclo[3.2.1]octan-8-amine (17.5 mg, 80.2 µmol) | 448.3 |
| 54 | N[(8 endo)-3-(6-methylpyrimidin-4-yl)-3-azabicyclo[3.2.1]octan-8-yl]-8-(2,2,3,3,3-pentafluoropropoxy)-[1,2,4]triazolo[1,5-a]pyridin-2-amine (41.9 mg, 55% yield) | 2-bromo-8-(2,2,3,3,3-pentafluoropropoxy)-[1,2,4]triazolo[1,5-a]pyridine (30 mg, 86.7 µmol) (intermediate III-14 on table 1) and (8 endo)-3-(6-methylpyrimidin-4-yl)-3-azabicyclo[3.2.1]octan-8-amine (22.7 mg, 104 µmol) | 484.3 |

Intermediate 2

(8 endo)-3-(2-methylpyrimidin-4-yl)-3-azabicyclo[3.2.1]octan-8-amine

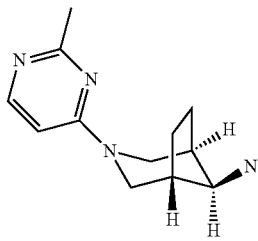 [SMILES: Cc1nccc(N2C[C@H]3CC[C@@H](C2)[C@@H]3N)n1]

Step 1

Tert-butyl N-[(8 endo)-3-(2-methylpyrimidin-4-yl)-3-azabicyclo[3.2.1]octan-8-yl]carbamate

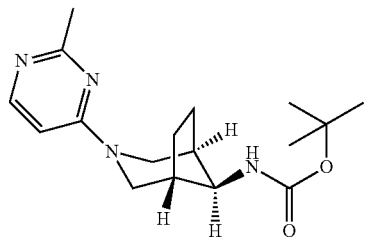 [SMILES: Cc1nccc(N2C[C@H]3CC[C@@H](C2)[C@@H]3NC(=O)OC(C)(C)C)n1]

The compound was prepared in analogy to example 50 (step 1, intermediate 2) using Tert-butyl (8 endo)-3-azabicyclo[3.2.1]octan-8-ylcarbamate (100 mg, 442 µmol) and of 4-chloro-2-methylpyrimidine (170 mg, 1.33 mmol) in a sealed tube at 130° C. using EtOH as solvent in the presence of triethylamine (179 mg, 246 µl, 1.77 mmol). The title compound was obtained after flash chromatoghraphy as an off-white solid (109.7 mg, 78% yield).

MS ES+ (m/z): 319.2 (100%) [(M+H)+]

Step 2

(8 endo)-3-(2-methylpyrimidin-4-yl)-3-azabicyclo[3.2.1]octan-8-amine

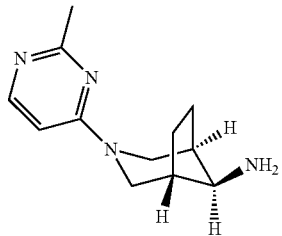 [SMILES: Cc1nccc(N2C[C@H]3CC[C@@H](C2)[C@@H]3N)n1]

The compound was prepared in analogy to example 50 (step 2, intermediate 2) using Tert-butyl N-[(8 endo)-3-(2-methylpyrimidin-4-yl)-3-azabicyclo[3.2.1]octan-8-yl] carbamate (107 mg, 336 µmol) in dichloromethane in the presence of TFA (383 mg, 259 µl, 3.36 mmol). The title compound was obtained after purification by ion exchange column (Si-SCX-2, 2 g) as a white solid (73 mg, 100% yield). MS ES+ (m/z): 219.2 [(M+H)+]

Further derivatives have been synthesized by Buchwald coupling according to the procedure described for the synthesis of example 1, using the corresponding intermediate 3 and the previously described intermediate 2 (8 endo)-3-(2-methylpyrimidin-4-yl)-3-azabicyclo[3.2.1]octan-8-amine. They comprise examples 55-56 in table 6.

TABLE 6

| Example | | Systematic name Yield of reaction | Starting materials | MW found (M + H)+ |
|---|---|---|---|---|
| 55 | ![structure] | N-[(8 endo)-3-(2-methylpyrimidin-4-yl)-3-azabicyclo[3.2.1]octan-8-yl]-8-(4,4,4-trifluorobutoxy)-[1,2,4]triazolo[1,5-a]pyridin-2-amine (9.2 mg, 25.8% yield) | 2-bromo-8-(4,4,4-trifluorobutoxy)-[1,2,4]triazolo[1,5-a]pyridine (25 mg, 77.1 µmol) (intermediate III, example 1) and (8 endo)-3-(2-methylpyrimidin-4-yl)-3-azabicyclo[3.2.1]octan-8-amine (16.8 mg, 77.1 µmol) | 462.3 |
| 56 | ![structure] | N-[(8 endo)-3-(2-methylpyrimidin-4-yl)-3-azabicyclo[3.2.1]octan-8-yl]-8-1,1,1-trifluoropropan-2-yloxy)-[1,2,4]triazolo[1,5-a]pyridin-2-amine (32 mg, 78.1%) | 2-bromo-8-(1,1,1-trifluoropropan-2-yloxy)-[1,2,4]triazolo[1,5-a]pyridine (31.2 mg, 101 µmol) (intermediate III, example 4) and (8 endo)-3-(6-methylpyrimidin-4-yl)-3-azabicyclo[3.2.1]octan-8-amine (20 mg, 91.6 µmol) | 448.2 |

Intermediate 2

(8 endo)-3-(6-(trifluoromethyl)pyrimidin-4-yl)-3-azabicyclo[3.2.1]octan-8-amine

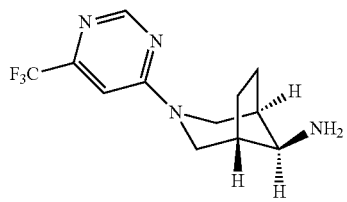 [SMILES: N[C@@H]1[C@@H]2CC[C@H]1CN(c1cc(C(F)(F)F)ncn1)C2]

Step 1

Tert-butyl N-[(8 endo)-3-(6-(trifluoromethyl)pyrimidin-4-yl)-3-azabicyclo[3.2.1]octan-8-yl]carbamate

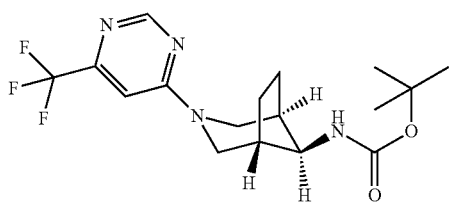 [SMILES: CC(C)(C)OC(=O)N[C@@H]1[C@@H]2CC[C@H]1CN(c1cc(C(F)(F)F)ncn1)C2]

The compound was prepared in analogy to example 50 (step 1, intermediate 2) using Tert-butyl (8 endo)-3-azabicyclo[3.2.1]octan-8-ylcarbamate (250 mg, 1.1 mmol of 4-chloro-6-(trifluoromethyl)pyrimidine (242 mg, 1.33 mmol) in a sealed tube at 130° C. using EtOH as solvent in the presence of triethylamine (447 mg, 616 μl, 4.42 mmol). The title compound was obtained as a white solid (400 mg, 1.07 mmol, 97.2% yield). MS ES+ (m/z): 373.3 [(M+H)+]

Step 2

(8 endo)-3-(6-(trifluoromethyl)pyrimidin-4-yl)-3-azabicyclo[3.2.1]octan-8-amine

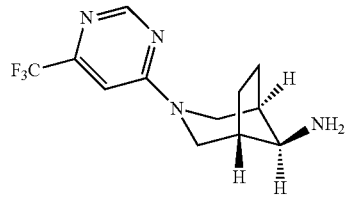 [SMILES: N[C@@H]1[C@@H]2CC[C@H]1CN(c1cc(C(F)(F)F)ncn1)C2]

The compound was prepared in analogy to example 50 (step 2, intermediate 2) using Tert-butyl N-[(8 endo)-3-(6-(trifluoromethyl)pyrimidin-4-yl]-3-azabicyclo[3.2.1]octan-8-yl)carbamate (400 mg, 1.07 mmol) in dichloromethane in the presence of HCl 37 (635 mg, 529 μl, 6.44 mmol) instead of TFA as acid. The title compound was obtained after extraction using 15 mL sat NaHCO₃ and DCM (6×15 mL) as a viscous colorless oil (289 mg, 98.8% yield).

MS ES+ (m/z): 273.2 [(M+H)+]

Example 57 (on table 7) has been synthesized by Buchwald coupling according to the procedure described for the synthesis of example 1, using the corresponding intermediate 3 and the previously described intermediate 2 (8 endo)-3-(6-(trifluoromethyl)pyrimidin-4-yl)-3-azabicyclo[3.2.1]octan-8-amine.

TABLE 7

| Example | Systematic name / Yield of reaction | Starting materials | MW found (M + H)+ |
|---|---|---|---|
| 57 | 8-(2,2,3,3,3-pentafluoropropoxy)-N-[(8 endo)-3-[6-(trifluoromethyl)pyrimidin-4-yl]-3-azabicyclo[3.2.1]octan-8-yl]-[1,2,4]triazolo[1,5-a]pyridin-2-amine (17 mg, 36.9%) | 2-bromo-8-(2,2,3,3,3-pentafluoropropoxy)-[1,2,4]triazolo[1,5-a]pyridine (30 mg, 86.7 μmol) (intermediate III-14 on table 1) and (8 endo)-3-(6-(trifluoromethyl)pyrimidin-4-yl)-3-azabicyclo[3.2.1]octan-8-amine (23.6 mg, 86.7 μmol) | 538.1 |

EXAMPLE 58

N-[(8 endo)-3-(5-fluoropyrimidin-4-yl)-3-azabicyclo[3.2.1]octan-8-yl]-8-(2,2,3,3,3-pentafluoropropoxy)-[1,2,4]triazolo[1,5-a]pyridin-2-amine

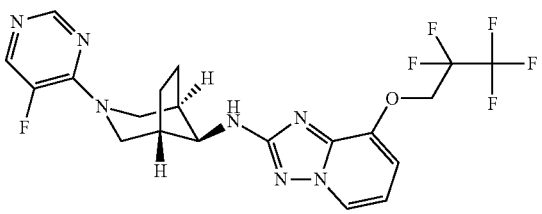 [SMILES: Fc1cncnc1N1C[C@H]2CC[C@@H](C1)[C@@H]2Nc1nc2c(OCC(F)(F)C(F)(F)F)cccn2n1]

Intermediate 2

Step 1

Tert-butyl N-[(8 endo)-3-(5-fluoropyrimidin-4-yl)-3-azabicyclo[3.2.1]octan-8-yl] carbamate

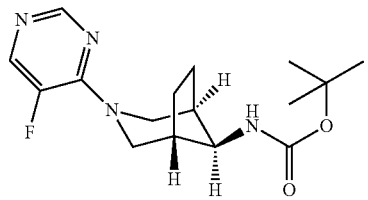 [SMILES: CC(C)(C)OC(=O)N[C@@H]1[C@@H]2CC[C@H]1CN(c1ncncc1F)C2]

The compound was prepared in analogy to example 50 (step 1, intermediate 2) using Tert-butyl (8 endo)-3-azabicyclo[3.2.1]octan-8-ylcarbamate (200 mg, 884 μmol) and 4,6-difluoropyrimidine (154 mg, 1.33 mmol) in a sealed tube at 100° C. using EtOH as solvent in the presence of triethylamine (358 mg, 3.53 mmol). The title compound was obtained as a white solid (247.3 mg, 86.8% yield). MS ES+ (m/z): 323.2 [(M+H)+]

Step 2

(8 endo)-3-(5-fluoropyrimidin-4-yl)-3-azabicyclo[3.2.1]octan-8-amine

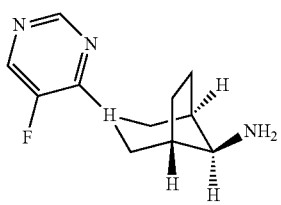

The compound was prepared in analogy to example 50 (step 2, intermediate 2) using Tert-butyl N-[(8 endo)-3-(5-fluoropyrimidin-4-yl)-3-azabicyclo[3.2.1]octan-8-yl] carbamate (240 mg, 743 μmol) in dichloromethane in the presence of HCl 37% (439 mg, 366 μl, 4.46 mmol). The title compound was obtained as a white powder (149 mg, 90% yield).

MS ES+ (m/z): 223.2 [(M+H)+]

Final Coupling Step 3

N-[(8 endo)-3-(5-fluoropyrimidin-4-yl)-3-azabicyclo[3.2.1]octan-8-yl]-8-(2,2,3,3,3-pentafluoropropoxy)-[1,2,4]triazolo[1,5-a]pyridin-2-amine

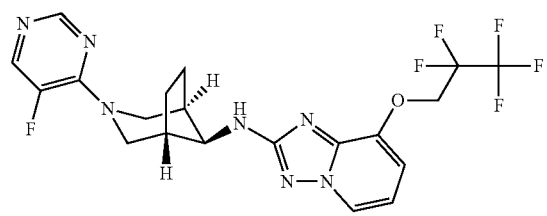 [SMILES: Fc1cncnc1N1C[C@H]2CC[C@@H](C1)[C@@H]2Nc1nc2c(OCC(F)(F)C(F)(F)F)cccn2n1]

The title compound, was prepared by Buchwald coupling in analogy to example 1, from 2-bromo-8-(2,2,3,3,3-pentafluoropropoxy)-[1,2,4]triazolo[1,5-a]pyridine (25 mg, 72.2 μmol) (intermediate 3-14 on table 1) and intermediate 2 (8 endo)-3-(5-fluoropyrimidin-4-yl)-3-azabicyclo[3.2.1]octan-8-amine (19.3 mg, 86.7 μmol) with Pd$_2$(dba)$_3$.CHCl$_3$ (5.98 mg, 5.78 μmol) in the presence of sodium tert-butoxide (13.9 mg, 144 μmol) and xantphos (6.69 mg, 11.6 μmol) in a microwave at 120° C. during 30 min. It was obtained as a white solid (5.2 mg, 14.8% yield) using preparative HPLC. MS ES+ (m/z): 488.2 [(M+H)+]

EXAMPLE 59

N-[(8 endo)-3-(5-fluoro-6-methylpyrimidin-4-yl)-3-azabicyclo[3.2.1]octan-8-yl]-8-(2,2,3,3,3-pentafluoropropoxy)-[1,2,4]triazolo[1,5-a]pyridin-2-amine

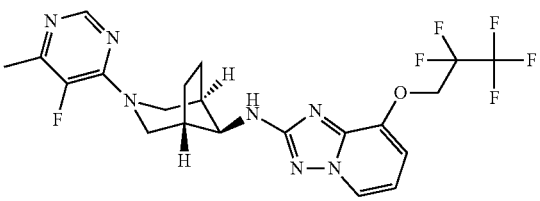 [SMILES: Cc1ncnc(N2C[C@H]3CC[C@@H](C2)[C@@H]3Nc2nc3c(OCC(F)(F)C(F)(F)F)cccn3n2)c1F]

Intermediate 2

Step 1

Tert-butyl N-[((8 endo)-3-(5-fluoro-6-methylpyrimidin-4-yl)-3-azabicyclo[3.2.1]octan-8-yl]carbamate

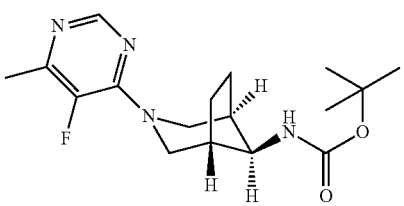 [SMILES: Cc1ncnc(N2C[C@H]3CC[C@@H](C2)[C@@H]3NC(=O)OC(C)(C)C)c1F]

The compound was prepared in analogy to example 50 (step 1, intermediate 2) using Tert-butyl (8 endo)-3-azabicyclo[3.2.1]octan-8-ylcarbamate (200 mg, 884 μmol) and 4-chloro-5-fluoro-6-methylpyrimidine (194 mg, 1.33 mmol) in a sealed tube at 100° C. using EtOH as solvent in the presence of triethylamine (358 mg, 493 μl, 3.53 mmol). The title compound was obtained as a white solid (255 mg, 758 μmol, 85.8% yield). MS ES+ (m/z): 337.3 [(M+H)+]

Step 2

(8 endo)-3-(5-fluoro-6-methylpyrimidin-4-yl)-3-azabicyclo[3.2.1]octan-8-amine

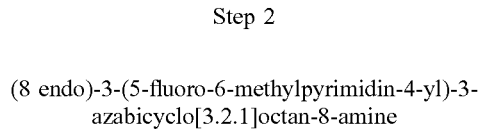

The compound was prepared in analogy to example 50 (step 2, intermediate 2) using Tert-butyl N-[(8 endo)-3-(5-fluoro-6-methylpyrimidin-4-yl)-3-azabicyclo[3.2.1]octan-8-yl]carbamate (253 mg, 752 μmol) in dichloromethane in the presence of HCl 37% (445 mg, 371 μl, 4.51 mmol). The title compound (170 mg, 719 μmol, 95.7% yield) was obtained as a white solid and used as a crude on the next steps. MS ES+ (m/z): 237.1 [(M+H)+]

Final Coupling Step 3

N-[(8 endo)-3-(5-fluoro-6-methylpyrimidin-4-yl)-3-azabicyclo[3.2.1]octan-8-yl]-8-(2,2,3,3,3-pentafluoropropoxy)-[1,2,4]triazolo[1,5-a]pyridin-2-amine

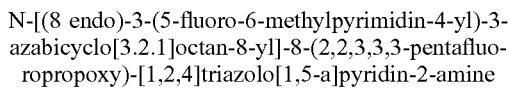

The title compound, was prepared by Buchwald coupling in analogy to example 1, from 2-bromo-8-(2,2,3,3,3-pentafluoropropoxy)-[1,2,4]triazolo[1,5-a]pyridine (40 mg, 116 μmol) (intermediate 3-14 on table 1) and intermediate 2 (8 endo)-3-(5-fluoro-6-methylpyrimidin-4-yl)-3-azabicyclo[3.2.1]octan-8-amine (32.8 mg, 139 μmol) with Pd₂(dba)₃.CHCl₃ (9.57 mg, 9.25 μmol) in the presence of sodium tert-butoxide (22.2 mg, 231 μmol) and xantphos (10.7 mg, 18.5 μmol, Eq: 0.16) in a microwave at 100° C. during 15 min to avoid fluoro elimination on the pentafluoropropoxy as by-product. It was obtained after preparative HPLC as a white solid (20.6 mg, 41.1 μmol, 35.5% yield). MS ES+ (m/z): 502.3 [(M+H)+]

EXAMPLE 60

N-[(8 endo)-3-(5-fluoro-2-methylpyrimidin-4-yl)-3-azabicylo[3.2.1]octan-8-yl]-8-(2,2,2-trifluoroethoxy)-[1,2,4]triazolo[1,5-a]pyridin-2-amine

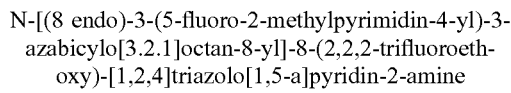

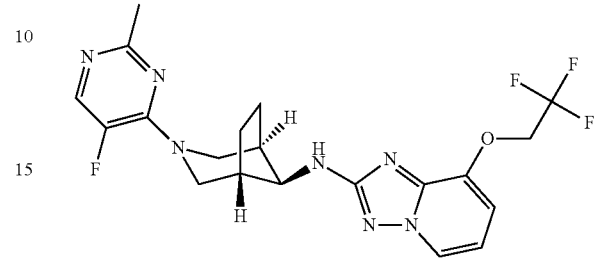

Intermediate 2

Step 1

Tert-butyl N-[(8 endo)-3-(5-fluoro-2-methylpyrimidin-4-yl)-3-azabicyclo[3.2.1]octan-8-yl]carbamate

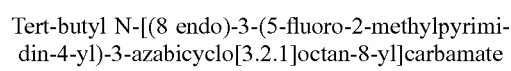

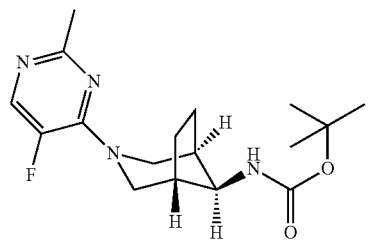 [SMILES: Cc1ncc(F)c(N2C[C@H]3CC[C@@H](C2)[C@@H]3NC(=O)OC(C)(C)C)n1]

The compound was prepared in analogy to example 50 (step 1, intermediate 2) using Tert-butyl (8 endo)-3-azabicyclo[3.2.1]octan-8-ylcarbamate (200 mg, 884 μmol) and 4-chloro-5-fluoro-2-methylpyrimidine (194 mg, 1.33 mmol) in a sealed tube at 100° C. using EtOH as solvent in the presence of triethylamine (358 mg, 3.53 mmol). The title compound was obtained as a white solid (278.7 mg, 93.7% yield). MS ES+ (m/z): 337.3 [(M+H)+]

Step 2

(8 endo)-3-(5-fluoro-2-methylpyrimidin-4-yl)-3-azabicyclo[3.2.1]octan-8-amine

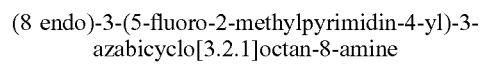

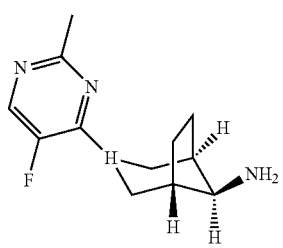

The compound was prepared in analogy to example 50 (step 2, intermediate 2) using Tert-butyl N-[(8 endo)-3-(5-fluoro-2-methylpyrimidin-4-yl)-3-azabicyclo[3.2.1]octan-8-yl]carbamate (276.9 mg, 823 µmol) in dichloromethane in the presence of HCl 37% (487 mg, 406 µl, 4.94 mmol). The title compound was obtained as a semi-solid (193 mg, 817 µmol, 99.2% yield) and use as a crude on the next steps. MS ES+ (m/z): 237.2 [(M+H)+]

Final Coupling Step 3

N-[(8 endo)-3-(5-fluoro-2-methylpyrimidin-4-yl)-3-azabicyclo[3.2.1]octan-8-yl]-8-(2,2,2-trifluoroethoxy)-[1,2,4]triazolo[1,5-a]pyridin-2-amine

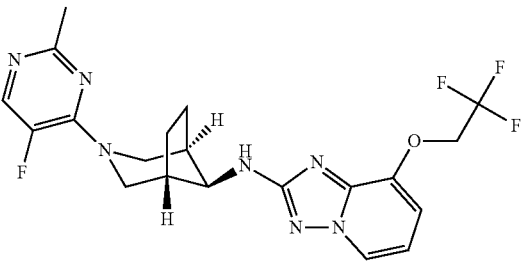 [SMILES: Cc1ncc(F)c(N2C[C@H]3CC[C@@H](C2)[C@@H]3Nc2nc3c(OCC(F)(F)F)cccn3n2)n1]

The title compound, was prepared by Buchwald coupling in analogy to example 1, from 2-bromo-8-(2,2,2-trifluoroethoxy)-[1,2,4]triazolo[1,5-a]pyridine (30 mg, 101 µmol), (intermediate 3 on example 3) and intermediate 2 (8 endo)-3-(5-fluoro-2-methylpyrimidin-4-yl)-3-azabicyclo[3.2.1]octan-8-amine (28.7 mg, 122 µmol) with Pd$_2$(dba)$_3$·CHCl$_3$ (9.57 mg, 9.25 mol) in the presence of sodium tert-butoxide (19.5 mg, 203 µmol) and xantphos (9.38 mg, 16.2 mol) in a microwave at 120° C. during 20 min. It was obtained as a white solid. (23 mg, 45.7 mol, 50.3% yield). MS ES+ (m/z): 452.3 (100%) [(M+H)+].

EXAMPLE 61

N-[(8 endo)-3-(6-chloropyrimidin-4-yl)-3-azabicyclo[3.2.1]octan-8-yl]-8-(2,2,2-trifluoroethoxy)-[1,2,4]triazolo[1,5-a]pyridin-2-amine

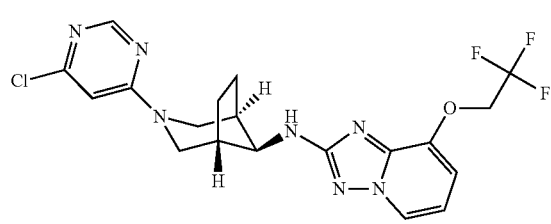 [SMILES: FC(F)(F)COc1cccn2nc(N[C@@H]3[C@@H]4CC[C@H]3CN(c3cc(Cl)ncn3)C4)nc12]

Intermediate 2

Step 1

Tert-butyl N-[(8 endo)-3-(6-chloropyrimidin-4-yl)-3-azabicyclo[3.2.1]octan-8-yl]carbamate

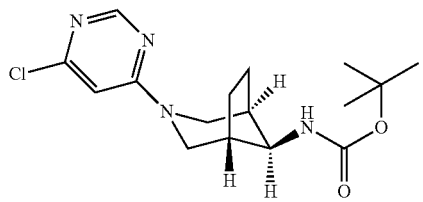 [SMILES: CC(C)(C)OC(=O)N[C@@H]1[C@@H]2CC[C@H]1CN(c1cc(Cl)ncn1)C2]

The compound was prepared in analogy to example 50 (step 1, intermediate 2) using Tert-butyl (8 endo)-3-azabicyclo[3.2.1]octan-8-ylcarbamate (250 mg, 1.1 mmol) and 4-chloro-6-fluoro-pyrimidine (220 mg, 1.66 mmol) in a sealed tube at 100° C. using EtOH as solvent in the presence of triethylamine (447 mg, 616 µl, 4.42 mmol). The title compound (329 mg, 87.9% yield) was obtained as a white solid. MS ES+ (m/z): 339.2 [(M+H)+]

Step 2

(8 endo)-3-(6-chloropyrimidin-4-yl)-3-azabicyclo[3.2.1]octan-8-amine

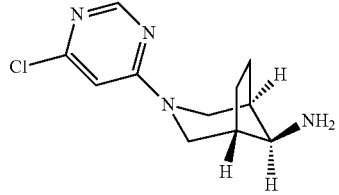 [SMILES: N[C@@H]1[C@@H]2CC[C@H]1CN(c1cc(Cl)ncn1)C2]

The compound was prepared in analogy to example 50 (step 2, intermediate 2) using Tert-butyl N-[(8 endo)-3-(6-chloropyrimidin-4-yl)-3-azabicyclo[3.2.1]octan-8-yl]carbamate (325 mg, 959 µmol) in dichloromethane in the presence of HCl 37% (567 mg, 473 µl, 5.76 mmol). The title compound (230 mg, 100% yield) was obtained as a white solid and used as a crude on the next steps. MS ES+ (m/z): 239.2 [(M+H)+]

Final Coupling Step 3

N-[(8 endo)-3-(6-chloropyrimidin-4-yl)-3-azabicyclo[3.2.1]octan-8-yl]-8-(2,2,2-trifluoroethoxy)-[1,2,4]triazolo[1,5-a]pyridin-2-amine

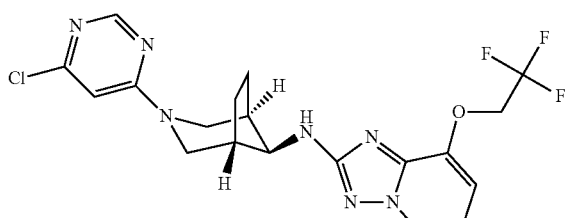

The title compound, was prepared by Buchwald coupling in analogy to example 1, from 2-bromo-8-(2,2,2-trifluoroethoxy)-[1,2,4]triazolo[1,5-a]pyridine (intermediate 3 on example 3) (30 mg, 101 µmol), (intermediate 3 on example 3) and intermediate 2 ((8 endo)-3-(6-chloropyrimidin-4-yl)-3-azabicyclo[3.2.1]octan-8-amine (29 mg, 122 µmol) with Pd$_2$(dba)$_3$.CHCl$_3$ (9.57 mg, 9.25 µmol) in the presence of sodium tert-butoxide (19.5 mg, 203 µmol) and xantphos (9.38 mg, 16.2 µmol) in a microwave at 120° C. during 20 min. It was obtained as a light yellow solid (11.2 mg, 24.7 µmol, 24.4% yield). MS ES+ (m/z): 454.2 [(M+H)$^+$].

EXAMPLE 62

8-(2,2,2-trifluoroethoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine

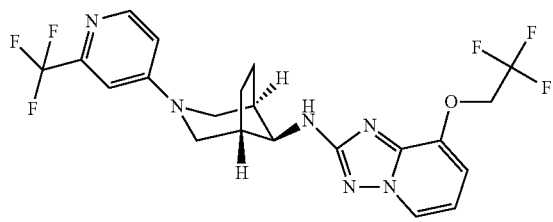 [SMILES: FC(F)(F)COc1cccn2nc(N[C@@H]3[C@@H]4CC[C@H]3CN(c3ccnc(C(F)(F)F)c3)C4)nc12]

Intermediate 2

Step 1

Tert-butyl N-[(8 endo)-3-(2-(trifluoromethyl)pyridin-4-yl)-3-azabicyclo[3.2.1]octan-8-yl]carbamate

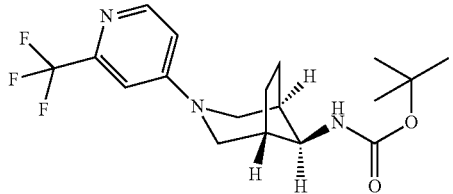 [SMILES: CC(C)(C)OC(=O)N[C@@H]1[C@@H]2CC[C@H]1CN(c1ccnc(C(F)(F)F)c1)C2]

To a solution of Tert-butyl (8 endo)-3-azabicyclo[3.2.1]octan-8-ylcarbamate (1.57 g, 6.93 mmol) in NMP (11 ml) in a tube and under argon, was added DIPEA (964 mg, 1.3 ml, 7.46 mmol) followed by 4-iodo-2-(trifluoromethyl)pyridine (1.5 g, 5.33 mmol). The vial was closed under Argon and the reaction mixture was stirred over night at 150° C. TLC and LC-MS showed the reaction was complete. The reaction mixture was diluted with 30 mL H$_2$O and extracted with EtOAc (3×30 mL). The organic layers were dried over MgSO$_4$ and concentrated in vacuum. The crude material was purified by flash chromatography (silica gel, 0% to 70% EtOAc in heptane) to afford the title compound (1.375 g, 69.5% yield). MS ES+ (m/z): 372.2 [(M+H)$^+$]

Step 2

(8 endo)-3-(2-(trifluoromethyl)pyridin-4-yl)-3-azabicyclo[3.2.1]octan-8-amine

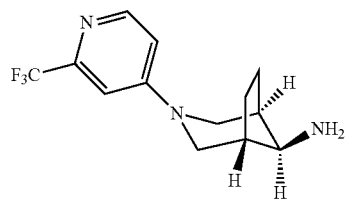 [SMILES: N[C@@H]1[C@@H]2CC[C@H]1CN(c1ccnc(C(F)(F)F)c1)C2]

The compound was prepared in analogy to example 50 (step 2, intermediate 2) using Tert-butyl N-[(8 endo)-3-(2-(trifluoromethyl)pyridin-4-yl)-3-azabicyclo[3.2.1]octan-8-yl]carbamate (1.049 g, 2.82 mmol) in dichloromethane in the presence of HCl 37% (1.68 g, 1.4 ml, 17 mmol). The title compound was obtained after extraction using sat NaHCO$_3$ and DCM as a light yellow solid (735 mg, 96% yield). MS ES+ (m/z): 272.2 [(M+H)$^+$]

Final Coupling Step 3

8-(2,2,2-trifluoroethoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine

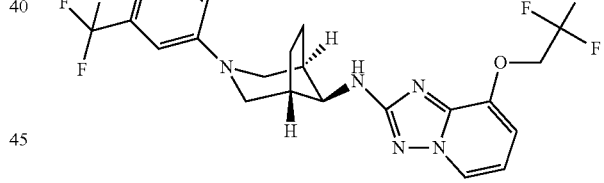

The title compound, was prepared by Buchwald coupling in analogy to example 1, from 2-bromo-8-(2,2,2-trifluoroethoxy)-[1,2,4]triazolo[1,5-a]pyridine (76.4 mg, 258 µmol), (intermediate 3 on example 3) and intermediate 2 (8 endo)-3-(2-(trifluoromethyl)pyridin-4-yl)-3-azabicyclo[3.2.1]octan-8-amine (70 mg, 258 µmol) with Pd$_2$(dba)$_3$.CHCl$_3$ (21.4 mg, 20.6 µmol) in the presence of sodium tert-butoxide (52.1 mg, 542 µmol) and xantphos (23.9 mg, 41.3 µmol) in a microwave at 145° C. during 30 min. It was obtained as a light yellow solid (75 mg, 59.8% yield). MS ES+ (m/z): 487.4 [(M+H)$^+$].

In analogy to example 62, several other derivatives have been synthesized, by Buchwald coupling using the corresponding intermediate 3 and the previously described intermediate 21 (8 endo)-3-(2-(trifluoromethyl)pyridin-4-yl)-3-azabicyclo[3.2.1]octan-8-amine. They comprise examples 63 to 67 in table 8.

TABLE 8

| Example | Systematic name<br>Yield of reaction | Starting materials | MW found<br>(M + H)+ |
|---|---|---|---|
| 63 | 8-[1,2,2,2-tetrafluoroethoxy]-N-[(8 endo)-3-[2-(trifluoromethyl)pyridin-4-yl]-3-azabicyclo[3.2.1]octan-8-yl]-[1,2,4]triazolo[1,5-a]pyridin-2-amine (19.6 mg, 70.3% yield) | 2-bromo-8-(1,2,2,2-tetrafluoroethoxy)-[1,2,4]triazolo[1,5-a]pyridine (intermediate III-10 on table 1) (19.1 mg, 60.8 µmol) and (8 endo)-3-(2-(trifluoromethyl)pyridin-4-yl)-3-azabicyclo[3.2.1]octan-8-amine (15 mg, 55.3 µmol) | 505.3 |
| 64 | 8-((1-(trifluoromethyl)cyclopropyl)methoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine (21.3 mg, 73.2% yield). | 2-bromo-8-((1-(trifluoromethyl)cyclopropyl)methoxy)-[1,2,4]triazolo[1,5-a]pyridine (intermediate III-7 on table 1), (19.5 mg, 58.1 µmol) and (8 endo)-3-(2-(trifluoromethyl)pyridin-4-yl)-3-azabicyclo[3.2.1]octan-8-amine (15 mg, 55.3 µmol) | 527.3 |
| 65 | 8-(2,2,3,3,3-pentafluoropropoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine (8 mg, 8.01% yield) | 2-bromo-8-(2,2,3,3,3-pentafluoropropoxy)-[1,2,4]triazolo[1,5-a]pyridine (intermediate III-14 on table 1) (63.8 mg, 184 µmol) and (8 endo)-3-(2-(trifluoromethyl)pyridin-4-yl)-3-azabicyclo[3.2.1]octan-8-amine (50 mg, 184 µmol) | 535.3 |
| 66 | N-((8 endo)-3-(2-(trifluoromethyl)pyridin-4-yl)-3-azabicyclo[3.21]octan-8-yl)-8-((1,1,1-trifluoropropan-2-yl)oxy)-[1,2,4]triazolo[1,5-a]pyrazin-2-amine (20 mg, 21.6% yield) | 2-bromo-8-((1,1,1-trifluoropropan-2-yl)oxy)-[1,2,4]triazolo[1,5-a]pyrazine (intermediate N-III 34 on table 4) (57.3 mg, 184 µmol) and (8 endo)-3-(2-(trifluoromethyl)pyridin-4-yl)-3-azabicyclo[3.2.1]octan-8-amine (50 mg, 184 µmol) | 502.2 |

TABLE 8-continued

| Example | Systematic name<br>Yield of reaction | Starting materials | MW found<br>(M + H)+ |
|---|---|---|---|
| 67 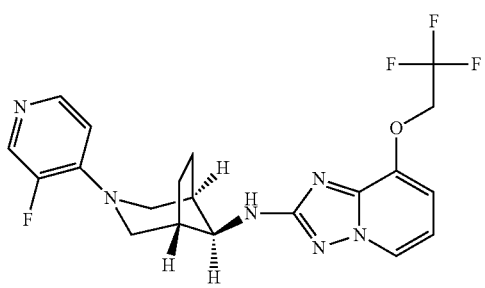 | 8-(2,2,3,3,3-pentafluoropropoxy)-N-((8 endo)-3-(2-(trifluoromethyl)pyridin-4-yl)-3-azabicyclo[3.2.1]octan-8-yl)-[1,2,4]triazolo[1,5-a]pyrazin-2-amine<br>(35 mg, 29.4% yield) | 2-bromo-8-(2,2,3,3,3-pentafluoropropoxy)-[1,2,4]triazolo[1,5-a]pyrazine (76.8 mg, 221 μmol) and (8 endo)-3-(2-(trifluoromethyl)pyridin-4-yl)-3-azabicyclo[3.2.1]octan-8-amine (60 mg, 221 μmol) | 538.2 |

N-[(8 endo)-3-(3-fluoropyridin-4-yl)-3-azabicyclo[3.2.1]octan-8-yl]-8-(2,2,2-trifluoroethoxy)-[1,2,4]triazolo[1,5-a]pyridin-2-amine

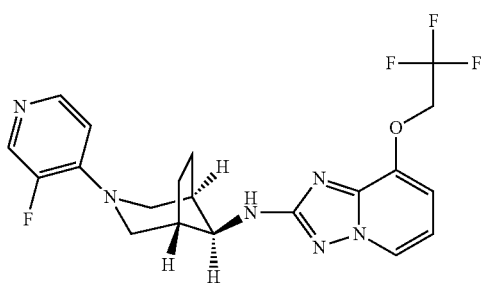 [SMILES: Fc1cnccc1N1C[C@H]2CC[C@@H](C1)[C@@H]2Nc1nc2c(OCC(F)(F)F)cccn2n1]

Intermediate 2

Step 1

Tert-butyl N-[(8 endo)-3-(3-fluoropyridin-4-yl)-3-azabicyclo[3.2.1]octan-8-yl]carbamate

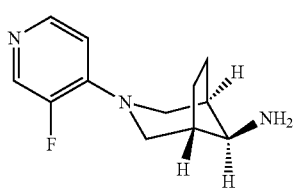 [SMILES: N[C@@H]1[C@@H]2CC[C@H]1CN(c1ccncc1F)C2]

The title compound was prepared in analogy to the intermediate 2 (step 1 on example 62) from Tert-butyl (8 endo)-3-azabicyclo[3.2.1]octan-8-ylcarbamate (150 mg, 663 mol)) and 4-bromo-3-fluoropyridine hydrochloride (211 mg, 994 μmol) in NMP (2 ml) and DIPEA (257 mg, 347 μl, 1.99 mmol) by stirring the reaction mixture over night at 150° C. The crude material was purified by flash chromatography (silica gel, 0% to 80% EtOAc in heptane) to obtain (93.5 mg, 291 μmol, 43.9% yield) of the title compound as a light yellow solid.

MS ES+ (m/z): 322.2 [(M+H)+]

Step 2

(8 endo)-3-(3-fluoropyridin-4-yl)-3-azabicyclo[3.2.1]octan-8-amine

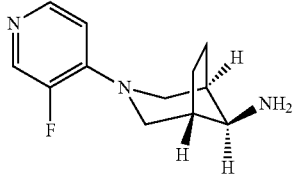 [SMILES: N[C@@H]1[C@@H]2CC[C@H]1CN(c1ccncc1F)C2]

The compound was prepared in analogy to example 50 (step 2, intermediate 2) using Tert-butyl N-[(8 endo)-3-(3-fluoropyridin-4-yl)-3-azabicyclo[3.2.1]octan-8-yl]carbamate (90 mg, 280 μmol) in dichloromethane in the presence of HCl 37% (166 mg, 138 μl, 1.68 mmol. The title compound was obtained after extraction using sat NaHCO₃ and dichloromethane as a white solid (60.5 mg, 273 μmol, 97.6% yield). MS ES+ (m/z): 222.1 [(M+H)+]

Final Coupling Step 3

N-[(8 endo)-3-(3-fluoropyridin-4-yl)-3-azabicyclo[3.2.1]octan-8-yl]-8-(2,2,2-trifluoroethoxy)-[1,2,4]triazolo[1,5-a]pyridin-2-amine The title compound, was prepared by Buchwald coupling in analogy to example 1, from 2-bromo-8-(2,2,2-trifluoroethoxy)-[1,2,4]triazolo[1,5-a]pyridine (30 mg, 101 μmol), (intermediate 3 on example 3) and intermediate 2 (8 endo)-3-(3-fluoropyridin-4-yl)-3-azabicyclo[3.2.1]octan-8-amine (24.5 mg, 111 μmol) with Pd₂(dba)3.CHCl₃ (8.39 mg, 8.11 μmol) in the presence of sodium tert-butoxide (19.5 mg, 203 μmol) and xantphos (9.38 mg, 16.2 μmol) in a microwave at 120° C. during 20 min. It was obtained as a white solid (16.4 mg, 37.5 μmol, 37% yield). MS ES+ (m/z): 437.2 [(M+H)+].

EXAMPLE 69

N-[(8 endo)-3-(2-chloropyridin-4-yl)-3-azabicyclo[3.2.1]octan-8-yl]-8-(2,2,2-trifluoroethoxy)-[1,2,4]triazolo[1,5-a]pyridin-2-amine

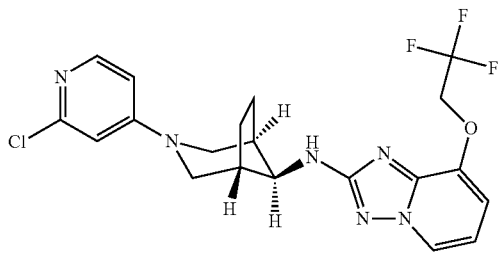 [SMILES: FC(F)(F)COc1cccn2nc(N[C@@H]3[C@@H]4CC[C@H]3CN(c3ccnc(Cl)c3)C4)nc12]

Intermediate 2

Step 1

Tert-butyl N-[(8 endo)-3-(2-chloropyridin-4-yl)-3-azabicyclo[3.2.1]octan-8-yl]carbamate

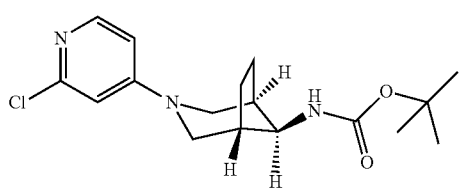 [SMILES: CC(C)(C)OC(=O)N[C@@H]1[C@@H]2CC[C@H]1CN(c1ccnc(Cl)c1)C2]

MS ES+ (m/z): 338.2 [(M+H)+]

Step 2

(8 endo)-3-(2-chloropyridin-4-yl)-3-azabicyclo[3.2.1]octan-8-amine

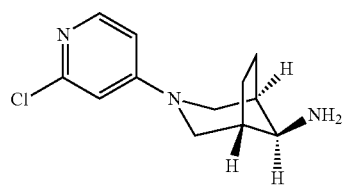 [SMILES: N[C@@H]1[C@@H]2CC[C@H]1CN(c1ccnc(Cl)c1)C2]

The compound was prepared in analogy to example 50 (step 2, intermediate 2) using Tert-butyl N [(8 endo)-3-(2-chloropyridin-4-yl)-3-azabicyclo[3.2.1]octan-8-yl] carbamate (146.9 mg, 435 μmol) in dichloromethane in the presence of HCl 37% (257 mg, 214 μl, 2.61 mmol). The title compound was obtained after extraction using sat NaHCO₃ and DCM as a white solid (89.9 mg, 378 μmol, 87% yield) MS ES+ (m/z): 238.1 [(M+H)+]

Final Coupling Step 3

N-[(8 endo)-3-(2-chloropyridin-4-yl)-3-azabicyclo[3.2.1]octan-8-yl]-8-(2,2,2-trifluoroethoxy)-[1,2,4]triazolo[1,5-a]pyridin-2-amine

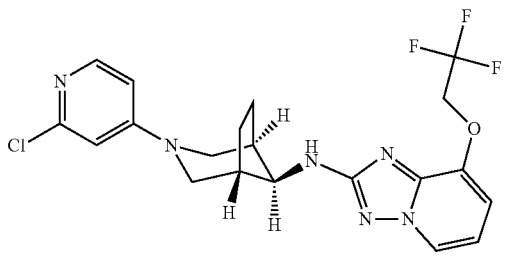 [SMILES: FC(F)(F)COc1cccn2nc(N[C@@H]3[C@@H]4CC[C@H]3CN(c3ccnc(Cl)c3)C4)nc12]

The title compound, was prepared by Buchwald coupling in analogy to example 1, from 2-bromo-8-(2,2,2-trifluoroethoxy)-[1,2,4]triazolo[1,5-a]pyridine (30 mg, 101 μmol), (intermediate 3 on example 3) and intermediate 2 (8 endo)-3-(2-chloropyridin-4-yl)-3-azabicyclo[3.2.1]octan-8-amine (26.5 mg, 111 μmol) with Pd₂(dba)3.CHCl3 (8.39 mg, 8.11 μmol) in the presence of sodium tert-butoxide (19.5 mg, 203 μmol) and xantphos (9.38 mg, 16.2 μmol) in a microwave at 120° C. during 20 min. It was obtained as a white solid (17 mg, 37.5 μmol, 37% yield). MS ES+(m/z): 453.2 [(M+H)+].

EXAMPLE 70

N-[(8 endo)-3-(5-fluoro-2-methylpyridin-4-yl)-3-azabicyclo[3.2.1]octan-8-yl]-8-(2,2,3,3,3-pentafluoropropoxy)-[1,2,4]triazolo[1,5-a]pyridin-2-amine

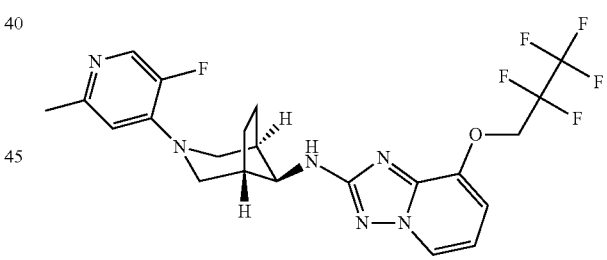

Step 1

Tert-butyl N-[(8 endo)-3-(5-fluoro-2-methylpyridin-4-yl)-3-azabicyclo[3.2.1]octan-8-yl]carbamate

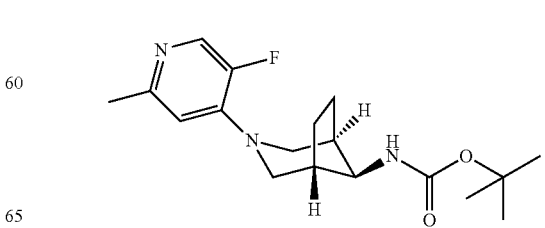

The title compound was prepared in analogy to the intermediate 2 (step 1 on example 62) from Tert-butyl (8 endo)-3-azabicyclo[3.2.1]octan-8-yl-carbamate (50 mg, 221 μmol) in NMP (1 ml) and DIPEA (57.1 mg, 77.2 μl, 442 μmol) followed by 4-bromo-5-fluoro-2-methylpyridine (63 mg, 331 μmol) by stirring under Argon, over night at 150° C. The compound was obtained a white solid (39.2 mg, 117 μmol, 52.9% yield). MS ES+ (m/z): 336.2 [(M+H)⁺]

Step 2

(8 endo)-3-(5-fluoro-2-methylpyridin-4-yl)-3-azabicyclo[3.2.1]octan-8-amine

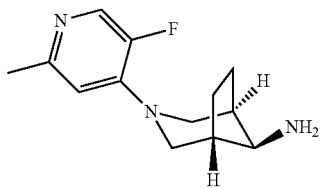 [SMILES: Cc1cc(N2C[C@H]3CC[C@@H](C2)[C@@H]3N)c(F)cn1]

The compound was prepared in analogy to example 50 (step 2, intermediate 2) using Tert-butyl N-[(8 endo)-3-(5-fluoro-2-methylpyridin-4-yl)-3-azabicyclo[3.2.1]octan-8-yl]carbamate (37 mg, 110 μmol) in dichloromethane in the presence of TFA (126 mg, 85 μl, 1.1 mmol). The crude reaction mixture was concentrated in vacuo. The crude material was purified by flash chromatography (silica gel, 0% to 10% MeOH in DCM, MeOH contains 7M NH₃) to afford the title compound (28.2 mg, 120 μmol, 109% yield). MS ES+ (m/z): 236.1 [(M+H)⁺]

Step 3

N-[(8 endo)-3-(5-fluoro-2-methylpyridin-4-yl)-3-azabicyclo[3.2.1]octan-8-yl]-8-(2,2,3,3,3-pentafluoropropoxy)-[1,2,4]triazolo[1,5-a]pyridin-2-amine

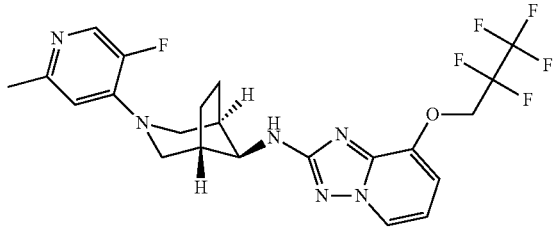 [SMILES: Cc1cc(N2C[C@H]3CC[C@@H](C2)[C@@H]3Nc2nc3c(OCC(F)(F)C(F)(F)F)cccn3n2)c(F)cn1]

The title compound, was prepared by Buchwald coupling in analogy to example 1, from 2-bromo-8-(2,2,3,3,3-pentafluoropropoxy)-[1,2,4]triazolo[1,5-a]pyridine (30 mg, 86.7 μmol) (intermediate 3-14 on table 1) and intermediate 2 N-(8 endo)-3-(5-fluoro-2-methylpyridin-4-yl)-3-azabicyclo[3.2.1]octan-8-amine (24.5 mg, 104 μmol) with Pd2(dba)3.CHCl₃ (8.39 mg, 8.11 μmol) in the presence of sodium tert-butoxide (16.7 mg, 173 μmol) and xantphos (8.03 mg, 13.9 μmol) in a microwave at 120° C. during 20 min. It was obtained as a light yellow solid (28 mg, 56 μmol, 64.5% yield). MS ES+ (m/z): 501.2 [(M+H)+].

EXAMPLE 71

N-[8-endo-3-(3-methylisothiazol-5-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

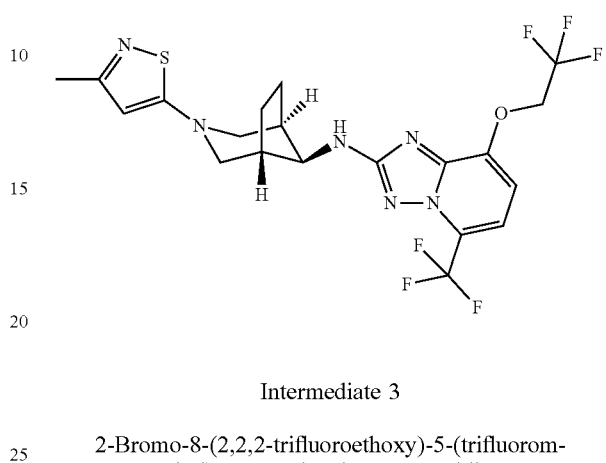

Intermediate 3

2-Bromo-8-(2,2,2-trifluoroethoxy)-5-(trifluoromethyl)-[1,2,4]triazolo[1,5-a]pyridine

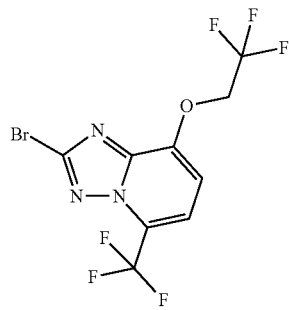 [SMILES: FC(F)(F)COc1ccc(C(F)(F)F)n2nc(Br)nc12]

Step 1

Ethyl N-[[3-bromo-6-(trifluoromethyl)-2-pyridyl]carbamothioyl]carbamate

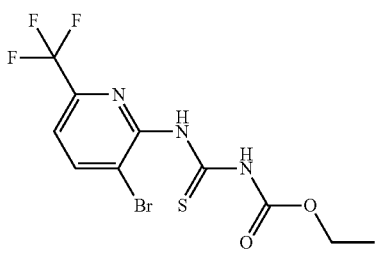 [SMILES: CCOC(=O)NC(=S)Nc1nc(C(F)(F)F)ccc1Br]

To a light yellow solution of 3-bromo-6-(trifluoromethyl) pyridin-2-amine (1 g, 4.15 mmol) in 1,4-dioxane (20 ml) was added ethoxycarbonyl isothiocyanate (599 mg, 539 μl, 4.56 mmol) under argon. The reaction mixture was stirred at 100° C. over night.

More ethoxycarbonyl isothiocyanate (109 mg, 830 μmol) was then added and the reaction mixture was stirred for further 4 hours at 100° C. It was then cooled to RT and concentrated in vacuo to obtain the title compound (1.48 g, 2.39 mmol, 57.5% yield) as a light yellow solid. MS ES+ (m/z): 371.9 [(M+H)$^+$]

Step 2

8-Bromo-5-(trifluoromethyl)-[1,2,4]triazolo[1,5-a]pyridin-2-amine

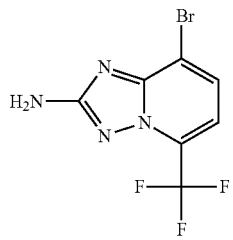 [SMILES: Nc1nc2c(Br)ccc(C(F)(F)F)n2n1]

To a light yellow solution of Ethyl N-[[3-bromo-6-(trifluoromethyl)-2-pyridyl]carbamothioyl]carbamate (1.48 g, 3.98 mmol) in ethanol (10 ml) and methanol (10 ml) was added under argon hydroxylamine hydrochloride (1.38 g, 19.9 mmol) followed by N,N-diisopropylethylamine (1.54 g, 2.08 ml, 11.9 mmol). The reaction mixture was warmed to 60° C. and stirred for 3 hours. TLC and LC-MS showed the reaction was complete. The reaction mixture was concentrated in vacuo and the crude material obtained was purified by flash chromatography (silica gel, 40 g, 0% to 40% EtOAc in heptane) to afford the title compound (680 mg, 60.8% yield) as a white solid. MS ES+ (m/z): 281.0 [(M+H)$^+$]

Step 3

8-(2,2,2-trifluoroethoxy)-5-(trifluoromethyl)-[1,2,4]triazolo[1,5-a]pyridin-2-amine

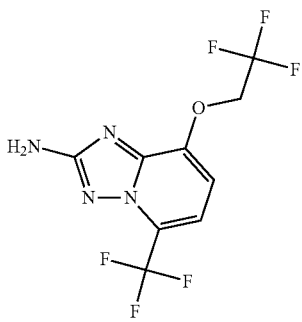 [SMILES: Nc1nc2c(OCC(F)(F)F)ccc(C(F)(F)F)n2n1]

NaH (8.54 mg, 196 µmol) was suspended in DMF (0.5 ml) and cooled to 0° C. with an ice-bath. Then 2,2,2-trifluoroethanol (23.1 mg, 16.6 µl, 231 µmol) in DMF (0.5 ml) was added dropwise over 10 min under argon. The ice-bath was removed and the reaction mixture stirred for 30 min. 8-Bromo-5-(trifluoromethyl)-[1,2,4]triazolo[1,5-a]pyridin-2-amine (50 mg, 178 µmol) in DMF (0.5 ml) was then added dropwise followed by the addition of copper (I) bromide (255 µg, 1.78 µmol). The reaction mixture was heated to 155° C. for 4 hours. TLC and LC-MS showed the reaction was complete. The reaction mixture was cooled to room temperature and solved in 15 mL sat NaHCO$_3$ and extracted with DCM (3×15 mL). The organic layers were dried over Na$_2$SO$_4$ and concentrated in vacuo. The crude material was purified by flash chromatography (silica gel, 0% to 40% EtOAc in heptane) to afford the title compound (38 mg, 114 µmol, 64% yield) as a white solid. MS ES+ (m/z): 301.1 [(M+H)$^+$]

Step 4

2-Bromo-8-(2,2,2-trifluoroethoxy)-5-(trifluoromethyl)-[1,2,4]triazolo[1,5-a]pyridine

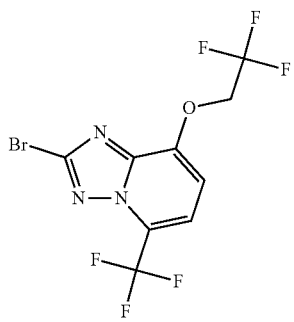 [SMILES: FC(F)(F)COc1ccc(C(F)(F)F)n2nc(Br)nc12]

To a dark brown solution of tert-butyl nitrite (18.6 mg, 21.5 µl, 180 µmol) and copper (II) bromide (40.2 mg, 180 µmol) in acetonitrile (1.5 ml) under argon was added dropwise at 60° C. a solution of 8-(2,2,2-trifluoroethoxy)-5-(trifluoromethyl)-[1,2,4]triazolo[1,5-a]pyridin-2-amine (36 mg, 120 µmol) in acetonitrile (1.5 ml). The reaction was warmed to 75° C. and stirred for 2 hours. LC-MS showed the reaction was complete. The reaction mixture quenched with 1 ml of 1M HCl, diluted with 10 mL H2O and extracted with DCM (3×15 mL). The organic layers were dried over MgSO$_4$ and concentrated in vacuo. The crude material was purified by flash chromatography (silica gel, 0% to 50% EtOAc in heptane) to afford the title compound (30 mg, 68.7% yield) as light-yellow oil. MS ES+ (m/z): 364.0 [(M+H)$^+$]

Final Coupling Step 5

N-[(8-endo)-3-(3-methylisothiazol-5-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

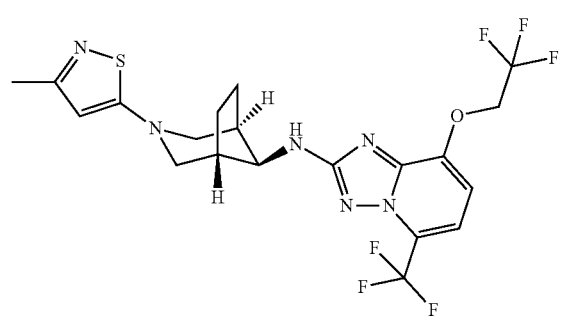 [SMILES: Cc1cc(N2C[C@H]3CC[C@@H](C2)[C@@H]3Nc2nc3c(OCC(F)(F)F)ccc(C(F)(F)F)n3n2)sn1]

A light yellow solution of 2-bromo-8-(2,2,2-trifluoroethoxy)-5-(trifluoromethyl)-[1,2,4]triazolo[1,5-a]pyridine (27.4 mg, 75.2 µmol), (8 endo)-3-(3-methylisothiazol-5-yl)-3-azabicyclo[3.2.1]octan-8-amine (16 mg, 71.6 µmol), intermediate 2 of example 14, and sodium tert-butoxide (20.7 mg, 215 µmol) in 1,4-dioxane (1 ml) was degased with argon in a ultra sound bath for 5 min. Then xantphos (6.63 mg, 11.5 µmol) and tris(dibenzylideneacetone)dipalladium (0) chloroform adduct (5.93 mg, 5.73 µmol) were added. The reaction mixture was degased for another 2 min before the vial was capped and heated in a microwave at 145° C. for 30 min. LC-MS showed the reaction was complete. The reaction mixture was poured into H$_2$O (10 ml) and extracted with DCM (3×10 mL). The organic layers were dried over MgSO$_4$ and concentrated in vacuo. The crude material was purified by flash chromatography (silica gel, 12 g, 0% to 100% EtOAc in heptane) to afford the title compound (17.1 mg, 47.1% yield) as a light yellow solid MS ES+ (m/z): 507.2 [(M+H)$^+$]

EXAMPLE 72

N-[(8-endo-3-(3-methylisothiazol-5-yl)-3-azabicyclo[33.2.1]octan-8-yl]-5-(trifluoromethyl)-8-[[1-(trifluoromethyl)cyclopropyl]methoxy]-[1,2,4]triazolo[1,5-a]pyridin-2-amine

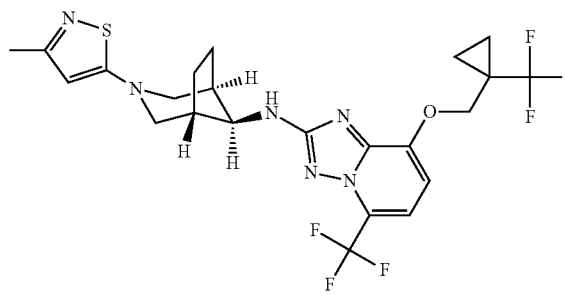

Intermediate 3

2-bromo-5-(trifluoromethyl)-8-((1-(trifluoromethyl)cyclopropyl)methoxy)-[1,2,4]triazolo[1,5-a]pyridine

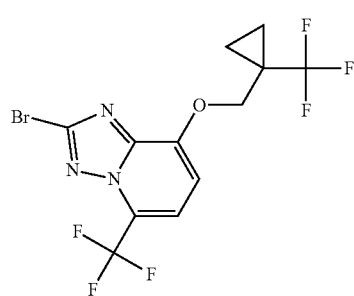 [SMILES: FC(F)(F)c1ccc(OCC2(C(F)(F)F)CC2)c2nc(Br)nn12]

5-(trifluoromethyl)-8-[[1-trifluoromethyl)cyclopropyl]methoxy]-[1,2,4]triazolo[1,5-a]pyridin-2-amine

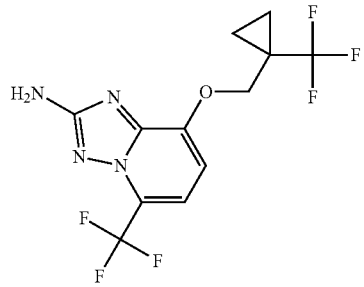 [SMILES: Nc1nc2c(OCC3(C(F)(F)F)CC3)ccc(C(F)(F)F)n2n1]

The title compound, was prepared in analogy to example 71, intermediate 3, step 3, from 8-bromo-5-(trifluoromethyl)-[1,2,4]triazolo[1,5-a]pyridin-2-amine (100 mg, 0.356 mmol, product of example 71, step 2, and (1-(trifluoromethyl)cyclopropyl)methanol (89.7 mg, 640 µmol) as a white solid, 72.5 mg, 59.93%). MS ES+ (m/z): 341.1 [(M+H)+]

Step 2

2-bromo-5-(trifluoromethyl)-8-((1-(trifluoromethyl)cyclopropyl)methoxy)-[1,2,4]triazolo[1,5-a]pyridine

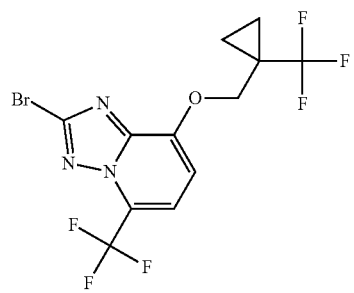 [SMILES: FC(F)(F)c1ccc(OCC2(C(F)(F)F)CC2)c2nc(Br)nn12]

The title compound, was prepared in analogy to example 1, intermediate 3, step 5, from 5-(trifluoromethyl)-8-((1-(trifluoromethyl)cyclopropyl)methoxy)-[1,2,4]triazolo[1,5-a]pyridin-2-amine (70 mg, 206 µmol), tert-butyl nitrite and copper (II) bromide as a white solid (77 mg, 92.6%). MS ES+ (m/z): 406.0 [(M+H)+]

Final Coupling Step 2

N-[(8-endo-3-(3-methylisothiazol-5-yl)-3-azabicyclo[3.2.1]octan-8-yl]-5-(trifluoromethyl)-8-[[1-(trifluoromethyl)cyclopropyl]methoxy]-[1,2,4]triazolo[1,5-a]pyridin-2-amine

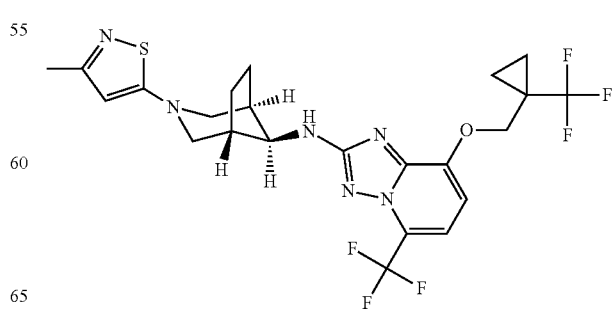

The title compound, was prepared by Buchwald coupling in analogy to example 1, from 2-bromo-5-(trifluoromethyl)-8-((1-(trifluoromethyl)cyclopropyl)methoxy)-[1,2,4]triazolo[1,5-a]pyridine (28.5 mg, 70.5 µmol) and 8-endo-3-(3-methylisothiazol-5-yl)-3-azabicyclo[3.2.1]octan-8-amine (15 mg, 67.2 µmol), intermediate II of example 14 with Pd2(dba)3.CHCl3 in the presence of sodium t-butoxide and xantphos as a off-white solid (23.4 mg, 63.7%). MS ES+ (m/z): 547.2 [(M+H)+]

EXAMPLE 73

N-[8-endo-3-(5-methyl-1,3,4-oxadiazol-2-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

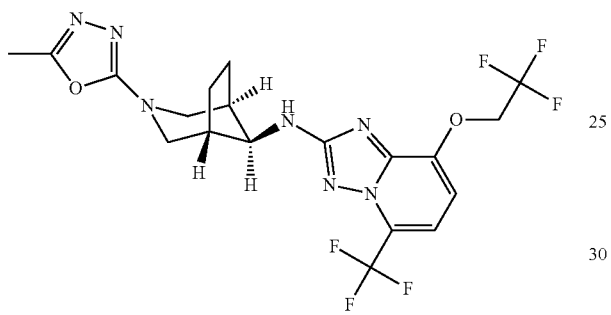

The title compound, was prepared by Buchwald coupling in analogy to example 1, from 2-bromo-8-(2,2,2-trifluoroethoxy)-5-(trifluoromethyl)-[1,2,4]triazolo[1,5-a]pyridine (40 mg, 110 mol), intermediate 3 of example 71 and 8-endo-3-(5-methyl-1,3,4-oxadiazol-2-yl)-3-azabicyclo[3.2.1]octan-8-amine (27.5 mg, 132 µmol) (intermediate 2 of example 41) with Pd2(dba)3.CHCl3 in the presence of sodium t-butoxide and xantphos as a light yellow solid (42.5 mg, 78.7%). MS ES+ (m/z): 492.2 [(M+H)+]

EXAMPLE 74

N-[(8-endo)-3-(5-methyl-1,3,4-oxadiazol-2-yl)-3-azabicyclo[3.2.1]octan-8-yl]-5-(trifluoromethyl)-8-(2,2,2-trifluoro-1-methyl-ethoxy)-[1,2,4]triazolo[1,5-a]pyridin-2-amine

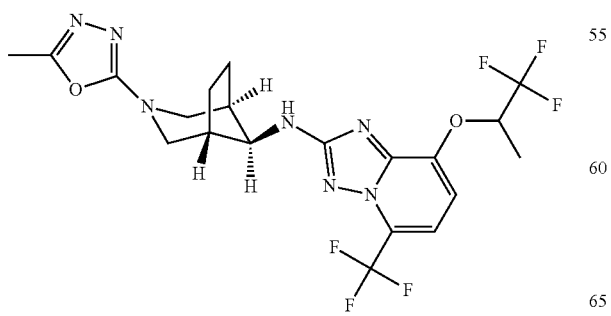

Intermediate 3

2-Bromo-5-(trifluoromethyl)-8-(2,2,2-trifluoro-1-methyl-ethoxy)-[1,2,4]triazolo[1,5-a]pyridine

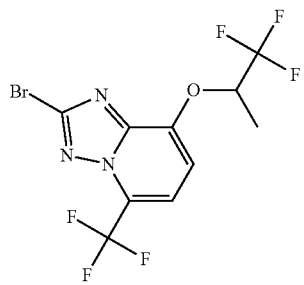 [SMILES: CC(Oc1ccc(C(F)(F)F)n2nc(Br)nc12)C(F)(F)F]

Step 1

5-(Trifluoromethyl)-8-(2,2,2-trifluoro-1-methyl-ethoxy)-[1,2,4]triazolo[1,5-a]pyridin-2-amine

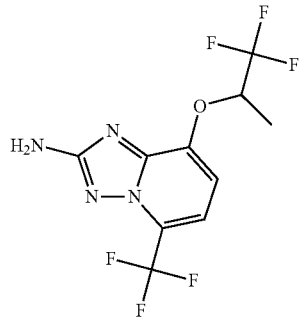 [SMILES: CC(Oc1ccc(C(F)(F)F)n2nc(N)nc12)C(F)(F)F]

The title compound, was prepared in analogy to example 71, intermediate 3, step 3, from 8-bromo-5-(trifluoromethyl)-[1,2,4]triazolo[1,5-a]pyridin-2-amine (100 mg, 0.356 mmol, product of example 71, step 2, and 1,1,1-trifluoro-2-propanol (60.9 mg, 534 µmol) as a white solid, 65.2 mg, 58.3%). MS ES+ (m/z): 315.1 [(M+H)+]

Step 2

2-bromo-5-(trifluoromethyl)-8-(2,2,2-trifluoro-1-methyl-ethoxy)-[1,2,4]triazolo[1,5-a]pyridine

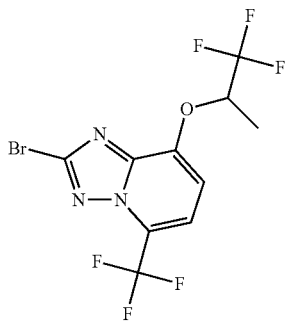 [SMILES: CC(Oc1ccc(C(F)(F)F)n2nc(Br)nc12)C(F)(F)F]

The title compound, was prepared in analogy to example 1, intermediate 3, step 4 from 5-(trifluoromethyl)-8-(2,2,2-trifluoro-1-methyl-ethoxy)-[1,2,4]triazolo[1,5-a]pyridin-2-amine (420 mg, 1.34 mmol), tert-butyl nitrite and copper (II) bromide as a white solid (432 mg, 85.5%).

MS ES+ (m/z): 378.0 [(M+H)+]

Final Coupling Step 3

N-[(rac)-8-endo-3-(5-methyl-1,3,4-oxadiazol-2-yl)-3-azabicyclo[3.2.1]octan-8-yl]-5-(trifluoromethyl)-8-(2,2,2-trifluoro-1-methyl-ethoxy)-[2,4]triazolo[1,5-a]pyridin-2-amine

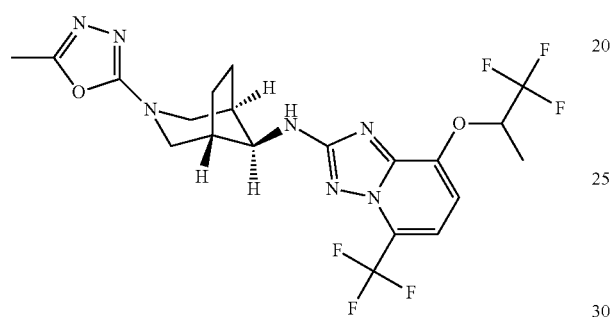

The title compound, was prepared by Buchwald coupling in analogy to example 1, from 2-bromo-5-(trifluoromethyl)-8-(2,2,2-trifluoro-1-methyl-ethoxy)-[1,2,4]triazolo[1,5-a]pyridine (50 mg, 132 µmol) and 8-endo-3-(5-methyl-1,3,4-oxadiazol-2-yl)-3-azabicyclo[3.2.1]octan-8-amine (33.1 mg, 159 µmol) (intermediate 2 of example 41) with Pd$_2$(dba)$_3$.CHCl$_3$ in the presence of sodium t-butoxide and xantphos as a light yellow solid (46.1 mg, 69%).

MS ES+ (m/z): 506.2 [(M+H)+]

EXAMPLE 75

N-[(8-endo)-3-(5-methyl-1,3,4-oxadiazol-2-yl)-3-azabicyclo[3.2.1]octan-8-yl]-5-(trifluoromethyl)-8-[(1R or 1S)-2,2,2-trifluoro-1-methyl-ethoxy]-[1,2,4]triazolo[1,5-a]pyridin-2-amine

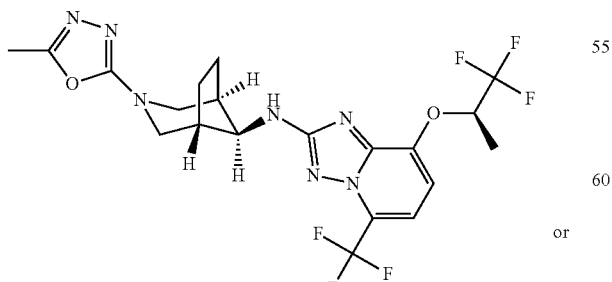

or

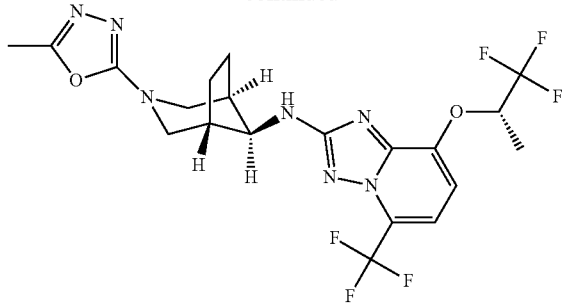 [SMILES: Cc1nnc(N2C[C@H]3CC[C@@H](C2)[C@@H]3Nc2nc3c(OC(C)C(F)(F)F)ccc(C(F)(F)F)n3n2)o1]

Intermediate 3

2-Bromo-5-(trifluoromethyl)-8-[(1R or 1S)-2,2,2-trifluoro-1-methyl-ethoxy]-[1,2,4]triazolo[1,5-a]pyridine

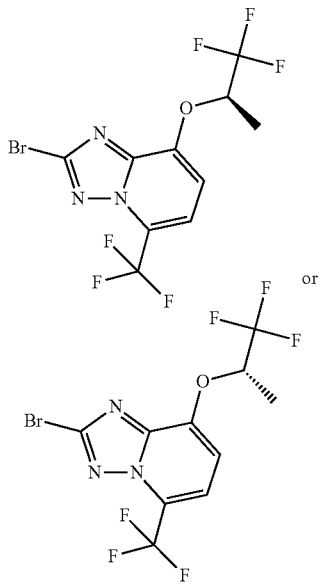

Step 1

5-(trifluoromethyl)-8-[(1R or 1S)-2,2,2-trifluoro-1-methyl-ethoxy]-[1,2,4]triazolo[1,5-a]pyridin-2-amine

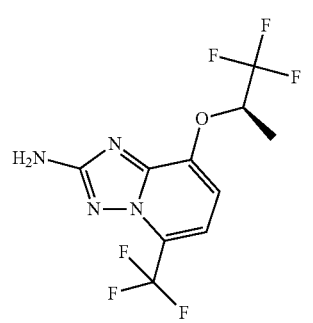

or

-continued

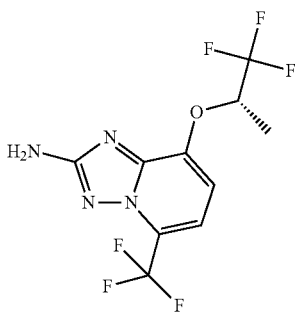

The title compound was obtained by chiral HPLC separation (Chiralpak AD, mobile phase heptane/ethanol/isopropanol) of racemic 5-(trifluoromethyl)-8-(2,2,2-trifluoro-1-methyl-ethoxy)-[1,2,4]triazolo[1,5-a]pyridin-2-amine (730 mg), product of example 74, step 1, as an off-white solid. The enantiomer A (283 mg, 38.75%) has a retention time of 7.4 min. under the indicated conditions. MS ES+ (m/z): 315.1 [(M+H)+].

Step 2

2-Bromo-5-(trifluoromethyl)-8-[(1R or 1S)-2,2,2-trifluoro-1-methyl-ethoxy]-[1,2,4]triazolo[1,5-a]pyridine

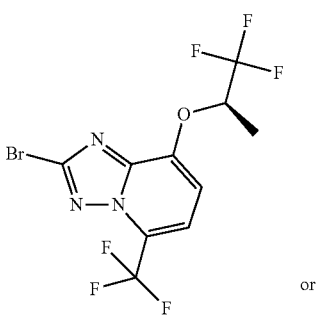

or

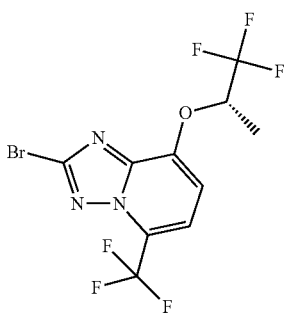

The title compound was prepared in analogy to intermediate 3 on example 1 (step 5) from 5-(trifluoromethyl)-8-[(1R or 1S)-2,2,2-trifluoro-1-methyl-ethoxy]-[1,2,4]triazolo[1,5-a]pyridin-2-amine (270 mg, 0.86 mmoles), tert-butyl nitrite and copper (II) bromide as a white solid (257 mg, 79.1% yield). MS ES+ (m/z): 377.9 [(M+H)+].

Final Coupling Step 3

N-[(8 endo)-3-(5-methyl-1,3,4-oxadiazol-2-yl)-3-azabicyclo[3.2.1]octan-8-yl]-5-(trifluoromethyl)-8-[(1R or 1S)-2,2,2-trifluoro-1-methyl-ethoxy]-[1,2,4]triazolo[1,5-a]pyridin-2-amine

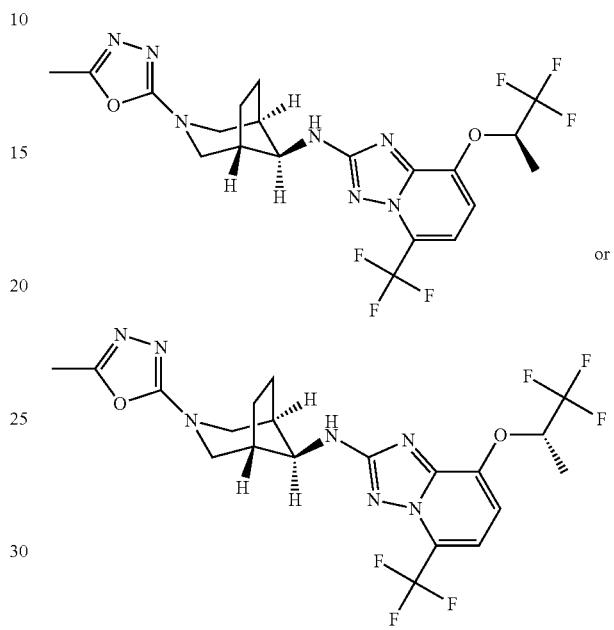

or

The title compound was prepared by Buchwald coupling in analogy to example 1, from 2-bromo-5-(trifluoromethyl)-8-[(1R or 1S)-2,2,2-trifluoro-1-methyl-ethoxy]-[1,2,4]triazolo[1,5-a]pyridine (30 mg, 79.4 µmol) and (8-endo)-3-(5-methyl-1,3,4-oxadiazol-2-yl)-3-azabicyclo[3.2.1]octan-8-amine (19.8 mg, 95.2 µmol) (intermediate 2 of example 41) with Pd$_2$(dba)$_3$.CHCl$_3$ in the presence of sodium t-butoxide and xantphos as a light yellow solid (24 mg, 60%). MS ES+ (m/z): 506.2 [(M+H)+].

EXAMPLE 76

N-[(8-endo)-3-(5-methyl-1,3,4-oxadiazol-2-yl)-3-azabicyclo[3.2.1]octan-8-yl]-5-(trifluoromethyl)-8-[(1S or 1R)-2,2,2-trifluoro-1-methyl-ethoxy]-[1,2,4]triazolo[1,5-a]pyridin-2-amine

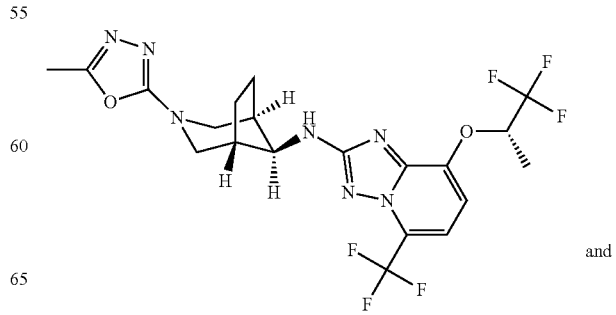

and

-continued

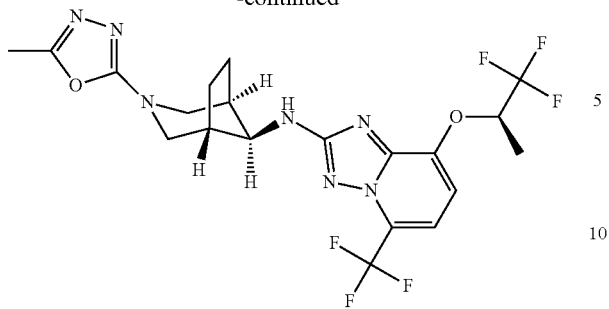

Intermediates 3

2-Bromo-5-(trifluoromethyl)-8-[(1S or 1R)-2,2,2-trifluoro-1-methyl-ethoxy]-[1,2,4]triazolo[1,5-a]pyridine

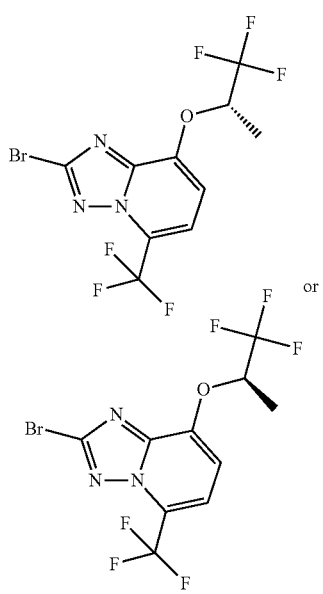

Step 1

5-(trifluoromethyl)-8-[(1S or 1R)-2,2,2-trifluoro-1-methyl-ethoxy]-[1,2,4]triazolo[1,5-a]pyridin-2-amine

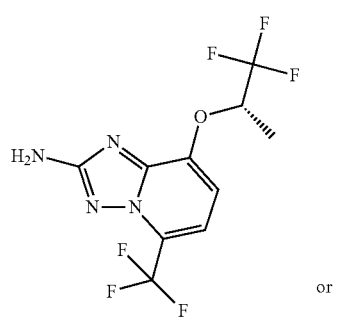

-continued

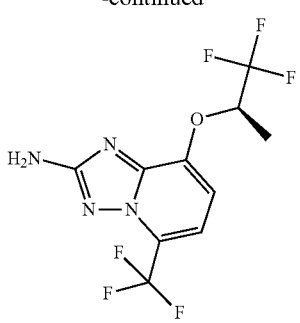

The title compound was obtained by chiral HPLC separation (Chiralpak AD, mobile phase heptane/ethanol/isopropanol) of racemic 5-(trifluoromethyl)-8-(2,2,2-trifluoro-1-methyl-ethoxy)-[1,2,4]triazolo[1,5-a]pyridin-2-amine (730 mg), product of example 74, step 1, as an off-white solid. This enantiomer B (321 mg, 41.75%) has a retention time of 8.48 min. under the mentioned conditions. MS ES$^+$ (m/z): 315.1 [(M+H)$^+$].

Step 2

2-bromo-5-(trifluoromethyl)-8-[(1S or 1R)-2,2,2-trifluoro-1-methyl-ethoxy]-[1,2,4]triazolo[1,5-a]pyridine

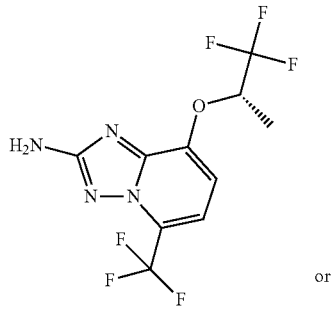

or

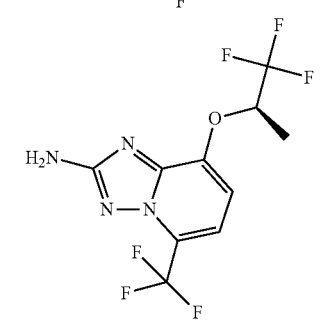

This enantiomer was prepared in analogy to example 1, intermediate 3, step 5, from 5-(trifluoromethyl)-8-[(1S or 1R)-2,2,2-trifluoro-1-methyl-ethoxy]-[1,2,4]triazolo[1,5-a]pyridin-2-amine (308 mg, 0.98 mmoles), tert-butyl nitrite and copper (II) bromide as a white solid (331 mg, 84.8% yield) MS ES+ (m/z): 377.9 [(M+H)$^+$].

Final Coupling Step 3

N-[(8-endo)-3-(5-methyl-1,3,4-oxadiazol-2-yl)-3-azabicyclo[3.2.1]octan-8-yl]-5-(trifluoromethyl)-8-[(1S or 1R)-2,2,2-trifluoro-1-methyl-ethoxy]-[1,2,4]triazolo[1,5-a]pyridin-2-amine

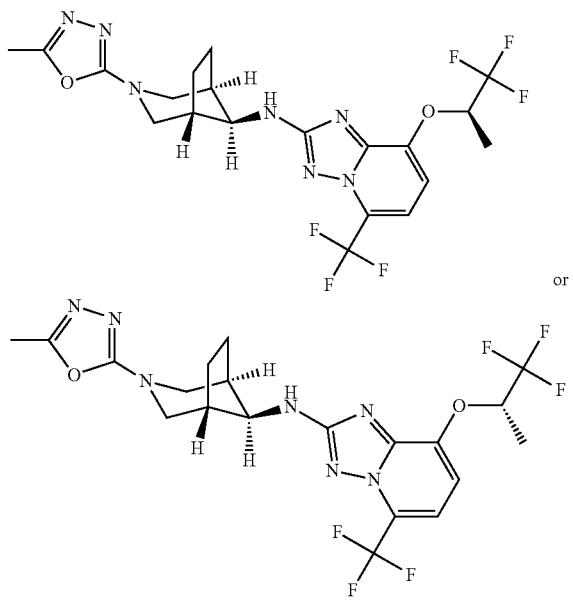

or

The title compound was prepared by Buchwald coupling in analogy to example 1, from 2-bromo-5-(trifluoromethyl)-8-[(1S or 1R)-2,2,2-trifluoro-1-methyl-ethoxy]-[1,2,4]triazolo[1,5-a]pyridine (30 mg, 79.4 µmol) and (8-endo)-3-(5-methyl-1,3,4-oxadiazol-2-yl)-3-azabicyclo[3.2.1]octan-8-amine (19.8 mg, 95.2 µmol) (intermediate 2 of example 41) with Pd$_2$(dba)$_3$.CHCl$_3$ in the presence of sodium t-butoxide and xantphos as a light yellow solid. (32.5 mg, 81%). MS ES+ (m/z): 506.2 [(M+H)$^+$].

EXAMPLE 77

N-[(8-endo)-3-(3-methylisoxazol-5-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

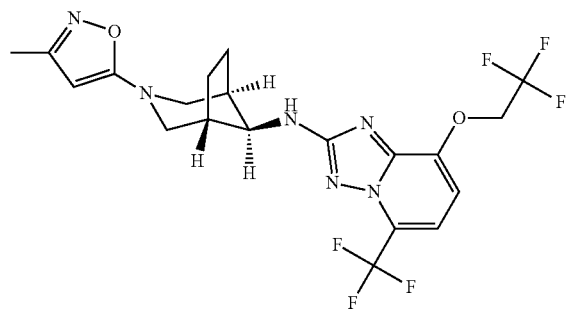 [SMILES: Cc1cc(N2C[C@H]3CC[C@@H](C2)[C@@H]3Nc2nc3c(OCC(F)(F)F)ccc(C(F)(F)F)n3n2)on1]

Step 1

Tert-butyl (8-endo)-[[8-(2,2,2-trifluoroethoxy)-5-(trifluoromethyl)-[1,2,4]triazolo[1,5-a]pyridin-2-yl]amino]-3-azabicyclo[3.2.1]octane-3-carboxylate

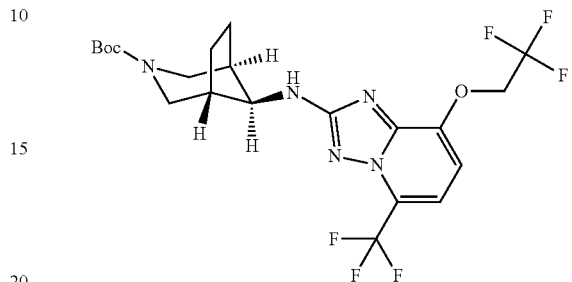

The title compound was prepared by Buchwald coupling in analogy to example 1, from 2-bromo-8-(2,2,2-trifluoroethoxy)-5-(trifluoromethyl)-[1,2,4]triazolo[1,5-a]pyridine (500 mg, 1.37 mmol) (intermediate 3 of example 71), tert-butyl (8 endo)-8-amino-3-azabicyclo[3.2.1]octane-3-carboxylate (373 mg, 1.65 mmol) (CAS Registry Number: 1330763-51-3) and sodium tert-butoxide (396 mg, 4.12 mmol) with Pd2(dba)3.CHCl$_3$ (114 mg, 110 µmol) in the presence of xantphos (127 mg, 220 µmol) in 1,4-dioxane (10 ml) at 145° C. during 30 min in a microwave. The compound was obtained as a light brown solid (303 mg, 43.3% yield).)

MS ES+ (m/z): 454.2 [((M–C$_4$H8)+H)+]

Step 2

N-[(8-endo)-3-azabicyclo[3.2.1]octan-8-yl]-8-(2,2,2-trifluoroethoxy)-5-(trifluoromethyl)-[1,2,4]triazolo[1,5-a]pyridin-2-amine

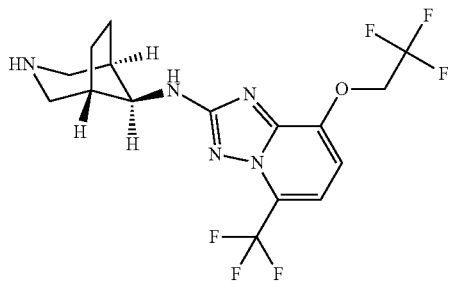 [SMILES: FC(F)(F)COc1ccc(C(F)(F)F)n2nc(N[C@@H]3[C@@H]4CC[C@H]3CNC4)nc12]

The title compound was prepared in analogy to example 42, step 2, from Tert-butyl (8-endo)-[[8-(2,2,2-trifluoroethoxy)-5-(trifluoromethyl)-[1,2,4]triazolo[1,5-a]pyridin-2-yl]amino]-3-azabicyclo[3.2.1]octane-3-carboxylate (300 mg, 589 µmol) by deprotection with TFA (671 mg, 5.89 mmol) in dichloromethane (10 ml) as a light brown solid (233 mg, 96.7%). MS ES+ (m/z): 410.1 [(M+H)+].

Step 3

N-[(8-endo)-3-(3-methylisoxazol-5-yl)-3-azabicyclo [3.2.1]octan-8-yl]-8-(2,2,2-trifluoroethoxy)-5-(trifluoromethyl)-[1,2,4]triazolo[1,5-a]pyridin-2-amine

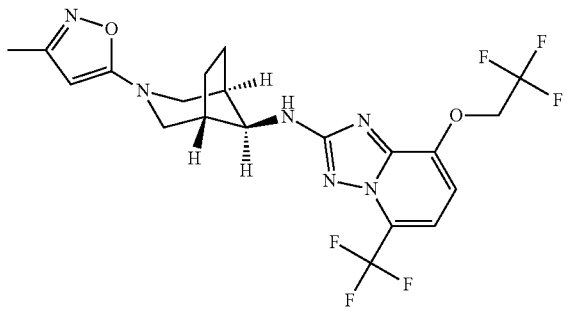

The title compound was prepared in analogy to example 42, step 3 from N-[8-endo-3-azabicyclo[3.2.1]octan-8-yl]-8-(2,2,2-trifluoroethoxy)-5-(trifluoromethyl)-[1,2,4]triazolo [1,5-a]pyridin-2-amine (230 mg, 562 µmol), 5-iodo-3-methylisoxazole (141 mg, 674 µmol), copper (I) iodide (10.7 mg, 56.2 µmol), tripotassium phosphate (239 mg, 1.12 mmol) and N,N-diethylsalicylamide (32.6 mg, 169 µmol) as an off-white solid (21.4 mg, 7.77%). MS ES+(m/z): 491.2 [(M+H)+].

EXAMPLE 78

N-[(8-endo)-3-(3-methylisoxazol-5-yl)-3-azabicyclo [3.2.1]octan-8-yl]-5-(trifluoromethyl)-8-[2,2,2-trifluoro-1-methyl-ethoxy]-[1,2,4]triazolo[1,5-a]pyridin-2-amine

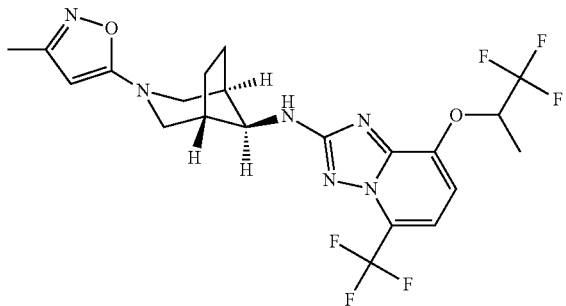 [SMILES: Cc1cc(N2C[C@H]3CC[C@@H](C2)[C@@H]3Nc2nc3c(OC(C)C(F)(F)F)ccc(C(F)(F)F)n3n2)on1]

Step 1

Tert-butyl (8-endo)-[5-(trifluoromethyl)-8-(2,2,2-trifluoro-1-methyl-ethoxy)-[1,2,4]triazolo[1,5-a] pyridin-2-yl]amino]-3-azabicyclo[3.2.1]octane-3-carboxylate

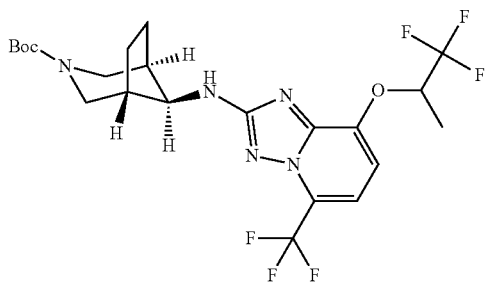 [SMILES: CC(Oc1ccc(C(F)(F)F)n2nc(N[C@@H]3[C@@H]4CC[C@H]3CN(C(=O)OC(C)(C)C)C4)nc12)C(F)(F)F]

The title compound was prepared by Buchwald coupling in analogy to example 1, from 2-bromo-5-(trifluoromethyl)-8-(2,2,2-trifluoro-1-methyl-ethoxy)-[1,2,4]triazolo[1,5-a] pyridine (200 mg, 529 µmol) (intermediate 3 from example 74), tert-butyl (8-endo)-8-amino-3-azabicyclo[3.2.1]octane-3-carboxylate (CAS Registry Number: 1330763-51-3) (144 mg, 635 µmol) and sodium tert-butoxide (102 mg, 1.06 mmol) with $Pd_2(dba)_3 \cdot CHCl_3$ (43.8 mg, 42.3 µmol) in the presence of xantphos (49 mg, 84.6 µmol) in 1,4-dioxane (3.5 ml) at 145° C. during 30 min in a microwave. The compound was obtained as a light yellow solid (211 mg, 76.2% yield).) MS ES+ (m/z): 524.2 [(M+H)+]

Step 2

N-[(8-endo)-3-azabicyclo[3.2.1]octan-8-yl]-5-(trifluoromethyl)-8-(2,2,2-trifluoro-1-methyl-ethoxy)-[1,2,4]triazolo[1,5-a]pyridin-2-amine

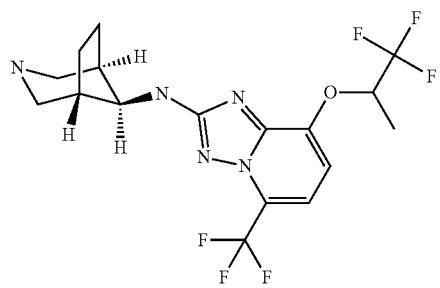 [SMILES: CC(Oc1ccc(C(F)(F)F)n2nc(N[C@@H]3[C@@H]4CC[C@H]3CNC4)nc12)C(F)(F)F]

The title compound was prepared in analogy to example 42, step 2, from Tert-butyl (8-endo)-[5-(trifluoromethyl)-8-(2,2,2-trifluoro-1-methy-1-ethoxy)-[1,2,4]triazolo[1,5-a] pyridin-2-yl]amino]-3-azabicyclo[3.2.1]octane-3-carboxylate (210 mg, 401 µmol) by deprotection with TFA (457 mg, 4.01 mmol) in dichlormethane (3 ml) as a light brown solid (164.2 mg, 96.7%). MS ES+(m/z): 424.2 [(M+H)+].

Step 3

N-[(8-endo)-3-(3-methylisoxazol-5-yl)-3-azabicyclo [3.2.1]octan-8-yl]-5-(trifluoromethyl)-8-[2,2,2-trifluoro-1-methyl-ethoxy]-[1,2,4]triazolo[1,5-a]pyridin-2-amine

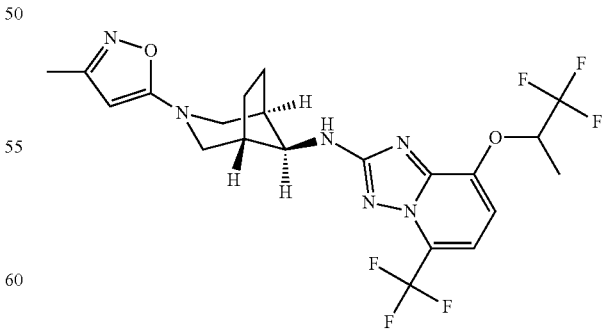

The title compound was prepared in analogy to example 42, step 3 from N-[(8-endo)-3-azabicyclo[3.2.1]octan-8-yl]-5-(trifluoromethyl)-8-(2,2,2-trifluoro-1-methyl-ethoxy)-[1, 2,4]triazolo[1,5-a]pyridin-2-amine (100 mg, 236 µmol), 5-iodo-3-methylisoxazole (59.2 mg, 283 µmol) in DMF (2.5 ml), copper (I) iodide (4.5 mg, 23.6 µmol), tripotassium phosphate (100 mg, 472 µmol) and N,N-diethylsalicylamide (13.7 mg, 70.9 µmol) as an light yellow solid (2.1 mg, 1.76%). MS ES+ (m/z): 505.2 [(M+H)+].

EXAMPLE 79

N-[(8-endo)-3-(3-methyl-1,2,4-oxadiazol-5-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

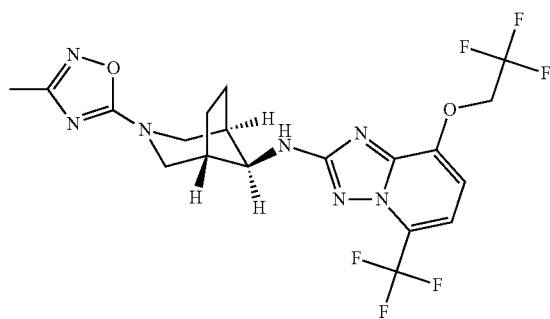 [SMILES: Cc1noc(N2C[C@H]3CC[C@@H](C2)[C@@H]3Nc2nc3c(OCC(F)(F)F)ccc(C(F)(F)F)n3n2)n1]

2-Bromo-8-(2,2,2-trifluoroethoxy)-5-(trifluoromethyl)-[1,2,4]triazolo[1,5-a]pyridine (80 mg, 220 mol), intermediate 3 of example 71, (8-endo)-3-(3-methyl-1,2,4-oxadiazol-5-yl)-3-azabicyclo[3.2.1]octan-8-amine (50.3 mg, 242 µmol), intermediate 2 of example 49, and sodium tert-butoxide (42.2 mg, 440 µmol) were added to 1,4-dioxane (2.5 ml) and degassed with argon in an ultra sound bath. Then dibromobis(tri-tert-butylphosphine)dipalladium(I) (17.1 mg, 22 µmol) was added and the reaction mixture and degassed with argon in an ultra sound bath. The vial was closed and heated to 110° C. for 2 hours. TLC and LC/MS showed that the reaction was completed. The reaction mixture was extracted with saturated NaHCO₃ (10 ml) and DCM (3×10 ml). The organic phase was dried with MgSO₄ and then removed in vacuo. The crude material was purified by flash chromatography (silica gel, 12 g, gradient: 0% to 80% EtOAc in heptane) to give the title compound (45.5 mg, 42% yield) as white solid. MS ES+ (m/z): 492.3 [(M+H)+].

EXAMPLE 80

N-[(8-endo)-3-(3-methyl-1,2,4-oxadiazol-5-yl)-3-azabicyclo[3.2.1]octan-8-yl]-5-(trifluoromethyl)-8-(2,2,2-trifluoro-1-methyl-ethoxy)-[1,2,4]triazolo[1,5-a]pyridin-2-amine

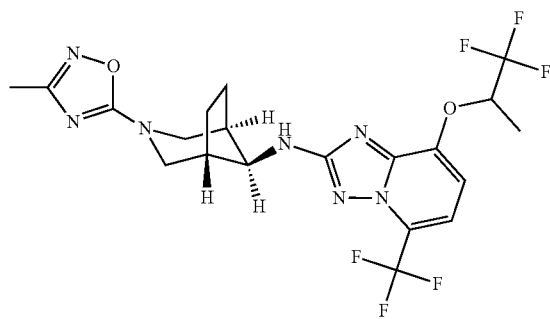 [SMILES: Cc1noc(N2C[C@H]3CC[C@@H](C2)[C@@H]3Nc2nc3c(OC(C)C(F)(F)F)ccc(C(F)(F)F)n3n2)n1]

Step 1

(8 endo)-[5-(trifluoromethyl)-8-(2,2,2-trifluoro-1-methyl-ethoxy)-[1,2,4]triazolo[1,5-a]pyridin-2-yl]amino]-3-azabicyclo[3.2.1]octane-3-carbonitrile

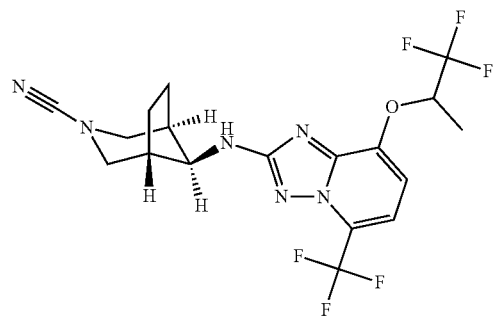 [SMILES: CC(Oc1ccc(C(F)(F)F)n2nc(N[C@@H]3[C@@H]4CC[C@H]3CN(C#N)C4)nc12)C(F)(F)F]

The title compound was prepared in analogy to example 46, step 1, from N-[(8-endo)-3-azabicyclo[3.2.1]octan-8-yl]-5-(trifluoromethyl)-8-((1,1,1-trifluoropropan-2-yl)oxy]-[1,2,4]triazolo[1,5-a]pyridin-2-amine (61 mg, 144 µmol) (prepared in example 78, step 2) and cyanogen bromide (16.8 mg, 158 µmol) with sodium bicarbonate (13.3 mg, 158 µmol) in EtOH (1.5 ml) to give the desired product (59.1 mg, 91.6% yield) as a light yellow solid. MS ES+(m/z): 449.2 [(M+H)+].

Step 2

N-[(8 endo)-3-(3-methyl-1,2,4-oxadiazol-5-yl)-3-azabicyclo[3.2.1]octan-8-yl]-5-(trifluoromethyl)-8-(2,2,2-trifluoro-1-methyl-ethoxy)-[1,2,4]triazolo[1,5-a]pyridin-2-amine

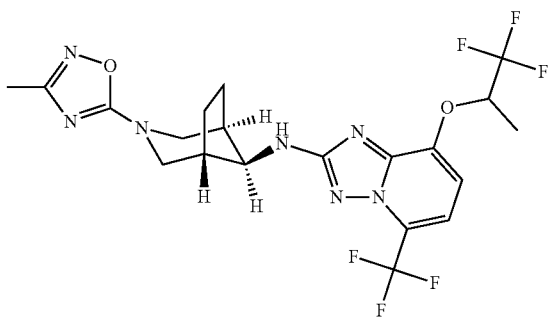 [SMILES: Cc1noc(N2C[C@H]3CC[C@@H](C2)[C@@H]3Nc2nc3c(OC(C)C(F)(F)F)ccc(C(F)(F)F)n3n2)n1]

The title compound was obtained in analogy to example 46, step 2, from (8 endo)-[5-(trifluoromethyl)-8-(2,2,2-trifluoro-1-methyl-ethoxy)-[1,2,4]triazolo[1,5-a]pyridin-2-yl]amino]-3-azabicyclo[3.2.1]octane-3-carbonitrile (56 mg, 125 mmol), N-hydroxyacetamidine (11.1 mg, 150 µmol), zinc chloride (20.4 mg, 150 µmol) in ethanol (1.35 ml) as a white solid (56 mg, 89% yield). MS ES+ (m/z): 506.2 [(M+H)+].

EXAMPLE 81

N-[(8-endo)-3-(3-methyl-1,2,4-oxadiazol-5-yl)-3-azabicyclo[3.2.1]octan-8-yl]-5-(trifluoromethyl)-8-[(1R or 1S)-2,2,2-trifluoro-1-methyl-ethoxy]-[1,2,4]triazolo[1,5-a]pyridin-2-amine

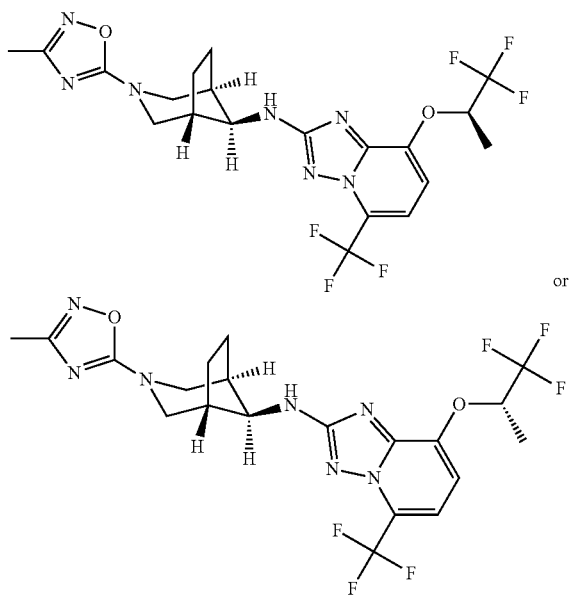

or

The title compound was prepared by Buchwald coupling in analogy to example 79 from 2-bromo-5-(trifluoromethyl)-8-[(1R or 1S)-2,2,2-trifluoro-1-methyl-ethoxy]-[1,2,4]triazolo[1,5-a]pyridine, enantiomer A of example 75 step 2, (30 mg, 79.4 μmol) and (8-endo)-3-(3-methyl-1,2,4-oxadiazol-5-yl)-3-azabicyclo[3.2.1]octan-8-amine, intermediate 2 of example 49 (18.2 mg, 87.3 μmol) in the presence of sodium tert-butoxide (15.6 mg, 163 μmol) and dibromobis(tri-tert-butylphosphine)dipalladium(I) (6.17 mg, 7.94 μmol) as a white solid (20.4 mg, 50.9%). MS ES+ (m/z): 506.2 [(M+H)+].

EXAMPLE 82

N-[(8 endo)-3-(1-methylpyrazol-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

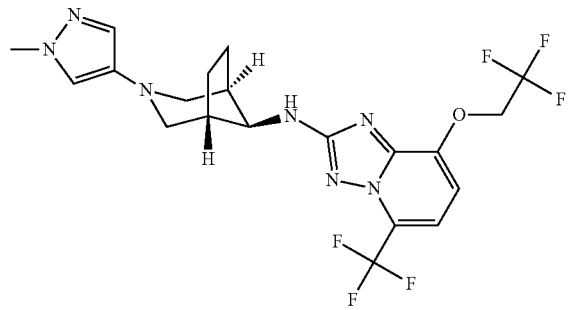 [SMILES: Cn1cc(N2C[C@H]3CC[C@@H](C2)[C@@H]3Nc2nc3c(OCC(F)(F)F)ccc(C(F)(F)F)n3n2)cn1]

Intermediate 2

(8 endo)-3-(1-methylpyrazol-4-yl)-3-azabicyclo[3.2.1]octan-8-amine

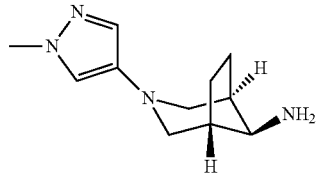

Step 1

Tert-butyl N-[(8-endo)-3-(1-methylpyrazol-4-yl)-3-azabicyclo[3.2.1]octan-8-yl]carbamate

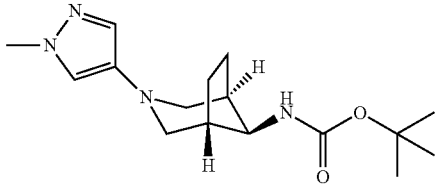 [SMILES: Cn1cc(N2C[C@H]3CC[C@@H](C2)[C@@H]3NC(=O)OC(C)(C)C)cn1]

A solution of 4-bromo-1-methyl-pyrazole (1.28 g, 7.95 mmol), tert-butyl N-[(8-endo)-3-azabicyclo[3.2.1]octan-8-yl]carbamate (0.45 g, 1.98 mmol), described in WO 2012116965, and NaOtBu (572.64 mg, 5.96 mmol) in toluene (15 ml) was degassed with argon. Brett-phos palladacycle (635.3 mg, 0.795 mmol) was added under argon. The reaction mixture was heated at 100° C. in microwave oven for 45 min. The crude material obtained was purified by column chromatography using 30% ethylacetate in hexane to afford (42 mg, 12.31% yield) of the desired compound as a yellow solid. ES+ (m/z): 307.1 [(M+H)+].

Step 2

(8 endo)-3-(1-methylpyrazol-4-yl)-3-azabicyclo[3.2.1]octan-8-amine

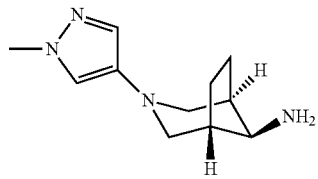

Tert-butyl N-[(8-endo)-3-(1-methylpyrazol-4-yl)-3-azabicyclo[3.2.1]octan-8-yl]carbamate (42 mg, 137 umol) in dichloromethane was stirred at 25° C. along with TFA (0.6 ml) for 7 h until TLC showed completion of reaction. The solvent was then evaporated under reduced pressure, toluene was added and evaporated several times. The residue was purified by column chromatography with 2% MeOH in dichloromethane as eluent to give the desired compound (28.3 mg, 91.8%) as a brown solid. ES+ (m/z): 207.1 [(M+H)+].

Final Coupling Step 3

N-[(8-endo)-3-(1-methylpyrazol-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

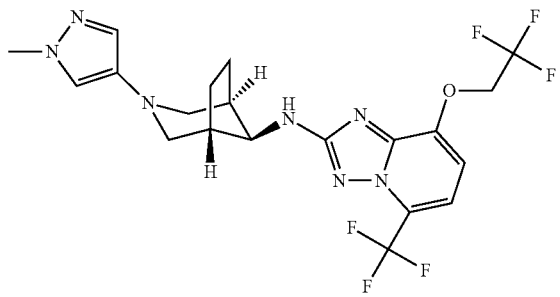 [SMILES: Cn1cc(N2C[C@H]3CC[C@@H](C2)[C@@H]3Nc2nc3c(OCC(F)(F)F)ccc(C(F)(F)F)n3n2)cn1]

The title compound, was prepared by Buchwald coupling in analogy to example 1, from 2-bromo-8-(2,2,2-trifluoroethoxy)-5-(trifluoromethyl)-[1,2,4]triazolo[1,5-a]pyridine (30 mg, 82.4 μmol), intermediate 2 of example 72, and (8-endo)-3-(1-methyl-1H-pyrazol-4-yl)-3-azabicyclo[3.2.1]octan-8-amine (20.4 mg, 98.9 μmol) with Pd$_2$(dba)$_3$.CHCl$_3$ in the presence of sodium t-butoxide and xantphos as a light yellow solid (12.3 mg, 30.5%).

MS ES+ (m/z): 490.2 [(M+H)+]

EXAMPLE 83

8-(2,2,2-trifluoroethoxy)-5-(trifluoromethyl)-N-[(8-endo)-3-[2-(trifluoromethyl)-4-pyridyl]-3-azabicyclo[3.2.1]octan-8-yl]-[1,2,4]triazolo[1,5-a]pyridin-2-amine

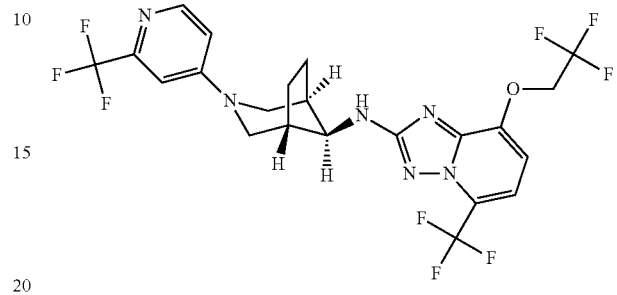

The title compound, was prepared by Buchwald coupling in analogy to example 1, from of 2-bromo-8-(2,2,2-trifluoroethoxy)-5-(trifluoromethyl)-[1,2,4]triazolo[1,5-a]pyridine (20 mg, 54.9 mol) intermediate 3 of example 71, and (8-endo)-3-(2-(trifluoromethyl)pyridin-4-yl)-3-azabicyclo[3.2.1]octan-8-amine (17.9 mg, 65.9 μmol) (intermediate 2 of example 62) with Pd$_2$(dba)$_3$.CHCl$_3$ in the presence of sodium t-butoxide and xantphos as a light yellow solid (15.1 mg, 49.6% yield). MS ES+ (m/z): 555.2 [(M+H)+]

According to the procedure described for the synthesis of example 83, further derivatives have been synthesized by Buchwald coupling from the respective intermediates 2 and intermediates 3. They comprise examples 84 to 91 of table 9.

| Example | | Systematic name Yield of reaction | Starting materials | MW found (M + H)+ |
|---|---|---|---|---|
| 84 | | 5-(trifluoromethyl)-8-(2,2,2-trifluoro-1-methyl-ethoxy)-N-[(8-endo)-3-[2-(trifluoromethyl)-4-pyridyl]-3-azabicyclo[3.2.1]octan-8-yl]-[1,2,4]triazolo[1,5-a]pyridin-2-amine (38.2 mg, 84.7% yield ) | 2-bromo-5-(trifluoromethyl)-8-((1,1,1-trifluoropropan-2-yl)oxy)-[1,2,4]triazolo[1,5-a]pyridine (30 mg, 79.4 μmol,) (intermediate III, example 74) and (8-endo)-3-(2-(trifluoromethyl)pyridin-4-yl)-3-azabicyclo[3.2.1]octan-8-amine (25.8 mg, 95.2 μmol)(intermediate II, example 62 | 569.2 |
| 85 | | N-[(8-endo)-3-(6-methylpyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine (40.8 mg, 74.1% yield) | 2-bromo-8-(2,2,2-trifluoroethoxy)-5-(trifluoromethyl)-[1,2,4]triazolo[1,5-a]pyridine (40 mg, 110 μmol), (intermediate III example 71) and (8-endo)-3-(6-methylpyrimidin-4-yl)-3-azabicyclo[3.2.1]octan-8-amin (28.8 mg, 132 μmol), (intermediate II, example 50) | 502.2 |

-continued

| Example | Systematic name Yield of reaction | Starting materials | MW found (M + H)+ |
|---|---|---|---|
| 86 | N-[(8-endo)-3-(5-fluoropyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine (63.2 mg, 25.3% yield) | 2-bromo-8-(2,2,2-trifluoroethoxy)-5-(trifluoromethyl)-[1,2,4]triazolo[1,5-a]pyridine (45.5 mg, 125 μmol,) (intermediate III, example 71) and (8-endo)-3-(5-fluoropyrimidin-4-yl)-3-azabicyclo[3.2.1]octan-8-amine (27.8 mg, 125 μmol), (intermediate II, example 58) | 506.15 |
| 87 | N-[(8-endo)-3-(5-fluoro-2-methyl-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine (24 mg, 56.2% yield) | 2-bromo-8-(2,2,2-trifluoroethoxy)-5-(trifluoromethyl)-[1,2,4]triazolo[1,5-a]pyridine (30 mg, 82.4 μmol), (intermediate III, example 71) and (8-endo)-3-(5-fluoro-2-methylpyridin-4-yl)-3-azabicyclo[3.2.1]octan-8-amine (23.3 mg, 98.9 μmol) (intermediate II, example 70 | 519.2 |
| 88 | N-[(8-endo)-3-(5-fluoro-6-methyl-pyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine amine (42.8 mg, 68.2% yield) | 2-bromo-8-(2,2,2-trifluoroethoxy)-5-(trifluoromethyl)-[1,2,4]triazolo[1,5-a]pyridine (30 mg, 82.4 μmol), (intermediate III example 71) and (8-endo)-3-(5-fluoro-6-methylpyrimidin-4-yl)-3-azabicyclo[3.2.1]octan-8-amine (23.4 mg, 98.9 μmol), (intermediate II of example 59) | 520.2 |
| 89 | N-[(8-endo)-3-(2-chloro-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine (42.9 mg, 58.9% yield) | 2-bromo-8-(2,2,2-trifluoroethoxy)-5-(trifluoromethyl)-[1,2,4]triazolo[1,5-a]pyridine (30 mg, 82.4 μmol), (intermediate III example 71) and (8-endo)-3-(2-chloropyridin-4-yl)-3-azabicyclo[3.2.1]octan-8-amine (21.5 mg, 90.6 μmol), (intermediate II of example 69) | 521.2 |

-continued

| Example | Systematic name Yield of reaction | Starting materials | MW found (M + H)+ |
|---|---|---|---|
| 90 | N-[(8 endo)-3-(3-fluoro-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine (41.6 mg, 71.5% yield) | 2-bromo-8-(2,2,2-trifluoroethoxy)-5-(trifluoromethyl)-[1,2,4]triazolo[1,5-a]pyridine (30 mg, 82.4 µmol), (intermediate III example 71) and (8-endo)-3-(3-fluoropyridin-4-yl)-3-azabicyclo[3.2.1]octan-8-amine (21.9 mg, 98.9 µmol), (intermediate II, example 68) | 505.2 |
| 91 | N-[(8-endo)-3-(6-chloropyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine (10.3 mg, 24% yield) | 2-bromo-8-(2,2,2-trifluoroethoxy)-5-(trifluoromethyl)-[1,2,4]triazolo[1,5-a]pyridine (30 mg, 82.4 µmol), (intermediate III example 71) and (8-endo)-3-(6-chloropyrimidin-4-yl)-3-azabicyclo[3.2.1]octan-8-amine (23.6 mg, 98.9 µmol), (intermediate II, example 61) | 522.3 |

EXAMPLE 92

N-[(8-endo)-3-pyrimidin-4-yl-3-azabicyclo[3.2.1]octan-8-yl]-8-(2,2,2-trifluoroethoxy)-5-(trifluoromethyl)-[1,2,4]triazolo[1,5-a]pyridin-2-amine

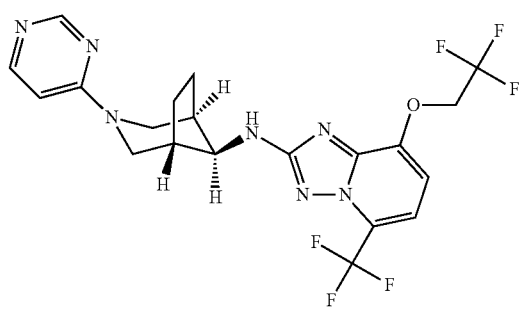 [SMILES: FC(F)(F)COc1ccc(C(F)(F)F)n2nc(N[C@@H]3[C@@H]4CC[C@H]3CN(c3ccncn3)C4)nc12]

To a light yellow solution of N-[8-endo)-3-azabicyclo[3.2.1]octan-8-yl]-8-(2,2,2-trifluoroethoxy)-5-(trifluoromethyl)-[1,2,4]triazolo[1,5-a]pyridin-2-amine (30 mg, 73.3 µmol) intermediate of example 77, step 2, in ethanol (1 ml) under argon was added triethylamine (29.7 mg, 293 µmol) followed by 4-chloropyrimidine hydrochloride (16.6 mg, 110 µmol). The vial was closed under argon and the reaction mixture was stirred over night at 10° C. TLC and LC-MS showed the reaction was complete. The reaction mixture was concentrated in vacuo. The crude material was purified by flash chromatography (silica gel, 12 g, 0% to 10% MeOH in DCM) to afford the title compound (32.9 mg, 92.1% yield) as a white powder. MS ES+ (m/z): 488.2 [(M+H)+]

EXAMPLE 93

N-[(8-endo)-3-(5-fluoro-2-methyl-pyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

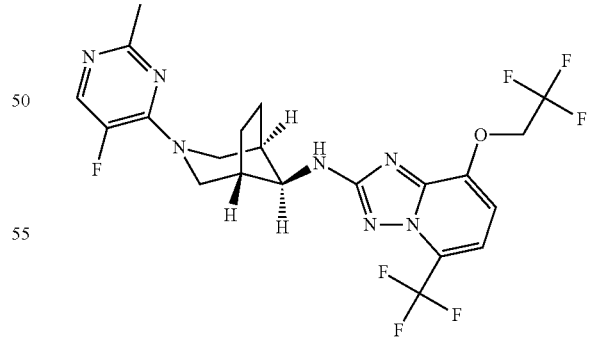

To a light yellow solution of N-[(8-endo)-3-azabicyclo[3.2.1]octan-8-yl]-8-(2,2,2-trifluoroethoxy)-5-(trifluoromethyl)-[1,2,4]triazolo[1,5-a]pyridin-2-amine (30 mg, 73.3 µmol), intermediate of example 77, step 2 in ethanol (1 ml) and under argon was added triethylamine (29.7 mg, 293 µmol) followed by 4-chloro-5-fluoro-2-methylpyrimidine (16.1 mg, 110 µmol). The vial was closed under argon and reaction mixture was stirred over night at 100° C. TLC and LC-MS showed the reaction was complete. The reaction mixture was concentrated in vacuo and the material was purified twice by flash chromatography (silica gel, 12 g, 0% to 60% EtOAc in heptane) to afford the title compound (25.5 mg, 67% yield) as a white solid. MS ES+(m/z): 520.2 [(M+H)+]

EXAMPLE 94

N-[(8-endo-3-(6-methoxypyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

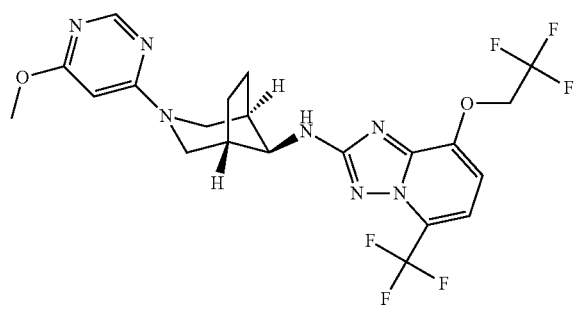 [SMILES: COc1cc(N2C[C@H]3CC[C@@H](C2)[C@@H]3Nc2nc3c(OCC(F)(F)F)ccc(C(F)(F)F)n3n2)ncn1]

Intermediate 2

(8-endo)-3-(6-methoxypyrimidin-4-yl)-3-azabicyclo[3.2.1]octan-8-amine

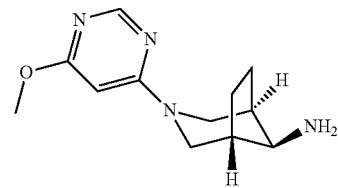 [SMILES: COc1cc(N2C[C@H]3CC[C@@H](C2)[C@@H]3N)ncn1]

Step 1 tert-butyl N-[(8-endo)-3-(6-methoxypyrimidin-4-yl)-3-azabicyclo[3.2.1]octan-8-yl]carbamate

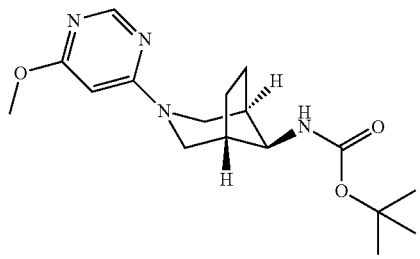 [SMILES: COc1cc(N2C[C@H]3CC[C@@H](C2)[C@@H]3NC(=O)OC(C)(C)C)ncn1]

To a light yellow solution of tert-butyl N-[(8 endo)-3-azabicyclo[3.2.1]octan-8-yl]carbamate (250 mg, 1.1 mmol), (CAS Registry Number: 1330763-51-3), in DMF (5 ml) was added K₂CO₃ (458 mg, 3.31 mmol) followed by 4-iodo-6-methoxypyrimidine (391 mg, 1.66 mmol). The vial was closed under argon and the reaction mixture was stirred at 100° C. over night. LC-MS showed the reaction was complete. The reaction mixture was diluted with 20 mL H₂O and extracted with DCM (3×25 mL). The organic layers were dried over MgSO₄ and concentrated in vacuo. The crude material was purified by flash chromatography (silica gel, 25 g, 0% to 60% EtOAc in heptane) to afford the title compound (315 mg, 85.3% yield) as a white powder. MS ES+ (m/z): 335.2 [(M+H)+]

Step 2

(8-endo)-3-(6-methoxypyrimidin-4-yl)-3-azabicyclo[3.2.1]octan-8-amine

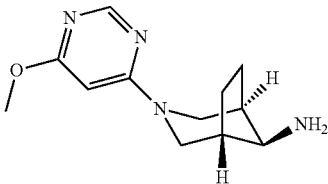 [SMILES: COc1cc(N2C[C@H]3CC[C@@H](C2)[C@@H]3N)ncn1]

To a light yellow solution of tert-butyl N-[(8-endo)-3-(6-methoxypyrimidin-4-yl)-3-azabicyclo[3.2.1]octan-8-yl]carbamate (330 mg, 987 µmol) (CAS Registry Number: 1330763-51-3) in DCM (5 ml) under argon was added TFA (1.13 g, 760 µl, 9.87 mmol). The reaction mixture was stirred over night at room temp. TLC and LC-MS showed the reaction was complete. The reaction mixture was quenched with 20 mL sat NaHCO₃ and extracted with DCM (3×20 mL). The organic layers were dried over MgSO₄ and concentrated in vacuo to obtain the title compound (222 mg, 96% yield) as light brown solid. MS ES+ (m/z): 235.2 [(M+H)+]

Final Coupling Step 3

N-[(8-endo)-3-(6-methoxypyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

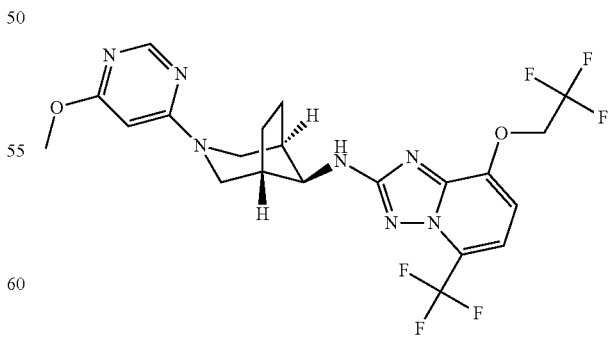

The title compound, was prepared by Buchwald coupling in analogy to example 1, from of 2-bromo-8-(2,2,2-trifluoroethoxy)-5-(trifluoromethyl)-[1,2,4]triazolo[1,5-a]pyridine (30 mg, 82.4 mol) intermediate 3 of example 71, and (8-endo)-3-(6-methoxypyrimidin-4-yl)-3-azabicyclo[3.2.1]octan-8-amine (23.2 mg, 98.9 μmol) with Pd$_2$(dba)$_3$.CHCl3 in the presence of sodium t-butoxide and xantphos as a white solid (34.8 mg, 81.6% yield). MS ES+ (m/z): 518.2 [(M+H)+]

EXAMPLE 95

N-[(8 endo)-3-(2-chloro-6-methyl-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine

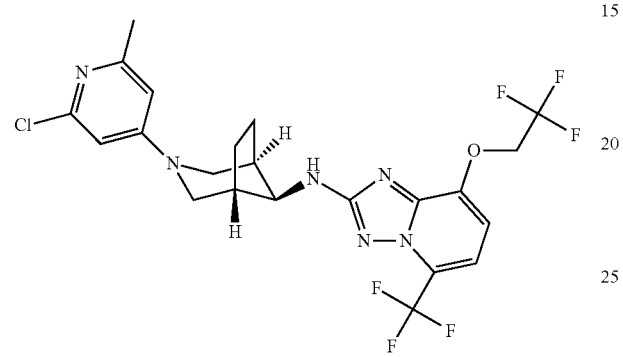

Intermediate 2

(8-endo)-3-(2-chloro-6-methyl-4-pyridyl)-3-azabicyclo[3.2.1]octan-8-amine

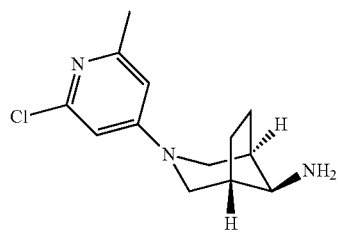 [SMILES: Cc1cc(N2C[C@H]3CC[C@@H](C2)[C@@H]3N)cc(Cl)n1]

Step 1 tert-butyl N-[(8-endo)-3-(2-chloro-6-methyl-4-pyridyl)-3-azabicyclo[3.2.1]octan-8-yl]carbamate

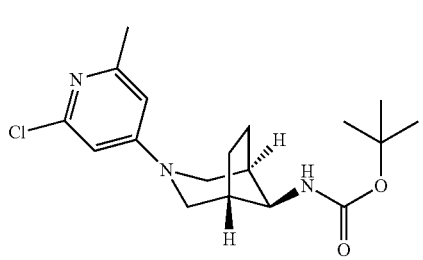 [SMILES: Cc1cc(N2C[C@H]3CC[C@@H](C2)[C@@H]3NC(=O)OC(C)(C)C)cc(Cl)n1]

To a light yellow solution of tert-butyl N-[(8-endo)-3-azabicyclo[3.2.1]octan-8-yl]carbamate (200 mg, 884 μmol) (CAS Registry Number: 1330763-51-3) in NMP (2 ml) was added under argon DIPEA (228 mg, 309 μl, 1.77 mmol) followed by 2,4-dichloro-6-methylpyridine (215 mg, 1.33 mmol). The vial was closed under argon and the reaction mixture was stirred over night at 150° C. TLC and LC-MS showed the reaction was complete. The reaction mixture was diluted with 15 mL H$_2$O and extracted with EtOAc (2×15 mL). The organic layer was back-extracted with saturated NaCl (1×15 mL). The organic layers were dried over MgSO$_4$ and concentrated in vacuo. The crude material was purified by flash chromatography (silica gel, 12 g, 0% to 100% EtOAc in heptane) to afford the title compound as a white solid (113 mg, 321 μmol, 36.3% yield). MS ES+ (m/z): 352.2 [(M+H)+]

Step 2

(8-endo-)-3-(2-chloro-6-methylpyridin-4-yl)-3-azabicyclo[3.2.1]octan-8-amine

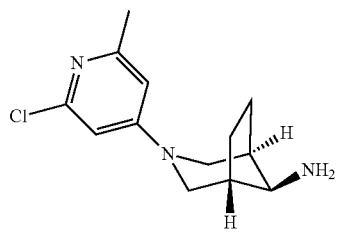 [SMILES: Cc1cc(N2C[C@H]3CC[C@@H](C2)[C@@H]3N)cc(Cl)n1]

To a light yellow solution of tert-butyl N-[(8-endo)-3-(2-chloro-6-methyl-4-pyridyl)-3-azabicyclo[3.2.1]octan-8-yl]carbamate (110 mg, 313 μmol) in DCM (1.5 ml) was added HCl 37% (185 mg, 154 μl, 1.88 mmol). The reaction mixture was stirred at room temp for 2 hours. TLC and LC-MS showed the reaction was complete. The reaction mixture was quenched with 10 mL sat NaHCO$_3$ and extracted with DCM (6×15 mL). The organic layers were dried over MgSO$_4$ and concentrated in vacuo to obtain the title compound as light yellow solid (75 mg, 95.3% yield). MS ES+ (m/z): 252.2 [(M+H)+]

Final Coupling Step 3

N-[8-endo-3-(2-chloro-6-methyl-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine

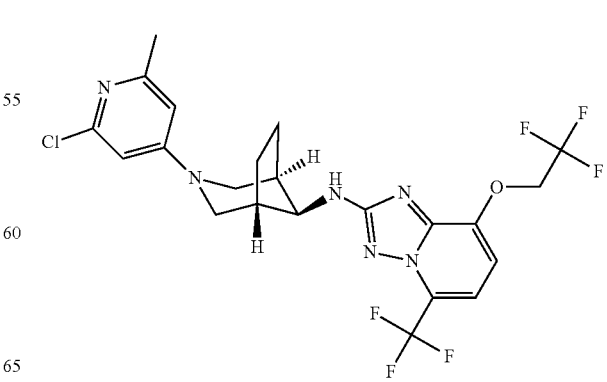

The title compound, was prepared by Buchwald coupling in analogy to example 1, from of 2-bromo-8-(2,2,2-trifluoroethoxy)-5-(trifluoromethyl)-[1,2,4]triazolo[1,5-a]pyridine (30 mg, 82.4 μmol) intermediate 3 of example 71, (8-endo)-3-(2-chloro-6-methylpyridin-4-yl)-3-azabicyclo[3.2.1]octan-8-amine (24.9 mg, 98.9 μmol) with Pd$_2$(dba)3.CHCl$_3$ in the presence of sodium t-butoxide and xantphos (7.63 mg, 13.2 μmol) as a light yellow solid (7.1 mg, 16.1% yield). MS ES+ (m/z): 535.2 [(M+H)+]

EXAMPLE 96

N-[(8-endo)-3-(6-fluoropyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

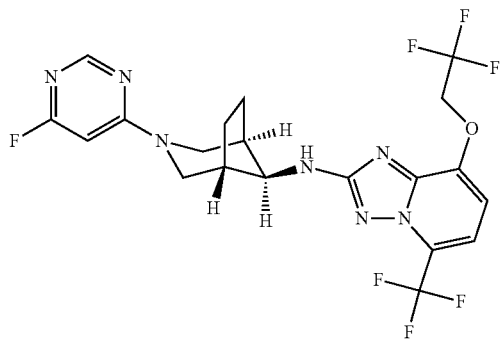 [SMILES: Fc1cc(N2C[C@H]3CC[C@@H](C2)[C@@H]3Nc2nc3c(OCC(F)(F)F)ccc(C(F)(F)F)n3n2)ncn1]

Intermediate 2

(8-endo)-3-(6-fluoropyrimidin-4-yl)-3-azabicyclo[3.2.1]octan-8-amine

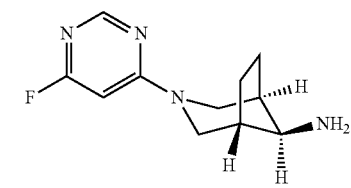 [SMILES: N[C@@H]1[C@@H]2CC[C@H]1CN(c1cc(F)ncn1)C2]

Step 1

Tert-butyl N-[(8-endo)-3-(6-fluoropyrimidin-4-yl)-3-azabicyclo[3.2.1]octan-8-yl]carbamate

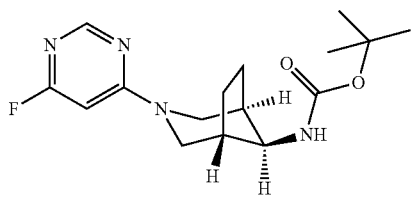 [SMILES: CC(C)(C)OC(=O)N[C@@H]1[C@@H]2CC[C@H]1CN(c1cc(F)ncn1)C2]

To a solution of 4,6-difluoropyrimidine (154 mg, 1.33 mmol) in ethanol (10 ml) under argon was added tert-butyl N-[(8-endo)-3-azabicyclo[3.2.1]octan-8-yl]carbamate (200 mg, 884 μmol) (CAS Registry Number: 1330763-51-3) followed by triethylamine (358 mg, 493 μl, 3.53 mmol). The reaction mixture was stirred at 100° C. over night. TLC showed the reaction was complete. The crude reaction mixture was concentrated in vacuo and then extracted with H$_2$O (10 ml) and DCM (3×20 ml) The crude material was purified by flash chromatography (silica gel, 24 g, 0% to 70% EtOAc in heptane) to afford the title compound as a white solid (247.3 mg, 86.8% yield). MS ES+ (m/z): 323.2 [(M+H)+]

Step 2

(8-endo)-3-(6-fluoropyrimidin-4-yl)-3-azabicyclo[3.2.1]octan-8-amine

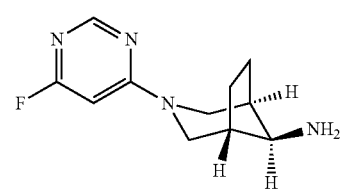 [SMILES: N[C@@H]1[C@@H]2CC[C@H]1CN(c1cc(F)ncn1)C2]

To a light yellow solution of tert-butyl N-[(8-endo)-3-(6-fluoropyrimidin-4-yl)-3-azabicyclo[3.2.1]octan-8-yl]carbamate (239.5 mg, 743 μmol) in DCM (4.0 ml) was added HCl 37% (439 mg, 366 μl, 4.46 mmol). The reaction mixture was stirred at room temp over 3 hours. TLC and LC-MS showed the reaction was complete. The reaction was then was quenched with NaOH (32%) to pH 10. The mixture was diluted with 5 mL H$_2$O and extracted with DCM (7×15 mL). The organic layers were dried over MgSO$_4$ and concentrated in vacuo to obtain the title compound as a white powder (148.4 mg, 89.9% yield). MS ES+ (m/z): 223.2 [(M+H)+]

Final Coupling Step 3

N-[8-endo-3-(6-fluoropyrimidin-4-yl)-3-azabicyclo[3.2.1]octan-8-yl]-8-(2,2,2-trifluoroethoxy)-5-(trifluoromethyl)-[1,2,1]triazolo[1,5-a]pyridin-2-amine

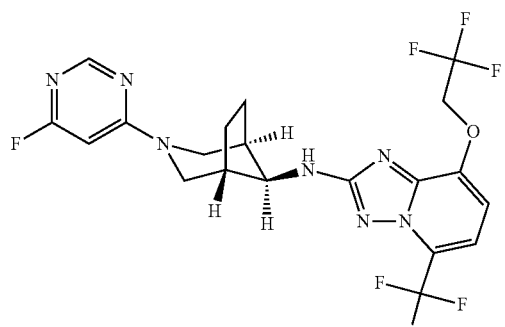

The title compound, was prepared by Buchwald coupling in analogy to example 1, from of 2-bromo-8-(2,2,2-trifluoroethoxy)-5-(trifluoromethyl)-[1,2,4]triazolo[1,5-a]pyridine (30 mg, 82.4 μmol) intermediate 3 of example 71, ((8-endo)-3-(6-fluoropyrimidin-4-yl)-3-azabicyclo[3.2.1]octan-8-amine (20.1 mg, 90.6 μmol) with Pd$_2$(dba)$_3$. CHCl$_3$ (6.82 mg, 6.59 µmol) in the presence of sodium t-butoxide (15.8 mg, 165 µmol) and xantphos (7.63 mg, 13.2 µmol) as a yellow solid (31.9 mg, 76.6% yield). MS ES+ (m/z): 506.3 [(M+H)+]

EXAMPLE 97

N-[(8-endo)-3-(2-chloro-5-fluoro-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine

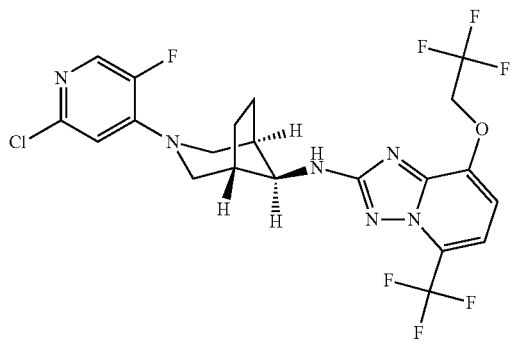 [SMILES: Fc1cnc(Cl)cc1N1C[C@H]2CC[C@@H](C1)[C@@H]2Nc1nc2c(OCC(F)(F)F)ccc(C(F)(F)F)n2n1]

Intermediate 2

(8-endo)-3-(2-chloro-5-fluoro-4-pyridyl)-3-azabicyclo[3.2.1]octan-8-amine

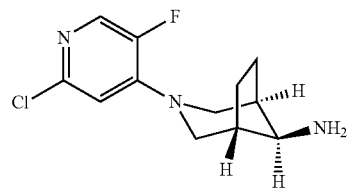 [SMILES: N[C@@H]1[C@@H]2CC[C@H]1CN(c1cc(Cl)ncc1F)C2]

Step 1

Tert-butyl N-[(8-endo)-3-(2-chloro-5-fluoro-4-pyridyl)-3-azabicyclo[3.2.1]octan-8-yl]carbamate

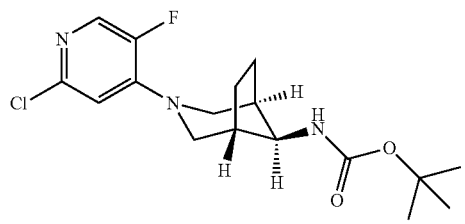 [SMILES: CC(C)(C)OC(=O)N[C@@H]1[C@@H]2CC[C@H]1CN(c1cc(Cl)ncc1F)C2]

To a solution of tert-butyl N-[(8-endo)-3-azabicyclo[3.2.1]octan-8-yl]carbamate (200 mg, 884 µmol) in NMP (3.33 ml) (CAS Registry Number: 1330763-51-3) was added DIPEA (228 mg, 309 µl, 1.77 mmol) followed by 2,4-dichloro-5-fluoropyridine (176 mg, 1.06 mmol). The reaction mixture was degassed with argon for 2 minutes. The vial was closed under argon and the dark red reaction mixture was stirred over night at 150° C. TLC showed reaction was complete. The reaction mixture was added to H₂O (20 ml) and extracted with EtOAc (3×50 ml). The organic phase was washed with brine and dried with MgSO₄. The crude material was purified by flash chromatography (silica gel, 12 g, 0% to 60% EtOAc in heptane) to afford the title compound as an off-white powder (253.8 mg, 713 µmol, 80.7% yield). MS ES+ (m/z): 356.2 [(M+H)⁺]

Step 2

(8-endo)-3-(2-chloro-5-fluoropyridin-4-yl)-3-azabicyclo[3.2.1]octan-8-amine

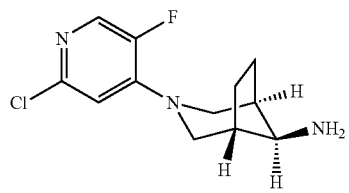 [SMILES: N[C@@H]1[C@@H]2CC[C@H]1CN(c1cc(Cl)ncc1F)C2]

To a light yellow solution of tert-butyl N-[(8-endo)-3-(2-chloro-5-fluoro-4-pyridyl)-3-azabicyclo[3.2.1]octan-8-yl] carbamate (243.3 mg, 684 µmol) in DCM (3.4 ml) was added HCl 37% (404 mg, 337 µl, 4.1 mmol). The reaction mixture was stirred at room temp over 3 hours. TLC and LC-MS showed the reaction was complete. RM was quenched with NaOH (32%) to pH 10. Then it was diluted with 5 mL H₂O and extracted with DCM (7×15 mL). The organic layers were dried over MgSO₄ and concentrated in vacuo to obtain the title compound as an off white solid. (167.7 mg, 95.9% yield). MS ES+ (m/z): 256.1 [(M+H)+]

Final Coupling Step 3

N-[(8-endo)-3-(2-chloro-5-fluoro-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine

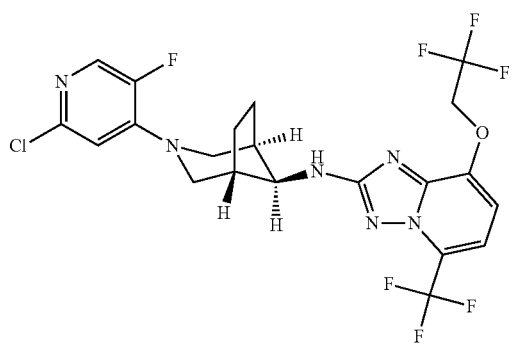 [SMILES: Fc1cnc(Cl)cc1N1C[C@H]2CC[C@@H](C1)[C@@H]2Nc1nc2c(OCC(F)(F)F)ccc(C(F)(F)F)n2n1]

The title compound, was prepared by Buchwald coupling in analogy to example 1, from of 2-bromo-8-(2,2,2-trifluoroethoxy)-5-(trifluoromethyl)-[1,2,4]triazolo[1,5-a]pyridine (30 mg, 82.4 mol) intermediate 3 of example 71, (8-endo)-3-(2-chloro-5-fluoropyridin-4-yl)-3-azabicyclo[3.2.1]octan- 8-amine (23.2 mg, 90.6 μmol) (20.1 mg, 90.6 μmol) with Pd$_2$(dba)$_3$·CHCl$_3$ in the presence of sodium t-butoxide and xantphos as a white solid (21.3 mg, 48% yield). MS ES+ (m/z): 539.3 [(M+H)+].

EXAMPLE 98

5-methyl-N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine

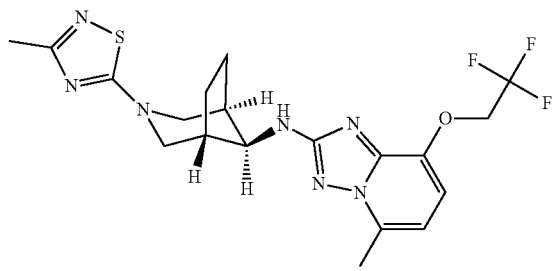 [SMILES: Cc1nsc(N2C[C@H]3CC[C@@H](C2)[C@@H]3Nc2nc3c(OCC(F)(F)F)ccc(C)n3n2)n1]

Intermediate 3

2-Bromo-5-methyl-8-(2,2,2-trifluoroethoxy)-[1,2,4]triazolo[1,5-a]pyridine

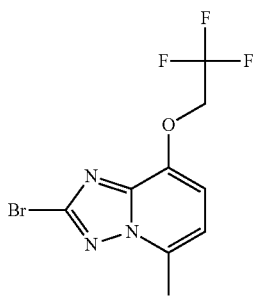 [SMILES: Cc1ccc(OCC(F)(F)F)c2nc(Br)nn12]

Step 1

6-Methyl-2-nitro-3-(2,2,2-trifluoroethoxy)pyridine

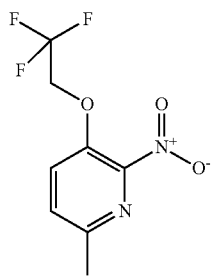

The title compound was prepared in analogy to example 3, intermediate 3, step 1, from 6-methyl-2-nitropyridin-3-ol (2 g, 13 mmol), 1,1,1-trifluoro-2-iodoethane (2.72 g, 1.28 ml, 13 mmol), and K$_2$CO$_3$ (3.59 g, 26 mmol) as base as a yellow solid (3.06 g, 48.3%). MS ES+ (m/z): 237.1 [(M+H)+].

Step 2

6-Methyl-3-(2,2,2-trifluoroethoxy)pyridin-2-amine

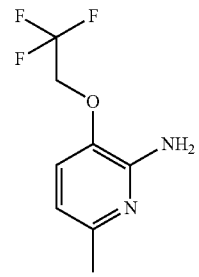

The title compound was prepared in analogy to example 3, intermediate 3, step 2, from 6-methyl-2-nitro-3-(2,2,2-trifluoroethoxy)pyridine (1.48 g, 6.27 mmol) as a light yellow solid (0.273 g, 21.1%). MS ES+ (m/z): 207.1 [(M+H)+].

Step 3

Ethyl N-[[6-methyl-3-(2,2,2-trifluoroethoxy)-2-pyridyl]carbamothioyl]carbamate

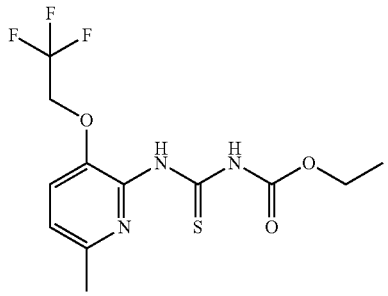 [SMILES: CCOC(=O)NC(=S)Nc1nc(C)ccc1OCC(F)(F)F]

The title compound was prepared in analogy to example 1, intermediate 3, step 3, from 6-methyl-3-(2,2,2-trifluoroethoxy)pyridin-2-amine (1.54 g, 7.47 mmol), ethoxycarbonyl isothiocyanate (2.02 g, 14.9 mmol) as a yellow solid (1.94 g, 77%).

MS ES+ (m/z): 338.0 [(M+H)+].

Step 4

5-Methyl-8-(2,2,2-trifluoroethoxy)-[1,2,4]triazolo[1,5-a]pyridin-2-amine

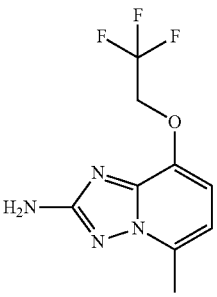 [SMILES: Cc1ccc(OCC(F)(F)F)c2nc(N)nn12]

The title compound was prepared in analogy to example 1, intermediate 3, step 4 from ethyl N-[[6-methyl-3-(2,2,2-trifluoroethoxy)-2-pyridyl]carbamothioyl]carbamate (1.94 g, 5.75 mmol) hydroxylamine hydrochloride (2.06 g, 28.8 mmol) and Hunig's base (2.23 g, 17.3 mmol) as a light yellow solid (1.18 g, 83.3%). MS ES+ (m/z): 247.1 [(M+H)+]

Step 5

2-Bromo-5-methyl-8-(2,2,2-trifluoroethoxy)-[1,2,4]triazolo[1,5-a]pyridine

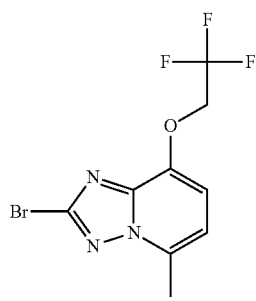 [SMILES: Cc1ccc(OCC(F)(F)F)c2nc(Br)nn12]

The title compound, was prepared in analogy to example 1, intermediate 3, step 5 from 5-methyl-8-(2,2,2-trifluoroethoxy)-[1,2,4]triazolo[1,5-a]pyridin-2-amine (200 mg, 812 □mol), tert-butyl nitrite and copper (II) bromide as a white solid (209 mg, 83%).

MS ES+ (m/z): 311.9 [(M+H)+]

Final Coupling Step 6

5-methyl-N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine

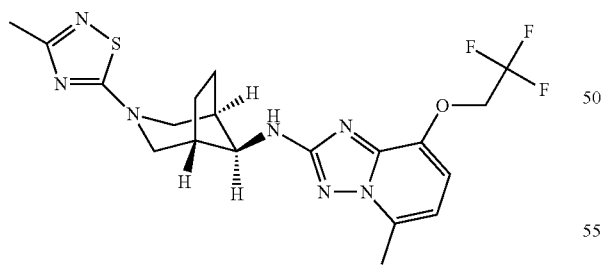

The title compound, was prepared by Buchwald coupling in analogy to example 1, from 2-bromo-5-methyl-8-(2,2,2-trifluoroethoxy)-[1,2,4]triazolo[1,5-a]pyridine (41.5 mg, 134 μmol), with (8-endo)-3-(3-methyl-1,2,4-thiadiazol-5-yl)-3-azabicyclo[3.2.1]octan-8-amine (30 mg, 134 μmol), intermediate 2 example 1, Pd₂(dba)₃. CHCl₃ (11.1 mg, 21.4 μmol) in the presence of sodium t-butoxide (27 mg, 281 μmol) and xantphos (12.4 mg, 13.2 μmol) as a white solid (26 mg, 42.9% yield). MS ES+ (m/z): 454.2 [(M+H)+]

EXAMPLE 99

5-Methyl-8-(2,2,2-trifluoroethoxy)-N-[(8-endo)-3-[2-(trifluoromethyl)-4-pyridyl]-3-azabicyclo[3.2.1]octan-8-yl]-[1,2,4]triazolo[1,5-a]pyridin-2-amine

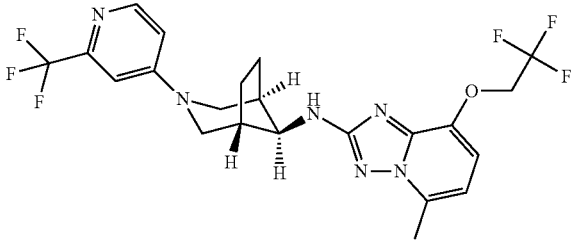 [SMILES: Cc1ccc(OCC(F)(F)F)c2nc(N[C@@H]3[C@@H]4CC[C@H]3CN(c3ccnc(C(F)(F)F)c3)C4)nn12]

The title compound, was prepared by Buchwald coupling in analogy to example 1, from 2-bromo-5-methyl-8-(2,2,2-trifluoroethoxy)-[1,2,4]triazolo[1,5-a]pyridine (51.4 mg, 166 μmol), intermediate 3 of example 98, with (8-endo)-3-(2-(trifluoromethyl)pyridin-4-yl)-3-azabicyclo[3.2.1]octan-8-amine (45 mg, 166 μmol), intermediate 2 of example 62, Pd₂(dba)₃.CHCl3 in the presence of sodium t-butoxide and xantphos as a white solid (40 mg, 48.2% yield). MS ES+ (m/z): 501.2 [(M+H)+]

EXAMPLE 100

5-Methyl-N-[8-endo-3-(3-methyl-1,2,4-oxadiazol-5-yl)-3-azabicyclo[3.2.1]octan-8-yl]-8-(2,2,3,3,3-pentafluoropropoxy)-[1,2,4]triazolo[1,5-a]pyridin-2-amine

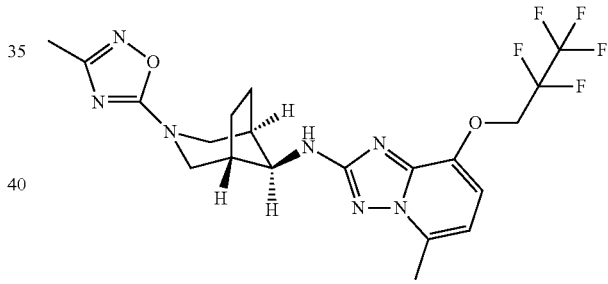

Intermediate 3

2-Bromo-5-methyl-8-(2,2,3,3,3-pentafluoropropoxy)-[1,2,4]triazolo[1,5-a]pyridine

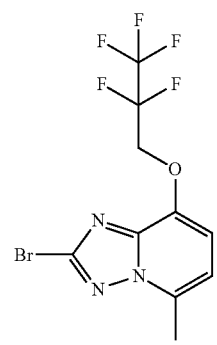 [SMILES: Cc1ccc(OCC(F)(F)C(F)(F)F)c2nc(Br)nn12]

Step 1

6-Methyl-2-nitro-3-(2,2,3,3,3-pentafluoropropoxy)pyridine

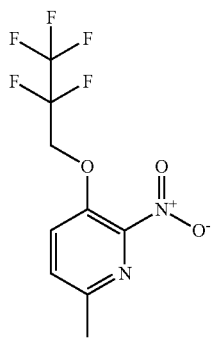

The title compound was prepared in analogy to example 3, intermediate 3, step 1, from 6-methyl-2-nitropyridin-3-ol (2 g, 13 mmol), 1 1,1,1,2,2-pentafluoro-3-iodopropane (5.06 g, 2.48 ml, 19.5 mmol), and K$_2$CO$_3$ (3.59 g, 26 mmol) as base as a yellow oil (3.71 g, 21.2%). MS ES+ (m/z): 237.1 [(M+H)$^+$].

Step 2

6-Methyl-3-(2,2,3,3,3-pentafluoropropoxy)pyridin-2-amine

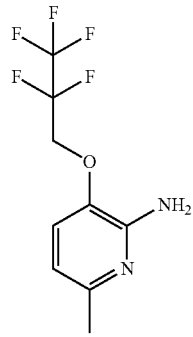 [SMILES: Cc1ccc(OCC(F)(F)C(F)(F)F)c(N)n1]

The title compound was prepared in analogy to example 1, intermediate 3, step 2, from 6-methyl-2-nitro-3-(2,2,3,3,3-pentafluoropropoxy)pyridine (200 mg, 699 μmol) as a light brown solid (0.146 g, 81.5%). MS ES+ (m/z): 257.1 [(M+H)$^+$].

Step 3

N-[[6-methyl-3-(2,2,3,3,3-pentafluoropropoxy)-2-pyridyl]carbamothioyl]carbamate

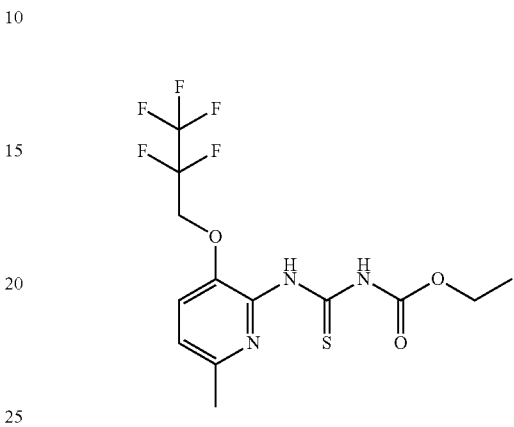

The title compound was prepared in analogy to example 1, intermediate 3, step 3, from 6-methyl-3-(2,2,3,3,3-pentafluoropropoxy)pyridin-2-amine (1.05 g, 4.1 mmol), ethoxycarbonyl isothiocyanate (1.11 g, 8.2 mmol) as a yellow solid (1.59 g, 93.2%). MS ES+ (m/z): 388.1 [(M+H)$^+$].

Step 4

5-Methyl-8-(2,2,3,3,3-pentafluoropropoxy)-[1,2,4]triazolo[1,5-a]pyridin-2-amine

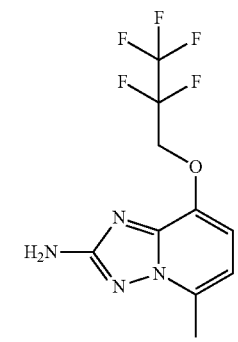 [SMILES: Cc1ccc(OCC(F)(F)C(F)(F)F)c2nc(N)nn12]

The title compound was prepared in analogy to example 1, intermediate 3, step 4 from ethyl N-[[6-methyl-3-(2,2,3,3,3-pentafluoropropoxy)-2-pyridyl]carbamothioyl]carbamate (1.48 g, 3.82 mmol) hydroxylamine hydrochloride (1.37 g, 19.1 mmol) and Hunig's base (1.48 g, 11.5 mmol) as a white solid (1.04 g, 91.9%). MS ES+ (m/z): 397.1 [(M+H)$^+$]

Step 5

2-Bromo-5-methyl-8-(2,2,3,3,3-pentafluoropropoxy)-[1,2,4]triazolo[1,5-a]pyridine

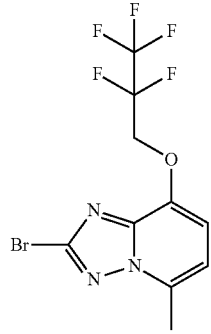 [SMILES: Cc1ccc(OCC(F)(F)C(F)(F)F)c2nc(Br)nn12]

The title compound, was prepared in analogy to example 1, intermediate 3, step 5 from 5-methyl-8-(2,2,3,3,3-pentafluoropropoxy)-[1,2,4]triazolo[1,5-a]pyridin-2-amine (300 mg, 1.01 mmol)), tert-butyl nitrite (174 mg, 1.52 mmol) and copper (II) bromide (343 mg, 1.52 mmol) as a yellow oil (343 mg, 94%). MS ES+ (m/z): 362 [(M+H)$^+$]

Final Coupling Step 6

5-methyl-N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine

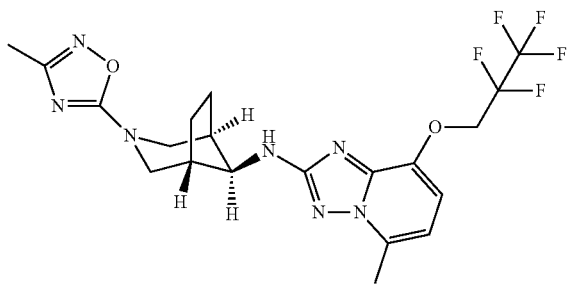 [SMILES: Cc1noc(N2C[C@H]3CC[C@@H](C2)[C@@H]3Nc2nc3c(OCC(F)(F)C(F)(F)F)ccc(C)n3n2)n1]

The title compound was prepared by Buchwald coupling in analogy to example 79 from (8-endo)-3-(3-methyl-1,2,4-oxadiazol-5-yl)-3-azabicyclo[3.2.1]octan-8-amine (50 mg, 240 μmol), intermediate 2, example 79, 2-bromo-5-methyl-8-(2,2,3,3,3-pentafluoropropoxy)-[1,2,4]triazolo[1,5-a]pyridine (86.4 mg, 240 μmol), dibromobis(tri-tert-butylphosphine)dipalladium(I) (18.7 mg, 24 μmol) and sodium tert-butoxide (47.3 mg, 492 μmol) as base as white solid (25 mg, 21.4%). MS ES+ (m/z): 488.3 [(M+H)+].

EXAMPLE 101

6-Methyl-N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine

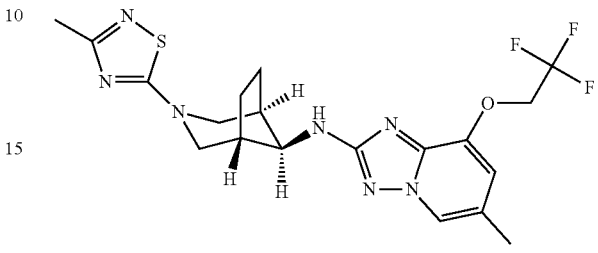

Intermediate 3

2-Bromo-6-methyl-8-(2,2,2-trifluoroethoxy)-[1,2,4]triazolo[1,5-a]pyridine

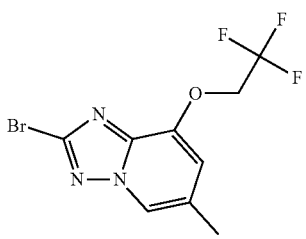 [SMILES: Cc1cc(OCC(F)(F)F)c2nc(Br)nn2c1]

Step 1

5-Methyl-2-nitro-3-(2,2,2-trifluoroethoxy)pyridine

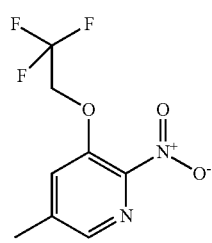

The title compound was prepared in analogy to example 3, intermediate 3, step 1, from 5-methyl-2-nitropyridin-3-ol (1.5 g, 9.44 mmol), 1,1,1-trifluoro-2-iodoethane (1.98 g, 9.44 mmol), and K2CO3 (2.61 g, 18.9 mmol) as base as a solid (1.23 g, 55.2%). MS ES+ (m/z): 237.1 [(M+H)$^+$].

Step 2

5-Methyl-3-(2,2,2-trifluoroethoxy)pyridin-2-amine

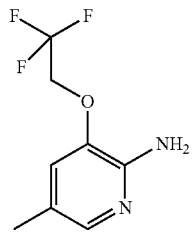

The title compound was prepared in analogy to example 3, intermediate 3, step 2, from 5-methyl-2-nitro-3-(2,2,2-trifluoroethoxy)pyridine (1.23 g, 6.27 mmol) as a light brown solid (1.07 g, 93.1%). MS ES+ (m/z): 207.1 [(M+H)$^+$].

Step 3

Ethyl N-[[5-methyl-3-(2,2,2-trifluoroethoxy)-2-pyridyl]carbamothioyl]carbamate

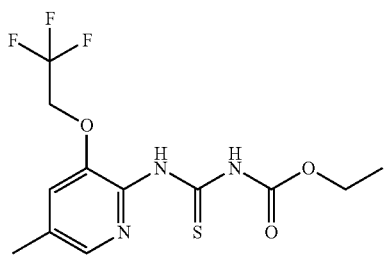 [SMILES: CCOC(=O)NC(=S)Nc1ncc(C)cc1OCC(F)(F)F]

The title compound was prepared in analogy to example 1, intermediate 3, step 3, from 5-methyl-3-(2,2,2-trifluoroethoxy)pyridin-2-amine (1 g, 4.85 mmol), ethoxycarbonyl isothiocyanate (1.31 g, 9.7 mmol) as a yellow solid (1.52 g, 92.9%). MS ES+ (m/z): 338.1 [(M+H)$^+$].

Step 4

6-Methyl-8-(2,2,2-trifluoroethoxy)-[1,2,4]triazolo[1,5-a]pyridin-2-amine

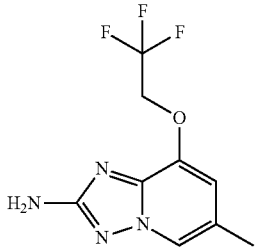 [SMILES: Cc1cc(OCC(F)(F)F)c2nc(N)nn2c1]

The title compound was prepared in analogy to example 1, intermediate 3, step 4 from ethyl N-[[5-methyl-3-(2,2,2-trifluoroethoxy)-2-pyridyl]carbamothioyl]carbamate (1.52 g, 4.51 mmol), hydroxylamine hydrochloride (1.61 g, 22.5 mmol) and Hunig's base (1.75 g, 13.5 mmol) as a light yellow solid (0.943 g, 85%). MS ES+ (m/z): 247.1 [(M+H)$^+$]

Step 5

2-Bromo-6-methyl-8-(2,2,2-trifluoroethoxy)-[1,2,4]triazolo[1,5-a]pyridine

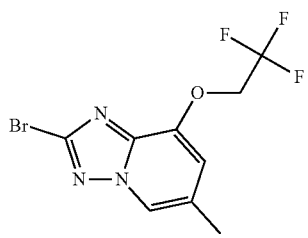 [SMILES: Cc1cc(OCC(F)(F)F)c2nc(Br)nn2c1]

The title compound, was prepared in analogy to example 1, intermediate 3, step 5 from 6-methyl-8-(2,2,2-trifluoroethoxy)-[1,2,4]triazolo[1,5-a]pyridin-2-amine (200 mg, 812 μmol), tert-butyl nitrite and copper (II) bromide as a white solid (204 mg, 81%).

MS ES+ (m/z): 312.0 [(M+H)$^+$]

Final Coupling Step 6

6-methyl-N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine

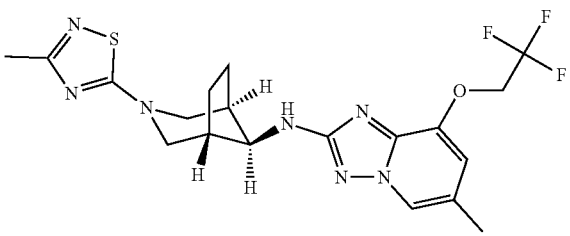 [SMILES: Cc1cc(OCC(F)(F)F)c2nc(N[C@@H]3[C@@H]4CC[C@H]3CN(c3nc(C)ns3)C4)nn2c1]

The title compound, was prepared by Buchwald coupling in analogy to example 1, from (8-endo)-3-(3-methyl-1,2,4-thiadiazol-5-yl)-3-azabicyclo[3.2.1]octan-8-amine (35 mg, 156 μmol), intermediate 2 of example 1, with 2-bromo-6-methyl-8-(2,2,2-trifluoroethoxy)-[1,2,4]triazolo[1,5-a]pyridine (48.4 mg, 156 μmol), Pd$_2$(dba)$_3$·CHCl$_3$ (12.9 mg, 12.5 μmol) in the presence of sodium t-butoxide (31.5 mg, 328 μmol) and xantphos (14.4 mg, 25 μmol) as a white solid (40 mg, 48.2% yield). MS ES+ (m/z): 454.2 [(M+H)+]

EXAMPLE 102

6-Fluoro-N-[(8-endo)-3-(3-methylisothiazol-5-yl)-3-azabicyclo[3.2.1]octan-8-yl]-8-(2,2,2-trifluoroethoxy)-[1,2,4]triazolo[1,5-a]pyridin-2-amine

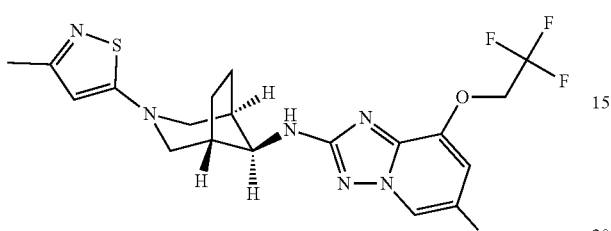

Intermediate 3

2-Bromo-6-fluoro-8-(2,2,2-trifluoroethoxy)-[1,2,4]triazolo[1,5-a]pyridine

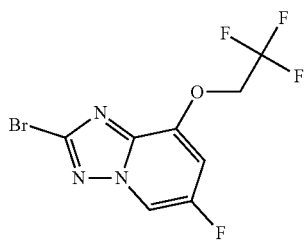 [SMILES: Fc1cc(OCC(F)(F)F)c2nc(Br)nn2c1]

Step 1

Ethyl N-[(5-fluoro-3-methoxy-2-pyridyl)carbamothioyl]carbamate

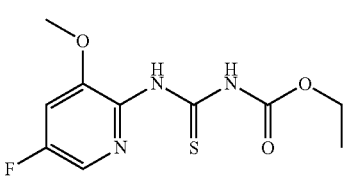 [SMILES: CCOC(=O)NC(=S)Nc1ncc(F)cc1OC]

The title compound was prepared in analogy to example 4, intermediate 3, step 1, from 5-fluoro-3-methoxypyridin-2-amine (496 mg, 3.49 mmol), ethoxycarbonyl isothiocyanate (0.458 g, 3.49 mmol) as a white solid (0.937 g, 98.3%). MS ES+ (m/z): 3274.1 [(M+H)+].

Step 2

6-Fluoro-8-methoxy-[1,2,4]triazolo[1,5-a]pyridin-2-amine

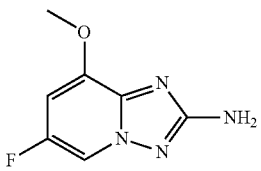

The title compound was preared in analogy to example 4, intermediate 3, step 2, from from ethyl N-[(5-fluoro-3-methoxy-2-pyridyl)carbamothioyl]carbamate (0.904 g, 3.31 mmol), hydroxylamine hydrochloride (1.15 g, 16.5 mmol) and Hunig's base (1.26 g, 9.73 mmol) as a white solid (0.603 g, 78.4%). MS ES+ (m/z): 183.1 [(M+H)+]

Step 3

2-Bromo-6-fluoro-8-methoxy-[1,2,4]triazolo[1,5-a]pyridine

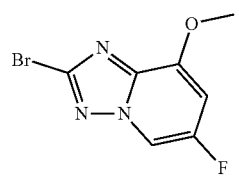

The title compound was prepared in analogy to example 4, intermediate 3, step 3, from 6-fluoro-8-methoxy-[1,2,4]triazolo[1,5-a]pyridin-2-amine (448 mg, 2.46 mmol) tert-butyl nitrite and copper (II) bromide as a white solid (605 mg, 82.2%). MS ES+ (m/z): 248.0 [(M+H)+]

Step 4

2-Bromo-6-fluoro-[1,2,4]triazolo[1,5-a]pyridin-8-ol

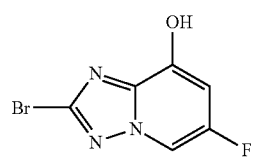 [SMILES: Oc1cc(F)cn2nc(Br)nc12]

The title compound was prepared in analogy to example 4, intermediate 3, step 4, from 2-bromo-6-fluoro-8-methoxy-[1,2,4]triazolo[1,5-a]pyridine (250 mg, 1.02 mmol) and BBr$_3$ 1M in dichlormethane (5 ml, 5 mmol) as a white powder (138.2 mg, 58.6%). MS ES+ (m/z): 233.9 [(M+H)+]

Step 5

2-Bromo-6-fluoro-8-(2,2,2-trifluoroethoxy)-[1,2,4]triazolo[1,5-a]pyridine

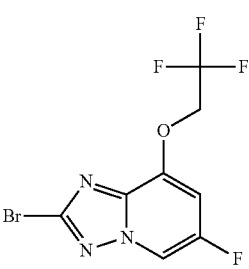 [SMILES: Fc1cc(OCC(F)(F)F)c2nc(Br)nn2c1]

The title compound was prepared in analogy to example 4, intermediate 3, step 5, from 2-bromo-6-fluoro-[1,2,4]triazolo[1,5-a]pyridin-8-ol (100 mg, 431 µmol), 1,1,1-trifluoro-2-iodoethane (136 mg, 63.7 µl, 647 µmol), and $K_2CO_3$ (119 mg, 862 µmol) as base as a white powder (69.6 mg, 51.4%). MS ES+ (m/z): 314.0 [(M+H)$^+$]

Final Coupling Step 6

6-Fluoro-N-[(8-endo-3-(3-methylisothiazol-5-yl)-3-azabicyclo[3.2.1]octan-8-yl]-8-(2,2,2-trifluoroethoxy)-[1,2,4]triazolo[1,5-a]pyridin-2-amine

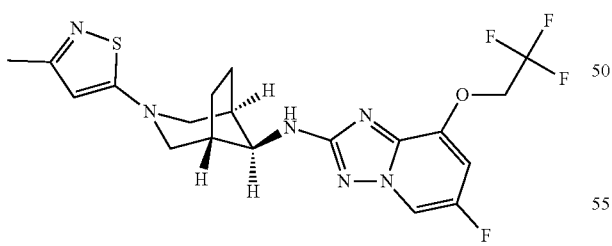

The title compound, was prepared by Buchwald coupling in analogy to example 1, (8-endo)-3-(3-methylisothiazol-5-yl)-3-azabicyclo[3.2.1]octan-8-amine (15 mg, 67.2 µmol), intermediate 2 of example 14, with 2-bromo-6-fluoro-8-(2,2,2-trifluoroethoxy)-[1,2,4]triazolo[1,5-a]pyridine (21.1 mg, 67.2 µmol), Pd$_2$(dba)$_3$·CHCl$_3$ in the presence of sodium t-butoxide and xantphos as a white solid (9.1 mg, 29.7% yield). MS ES+ (m/z): 457.2 [(M+H)+]

EXAMPLE 103

6-chloro-N-[8-endo-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine

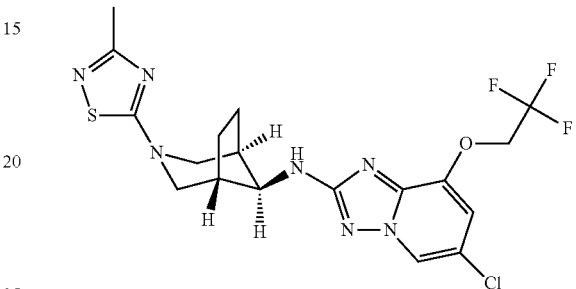

Intermediate 3

2-Bromo-6-chloro-8-(2,2,2-trifluoroethoxy)-[1,2,4]triazolo[1,5-a]pyridine

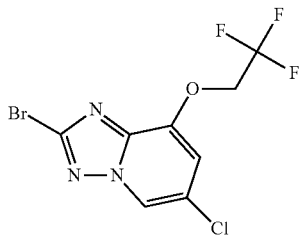 [SMILES: FC(F)(F)COc1cc(Cl)cn2nc(Br)nc12]

Step 1

Ethyl N-[(3-bromo-5-chloro-2-pyridyl)carbamothioyl]carbamate

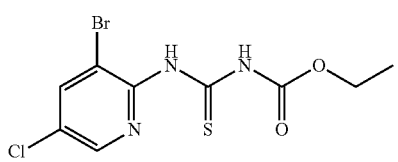 [SMILES: CCOC(=O)NC(=S)Nc1ncc(Cl)cc1Br]

The title compound was prepared in analogy to example 71, intermediate 3, step 1, from 3-bromo-5-chloropyridin-2-amine (2 g, 9.64 mmol) and ethoxycarbonyl isothiocyanate (1.33 g, 10.1 mmol) as a light brown solid. HRMS: 339.93323 [(M+H)$^+$]

Step 2

8-Bromo-6-chloro-[1,2,4]triazolo[1,5-a]pyridin-2-amine

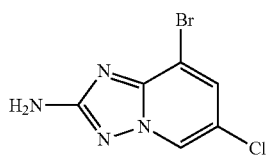 [SMILES: Nc1nc2c(Br)cc(Cl)cn2n1]

The title compound was prepared in analogy to example 71, intermediate 3, step 2 from ethyl N-[(3-bromo-5-chloro-2-pyridyl)carbamothioyl]carbamate (3.1 g, 9.16 mmol), hydroxylamine hydrochloride (636 mg, 9.16 mmol) and Hunig's base (1.18 g, 9.16 mmol) as a light yellow solid. HRMS: 248.93598 [(M+H)$^+$]

Step 3

6-Chloro-8-(2,2,2-trifluoroethoxy)-[1.24]triazolo[1,5-a]pyridin-2-amine

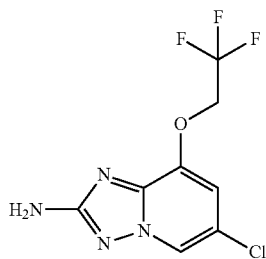 [SMILES: Nc1nc2c(OCC(F)(F)F)cc(Cl)cn2n1]

The title compound was prepared in analogy to example 71, intermediate 3, step 3, from 8-bromo-6-chloro-[1,2,4]triazolo[1,5-a]pyridin-2-amine (150 mg, 606 μmol), 2,2,2-trifluoroethanol (91 mg, 909 μmol), NaH (34.4 mg, 788 μmol, copper (I) bromide (869 μg, 6.06 mol) as a light yellow solid (54 mg, 33.4%). HRMS: 267.0256 [(M+H)$^+$]

Step 4

2-Bromo-6-chloro-8-(2,2,2-trifluoroethoxy)-[1,2,4]triazolo[1,5-a]pyridine

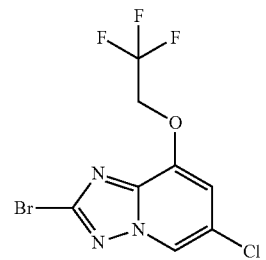 [SMILES: FC(F)(F)COc1cc(Cl)cn2nc(Br)nc12]

The title compound, was prepared in analogy to example 1, intermediate 3, step 5 from 6-chloro-8-(2,2,2-trifluoroethoxy)-[1,2,4]triazolo[1,5-a]pyridin-2-amine (52 mg, 195 μmol), tert-butyl nitrite and copper (II) bromide as a white solid (48 mg, 74.5%). HR-MS: 331.92166 [(M+H)$^+$]

Final Coupling Step 5

6-chloro-N-[(8-endo)-3-(3-methyl-1,2,4-thiadiazol-5-yl)-3-azabicyclo[3.2.1]octan-8-yl]-8-(2,2,2-trifluoroethoxy)-[1.2.4]triazolo[1,5-a]pyridin-2-amine

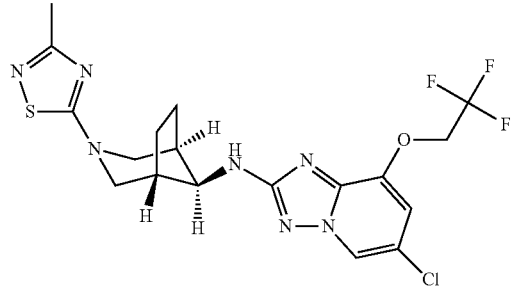 [SMILES: Cc1nsc(N2C[C@H]3CC[C@@H](C2)[C@@H]3Nc2nc3c(OCC(F)(F)F)cc(Cl)cn3n2)n1]

The title compound was prepared by Buchwald coupling in analogy to example 79 from (8 endo)-3-(3-methyl-1,2,4-thiadiazol-5-yl)-3-azabicyclo[3.2.1]octan-8-amine (16.8 mg, 74.9 μmol, Eq: 1), intermediate 2, example 1, 2-bromo-6-chloro-8-(2,2,2-trifluoroethoxy)-[1,2,4]triazolo[1,5-a] pyridine (24.8 mg, 75 μmol), dibromobis(tri-tert-butylphosphine)dipalladium(I) (5.82 mg, 7.49 μmol) and sodium tert-butoxide (14.8 mg, 154 μmol) as base as an off-white solid (35.5 mg, 44.2%). MS ES+ (m/z): 474.1 [(M+H)+].

EXAMPLE 104

2-[2-[[(8 endo)-3-(6-methylpyrimidin-4-yl)-3-azabicyclo[3.2.1]octan-8-yl]amino]-8-(2,2,2-trifluoroethoxy)-[1,2,4]triazolo[1,5-a]pyridin-5-yl]propan-2-ol

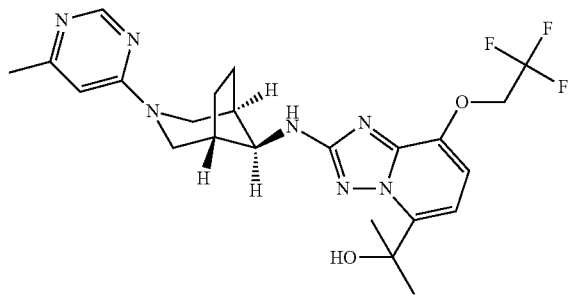 [SMILES: Cc1cc(N2C[C@H]3CC[C@@H](C2)[C@@H]3Nc2nc3c(OCC(F)(F)F)ccc(C(C)(C)O)n3n2)ncn1]

Intermediate 3

Step 1

6-methyl-2-nitro-3-(2,2,2-trifluoroethoxy)pyridine

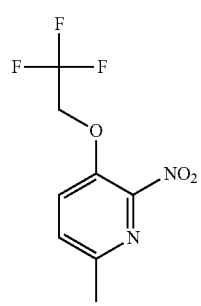

To a solution of 6-methyl-2-nitropyridin-3-ol (5 g, 32.4 mmol) in DMF (60 ml) was added K$_2$CO$_3$ (8.97 g, 64.9 mmol) and the reaction mixture was warmed to 90° C. and stirred during 1 hour. The reaction was cooled down to room temperature before 1,1,1-trifluoro-2-iodoethane (13.6 g, 6.4 ml, 64.9 mmol) was added and the mixture was heated to 125° C. under Argon during 2 days in a closed vial. TLC and LC-MS showed the reaction was complete. The reaction mixture was diluted with 75 mL H$_2$O and the water phase was extracted with DCM (3×75 mL). The organic layers were dried over MgSO$_4$ and concentrated in vacuum. The crude material was purified by flash chromatography (silica gel, 0% to 60% EtOAc in heptane) to afford the title compound (5.12 g, 21.7 mmol, 66.8% yield). MS ES+ (m/z): 237.0 [(M+H)+].

Step 2

6-Methyl-3-(2,2,2-trifluoro-ethoxy)-pyridin-2-ylamine

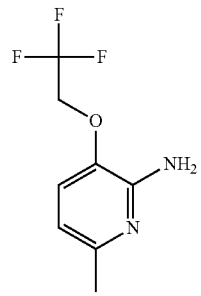

Under Argon, in a four-necked flask with a mechanical stirrer 6-methyl-2-nitro-3-(2,2,2-trifluoroethoxy)pyridine (5.1 g, 21.6 mmol) was solved in Ethanol (166 ml) and Hydrochloric acid (120 g, 99.7 ml, 821 mmol) was added followed by iron (7.24 g, 130 mmol). The reaction was warmed to 90° C. and stirred for 2 hours. The organic solvent was removed in vacuum. The residue was solved in dichloromethane and a sat aqueous solution of NaHCO$_3$ was added. The water phase was extracted with DCM (3×100 mL). The organic layers were dried over MgSO$_4$ and concentrated in vacuum. The crude material was purified by flash chromatography (silica gel, 0% to 100% EtOAc in heptane) to afford the title compound (3.88 g, 18.8 mmol, 87.1% yield) as a yellow solid. MS ES+ (m/z): 207.1 [(M+H)+].

Step 3

N-(6-methyl-3-(2,2,2-trifluoroethoxy)pyridin-2-yl)acetamide

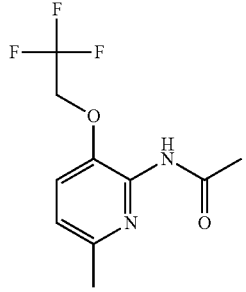 [SMILES: CC(=O)Nc1nc(C)ccc1OCC(F)(F)F]

To a solution of 6-methyl-3-(2,2,2-trifluoroethoxy)pyridin-2-amine (3.8 g, 18.4 mmol) in Dichloromethane (80 ml) was added triethylamine (2.8 g, 3.85 ml, 27.6 mmol) followed by acetic anhydride (3.76 g, 3.48 ml, 36.9 mmol). The reaction was stirred over night at room temp. LC-MS showed the reaction was incomplete with remaining starting material so triethylamine (1.4 g, 1.93 ml, 13.8 mmol) and acetic anhydride (1.88 g, 1.74 ml, 18.4 mmol) were added and the reaction was stirred another 24 hours at room temp to arrive to completion. The reaction was quenched by adding 150 mL H$_2$O and was extracted with DCM (3×100 mL). The organic layers were dried over MgSO$_4$ and concentrated in vacuum to obtain the title compound as a light yellow solid (3.89 g, 15.7 mmol, 85% yield). MS ES+ (m/z): 249.1 [(M+H)+].

Step 4 methyl 6-amino-5-(2,2,2-trifluoroethoxy)pyridine-2-carboxylate

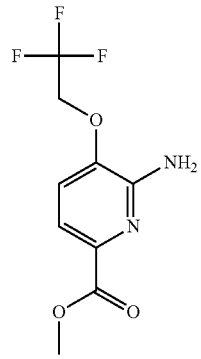 [SMILES: COC(=O)c1ccc(OCC(F)(F)F)c(N)n1]

Step 4A 6-acetamido-5-(2,2,2-trifluoroethoxy)picolinic acid

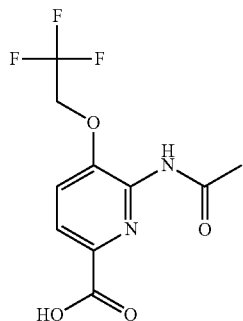 [SMILES: CC(=O)Nc1nc(C(=O)O)ccc1OCC(F)(F)F]

A suspension of N-(6-methyl-3-(2,2,2-trifluoroethoxy)pyridin-2-yl)acetamide (3.9 g, 15.7 mmol) in water (78 ml) was warmed to 85° C. Potassium dihydrogen phosphate (4.28 g, 31.4 mmol) was added to the solution followed by sodium permanganate monohydrate (NaMgO$_4$) (7.54 g, 47.1 mmol) that was added portion wise to the white suspension. After the addition the reaction was stirred for 1 hour at 85° C. and more sodium permanganate monohydrate (3.77 g, 23.6 mmol) was added portionwise and the reaction was stirred 1 hr at 85°. The MnO₂ was filtered off and the aqueous layer was extracted with EtOAc (2×20 mL) to remove impurities. The water phase was concentrated in vacuo and dried on high vacuum pump over night to obtain 6-acetamido-5-(2,2,2-trifluoroethoxy)picolinic acid as crude intermediate. MS ES+ (m/z): 279.1 [(M+H)+].

Step 4B methyl 6-amino-5-(2,2,2-trifluoroethoxy)picolinate

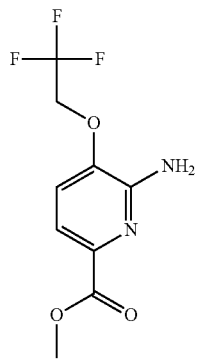 [SMILES: COC(=O)c1ccc(OCC(F)(F)F)c(N)n1]

The crude intermediate 6-acetamido-5-(2,2,2-trifluoroethoxy)picolinic acid was suspended in HCl 3M in Methanol (60 g, 50 ml, 150 mmol) and the mixture was refluxed overnight. The crude reaction mixture was concentrated in vacuo. The residue was extracted from 100 mL of sat NaHCO₃ using DCM (3×100 mL). The organic layers were dried over MgSO₄ and concentrated in vacuo to obtain the title compound (1.2 g, 4.8 mmol, 30.5% yield) as crude. MS ES+ (m/z): 251.1 [(M+H)+].

Step 5 methyl 6-(ethoxycarbonylcarbamothioylamino)-5-(2,2,2-trifluoroethoxy)pyridine-2-carboxylate

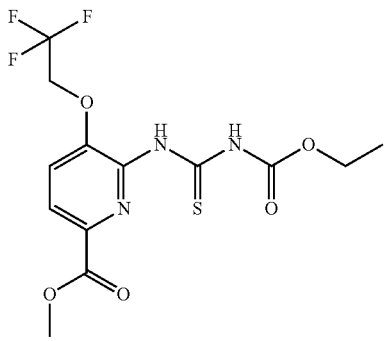 [SMILES: CCOC(=O)NC(=S)Nc1nc(C(=O)OC)ccc1OCC(F)(F)F]

To a light yellow solution of methyl 6-amino-5-(2,2,2-trifluoroethoxy)picolinate (1.15 g, 4.6 mmol in 1,4-Dioxane (20 ml) was added ethoxycarbonylisothiocyanate (904 mg, 815 µl, 6.9 mmol) and the reaction mixture was stirred at 100° C. over 6 hours. LC-MS and TLC showed the reaction was complete. The crude reaction mixture was concentrated in vacuo to obtain the title compound (1.8 g, 4.72 mmol, 103% yield) as crude. MS ES+ (m/z): 382.1 (100%) [(M+H)+].

Step 6 methyl 2-amino-8-(2,2,2-trifluoroethoxy)-[1,2,4]triazolo[1,5-a]pyridine-5-carboxylate

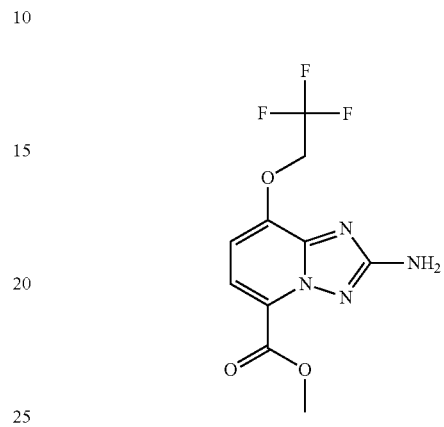

To a yellow suspension of methyl 6-(3-(ethoxycarbonyl)thioureido)-5-(2,2,2-trifluoroethoxy)picolinate (1.75 g, 4.59 mmol in MeOH (10 ml) and EtOH (10 ml) Hunig's base (1.78 g, 2.4 ml, 13.8 mmol and hydroxylamine hydrochloride (1.59 g, 22.9 mmol) were added at room temperature. The reaction mixture was heated up to 60° C. and TLC and LC/MS showed the reaction was complete after 2 hours, The solvent was removed in vacuo. and the residue was taken up in 100 mL H₂O and extracted with DCM. The organic layers were dried over MgSO₄ and concentrated in vacuo. The crude material was purified by flash chromatography (silica gel, 0 to 100% EtOAc in heptane) to afford the title compound as a white solid (832 mg, 62.5% yield) MS ES+ (m/z): 291.1 [(M+H)+].

Step 7 methyl 2-bromo-8-(2,2,2-trifluoroethoxy)-[1,2,4]triazolo[1,5-a]pyridine-5-carboxylate

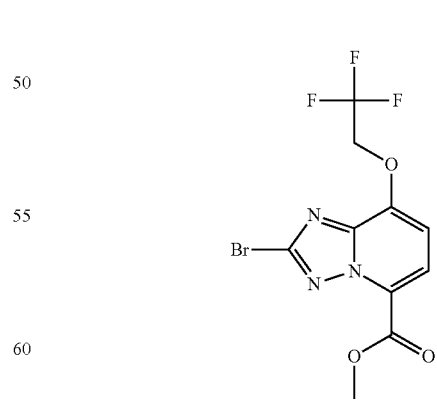

The title compound, was prepared in analogy to example 1, intermediate 3, step 5 by adding methyl 2-amino-8-(2,2,2-trifluoroethoxy)-[1,2,4]triazolo[1,5-a]pyridine-5-carboxylate (700 mg, 2.41 mmol) portionwise during 15 minutes to a dark brown solution of tert-butyl nitrite (373 mg, 432 μl, 3.62 mmol) and copper (II) bromide (808 mg, 3.62 mmol) in Acetonitrile (20 ml) previously heated to 60° C. and stirring the reaction mixture at 75° C. for 2 hours in this example. An aqueous HCl solution (1M, 20 ml) was added, the aqueous phase was separated and extracted with DCM (3×50 mL). The reaction mixture quenched with 20 ml of 1M HCl, diluted with H₂O (25 ml) and extracted with DCM (3×50 mL). The combined organic layers were dried over MgSO₄ and the solvent was removed in vacuo. The crude material was purified by flash chromatography (silica gel, 0% to 60% EtOAc in heptane) to afford the title compound (752 mg, 88% yield) as a white solid. MS ES+ (m/z): 356.1 [(M+H)⁺]

Step 8

2-[2-bromo-8-(2,2,2-trifluoroethoxy)-[1,2,4]triazolo[1,5-a]pyridin-5-yl]propan-2-ol

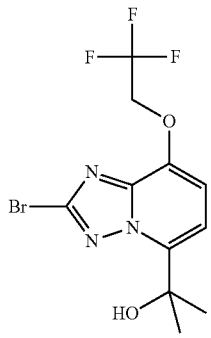 [SMILES: CC(C)(O)c1ccc(OCC(F)(F)F)c2nc(Br)nn12]

A methyl magnesium bromide solution (2.82 ml, 8.47 mmol) was added dropwise to a colorless solution of methyl 2-bromo-8-(2,2,2-trifluoroethoxy)-[1,2,4]triazolo[1,5-a]pyridine-5-carboxylate (750 mg, 2.12 mmol) in THF (25 ml) at −30° C. and the reaction mixture was stirred at −30° C. during 1 hour, allowed to warm to 0° C. and stirred at this temperature for 1 hour for reaction completion. 25 mL of an aqueous saturated solution of NH₄Cl was slowly added followed by 25 ml of water. The water phase was extracted with DCM (3×50 mL) and the combined organic layers were dried over MgSO₄ and concentrated in vacuo. The crude material was purified by flash chromatography (silica gel, 0% to 60% EtOAc in heptane) to afford the title compound (511 mg, 68.1% yield). MS ES+ (m/z): 356.1 [(M+H)⁺]

Final Coupling

2-[2-[[(8 endo)-3-(6-methylpyrimidin-4-yl)-3-azabicyclo[3.2.1]octan-8-yl]amino-8-(2,2,2-trifluoroethoxy)-[1,2,4]triazolo[1,5]-a]pyridin-5-yl]propan-2-ol

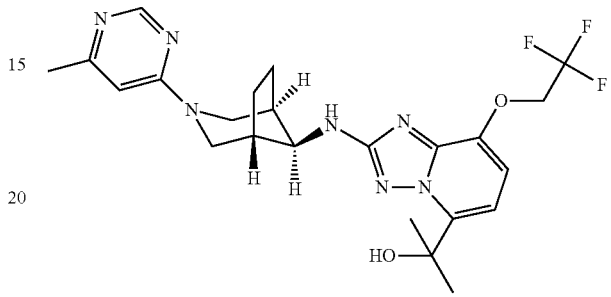

The title compound, was prepared by Buchwald coupling in analogy to example 1, from the described intermediate 3 2-(2-bromo-8-(2,2,2-trifluoroethoxy)-[1,2,4]triazolo[1,5-a]pyridin-5-yl)propan-2-ol (27 mg, 76.2 μmol), and intermediate 2 (example 50) (8 endo)-3-(6-methylpyrimidin-4-yl)-3-azabicyclo[3.2.1]octan-8-amine (20 mg, 91.5 μmol) with Pd₂(dba)₃·CHCl₃ (6.31 mg, 6.1 μmol) in the presence of sodium tert-butoxide (14.7 mg, 152 mol) and xantphos (7.06 mg, 12.2 μmol) heating in a microwave at 120° C. during 20 min. as a light yellow solid (20 mg, 53.4% yield).

MS ES+ (m/z): 492.4 [(M+H)⁺]

In analogy to example 104, several other derivatives have been synthesized, by Buchwald coupling using the described intermediate 3, 2-(2-bromo-8-(2,2,2-trifluoroethoxy)-[1,2,4]triazolo[1,5-a]pyridin-5-yl)propan-2-ol and the already described intermediates 2

They comprise examples 105 to 110 in table 9

TABLE 9

| Example | Systematic name<br>Yield of reaction | Starting materials | MW found<br>(M + H)⁺ |
|---|---|---|---|
| 105 | 2-[2-[[(8 endo)-3-(5-fluoropyrimidin-4-yl)-3-azabicyclo[3.2.1]octan-8-yl]amino]-8-(2,2,2-trifluoroethoxy)-[1,2,4]triazolo[1,5-a]pyridin-5-yl]propan-2-ol (16 mg, 38.1% yield) | 2-(2-bromo-8-(2,2,2-trifluoroethoxy)-[1,2,4]triazolo[1,5-a]pyridin-5-yl)propan-2-ol (30 mg, 84.7 μmol) and (8 endo) 3-(5-fluoropyrimidin-4-yl)-3-azabicyclo[3.2.1]octan-8-amine (intermediate II, example 58) (21.7 mg, 97.6 μmol) | 496.4 |

TABLE 9-continued

| Example | Systematic name Yield of reaction | Starting materials | MW found (M + H)+ |
|---|---|---|---|
| 106 | 2-[2-[[(8 endo)-3-(5-fluoro-6-methylpyrimidin-4-yl)-3-azabicyclo[3.2.1]octan-8-yl]amino]-8-(2,2,2-trifluoroethoxy)-[1,2,4]triazolo[1,5-a]pyridin-5-yl]propan-2-ol (29.4 mg, 68.1% yield). | 2-(2-bromo-8-(2,2,2-trifluoroethoxy)-[1,2,4]triazolo[1,5-a]pyridin-5-yl)propan-2-ol (30 mg, 84.7 μmol) and (8 endo)-3-(5-fluoro-6-methylpyrimidin-4-yl)-3-azabicyclo[3.2.1]octan-8-amine (intermediate II, example 59) (24 mg, 102 μmol,) | 510.4 |
| 107 | 2-[2-[[(8endo)-3-(5-fluoro-2-methylpyrimidin-4-yl)-3-azabicyclo[3.2.1]octan-8-yl]amino]-8-(2,2,2-trifluoroethoxy)-[1,2,4]triazolo[1,5-a]pyridin-5-yl]propan-2-ol (26.7 mg, 61.9% yield) | 2-(2-bromo-8-(2,2,2-trifluoroethoxy)-[1,2,4]triazolo[1,5-a]pyridin-5-yl)propan-2-ol (30 mg, 84.7 μmol) and (8 endo)-3-(5-fluoro-2-methylpyrimidin-4-yl)-3-azabicyclo[3.2.1]octan-8-amine (intermediate II, example 60) (24 mg, 102 μmol) | 510.3 |
| 108 | 2-[8-(2,2,2-trifluoroethoxy)-2-[[(8 endo)-3-[2-(trifluoromethyl)pyridin-4-yl]-3-azabicyclo[3.2.1]octan-8-yl]amino]-[1,2,4]triazolo[1,5-a]pyridin-5-yl]propan-2-ol (30.2 mg, 65.5% yield) | 2-(2-bromo-8-(2,2,2-trifluoroethoxy)-[1,2,4]triazolo[1,5-a]pyridin-5-yl)propan-2-ol (30 mg, 84.7 μmol) and (8 endo)-3-(2-(trifluoromethyl)pyridin-4-yl)-3-azabicyclo[3.2.1]octan-8-amine (intermediate II, example 62) (27.6 mg, 102 μmol) | 545.3 |
| 109 | 2-[2-[[(8endo)-3-(2-chloropyridin-4-yl)-3-azabicyclo[3.2.1]octan-8-yl]amino]-8-(2,2,2-trifluoroethoxy)-[1,2,4]triazolo[1,5-a]pyridin-5-yl]propan-2-ol (17 mg, 39.3% yield) | 2-(2-bromo-8-(2,2,2-trifluoroethoxy)-[1,2,4]triazolo[1,5-a]pyridin-5-yl)propan-2-ol (30 mg, 84.7 μmol) and (8 endo)-3-(2-chloropyridin-4-yl)-3-azabicyclo[3.2.1]octan-8-amine (intermediate II, example 69) (24.2 mg, 102 μmol) | 511.3 |

TABLE 9-continued

| Example | Systematic name Yield of reaction | Starting materials | MW found (M + H)+ |
|---|---|---|---|
| 110 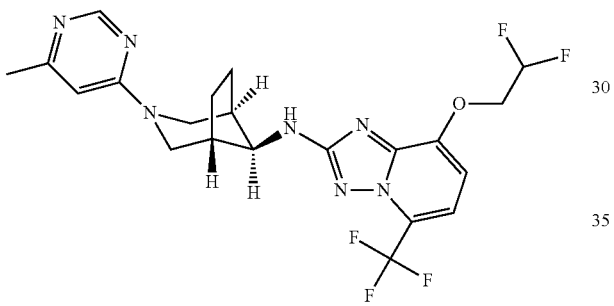 | 2-[2-[[(8 endo)-3-(2-chloro-5-fluoropyridin-4-yl)-3-azabicyclo[3.2.1]octan-8-yl]amino]-8-(2,2,2-trifluoroethoxy)-[1,2,4]triazolo[1,5-a]pyridin-5-yl]propan-2-ol (18.3 mg, 40.8% yield) | 2-(2-bromo-8-(2,2,2-trifluoroethoxy)-[1,2,4]triazolo[1,5-a]pyridin-5-yl)propan-2-ol (30 mg, 84.7 μmol) and (8 endo)-3-(2-chloro-5-fluoropyridin-4-yl)-3-azabicyclo[3.2.1]octan-8-amine (intermediate II, example 97) (26 mg, 102 μmol) | 529.2 |

EXAMPLE 111

8-(2,2-difluoroethoxy)-N-[(8 endo)-3-(6-methylpyrimidin-4-yl)-3-azabicyclo[3.2.1]octan-8-yl]-5-(trifluoromethyl)-[1,2,4]triazolo[1,5-a]pyridin-2-amine

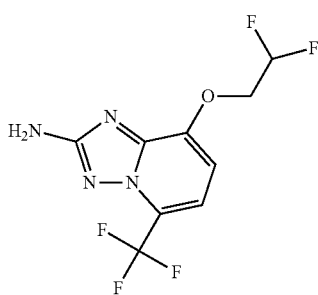 [SMILES: Nc1nc2c(OCC(F)F)ccc(C(F)(F)F)n2n1]

Intermediate 3

Step 1

8-(2,2-difluoroethoxy)-5-(trifluoromethyl)-[1,2,4]triazolo[1,5-a]pyridin-2-amine

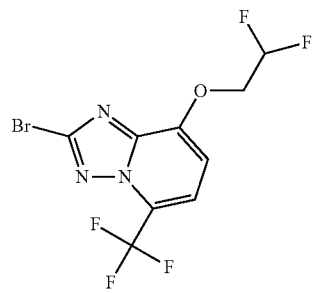 [SMILES: FC(F)COc1ccc(C(F)(F)F)n2nc(Br)nc12]

The title compound, was prepared in analogy to example 71, intermediate 3, step 3, from 8-bromo-5-(trifluoromethyl)-[1,2,4]triazolo[1,5-a]pyridin-2-amine (150 mg, 534 μmol) product of example 71, step 2, and 2,2-difluoroethanol (65.7 mg, 50.7 μl, 801 μmol) as an off-white solid (124 mg, 439 μmol, 61.6% yield). MS ES+ (m/z): 283.1 [(M+H)+].

Step 2

2-bromo-8-(2,2-difluoroethoxy)-5-(trifluoromethyl)-[1,2,4]triazolo[1,5-a]pyridine The title compound, was prepared in analogy to example 1, intermediate 3, step 4 from 8-(2,2-difluoroethoxy)-5-(trifluoromethyl)-[1,2,4]triazolo[1,5-a]pyridin-2-amine (120 mg, 425 μmol), tert-butyl nitrite and copper (II) bromide as a white solid (123.9 mg, 84.2% yield). MS ES+(m/z): 346.0 [(M+H)+]

Final Coupling Step 3

8-(2,2-difluoroethoxy)-N-[(8 endo)-3-(6-methylpyrimidin-4-yl)-3-azabicyclo[3.2.1]octan-8-yl]-5-(trifluoromethyl)-[1,2,4]triazolo[1,5-a]pyridin-2-amine

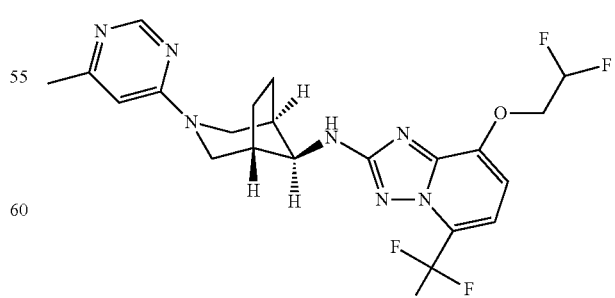

The title compound, was prepared by Buchwald coupling in analogy to example 1, from the described intermediate 3

2-bromo-8-(2,2-difluoroethoxy)-5-(trifluoromethyl)-[1,2,4]triazolo[1,5-a]pyridine (30 mg, 86.7 μmol), and intermediate 2 (example 50) (8 endo)-3-(6-methylpyrimidin-4-yl)-3-azabicyclo[3.2.1]octan-8-amine ((22.7 mg, 104 μmol) with Pd$_2$(dba)$_3$.CHCl$_3$ (7.18 mg, 6.94 μmol) in the presence of sodium tert-butoxide (16.7 mg, 173 μmol) and xantphos (8.03 mg, 13.9 μmol) heating in a microwave at 130° C. during 30 min. as a light yellow solid (32.8 mg, 67.8 μmol, 78.3% yield). MS ES+ (m/z): 484.2 [(M+H)$^+$].

EXAMPLE 112

N-[(8 endo)-3-(2-chloropyridin-4-yl)-3-azabicyclo[3.2.1]octan-8-yl]-8-(2,2-difluoroethoxy)-5-(trifluoromethyl)-[1,2,4]triazolo[1,5-a]pyridin-2-amine

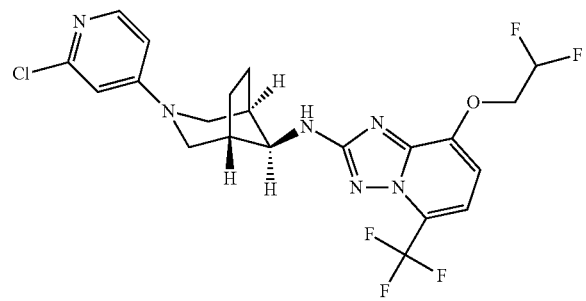 [SMILES: FC(F)COc1ccc(C(F)(F)F)n2nc(N[C@@H]3[C@@H]4CC[C@H]3CN(c3ccnc(Cl)c3)C4)nc12]

The title compound, was prepared by Buchwald coupling in analogy to example 1, from the described intermediate 3 (on example 111) 2-bromo-8-(2,2-difluoroethoxy)-5-(trifluoromethyl)-[1,2,4]triazolo[1,5-a]pyridine (30 mg, 86.7 μmol), and intermediate 2 (example 69) (8 endo)-3-(2-chloropyridin-4-yl)-3-azabicyclo[3.2.1]octan-8-amine (22.7 mg, 95.4 μmol) with Pd$_2$(dba)$_3$.CHCl$_3$ (7.18 mg, 6.94 μmol) in the presence of sodium tert-butoxide (16.7 mg, 173 μmol) and xantphos (8.03 mg, 13.9 μmol) heating in a microwave at 130° C. during 30 min. as a light yellow solid (21.6 mg, 49.5% yield). MS ES+ (m/z): 503.2 [(M+H)$^+$].

EXAMPLE 113

8-(2-fluoroethoxy)-N-[(8 endo)-3-(6-methylpyrimidin-4-yl)-3-azabicyclo[3.2.1]octan-8-yl]-5-(trifluoromethyl)-[1,2,4]triazolo[1,5-a]pyridin-2-amine

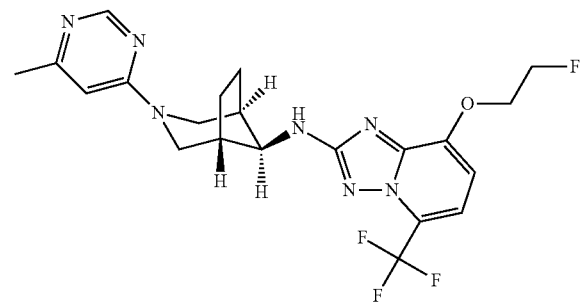 [SMILES: Cc1cc(N2C[C@H]3CC[C@@H](C2)[C@@H]3Nc2nc3c(OCCF)ccc(C(F)(F)F)n3n2)ncn1]

Intermediate 3

Step 1

8-(2-fluoroethoxy)-5-(trifluoromethyl)-[1,2,4]triazolo[1,5-a]pyridin-2-amine

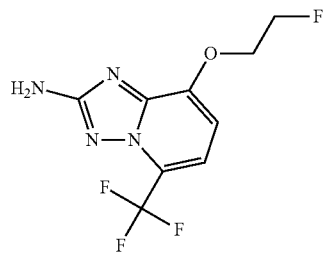 [SMILES: Nc1nc2c(OCCF)ccc(C(F)(F)F)n2n1]

The title compound, was prepared in analogy to example 71, intermediate 3, step 3, from 8-bromo-5-(trifluoromethyl)-[1,2,4]triazolo[1,5-a]pyridin-2-amine (500 mg, 1.78 mmol) product of example 71, step 2, and 2-fluoroethanol (171 mg, 157 μl, 2.67 mmol) as an off-white solid (230.5 mg, 873 μmol, 49% yield). MS ES$^+$ (m/z): 265.1 [(M+H)$^+$].

Step 2

2-bromo-8-(2,2-difluoroethoxy)-5-(trifluoromethyl)-[1,2-a]triazolo[1,5-a]pyridine

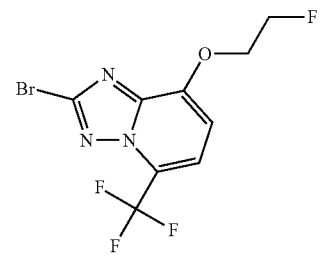 [SMILES: FCCOc1ccc(C(F)(F)F)n2nc(Br)nc12]

The title compound, was prepared in analogy to example 1, intermediate 3, step 4 from 8-(2-fluoroethoxy)-5-(trifluoromethyl)-[1,2,4]triazolo[1,5-a]pyridin-2-amine (230 mg, 871 μmol), tert-butyl nitrite and copper (II) bromide as a white solid (221.8 mg, 676 μmol, 78% yield). MS ES+ (m/z): 330.0 [(M+H)$^+$].

Final Coupling Step 3

8-(2-fluoroethoxy)-N-[(8 endo)-3-(6-methylpyrimidin-4-yl)-3-azabicyclo[3.2.1]octan-8-yl]-5-(trifluoromethyl)-[1,2,4]triazolo[1,5-a]pyridin-2-amine

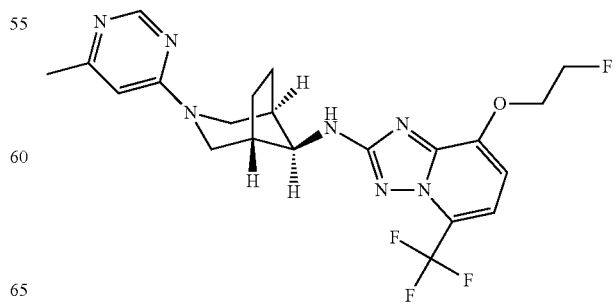

The title compound, was prepared by Buchwald coupling in analogy to example 1, from the described intermediate 3 2-bromo-8-(2-fluoroethoxy)-5-(trifluoromethyl)-[1,2,4]triazolo[1,5-a]pyridine (30 mg, 91.4 µmol), and intermediate 2 (example 50) (8 endo)-3-(6-methylpyrimidin-4-yl)-3-azabicyclo[3.2.1]octan-8-amine ((24 mg, 110 µmol) with Pd$_2$(dba)$_3$.CHCl$_3$ (7.57 mg, 7.32 µmol) in the presence of sodium tert-butoxide (17.6 mg, 183 µmol) and xantphos (8.47 mg, 14.6 µmol) heating in a microwave at 120° C. during 20 min. as a light yellow solid (36.8 mg, 79.1 µmol, 86.5% yield). MS ES+ (m/z): 466.3 (100%) [(M+H)$^+$]

EXAMPLE 114

N-[(8 endo)-3-(2-chloropyridin-4-yl)-3-azabicyclo[3.2.1]octan-8-yl]-8-(2-fluoroethoxy)-5-(trifluoromethyl)-[1,2,4]triazolo[1,5-a]pyridin-2-amine

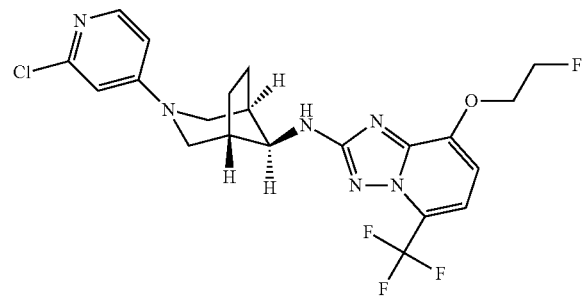 [SMILES: FCCOc1ccc(C(F)(F)F)n2nc(N[C@@H]3[C@@H]4CC[C@H]3CN(c3ccnc(Cl)c3)C4)nc12]

The title compound, was prepared by Buchwald coupling in analogy to example 1, from the described intermediate 3 (on example 113) 2-bromo-8-(2,2-difluoroethoxy)-5-(trifluoromethyl)-[1,2,4]triazolo[1,5-a]pyridine (30 mg, 91.4 µmol), and intermediate 2 (example 69) (8 endo)-3-(2-chloropyridin-4-yl)-3-azabicyclo[3.2.1]octan-8-amine (23.9 mg, 101 µmol) with Pd$_2$(dba)$_3$.CHCl$_3$ (7.57 mg, 67.32 µmol) in the presence of sodium tert-butoxide (17.6 mg, 183 µmol) and xantphos (8.47 mg, 14.6 µmol) heating in a microwave at 120° C. during 20 min. as a light yellow solid (20.7 mg, 42.7 µmol, 46.7% yield). MS ES+ (m/z): 485.3 [(M+H)$^+$].

EXAMPLE 115

2-[2-[[(1R,5S,8s)-3-(5-fluoro-2-methyl-4-pyridyl)-3-azabicyclo[3.2.1]octan-8-yl]amino]-8-(2,2,2-trifluoroethoxy)-[1,2,4]triazolo[1,5-a]pyridin-5-yl]propan-2-ol

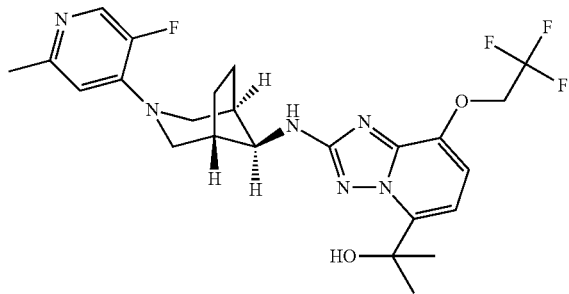 [SMILES: Cc1cc(N2C[C@H]3CC[C@@H](C2)[C@@H]3Nc2nc3c(OCC(F)(F)F)ccc(C(C)(C)O)n3n2)c(F)cn1]

The title compound, was prepared by Buchwald coupling in analogy to example 1, from 2-[2-bromo-8-(2,2,2-trifluoroethoxy)-[1,2,4]triazolo[1,5-a]pyridin-5-yl]propan-2-ol (30 mg, 84.7 µmol) (preparation described in example 104) and (1R,5S,8s)-3-(5-fluoro-2-methyl-4-pyridyl)-3-azabicyclo[3.2.1]octan-8-amine (23.9 mg, 102 µmol) (preparation described in example 70) with Pd$_2$(dba)$_3$. CHCl$_3$ (7.02 mg, 6.78 µmol) in the presence of sodium tert-butoxide (16.3 mg, 169 µmol) and xantphos (7.84 mg, 13.6 µmol) in a microwave at 120° C. during 20 min. It was obtained as an off white solid (43 mg, 85 µmol, 63.4% yield). MS ES+ (m/z): 509.2 [(M+H)+].

EXAMPLE 116

2-[2-[[(1R,5S,8s)-3-(3-fluoro-4-pyridyl)-3-azabicyclo[3.2.1]octan-8-yl]amino]-8-(2,2,2-trifluoroethoxy)-[1,2,4]triazolo[1,5-a]pyridin-5-yl]propan-2-ol

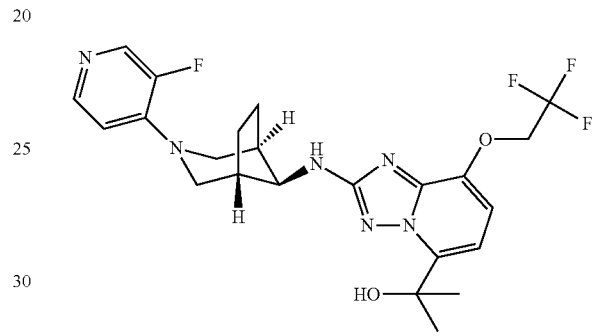

The title compound, was prepared by Buchwald coupling in analogy to example 1, from 2-[2-bromo-8-(2,2,2-trifluoroethoxy)-[1,2,4]triazolo[1,5-a]pyridin-5-yl]propan-2-ol (30 mg, 84.7 µmol) (preparation described in example 104) and (1R,5S,8s)-3-(3-fluoro-4-pyridyl)-3-azabicyclo[3.2.1]octan-8-amine (22.5 mg, 102 µmol) (preparation described in example 90) with Pd$_2$(dba)$_3$.CHCl$_3$ (7.02 mg, 6.78 µmol) in the presence of sodium tert-butoxide (16.3 mg, 169 µmol) and xantphos (7.84 mg, 13.6 µmol) in a microwave at 120° C. during 20 min. It was obtained as an off white solid (41.9 mg, 84.7 µmol, 62.3% yield). MS ES+ (m/z): 495.4 [(M+H)+].

EXAMPLE 117

5-cyclopropyl-N-[(1R,5S,8s)-3-(6-methylpyrimidin-4-yl)-3-azabicyclo[3.2.1]octan-8-yl]-8-(2,2,2-trifluoroethoxy)-[1,2,4]triazolo[1,5-a]pyridin-2-amine

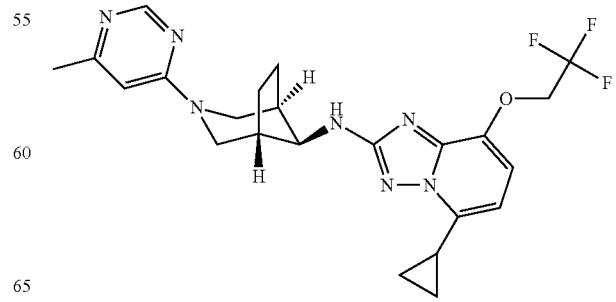

Step 1: 6-bromo-2-nitro-pyridin-3-ol

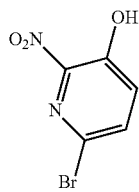 [SMILES: O=[N+]([O-])c1nc(Br)ccc1O]

A solution of 2-nitropyridin-3-ol (15 g, 104 mmol) in DMF (189 mL) was cooled to 0° C. then N-bromosuccinimide (24 g, 135 mmol) was added gradually over 25 minutes. The solution was stirred at 0° C. for an additional 15 minutes and then the mixture was allowed to warm to RT, and stirred over night. The reaction mixture was concentrated in vacuo and purified by column chromatography using 100% $CH_2Cl_2$ to afford 6-bromo-2-nitro-pyridin-3-ol (13.67 g, 56.2 mmol, 54.1% yield) as a yellow solid. MS ES+ (m/z): 219.1 [(M+H)+].

Step 2: 6-bromo-2-nitro-3-(2,2,2-trifluoroethoxy)pyridine

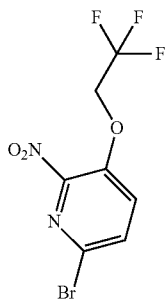 [SMILES: O=[N+]([O-])c1nc(Br)ccc1OCC(F)(F)F]

To a yellow solution of 6-bromo-2-nitro-pyridin-3-ol (11.9 g, 48.9 mmol) in DMF (256 mL) 0° C. was added $K_2CO_3$ (10.1 g, 73.4 mmol). 2,2,2-trifluoroethyl trifluoromethanesulfonate (17.6 g, 10.9 ml, 73.4 mmol) was then added dropwise and the reaction mixture was allowed to warm to RT and stirred over night. The reaction mixture was concentrated in vacuo (HV), diluted with EtOAc and washed with water and 1M NaOH. The organic layer was dried over sodium sulfate, filtered and concentrated in vacuo. A column chromatography using (Hept:EtOAc 2:1 to 1:1) afforded 6-bromo-2-nitro-3-(2,2,2-trifluoroethoxy)pyridine (13.71 g, 45.5 mmol, 93.1% yield) as a yellow oil.

Step 3: 6-cyclopropyl-2-nitro-3-(2,2,2-trifluoroethoxy)pyridine

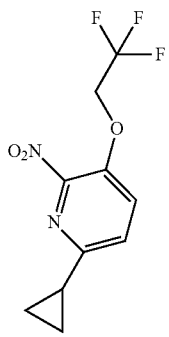 [SMILES: O=[N+]([O-])c1nc(C2CC2)ccc1OCC(F)(F)F]

In a sealed tube under argon 6-bromo-2-nitro-3-(2,2,2-trifluoroethoxy)pyridine (1.00 g, 3.32 mmol) was dissolved in toluene (11.7 mL) and water (1.17 mL). Cyclopropylboronic acid (514 mg, 5.98 mmol), potassium phosphate tribasic (1.41 g, 6.64 mmol), tricyclohexylphosphine (93.2 mg, 332 μmol) and palladium (II) acetate (37.3 mg, 166 μmol) were added and the resulting reaction mixture was stirred at 100° C. over night. The reaction mixture was diluted with EtOAc and washed with water twice. The organic layer was dried over sodium sulfate, filtered and concentrated in vacuo. Column chromatography (Hept:EtOAc 100:0 to 70:30) afforded 6-cyclopropyl-2-nitro-3-(2,2,2-trifluoroethoxy)pyridine (801 mg, 3.06 mmol, 92% yield) as a light-brown oil. MS ES+ (m/z): 263.1 [(M+H)+].

Step 4: 6-cyclopropyl-3-(2,2,2-trifluoroethoxy)pyridin-2-amine

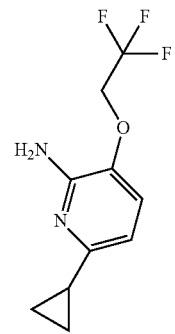

To a solution of 6-cyclopropyl-2-nitro-3-(2,2,2-trifluoroethoxy)pyridine (7.5 g, 28.6 mmol) in ethanol (150 mL) was added Fe powder (6.5 g, 116 mmol) and acetic acid (76 mL). The reaction mixture was stirred at 80° C. for 5 hours and then was concentrated in vacuo. The residue was diluted with EtOAc and water, basified to pH 9 using solid NaOH and 1M NaOH and filtered through celite. The organic phase was dried over sodium sulfate, filtered and concentrated in vacuo. A column chromatography (Hept:EtOAc 2:1) afforded 6-cyclopropyl-3-(2,2,2-trifluoroethoxy)pyridin-2-amine (6.28 g, 27 mmol, 94.5% yield) as an off-white solid. MS ES+(m/z): 233.1 [(M+H)+].

Step 5: ethyl N-[[6-cyclopropyl-3-(2,2,2-trifluoroethoxy)-2-pyridyl]carbamothioyl]carbamate

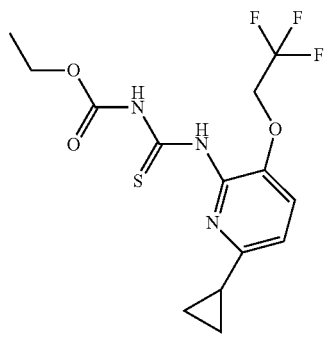 [SMILES: CCOC(=O)NC(=S)Nc1nc(C2CC2)ccc1OCC(F)(F)F]

To a solution of 6-cyclopropyl-3-(2,2,2-trifluoroethoxy) pyridin-2-amine (6.28 g, 27 mmol) in 1,4-dioxane (100 mL) was added ethoxycarbonyl isothiocyanate (3.84 g, 3.46 ml, 28.4 mmol) and the reaction mixture was stirred at RT for 75 min. The resulting precipitate was collected by filtration (6.34 g) and the filtrate was concentrated in vacuo and purified by column chromatography (Hept:EtOAc 90:10 to 50:50) to afford another 2.9 g of product. No further purification was requiring (9.24 g, 94% yield). MS ES+ (m/z): 364.2 [(M+H)+].

Step 6: 5-cyclopropyl-8-(2,2,2-trifluoroethoxy)-[1,2,4]triazolo[1,5-a]pyridin-2-amine

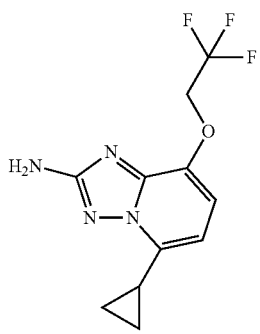 [SMILES: Nc1nc2c(OCC(F)(F)F)ccc(C3CC3)n2n1]

To a mixture of ethyl N-[[6-cyclopropyl-3-(2,2,2-trifluoroethoxy)pyridin-2-yl]carbamothioyl]-carbamate (6.34 g, 17.4 mmol) and hydroxylamine hydrochloride (6.12 g, 87.2 mmol) in EtOH (52 mL) and MeOH (52 mL) was added N,N-diisopropylethylamine (6.77 g, 9.06 mL, 52.3 mmol). The reaction mixture was stirred at 70° C. for 45 minutes, concentrated under vacuo, diluted in EtOAc and washed with water. The organic phase was separated and dried over sodium sulfate, filtered and concentrated in vacuo. A column chromatography (Hept:EtOAc 1:1 to 1:2) afforded 5-cyclopropyl-8-(2,2,2-trifluoroethoxy)-[1,2,4]triazolo[1,5-a]pyridin-2-amine (4.41 g, 16.2 mmol, 92.8% yield) as a white solid. MS ES+ (m/z): 273.2 [(M+H)+].

Step 7: 2-bromo-5-cyclopropyl-8-(2,2,2-trifluoroethoxy)-[1,2,4]triazolo[1,5-a]pyridine

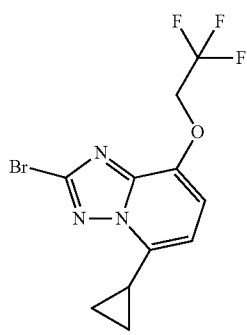 [SMILES: FC(F)(F)COc1ccc(C2CC2)n2nc(Br)nc12]

To a solution of cupric bromide (5.54 g, 24.3 mmol) and tert-butyl nitrite (2.78 g, 3.21 ml, 24.3 mmol) in CH₃CN (80 mL) was added a solution of 5-cyclopropyl-8-(2,2,2-trifluoroethoxy)-[1,2,4]triazolo[1,5-a]pyridin-2-amine (4.41 g, 16.2 mmol) in CH₃CN (20 mL) at 60° C. The reaction mixture was stirred for 5 min at 75° C. The reaction mixture was concentrated in vacuo, diluted with EtOAc and washed with water. The organic phase was separated and dried over sodium sulfate, filtered and concentrated in vacuo. A column chromatography (Hept:EtOAc 6:1 to 4:1) gave 2-bromo-5-cyclopropyl-8-(2,2,2-trifluoroethoxy)-[1,2,4]triazolo[1,5-a]pyridine (4.81 g, 14.3 mmol, 88.3% yield) as a colourless oil. MS ES+ (m/z): 336.1 [(M+H)+].

Step 8: 5-cyclopropyl-N-[(1R,5S,8s)-3-(6-methylpyrimidin-4-yl)-3-azabicyclo[3.2.1]octan-8-yl]-8-(2,2,2-trifluoroethoxy)-[1,2,4]triazolo[1,5-a]pyridin-2-amine

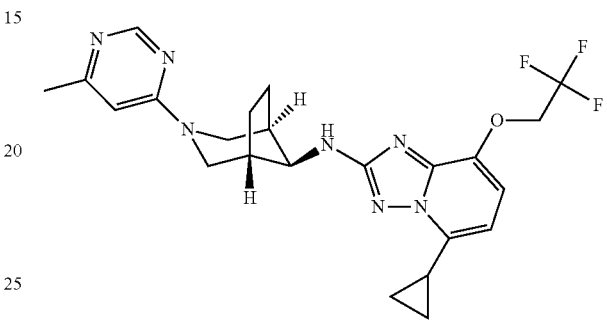

2-bromo-5-cyclopropyl-8-(2,2,2-trifluoroethoxy)-[1,2,4]triazolo[1,5-a]pyridine (700 mg, 2.08 mmol), (1R,5S,8s)-3-(6-methylpyrimidin-4-yl)-3-azabicyclo[3.2.1]octan-8-amine (500 mg, 2.29 mmol) (preparation described in example 50) and sodium tert-butoxide (801 mg, 8.33 mmol) were combined in MeTHF (83 mL), flushed with argon then followed by the addition of 2-di-tert-butylphosphino-2',4',6'-triisopropylbiphenyl (26.5 mg, 62.5 μmol) and tris(dibenzylidene-acetone)dipalladium (0) (28.6 mg, 31.2 μmol). The reaction mixture was stirred at 80° C. for 2 hours. The reaction mixture was diluted with water and EtOAc, the organic phase separated and dried over sodium sulfate, filtered and concentrated in vacuo. A column chromatography (Hept:EtOAc 40:60 to 0:100) afforded the title compound 5-cyclopropyl-N-[(1R,5S,8s)-3-(6-methylpyrimidin-4-yl)-3-azabicyclo[3.2.1]octan-8-yl]-8-(2,2,2-trifluoroethoxy)[1,2,4]triazolo-[1,5-a]pyridin-2-amine (633 mg, 1.34 mmol, 64.2% yield) as a light-yellow foam. MS ES+(m/z): 474.3 [(M+H)+].

EXAMPLE 118

N-[(1R,5S,8s)-3-(6-chloropyridazin-4-yl)-3-azabicyclo[3.2.1]octan-8-yl]-5-cyclopropyl-8-(2,2,2-trifluoroethoxy)-[1,2,4]triazolo[1,5-a]pyridin-2-amine

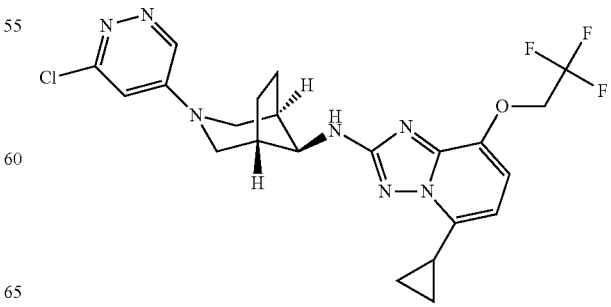

The title compound, was prepared by Buchwald coupling in analogy to example 1, from 2-bromo-5-cyclopropyl-8-(2,2,2-trifluoroethoxy)-[1,2,4]triazolo[1,5-a]pyridine (98 mg, 293 μmol) (preparation described in example 117) and (1R,5S,8s)-3-(6-chloropyridazin-4-yl)-3-azabicyclo[3.2.1]octan-8-amine (70 mg, 293 μmol) (preparation described herein below) with Pd$_2$(dba)$_3$.CHCl$_3$ (24.3 mg, 23.5 μmol) in the presence of sodium tert-butoxide (59.2 mg, 616 μmol) and xantphos (27.1 mg, 46.9 μmol) in a microwave at 120° C. during 30 min. It was obtained as a light yellow solid (44 mg, 89 μmol, 30% yield). MS ES+ (m/z): 494.3 [(M+H)+].

Preparation of (1R,5S,8s)-3-(6-chloropyridazin-4-yl)-3-azabicyclo[3.2.1]octan-8-amine

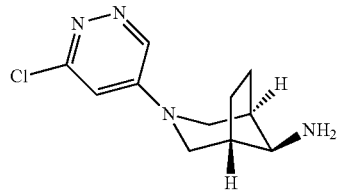 [SMILES: N[C@@H]1[C@@H]2CC[C@H]1CN(c1cnnc(Cl)c1)C2]

First Step

A solution of tert-butyl N-[(1R,5S,8s)-3-azabicyclo[3.2.1]octan-8-yl]carbamate (700 mg, 3.09 mmol), 3,5-dichloropyridazine (691 mg, 4.64 mmol) in ethanol (42 mL) with triethylamine (1.25 g, 12.4 mmol) was stirred for 3 h at 85° C. and then 60 h at RT. The reaction mixture was diluted with 30 mL H$_2$O and extracted with EtOAc (3×30 mL). The organic layers were dried over MgSO$_4$ and concentrated in vacuum. The crude material was purified by flash chromatography (silica gel 20 g, eluent 0% to 70% EtOAc in heptane) to afford tert-butyl N-[(1R,5S,8s)-3-(6-chloropyridazin-4-yl)-3-azabicyclo[3.2.1]octan-8-yl]carbamate 923 mg, 88%. MS ES+ (m/z): 339.2 [(M+H)+].

Second Step

To a solution of tert-butyl N-[(1R,5S,8s)-3-(6-chloropyridazin-4-yl)-3-azabicyclo-[3.2.1]octan-8-yl]carbamate (923 mg, 2.72 mmol) in CH$_2$Cl$_2$ was added aqueous HCl 37% (1.61 g, 16.3 mmol). The title compound was obtained after extraction using sat NaHCO$_3$ and DCM as a brown solid (651 mg, 100% yield) MS ES+ (m/z): 239.1 [(M+H)$^+$].

EXAMPLE 119

5-cyclopropyl-N-[(1R,5S,8s)-3-(6-methoxypyridazin-4-yl)-3-azabicyclo[3.2.1]octan-8-yl]-8-(2,2,2-trifluoroethoxy)-[1,2,4]triazolo[1,5-a]pyridin-2-amine

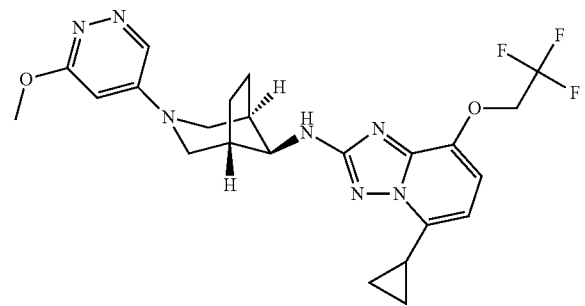 [SMILES: COc1cc(N2C[C@H]3CC[C@@H](C2)[C@@H]3Nc2nc3c(OCC(F)(F)F)ccc(C4CC4)n3n2)cnn1]

The title compound, was prepared by Buchwald coupling in analogy to example 1, from 2-bromo-5-cyclopropyl-8-(2,2,2-trifluoroethoxy)-[1,2,4]triazolo[1,5-a]pyridine (57 mg, 171 μmol) (preparation described in example 117) and (1R,5S,8s)-3-(6-methoxypyridazin-4-yl)-3-azabicyclo[3.2.1]octan-8-amine (40 mg, 171 μmol) (preparation described herein below) with Pd$_2$(dba)$_3$.CHCl$_3$ (14.1 mg, 13.7 μmol) in the presence of sodium tert-butoxide (34.5 mg, 359 μmol) and xantphos (15.8 mg, 27.3 μmol) in a microwave at 120° C. during 30 min. It was obtained as a light yellow solid (47 mg, 96 μmol, 56% yield). MS ES+ (m/z): 490.3 [(M+H)+].

Preparation of (1R,5S,8s)-3-(6-methoxypyridazin-4-yl)-3-azabicyclo[3.2.1]octan-8-amine

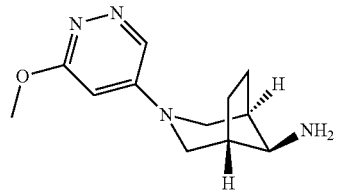 [SMILES: COc1cc(N2C[C@H]3CC[C@@H](C2)[C@@H]3N)cnn1]

Step 1

Tert-butyl N-[(1R,5S,8s)-3-(6-chloropyridazin-4-yl)-3-azabicyclo[3.2.1]octan-8-yl]carbamate (4.314 g, 12.1 mmol), material of example 118, was partially dissolved in 150 mL of methanol. The vial was flushed with argon. A sodium methoxide solution, 25% in methanol (7.94 g, 8.4 ml, 36.7 mmol) was added drop-wise, the vial was flushed again with argon and closed. The reaction mixture was stirred at 85° C. overnight. The LC/MS showed still starting material. The reaction mixture was cooled to room temperature. Sodium methoxide solution, 25% in methanol (2.65 g, 2.8 ml, 12.2 mmol) was added and the reaction mixture was stirred at 85° C. for further six days. The reaction mixture was cooled to room temperature and then adsorbed on ISOLUTE HM-N and chromatographed over 120 g of silica gel with EtOAc in heptane, 0-100%. All fractions containing product were combined and concentrated to afford tert-butyl N-[(1R,5S,8s)-3-(6-methoxypyridazin-4-yl)-3-azabicyclo[3.2.1]octan-8-yl]carbamate (2.423 g, 7.25 mmol, 59.9% yield) as an off-white solid. MS ES+ (m/z): 335.2 [(M+H)+].

Step 2 tert-butyl N-[(1R,5S,8s)-3-(6-methoxypyridazin-4-yl)-3-azabicyclo[3.2.1]octan-8-yl]carbamate (500 mg, 1.5 mmol) and TFA (3.4 g, 2.3 mL, 29.9 mmol) were combined in CH$_2$Cl$_2$ (10 mL). The reaction mixture was stirred at RT for 1 hr. The reaction mixture was evaporated under high vacuum, re-dissolved in CH$_2$Cl$_2$ and washed once with saturated aqueous K$_2$CO$_3$. The aqueous layer was extracted twice with CH$_2$Cl$_2$. The aqueous phase was extracted further 6 times with MeOH:DCM, 5%. The organic layers were combined, dried over sodium sulfate and evaporated under vacuum to afford (1R,5S,8s)-3-(6-methoxypyridazin-4-yl)-3-azabicyclo[3.2.1]octan-8-amine (338 mg, 1.44 mmol, 96.5% yield) as an off-white solid. MS ES+ (m/z): 235.2 [(M+H)+].

EXAMPLE 120

N-[(1R,5S,8s)-3-(6-chloropyridazin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

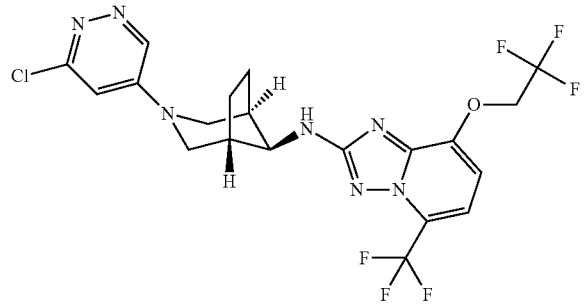 [SMILES: FC(F)(F)COc1ccc(C(F)(F)F)n2nc(N[C@@H]3[C@@H]4CC[C@H]3CN(c3cnnc(Cl)c3)C4)nc12]

The title compound, was prepared by Buchwald coupling in analogy to example 1, from 2-bromo-8-(2,2,2-trifluoroethoxy)-5-(trifluoromethyl)-[1,2,4]triazolo[1,5-a]pyridine (91 mg, 251 mol) (preparation described in example 71) and (1R,5S,8s)-3-(6-chloropyridazin-4-yl)-3-azabicyclo[3.2.1]octan-8-amine (60 mg, 251 μmol) (preparation described in example 118) with Pd$_2$(dba)$_3$.CHCl$_3$ (20.8 mg, 20.1 μmol) in the presence of sodium tert-butoxide (48.3 mg, 503 mol) and xantphos (23.3 mg, 40.2 μmol) in a microwave at 110° C. during 30 min. It was obtained as a light yellow solid (41 mg, 78 μmol, 31% yield). MS ES+(m/z): 522.2 [(M+H)+].

EXAMPLE 121

N-[(1R,5S,8s)-3-(6-chloropyrimidin-4-yl)-3-azabicyclo[3.2.1]octan-8-yl]-5-cyclopropyl-8-(2,2,2-trifluoroethoxy)-[1,2,4]triazolo[1,5-a]pyridin-2-amine

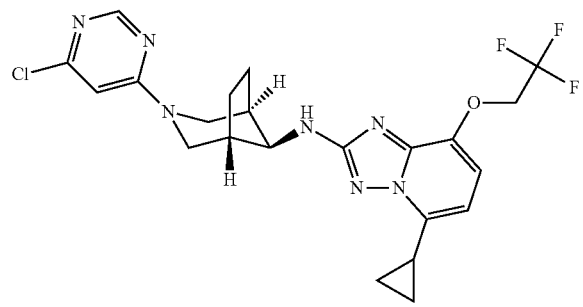 [SMILES: FC(F)(F)COc1ccc(C2CC2)n2nc(N[C@@H]3[C@@H]4CC[C@H]3CN(c3cc(Cl)ncn3)C4)nc12]

The title compound, was prepared by Buchwald coupling in analogy to example 1, from 2-bromo-5-cyclopropyl-8-(2,2,2-trifluoroethoxy)-[1,2,4]triazolo[1,5-a]pyridine (56 mg, 168 μmol) (preparation described in example 117) and (1R,5S,8s)-3-(6-chloropyrimidin-4-yl)-3-azabicyclo[3.2.1]octan-8-amine (40 mg, 168 μmol) (preparation described in example 61) with Pd$_2$(dba)$_3$.CHCl$_3$ (13.9 mg, 13.4 μmol) in the presence of sodium tert-butoxide (33.8 mg, 352 mol) and xantphos (15.5 mg, 26.8 μmol) in a microwave at 120° C. during 30 min. It was obtained as a white solid (14 mg, 28 μmol, 16% yield). MS ES+ (m/z): 494.2 [(M+H)+].

EXAMPLE 122

N-[(1R,5S,8s)-3-(6-methoxypyridazin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine

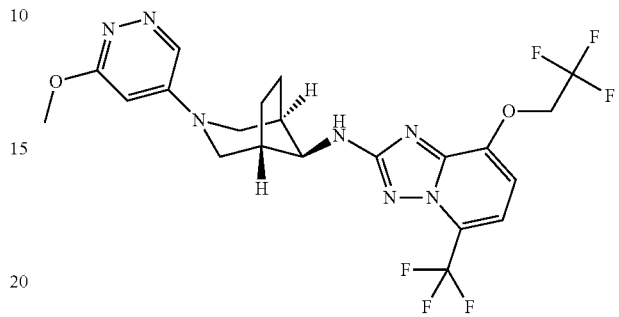

The title compound, was prepared by Buchwald coupling in analogy to example 1, from 2-bromo-8-(2,2,2-trifluoroethoxy)-5-(trifluoromethyl)-[1,2,4]triazolo[1,5-a]pyridine (46 mg, 128 mol) (preparation described in example 71) and (1R,5S,8s)-3-(6-methoxypyridazin-4-yl)-3-azabicyclo[3.2.1]octan-8-amine (30 mg, 128 μmol) (preparation described in example 119) with Pd$_2$(dba)$_3$.CHCl$_3$ (10.6 mg, 10.2 μmol) in the presence of sodium tert-butoxide (24.6 mg, 256 mol) and xantphos (11.9 mg, 20.5 μmol) in a microwave at 110° C. during 30 min. It was obtained as a white solid (33 mg, 64 μmol, 50% yield). MS ES+ (m/z): 518.3 [(M+H)+].

EXAMPLE 123

N-[(1R,5S,8s)-3-(2-chloro-4-pyridyl)-3-azabicyclo[3.2.1]octan-8-yl]-5-cyclopropyl-8-(2,2,2-trifluoroethoxy)-[1,2,4]triazolo[1,5-a]pyridin-2-amine

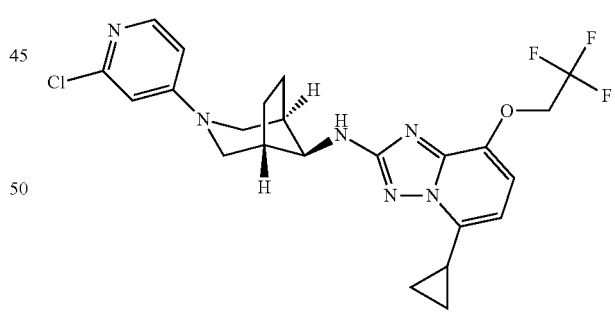

The title compound, was prepared by Buchwald coupling in analogy to example 1, from 2-bromo-5-cyclopropyl-8-(2,2,2-trifluoroethoxy)-[1,2,4]triazolo[1,5-a]pyridine (63 mg, 189 μmol) (preparation described in example 117) and (1R,5S,8s)-3-(2-chloro-4-pyridyl)-3-azabicyclo[3.2.1]octan-8-amine (45 mg, 189 μmol) (preparation described in example 69) with Pd$_2$(dba)$_3$.CHCl$_3$ (15.7 mg, 15.1 μmol) in the presence of sodium tert-butoxide (38.2 mg, 398 mol) and xantphos (17.5 mg, 30.3 μmol) in a microwave at 120° C. during 30 min. It was obtained as a yellow solid (43 mg, 87 μmol, 46% yield). MS ES+ (m/z): 493.3 [(M+H)+].

The invention claimed is:
1. A compound of formula I

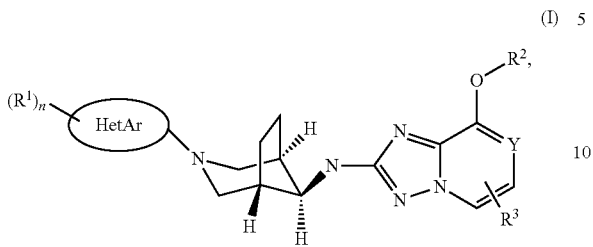

or a pharmaceutically acceptable salt thereof, wherein:
HetAr is a five or six membered hetaryl group, containing one, two or three heteroatoms, selected from N, O or S;
$R^1$ is hydrogen, lower alkyl, lower alkyl substituted by halogen, halogen, or lower alkoxy;
$R^2$ is lower alkyl substituted by halogen, —$CH_2$—$C_{3-6}$-cycloalkyl, substituted by one or two substituents, selected from lower alkyl substituted by halogen or halogen, or is lower alkenyl substituted by halogen;
$R^3$ is hydrogen, lower alkyl substituted by halogen, lower alkyl, halogen or lower alkyl substituted by hydroxy;
n is 1 or 2; for n=2, $R^1$ can be independent of each other; and
Y is CH or N.

2. A compound of formula I-1 according to claim 1

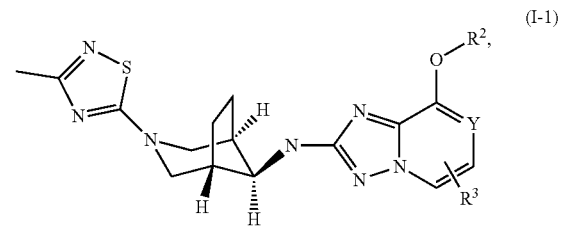

or a pharmaceutically acceptable salt thereof, wherein:
$R^2$ is lower alkyl substituted by halogen,

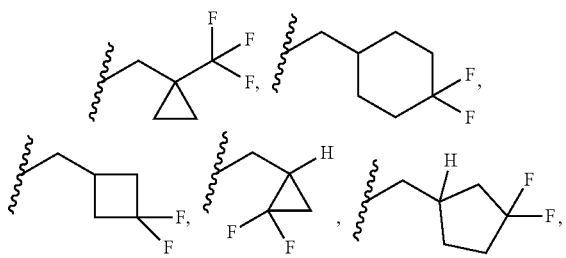

or is lower alkenyl substituted by halogen;
$R^3$ is hydrogen, lower alkyl substituted by halogen, lower alkyl, halogen or lower alkyl substituted by hydroxy; and
Y is CH or N.

3. A compound of formula I-1 according to claim 2, or a pharmaceutically acceptable salt thereof, wherein the compound is selected from the group consisting of:
N-(8 endo)-3-(3-methyl-1,2,4-thiadiazol-5-yl)-3-azabicyclo[3.2.1]octan-8-yl)-8-(4,4,4-trifluorobutoxy)-[1,2,4]triazolo[1,5-a]pyridin-2-amine;

N-[(8-endo)-3-(3-methyl-1,2,4-thiadiazol-5-yl)-3-azabicyclo[3.2.1]octan-8-yl]-8-(3,3,3-trifluoropropoxy)-[1,2,4]triazolo[1,5-a]pyridin-2-amine;

N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine;

N-[(8-endo) 3-(3-methyl-1,2,4-thiadiazol-5-yl)-3-azabicyclo[3.2.1]octan-8-yl]-8-[(2R/S)-1,1,1-trifluoropropan-2-yl]oxy-[1,2,4]triazolo[1,5-a]pyridin-2-amine;

N-[(8-endo)-3-(3-methyl-1,2,4-thiadiazol-5-yl)-3-azabicyclo[3.2.1]octan-8-yl]-8-[(2R or 2S)-1,1,1-trifluoropropan-2-yl]oxy-[1,2,4]triazolo[1,5-a]pyridin-2-amine;

N-[(8-endo)-3-(3-methyl-1,2,4-thiadiazol-5-yl)-3-azabicyclo[3.2.1]octan-8-yl]-8-[(2S or 2R)-1,1,1-trifluoropropan-2-yl]oxy-[1,2,4]triazolo[1,5-a]pyridin-2-amine;

N-[(8-endo)-3-(3-methyl-1,2,4-thiadiazol-5-yl)-3-azabicyclo[3.2.1]octan-8-yl]-8-[[1-(trifluoromethyl)cyclopropyl]methoxy]-[1,2,4]triazolo[1,5-a]pyridin-2-amine;

8-[(4,4-difluorocyclohexyl)methoxy]-N-[(8-endo)-3-(3-methyl-1,2,4-thiadiazol-5-yl)-3-azabicyclo[3.2.1]octan-8-yl]-[1,2,4]triazolo[1,5-a]pyridin-2-amine;

8-[(3,3-difluorocyclobutyl)methoxy]-N-[(8 endo)-3-(3-methyl-1,2,4-thiadiazol-5-yl)-3-azabicyclo[3.2.1]octan-8-yl]-[1,2,4]triazolo[1,5-a]pyridin-2-amine;

N-[(8 endo)-3-(3-methyl-1,2,4-thiadiazol-5-yl)-3-azabicyclo[3.2.1]octan-8-yl]-8-(1,2,2,2-tetrafluoroethoxy)-[1,2,4]triazolo[1,5-a]pyridin-2-amine;

8-[2,2-difluorocyclopropyl] methoxy]-N-[(8endo)-3-(3-methyl-1,2,4-thiadiazol-5-yl)-3-azabicyclo[3.2.1]octan-8-yl]-[1,2,4]triazolo[1,5-a]pyridin-2-amine;

8-((3,3-difluorocyclopentyl)methoxy)-N-[(8 endo) 3-(3-methyl-1,2,4-thiadiazol-5-yl)-3-azabicyclo[3.2.1]octan-8-yl]-[1,2,4]triazolo[1,5-a]pyridin-2-amine;

N-[(8-endo)-3-(3-methyl-1,2,4-thiadiazol-5-yl)-3-azabicyclo[3.2.1]octan-8-yl]-8-(3,3,3-trifluoro-2,2-dimethylpropoxy)-[1,2,4]triazolo[1,5-a]pyridin-2-amine;

5-methyl-N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine;

6-Methyl-N-[(8-endo)-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine; and 6-chloro-N-[8-endo-3-(3-methyl-1,2,4-thiadiazol-5-yl)-3-azabicyclo[3.2.1]octan-8-yl]-8-(2,2,2-trifluoroethoxy)-[1,2,4]triazolo[1,5-a]pyridin-2-amine.

4. A compound of formula I-2 according to claim 1

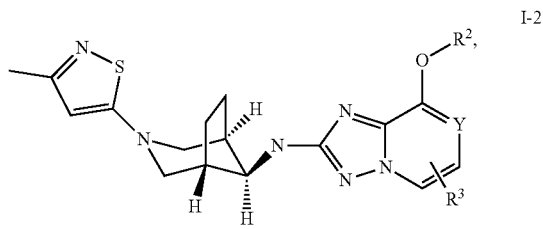

or a pharmaceutically acceptable salt thereof, wherein:
R² is lower alkyl substituted by halogen,

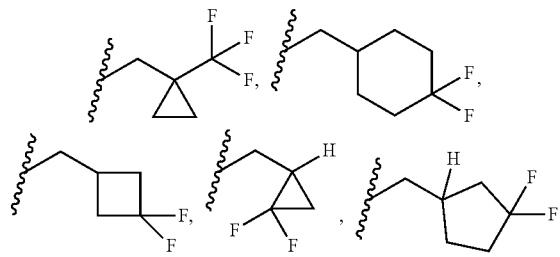

or is lower alkenyl substituted by halogen;
R³ is hydrogen, lower alkyl substituted by halogen, lower alkyl, halogen or lower alkyl substituted by hydroxy; and
Y is CH or N.

5. A compound of formula I-2 according to claim 4, or a pharmaceutically acceptable salt thereof, wherein the compound is selected from the group consisting of:
N-[(8-endo)-3-(3-methyl-1,2-thiazol-5-yl)-3-azabicyclo[3.2.1]octan-8-yl]-8-(3,3,3-trifluoropropoxy)-[1,2,4]triazolo[1,5-a]pyridin-2-amine;
N-[(8 endo)-3-(3-methylisothiazol-5-yl)-3-azabicyclo[3.2.1]octan-8-yl]-8-(2,2,3,3,3-pentafluoropropoxy)-[1,2,4]triazolo[1,5-a]pyridin-2-amine;
N-[(8 endo) 3-(3-methylisothiazol-5-yl)-3-azabicyclo[3.2.1]octan-8-yl)]-8-(2,2,2-trifluoroethoxy)-[1,2,4]triazolo[1,5-a]pyridin-2-amine;
N-[(8 endo)-3-(3-methylisothiazol-5-yl)-3-azabicyclo[3.2.1]octan-8-yl]-8-((1,1,1,1-trifluoropropan-2-yl)oxy)-[1,2,4]triazolo[1,5-a]pyridin-2-amine;
N-((8 endo)-3-(3-methylisothiazol-5-yl)-3-azabicyclo[3.2.1]octan-8-yl)-8-((2R or 2S)-1,1,1-trifluoropropan-2-yl)oxy)-[1,2,4]triazolo[1,5-a]pyridin-2-amine;
N-[(8-endo)-3-(3-methylisothiazol-5-yl)-3-azabicyclo[3.2.1]octan-8-yl)]-8-((2S or 2R)-1,1,1-trifluoropropan-2-yl)oxy)-[1,2,4]triazolo[1,5-a]pyridin-2-amine;
N-[(8 endo)-3-(3-methylisothiazol-5-yl)-3-azabicyclo[3.2.1]octan-8-yl]-8-(trifluoromethoxy)-[1,2,4]triazolo[1,5-a]pyridin-2-amine;
N-[(8 endo)-3-(3-methyl-1,2-thiazol-5-yl)-3-azabicyclo[3.2.1]octan-8-yl]-8-[[1-(trifluoromethyl) cyclopropyl]methoxy]-[1,2,4]triazolo[1,5-a]pyridin-2-amine;
8-[(4,4-difluorocyclohexyl)methoxy]-N-[(8 endo)-3-(3-methyl-1,2-thiazol-5-yl)-3-azabicyclo[3.2.1]octan-8-yl]-[1,2,4]triazolo[1,5-a]pyridin-2-amine;
8-[(3,3-difluorocyclobutyl)methoxy]-N-[(8 endo)-3-(3-methyl-1,2-thiazol-5-yl)-3-azabicyclo[3.2.1]octan-8-yl]-[1,2,4]triazolo[1,5-a]pyridin-2-amine;
N-[(8-endo)-3-(3-methyl-1,2-thiazol-5-yl)-3-azabicyclo[3.2.1]octan-8-yl]-8-[1,2,2,2-tetrafluoroethoxy]-[1,2,4]triazolo[1,5-a]pyridin-2-amine;
8-[2,2-difluorocyclopropyl]methoxy]-N[(8-endo)-3-(3-methylisothiazol-5-yl)-3-azabicyclo[3.2.1]octan-8-yl)]-[1,2,4]triazolo[1,5-a]pyridin-2-amine;
8-[3,3-difluorocyclopentyl] methoxy]-N-[(8 endo)-3-(3-methyl-1,2-thiazol-5-yl)-3-azabicyclo[3.2.1]octan-8-yl]-[1,2,4]triazolo[1,5-a]pyridin-2-amine;
N-[(8 endo)-3-(3-methyl-1,2-thiazol-5-yl)-3-azabicyclo[3.2.1]octan-8-yl]-8-(3,3,3-trifluoro-2,2-dimethylpropoxy)-[1,2,4]triazolo[1,5-a]pyridin-2-amine;
N-[(8 endo) (3-(3-methylisothiazol-5-yl)-3-azabicyclo[3.2.1]octan-8-yl)]-8-(2,2,2-trifluoroethoxy)-[1,2,4]triazolo[1,5-a]pyridin-2-amine;
N-[(8 endo)-3-(3-methylisothiazol-5-yl)-3-azabicyclo[3.2.1]octan-8-yl)]-8-(3,3,3-trifluoropropoxy)-[1,2,4]triazolo[1,5-a]pyrazin-2-amine;
8-(2,2-difluoroethoxy)-N-[(8-endo)-3-(3-methylisothiazol-5-yl)-3-azabicyclo[3.2.1]octan-8-yl]-[1,2,4]triazolo[1,5-a]pyrazin-2-amine;
N-[(8-endo)-3-(3-methylisothiazol-5-yl)-3-azabicyclo[3.2.1]octan-8-yl]-8-(2,2,3,3,3-pentafluoropropoxy)-[1,2,4]triazolo[1,5-a]pyrazin-2-amine;
8-((1,1,1,3,3,3-hexafluoropropan-2-yl)oxy)-N-[(8-endo)-3-(3-methylisothiazol-5-yl)-3-azabicyclo[3.2.1]octan-8-yl)-[1,2,4]triazolo[1,5-a]pyrazin-2-amine;
N-[(8-endo)-3-(3-methylisothiazol-5-yl)-3-azabicyclo[3.2.1]octan-8-yl]-8-((1-(trifluoromethyl)cyclopropyl)methoxy)-[1,2,4]triazolo[1,5-a]pyrazin-2-amine;
N-[(8-endo)-3-(3-methylisothiazol-5-yl)-3-azabicyclo[3.2.1]octan-8-yl]-8-((1,1,1-trifluoropropan-2-yl)oxy)-[1,2,4]triazolo[1,5-a]pyrazin-2-amine;
N-[(8-endo)-3-(3-methylisothiazol-5-yl)-3-azabicyclo[3.2.1]octan-8-yl]-8-((2R or 2S)-1,1,1-trifluoropropan-2-yl)oxy)-[1,2,4]triazolo[1,5-a]pyrazin-2-amine;
N-[(8-endo)-3-(3-methylisothiazol-5-yl)-3-azabicyclo[3.2.1]octan-8-yl]-8-((2S or 2R)-1,1,1-trifluoropropan-2-yl)oxy)-[1,2,4]triazolo[1,5-a]pyrazin-2-amine;
N-[8-endo-3-(3-methylisothiazol-5-yl)-3-azabicyclo[3.2.1]octan-8-yl]-8-(2,2,2-trifluoroethoxy)-5-(trifluoromethyl)-[1,2,4]triazolo[1,5-a]pyridin-2-amine;
N-[(8-endo-3-(3-methylisothiazol-5-yl)-3-azabicyclo[3.2.1]octan-8-yl]-5-(trifluoromethyl)-8-[[1-(trifluoromethyl)cyclopropyl]methoxy]-[1,2,4]triazolo[1,5-a]pyridin-2-amine; and
6-fluoro-N-[(8-endo)-3-(3-methylisothiazol-5-yl)-3-azabicyclo[3.2.1]octan-8-yl]-8-(2,2,2-trifluoroethoxy)-[1,2,4]triazolo[1,5-a]pyridin-2-amine.

6. A compound of formula I-3 according to claim 1

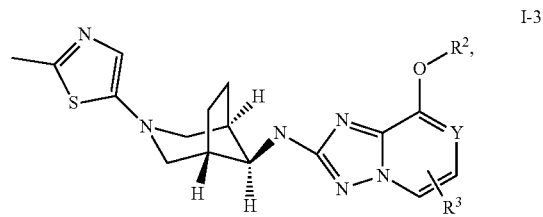

or a pharmaceutically acceptable salt thereof, wherein:
R² is lower alkyl substituted by halogen,

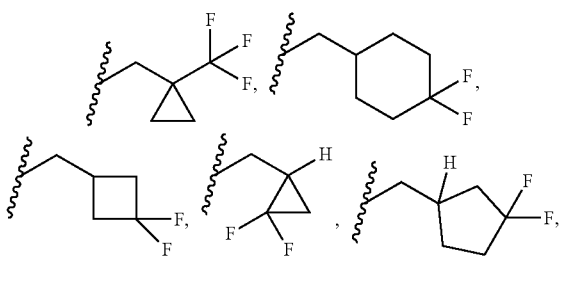

or is lower alkenyl substituted by halogen;
R³ is hydrogen, lower alkyl substituted by halogen, lower alkyl, halogen or lower alkyl substituted by hydroxy; and
Y is CH or N.

7. A compound of formula I-3 according to claim 6, or a pharmaceutically acceptable salt thereof, wherein the compound is selected from the group consisting of:
N-[(8-endo)-3-(2-methyl-1,3-thiazol-5-yl)-3-azabicyclo[3.2.1]octan-8-yl]-8-(4,4,4-trifluorobutoxy)-[1,2,4]triazolo[1,5-a]pyridin-2-amine;
N-[(8-endo)-3-(2-methyl-1,3-thiazol-5-yl)-3-azabicyclo[3.2.1]octan-8-yl]-8-(3,3,3-trifluoropropoxy)-[1,2,4]triazolo[1,5-a]pyridin-2-amine;
N-[8-endo-3-(2-methyl-1,3-thiazol-5-yl)-3-azabicyclo[3.2.1]octan-8-yl]-8-(2,2,2-trifluoroethoxy)-[1,2,4]triazolo[1,5-a]pyridin-2-amine; and
N-[(8-endo-3-(2-methyl-1,3-thiazol-5-yl)-3-azabicyclo[3.2.1]octan-8-yl]-8-[1,1,1-trifluoropropan-2-yl]oxy-[1,2,4]triazolo[1,5-a]pyridin-2-amine.

8. A compound of formula I-4 according to claim 1

I-4 or a pharmaceutically acceptable salt thereof, wherein R² is lower alkyl substituted by halogen, or is lower alkenyl substituted by halogen;
R³ is hydrogen, lower alkyl substituted by halogen, lower alkyl, halogen or lower alkyl substituted by hydroxy; and
Y is CH or N.

9. A compound of formula I-4 according to claim 8, or a pharmaceutically acceptable salt thereof, wherein the compound is selected from the group consisting of:
N-[(8-endo)-3-(5-methyl-1,3,4-oxadiazol-2-yl)-3-azabicyclo[3.2.1]octan-8-yl]-8-(4,4,4-trifluorobutoxy)-[1,2,4]triazolo[1,5-a]pyridin-2-amine;
N-[8-endo-3-(5-methyl-1,3,4-oxadiazol-2-yl)-3-azabicyclo[3.2.1]octan-8-yl]-8-(2,2,2-trifluoroethoxy)-5-(trifluoromethyl)-[1,2,4]triazolo[1,5-a]pyridin-2-amine;
N-[(8-endo)-3-(5-methyl-1,3,4-oxadiazol-2-yl)-3-azabicyclo[3.2.1]octan-8-yl]-5-(trifluoromethyl)-8-(2,2,2-trifluoro-1-methyl-ethoxy)-[1,2,4]triazo[1,5-a]pyridin-2-amine;
N-[(8-endo)-3-(5-methyl-1,3,4-oxadiazol-2-yl)-3-azabicyclo[3.2.1]octan-8-yl]-5-(trifluoromethyl)-8-[(1R or 1S)-2,2,2-trifluoro-1-methyl-ethoxy]-[1,2,4]triazolo[1,5-a]pyridin-2-amine; and
N-[(8-endo)-3-(5-methyl-1,3,4-oxadiazol-2-yl)-3-azabicyclo[3.2.1]octan-8-yl]-5-(trifluoromethyl)-8-[(1S or 1R)-2,2,2-trifluoro-1-methyl-ethoxy]-[1,2,4]triazolo[1,5-a]pyridin-2-amine.

10. A compound of formula I-5 according to claim 1

I-5 or a pharmaceutically acceptable salt thereof, wherein:
R² is lower alkyl substituted by halogen, or is lower alkenyl substituted by halogen;
R³ is hydrogen, lower alkyl substituted by halogen, lower alkyl, halogen or lower alkyl substituted by hydroxy; and
Y is CH or N.

11. A compound of formula I-5 according to claim 10, or a pharmaceutically acceptable salt thereof, wherein the compound is selected from the group consisting of:
N-[(8-endo)-3-(3-methyl-1,2-oxazol-5-yl)-3-azabicyclo[3.2.1]octan-8-yl]-8-[1,1,1-trifluoropropan-2-yl]oxy-[1,2,4]triazolo[1,5-a]pyridin-2-amine;
N-[(8-endo)-3-(3-methyl-1,2-oxazol-5-yl)-3-azabicyclo[3.2.1]octan-8-yl]-8-[(2R or 2S)-1,1,1-trifluoropropan-2-yl]oxy-[1,2,4]triazolo[1,5-a]pyridin-2-amine;
N-[(8-endo)-3-(3-methyl-1,2-oxazol-5-yl)-3-azabicyclo[3.2.1]octan-8-yl]-8-[[1 (trifluoromethyl)cyclopropyl]methoxy]-[1,2,4]triazolo[1,5-a]pyridin-2-amine;
N-[(8-endo)-3-(3-methyl-1,2-oxazol-5-yl)-3-azabicyclo[3.2.1]octan-8-yl]-8-(2,2,3,3,3-pentafluoropropoxy)-[1,2,4]triazolo[1,5-a]pyridin-2-amine;
N-[(8-endo)-3-(3-methylisoxazol-5-yl)-3-azabicyclo[3.2.1]octan-8-yl]-8-(2,2,2-trifluoroethoxy)-5-(trifluoromethyl)-[1,2,4]triazolo[1,5-a]pyridin-2-amine; and
N-[(8-endo)-3-(3-methylisoxazol-5-yl)-3-azabicyclo[3.2.1]octan-8-yl]-5-(trifluoromethyl)-8-[2,2,2-trifluoro-1-methyl-ethoxy]-[1,2,4]triazolo[1,5-a]pyridin-2-amine.

12. A compound of formula I-6 according to claim 1

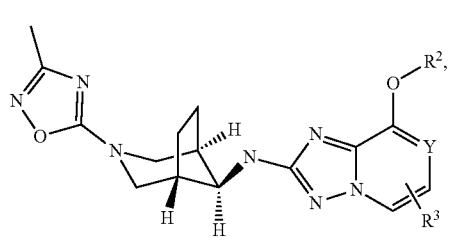

or a pharmaceutically acceptable salt thereof, wherein:
R² is lower alkyl substituted by halogen,

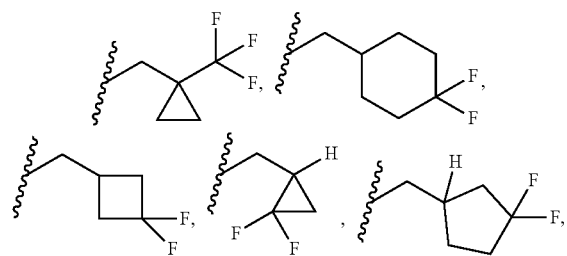

or is lower alkenyl substituted by halogen;
R³ is hydrogen, lower alkyl substituted by halogen, lower alkyl, halogen or lower alkyl substituted by hydroxy; and
Y is CH or N.

13. A compound of formula I-6 according to claim 12, or a pharmaceutically acceptable salt thereof, wherein the compound is selected from the group consisting of:

N-[(8 endo)-3-(3-methyl-1,2,4-oxadiazol-5-yl)-3-azabicyclo[3.2.1]octan-8-yl]-8-(1,1,1-trifluoropropan-2-yloxy)-[1,2,4]triazolo[1,5-a]pyridin-2-amine;

N-[(8 endo)-3-(3-methyl-1,2,4-oxadiazol-5-yl)-3-azabicyclo[3.2.1]octan-8-yl]-8-(2,2,3,3,3-pentafluoropropoxy)-[1,2,4]triazolo[1,5-a]pyridin-2-amine;

N-[(8 endo)-3-(3-methyl-1,2,4-oxadiazol-5-yl)-3-azabicyclo[3.2.1]octan-8-yl]-8-[(Z)-2,3,3,3-tetrafluoroprop-1-enoxy]-[1,2,4]triazolo[1,5-a]pyridin-2-amine;

N-[(8 endo)-3-(3-methyl-1,2,4-oxadiazol-5-yl)-3-azabicyclo[3.2.1]octan-8-yl]-8-(2,2,3,3,3-pentafluoropropoxy)-[1,2,4]triazolo[1,5-a]pyrazin-2-amine;

N-[(8-endo)-3-(3-methyl-1,2,4-oxadiazol-5-yl)-3-azabicyclo[3.2.1]octan-8-yl]-8-(2,2,2-trifluoroethoxy)-5-(trifluoromethyl)-[1,2,4]triazolo[1,5-a]pyridin-2-amine;

N-[(8-endo)-3-(3-methyl-1,2,4-oxadiazol-5-yl)-3-azabicyclo[3.2.1]octan-8-yl]-5-(trifluoromethyl)-8-(2,2,2-trifluoro-1-methyl-ethoxy)-[1,2,4]triazolo[1,5-a]pyridin-2-amine;

N-[(8-endo)-3-(3-methyl-1,2,4-oxadiazol-5-yl)-3-azabicyclo[3.2.1]octan-8-yl]-5-(trifluoromethyl)-8-[(1R or 1S)-2,2,2-trifluoro-1-methyl-ethoxy]-[1,2,4]triazolo[1,5-a]pyridin-2-amine; and 5-Methyl-N-[8-endo-3-(3-methyl-1,2,4-oxadiazol-5-yl)-3-azabicyclo[3.2.1]octan-8-yl]-8-(2,2,3,3,3-pentafluoropropoxy)-[1,2,4]triazolo[1,5-a]pyridin-2-amine.

14. A compound of formula I-7 according to claim 1

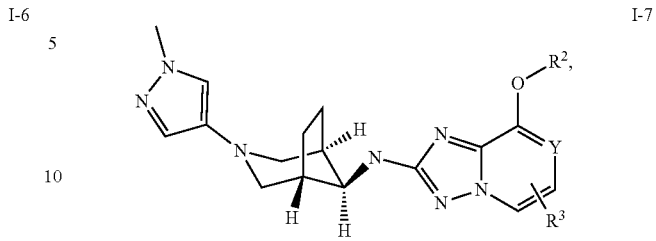

or a pharmaceutically acceptable salt thereof, wherein:
R² is lower alkyl substituted by halogen,

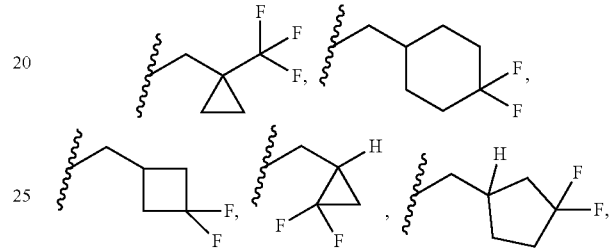

or is lower alkenyl substituted by halogen;
R³ is hydrogen, lower alkyl substituted by halogen, lower alkyl, halogen or lower alkyl substituted by hydroxy; and
Y is CH or N.

15. A compound of formula I-7 according to claim 14, which compound is N-[(8 endo)-3-(1-methylpyrazol-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine.

16. A compound of formula I-8 according to claim 1

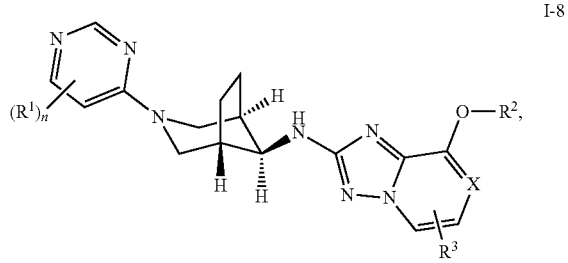

or a pharmaceutically acceptable salt thereof, wherein:
R¹ is hydrogen, lower alkyl, lower alkyl substituted by halogen or halogen;
R² is lower alkyl substituted by halogen,

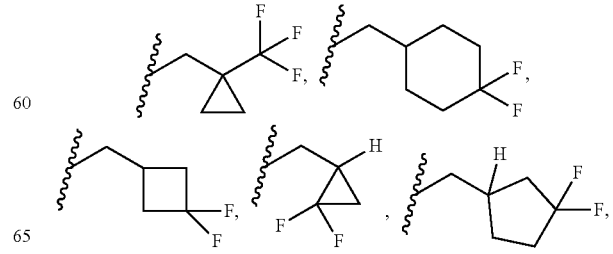

or is lower alkenyl substituted by halogen;
R³ is hydrogen, lower alkyl substituted by halogen, lower alkyl, halogen or lower alkyl substituted by hydroxy;
Y is CH or N; and
n is 1 or 2.

17. A compound of formula I-8 according to claim 16, or a pharmaceutically acceptable salt thereof, wherein the compound is selected from the group consisting of:
N-[(8-endo)-3-(6-methylpyrimidin-4-yl)-3-azabicyclo[3.2.1]octan-8-yl]-8-(3,3,3-trifluoropropoxy)-[1,2,4]triazolo[1,5-a]pyridin-2-amine;
N-[(8-endo)-3-(6-methylpyrimidin-4-yl)-3-azabicyclo[3.2.1]octan-8-yl]-8-(2,2,2-trifluoroethoxy)-[1,2,4]triazolo[1,5-a]pyridin-2-amine;
N-[(8-endo)-3-(6-methylpyrimidin-4-yl)-3-azabicyclo[3.2.1]octan-8-yl]-8-1,1,1-trifluoropropan-2-yloxy)-[1,2,4]triazolo[1,5-a]pyridin-2-amine;
N[(8-endo)-3-(6-methylpyrimidin-4-yl)-3-azabicyclo[3.2.1]octan-8-yl]-8-(2,2,3,3,3-pentafluoropropoxy)-[1,2,4]triazolo[1,5-a]pyridin-2-amine;
N-[(8-endo)-3-(2-methyl pyrimidin-4-yl)-3-azabicyclo[3.2.1]octan-8-yl]-8-(4,4,4-trifluorobutoxy)-[1,2,4]triazolo[1,5-a]pyridin-2-amine;
N-[(8-endo)-3-(2-methylpyrimidin-4-yl)-3-azabicyclo[3.2.1]octan-8-yl]-8-1,1,1-trifluoropropan-2-yloxy)-[1,2,4]triazolo[1,5-a]pyridin-2-amine;
8-(2,2,3,3,3-pentafluoropropoxy)-N-[(8 endo)-3-[6-(trifluoromethyl)pyrimidin-4-yl]-3-azabicyclo[3.2.1]octan-8-yl]-[1,2,4]triazolo[1,5-a]pyridin-2-amine;
N-[(8-endo)-3-(5-fluoropyrimidin-4-yl)-3-azabicyclo[3.2.1]octan-8-yl]-8-(2,2,3,3,3-pentafluoropropoxy)-[1,2,4]triazolo[1,5-a]pyridin-2-amine;
N-[(8-endo)-3-(5-fluoro-6-methylpyrimidin-4-yl)-3-azabicyclo[3.2.1]octan-8-yl]-8-(2,2,3,3,3-pentafluoropropoxy)-[1,2,4]triazolo[1,5-a]pyridin-2-amine;
N-[(8-endo)-3-(5-fluoro-2-methylpyrimidin-4-yl)-3-azabicyclo[3.2.1]octan-8-yl]-8-(2,2,2-trifluoroethoxy)-[1,2,4]triazolo[1,5-a]pyridin-2-amine;
N-[(8-endo)-3-(6-chloropyrimidin-4-yl)-3-azabicyclo[3.2.1]octan-8-yl]-8-(2,2,2-trifluoroethoxy)-[1,2,4]triazolo[1,5-a]pyridin-2-amine;
N-[(8-endo)-3-(6-methyl pyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine;
N-[(8-endo)-3-(5-fluoropyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine;
N-[(8-endo)-3-(5-fluoro-6-methyl-pyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine amine;
N-[(8-endo)-3-(6-chloropyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine;
N-[(8-endo)-3-pyrimidin-4-yl-3-azabicyclo[3.2.1]octan-8-yl]-8-(2,2,2-trifluoroethoxy)-5-(trifluoromethyl)-[1,2,4]triazolo[1,5-a]pyridin-2-amine;
N-[(8-endo)-3-(5-fluoro-2-methyl-pyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine;
N-[(8-endo-3-(6-methoxypyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine;
N-[(8-endo)-3-(6-fluoropyrimidin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine;
2-[2-[[(8 endo)-3-(6-methylpyrimidin-4-yl)-3-azabicyclo[3.2.1]octan-8-yl]amino]-8-(2,2,2-trifluoroethoxy)-[1,2,4]triazolo[1,5-a]pyridin-5-yl]propan-2-ol;
2-[2-[[(8 endo)-3-(5-fluoropyrimidin-4-yl)-3-azabicyclo[3.2.1]octan-8-yl]amino]-8-(2,2,2-trifluoroethoxy)-[1,2,4] triazolo[1,5-a]pyridin-5-yl]propan-2-ol;
2-[2-[[(8 endo)-3-(5-fluoro-6-methylpyrimidin-4-yl)-3-azabicyclo[3.2.1]octan-8-yl]amino]-8-(2,2,2-trifluoroethoxy)-[1,2,4]triazol o[1,5-a]pyridin-5-yl]propan-2-ol;
2-[2-[[(8endo)-3-(5-fluoro-2-methylpyrimidin-4-yl)-3-azabicyclo[3.2.1]octan-8-yl]amino]-8-(2,2,2-trifluoroethoxy)-[1,2,4] triazolo [1,5-a]pyridin-5-yl]propan-2-ol;
8-(2,2-difluoroethoxy)-N-[(8 endo)-3-(6-methylpyrimidin-4-yl)-3-azabicyclo[3.2.1]octan-8-yl]-5-(trifluoromethyl)-[1,2,4]triazolo[1,5-a]pyridin-2-amine; and
8-(2-fluoroethoxy)-N-[(8 endo)-3-(6-methylpyrimidin-4-yl)-3-azabicyclo[3.2.1]octan-8-yl]-5-(trifluoromethyl)-[1,2,4]triazolo[1,5-a]pyridin-2-amine.

18. A compound of formula I-9 according to claim 1

I-9 or a pharmaceutically acceptable salt thereof, wherein
R¹ is hydrogen, lower alkyl, lower alkyl substituted by halogen or halogen;
R² is lower alkyl substituted by halogen, or is lower alkenyl substituted by halogen;
R³ is hydrogen, lower alkyl substituted by halogen, lower alkyl, halogen or lower alkyl substituted by hydroxy;
Y is CH or N; and
n is 1 or 2.

19. A compound of formula I-9 according to claim 18, or a pharmaceutically acceptable salt thereof, wherein the compound is selected from the group consisting of:
8-(2,2,2-trifluoroethoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine;
8-[1,2,2,2-tetrafluoroethoxy]-N-[(8 endo)-3-[2-(trifluoromethyl)pyridin-4-yl]-3-azabicyclo[3.2.1]octan-8-yl]-[1,2,4]triazolo[1,5-a] pyridin-2-amine;

8-((1-(trifluoromethyl) cyclopropyl)methoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine;

8-(2,2,3,3,3-pentafluoropropoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine;

N-((8-endo)-3-(2-(trifluoromethyl)pyridin-4-yl)-3-azabicyclo[3.2.1]octan-8-yl)-8-((1,1,1-trifluoropropan-2-yl)oxy)-[1,2,4]triazolo[1,5-a]pyrazin-2-amine;

8-(2,2,3,3,3-pentafluoropropoxy)-N-((8 endo)-3-(2-(trifluoromethyl)pyridin-4-yl)-3-azabicyclo[3.2.1]octan-8-yl)-[1,2,4]triazolo[1,5-a]pyrazin-2-amine;

N-[(8-endo)-3-(3-fluoropyridin-4-yl)-3-azabicyclo[3.2.1]octan-8-yl]-8-(2,2,2-trifluoroethoxy)-[1,2,4]triazolo[1,5-a]pyridin-2-amine;

N-[(8-endo)-3-(2-chloropyridin-4-yl)-3-azabicyclo[3.2.1]octan-8-yl]-8-(2,2,2-trifluoroethoxy)-[1,2,4]triazolo[1,5-a]pyridin-2-amine;

N-[(8-endo)-3-(5-fluoro-2-methylpyridin-4-yl)-3-azabicyclo[3.2.1]octan-8-yl]-8-(2,2,3,3,3-pentafluoropropoxy)-[1,2,4]triazolo[1,5-a]pyridin-2-amine;

8-(2,2,2-trifluoroethoxy)-5-(trifluoromethyl)-N-[(8-endo)-3-[2-(trifluoromethyl)-4-pyridyl]-3-azabicyclo[3.2.1]octan-8-yl]-[1,2,4]triazolo[1,5-a]pyridin-2-amine;

5-(trifluoromethyl)-8-(2,2,2-trifluoro-1-methyl-ethoxy)-N-[8-endo-3-[2-(trifluoromethyl)-4-pyridyl]-3-azabicyclo[3.2.1]octan-8-yl]-[1,2,4]triazolo[1,5-a]pyridin-2-amine;

N-[(8-endo)-3-(5-fluoro-2-methyl-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine;

N-[(8-endo)-3-(2-chloro-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine;

N-[(8-endo)-3-(3-fluoro-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine;

N-[(8 endo)-3-(2-chloro-6-methyl-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine;

N-[(8-endo)-3-(2-chloro-5-fluoro-4-pyridyl)-3-azabicyclo[3.2.1]octan-8-yl]-8-(2,2,2-trifluoroethoxy)-5-(trifluoromethyl)-[1,2,4]triazolo[1,5-a]pyridin-2-amine;

5-Methyl-8-(2,2,2-trifluoroethoxy)-N-[(8-endo)-3-[2-(trifluoromethyl)-4-pyridyl]-3-azabicyclo[3.2.1]octan-8-yl]-[1,2,4]triazolo[1,5-a]pyridin-2-amine;

2-[8-(2,2,2-trifluoroethoxy)-2-[[(8 endo)-3-[2-(trifluoromethyl)pyridin-4-yl]-3-azabicyclo [3.2.1]octan-8-yl]amino]-[1,2,4]triazolo [1,5-a]pyridin-5-yl]propan-2-ol;

2-[2-[[(8-endo)-3-(2-chloropyridin-4-yl)-3-azabicyclo[3.2.1]octan-8-yl]amino]-8-(2,2,2-trifluoroethoxy)-[1,2,4] triazolo [1,5-a]pyridin-5-yl]propan-2-ol;

2-[2-[[(8-endo)-3-(2-chloro-5-fluoropyridin-4-yl)-3-azabicyclo[3.2.1]octan-8-yl]amino]-8-(2,2,2-trifluoroethoxy)-[1,2,4]triazolo[1,5-a]pyridin-5-yl]propan-2-ol;

N-[(8-endo)-3-(2-chloropyridin-4-yl)-3-azabicyclo[3.2.1]octan-8-yl]-8-(2,2-difluoroethoxy)-5-(trifluoromethyl)-[1,2,4]triazolo[1,5-a]pyridin-2-amine; and N-[(8-endo)-3-(2-chloropyridin-4-yl)-3-azabicyclo[3.2.1]octan-8-yl]-8-(2-fluoroethoxy)-5-(trifluoromethyl)-[1,2,4]triazolo[1,5-a]pyridin-2-amine.

20. A compound of formula I-10 according to claim 1

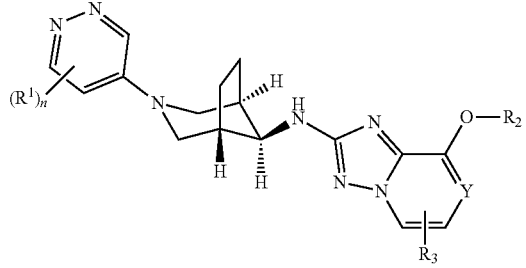

I-10 or a pharmaceutically acceptable salt thereof, wherein:
R¹ is hydrogen, lower alkyl, lower alkyl substituted by halogen, halogen, or lower alkoxy;
R² is lower alkyl substituted by halogen,

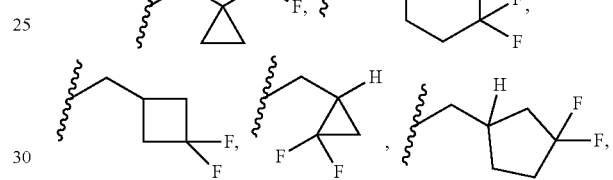

or is lower alkenyl substituted by halogen;
R³ is hydrogen, lower alkyl substituted by halogen, lower alkyl, halogen, $C_{3-6}$-cycloalkyl or lower alkyl substituted by hydroxy;
Y is CH or N;
n is 1 or 2, wherein for n=2 each R¹ can be independent of each other.

21. A compound of formula I-10 according to claim 20, or a pharmaceutically acceptable salt thereof, wherein the compound is selected from the group consisting of:
N-[(1R,5 S,8s)-3-(6-chloropyridazin-4-yl)-3-azabicyclo[3.2.1]octan-8-yl]-[1,2,4]triazolo[1,5-a]pyridin-2-amine;

5-cyclopropyl-N-[(1R,5S,8s)-3-(6-methoxypyridazin-4-yl)-3-azabicyclo[3.2.1]octan-8-yl]-8-(2,2,2-trifluoroethoxy)-[1,2,4]triazolo[1,5-a]pyridin-2-amine;

N-[(1R,5 S,8s)-3-(6-chloropyridazin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine; and N-[(1R,5 S,8s)-3-(6-methoxypyridazin-4-yl)-3-azabicyclo[3.2.1]octan-8-yl]-8-(2,2,2-trifluoroethoxy)-5-(trifluoromethyl)-[1,2,4]triazolo[1,5-a]pyridin-2-amine.

22. A process for preparing a compound of formula I as defined in claim 1, which process comprises:
a) reacting a compound of formula 2:

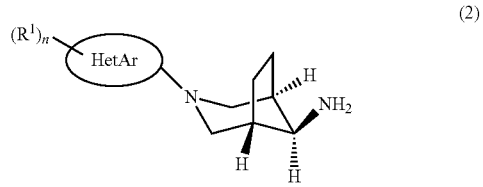

(2)

with a compound of formula 3:

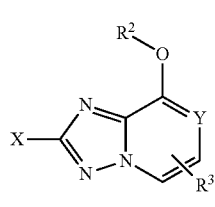
(3)

to form a compound of formula I:

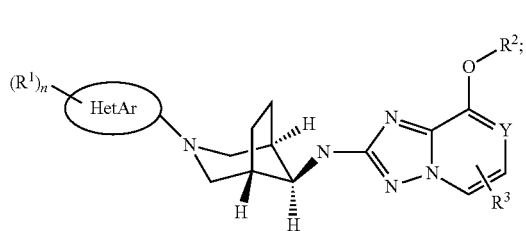
(I)

wherein X is halogen, and, optionally, converting the compound of formula I into a pharmaceutically acceptable salt;
or
b) reacting a compound of formula 6:

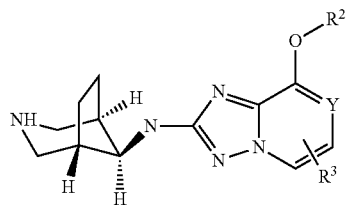
(6)

with a compound of formula 7:

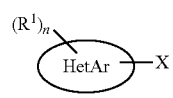
(7)

to form a compound of formula I:

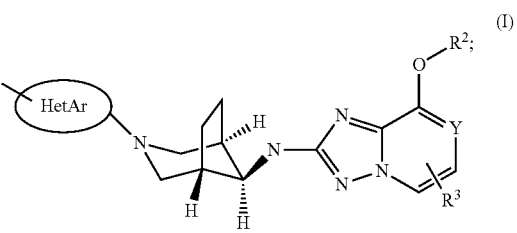
(I)

or a pharmaceutically acceptable salt thereof.

23. A medicament comprising a compound of claim 1 and one or more pharmaceutically acceptable excipients.

24. A method for the treatment of cerebral amyloid angiopathy, or hereditary cerebral hemorrhage with amyloidosis, Dutch-type, which method comprises administering an effective amount of a compound as defined in claim 1, or a pharmaceutically acceptable salt thereof, to a subject in need thereof.

* * * * *